(12) United States Patent
Salomon et al.

(10) Patent No.: US 11,993,762 B2
(45) Date of Patent: May 28, 2024

(54) POLYPEPTIDES HAVING ALPHA-MANNAN DEGRADING ACTIVITY AND POLYNUCLEOTIDES ENCODING SAME

(71) Applicant: Novozymes A/S, Bagsvaerd (DK)

(72) Inventors: Jesper Salomon, Holte (DK); Klaus Gori, Dyssegaard (DK); Lorena González Palmén, Åkarp (SE); Kenneth Jensen, Delsted (DK); Nikolaj Spodsberg, Holte (DK); Mary Ann Stringer, Søborg (DK); Kristian Bertel Roemer M. Krogh, Bagsvaerd (DK); Morten Gjermansen, Greve (DK)

(73) Assignee: Novozymes A/S, Bagsvaerd (DK)

( * ) Notice: Subject to any disclaimer, the term of this patent is extended or adjusted under 35 U.S.C. 154(b) by 662 days.

(21) Appl. No.: 17/280,798

(22) PCT Filed: Oct. 2, 2019

(86) PCT No.: PCT/EP2019/076728
§ 371 (c)(1),
(2) Date: Mar. 26, 2021

(87) PCT Pub. No.: WO2020/070199
PCT Pub. Date: Apr. 9, 2020

(65) Prior Publication Data
US 2022/0089977 A1 Mar. 24, 2022

(30) Foreign Application Priority Data
Oct. 3, 2018 (EP) .................................. 18198448

(51) Int. Cl.
| | | |
|---|---|---|
| *C11D 3/386* | (2006.01) | |
| *C12N 9/24* | (2006.01) | |
| *C12N 15/09* | (2006.01) | |
| *C12N 15/11* | (2006.01) | |
| *C12P 21/00* | (2006.01) | |
| *C12P 21/02* | (2006.01) | |

(52) U.S. Cl.
CPC ........ *C11D 3/38636* (2013.01); *C12N 9/2402* (2013.01); *C12Y 302/01078* (2013.01); *C12N 15/09* (2013.01); *C12N 15/11* (2013.01); *C12P 21/00* (2013.01); *C12P 21/02* (2013.01)

(58) Field of Classification Search
None
See application file for complete search history.

(56) References Cited

U.S. PATENT DOCUMENTS
2009/0176682 A1  7/2009 Boutique et al.

FOREIGN PATENT DOCUMENTS
WO  2009087525 A1  7/2009

OTHER PUBLICATIONS

Anonymous, 2020, NCBI reference No. WP_090577824.1.
Anonymous, 2020, NCBI Reference No. WP_091188622.1.
Dhawan et al., 2007, CRC Critical reviews in biotechnology 27(4), 197-216.
Fiorini, 2014, Chemistry world, 1-3.
Lucas et al., 2013, GenBank No. ACT03643.1.

*Primary Examiner* — Suzanne M Noakes
*Assistant Examiner* — Jae W Lee
(74) *Attorney, Agent, or Firm* — Kelly K. Reynolds

(57) ABSTRACT

The invention relates to compositions comprising and uses of polypeptides having alpha-mannan degrading activity. The present invention relates to polypeptides having alpha-mannan degrading activity, and polynucleotides encoding the polypeptides. The invention also relates to nucleic acid constructs, vectors, and host cells comprising the polynucleotides as well as methods of producing and using the polypeptides.

18 Claims, No Drawings
Specification includes a Sequence Listing.

POLYPEPTIDES HAVING ALPHA-MANNAN DEGRADING ACTIVITY AND POLYNUCLEOTIDES ENCODING SAME

CROSS-REFERENCE TO RELATED APPLICATIONS

This application is a 35 U.S.C. 371 national application of international application no. PCT/EP2019/076728 filed Oct. 2, 2019, which claims priority or the benefit under 35 U.S.C. 119 of European application no. 18198448.5 filed Oct. 3, 2018, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The invention relates to compositions comprising and uses of polypeptides having alpha-mannan degrading activity. The present invention relates to polypeptides having alpha-mannan degrading activity, and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets it specific substrate, e.g., amylases are active towards starch stains, proteases towards protein stains, and so forth.

Mannans are known in the art as plant polysaccharides with a backbone of β-1,4-linked D-mannopyranosyl residues, which can contain galactose or acetyl substitutions and may have glucose residues in the backbone. The main enzyme type participating in the degradation of mannans are endo-1,4-β-mannanases (EC 3.2.1.78), which hydrolyze the internal glycoside bonds in the mannan backbone. Beta-mannanases, which are often simply referred to in the literature as mannanases, have been used for many years in the detergent industry for effective stain removal of plant-based stains.

Another important type of mannan is the cell wall polysaccharide found, for example, in yeast cell walls, and known as alpha-mannan. In contrast to the plant-based beta-mannan polysaccharides noted above, these alpha-mannans contain mannose residues connected through an alpha-(1,6)-linked linear backbone, with alpha-(1,2) and alpha-(1,3) linked branches, which may also be phosphorylated.

Alpha-mannans are also components of biofilm. Textiles surface and hard surfaces, such as dishes or the inner space of a laundry machine enduring a number of wash cycles, become soiled with many different types of soiling which may compose of proteins, grease, starch etc. One type of soiling may be organic matter, such as biofilm, extracellular polymeric substance (EPS), etc. Organic matter composes different molecules such as polysaccharides, extracellular DNA (eDNA), and proteins. Some organic matter composes an extracellular polymeric matrix, which may be sticky or glueing, which when present on textile, attracts soils and may course redeposition or backstaining of soil resulting in a greying of the textile. Additionally, organic matters such as biofilms often cause malodor issue as various malodor molecules can be adhered by the polysaccharides, extracellular DNA (eDNA), and proteins in the complex extracellular matrix and be slowly released out to cause consumer noticeable malodor issue.

Thus, it could be advantageous to use enzymes in applications where alpha-mannan needs to be degraded.

According to the online carbohydrate-active enzyme ("CAZy") database (available at cazy.org), alpha-mannan degrading enzymes have been found in glycoside hydrolase families including 76, 92, and 99. The present invention provides polypeptides having alpha-mannanase activity and polynucleotides encoding the polypeptides that are highly active in degrading alpha-mannan, and therefore could be used in the aforementioned applications.

SUMMARY OF THE INVENTION

The invention relates to cleaning compositions comprising at least one polypeptide having alpha-mannan degrading activity or a variant or a fragment thereof having alpha-mannan degrading activity; and a cleaning composition component.

The present invention provides isolated or purified polypeptides having alpha-mannan degrading activity and polynucleotides encoding the polypeptides. In an embodiment, the polypeptide having alpha-mannan degrading activity belongs to glycosyl hydrolase family 76 (GH76), glycosyl hydrolase family 92 (GH92), glycosyl hydrolase family 99 (GH99), in particular to glycosyl hydrolase family 76.

One aspect relates to polypeptides comprising one or more of the motifs

[YND]DD[QINLEM]     (SEQ ID NO: 60)
and

GG[ILMV]X[WS].     (SEQ ID NO: 61)

One aspect relates to polypeptides comprises the motif [RK][NLT]XXX[NTV]XP[GTLYISAVFNM] (SEQ ID NO: 64).

One aspect relates to polypeptides of the KNTPA clade and of bacterial origin.

One aspect relates to polypeptides comprising the motif

GA]XX[AVL][ML]X[MA][ATV][EATV]     (SEQ ID NO: 62)
or the motif

LA[EQ]X[VL][YF].     (SEQ ID NO: 63)

One aspect relates to polypeptides of the AMXAAE clade and of fungal origin.

One aspect relates to polypeptides comprising the motif N[EQD][WFY][HG]E (SEQ ID NO: 66).

Accordingly, the present invention relates to isolated or purified polypeptides having alpha-mannan degrading activity selected from the group consisting of: a polypeptide having at least 60% sequence identity to the polypeptide of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, or SEQ ID NO: 57 or a fragment thereof having alpha-mannan degrading activity.

Accordingly, the present invention relates to isolated or purified polypeptides having alpha-mannan degrading activity selected from the group consisting of:

(a) a polypeptide having at least 60% sequence identity to the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 53, SEQ ID NO: 56;

(b) a polypeptide encoded by a polynucleotide that hybridizes under medium stringency conditions with the full-length complement of the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 49 or the cDNA sequence thereof, SEQ ID NO: 52 or the cDNA sequence thereof, SEQ ID NO: 55;

(c) a polypeptide encoded by a polynucleotide having at least 60% sequence identity to the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 46 or the cDNA sequence thereof, SEQ ID NO: 49 or the cDNA sequence thereof, SEQ ID NO: 52 or the cDNA sequence thereof, SEQ ID NO: 55;

(d) a fragment of the polypeptide of (a), (b), or (c), that has alpha-mannan degrading activity.

The present invention also relates to isolated or purified polynucleotides encoding the polypeptides of the present invention; nucleic acid constructs; recombinant expression vectors; recombinant host cells comprising the polynucleotides; and methods of producing the polypeptides.

The present invention further relates to granules comprising a core particle and one or more coatings, wherein the granule comprises a polypeptide having alpha-mannan degrading activity as defined above, and liquid compositions comprising a polyol and a polypeptide having alpha-mannan degrading activity, wherein the polypeptide is as defined above.

The invention further relates to uses of the peptide in various applications such as degrading alpha-mannan, laundering, washing, cleaning, feed, food, extracting coffee, degrading cellulosic material, producing a fermentation product, isolated polynucleotides encoding the polypeptides of the invention, recombinant host cells and method of producing the polypeptide of the invention.

Overview of Sequences

SEQ ID NO: 1 DNA encoding full length polypeptide from *Paenibacillus glycanilyticus*
SEQ ID NO: 2 polypeptide derived from SEQ ID NO: 1
SEQ ID NO: 3 mature polypeptide obtained from *Paenibacillus glycanilyticus*
SEQ ID NO: 4 DNA encoding full length polypeptide from *Bacillus acidicola*
SEQ ID NO: 5 polypeptide derived from SEQ ID NO: 4
SEQ ID NO: 6 mature polypeptide obtained from *Bacillus acidicola*
SEQ ID NO: 7 DNA encoding full length polypeptide from *Bacillus* sp.
SEQ ID NO: 8 polypeptide derived from SEQ ID NO: 7
SEQ ID NO: 9 mature polypeptide obtained from *Bacillus* sp.
SEQ ID NO: 10 DNA encoding full length polypeptide from *Paenibacillus* sp. A
SEQ ID NO: 11 polypeptide derived from SEQ ID NO: 10
SEQ ID NO: 12 mature polypeptide obtained from *Paenibacillus* sp. A
SEQ ID NO: 13 DNA encoding full length polypeptide from *Paenibacillus* sp. B
SEQ ID NO: 14 polypeptide derived from SEQ ID NO: 13
SEQ ID NO: 15 mature polypeptide obtained from *Paenibacillus* sp. B
SEQ ID NO: 16 DNA encoding full length polypeptide from *Paenibacillus* sp. C
SEQ ID NO: 17 polypeptide derived from SEQ ID NO: 16
SEQ ID NO: 18 mature polypeptide obtained from *Paenibacillus* sp. C
SEQ ID NO: 19 DNA encoding full length polypeptide from Microbial community B
SEQ ID NO: 20 polypeptide derived from SEQ ID NO: 19
SEQ ID NO: 21 mature polypeptide obtained from Microbial community B
SEQ ID NO: 22 DNA encoding full length polypeptide from Microbial community H
SEQ ID NO: 23 polypeptide derived from SEQ ID NO: 22
SEQ ID NO: 24 mature polypeptide obtained from Microbial community H
SEQ ID NO: 25 DNA encoding full length polypeptide from *Bacillus novalis*
SEQ ID NO: 26 polypeptide derived from SEQ ID NO: 25
SEQ ID NO: 27 mature polypeptide obtained from *Bacillus novalis*
SEQ ID NO: 28 DNA encoding full length polypeptide from *Chryseobacterium* sp.
SEQ ID NO: 29 polypeptide derived from SEQ ID NO: 28
SEQ ID NO: 30 mature polypeptide obtained from *Chryseobacterium* sp.
SEQ ID NO: 31 DNA encoding full length polypeptide from *Aspergillus aculeatus*
SEQ ID NO: 32 polypeptide derived from SEQ ID NO: 31
SEQ ID NO: 33 mature polypeptide obtained from *Aspergillus aculeatus*
SEQ ID NO: 34 DNA encoding full length polypeptide from *Aspergillus aculeatus*
SEQ ID NO: 35 polypeptide derived from SEQ ID NO: 34
SEQ ID NO: 36 mature polypeptide obtained from *Aspergillus aculeatus*
SEQ ID NO: 37 DNA encoding full length polypeptide from *Aspergillus aculeatus*
SEQ ID NO: 38 polypeptide derived from SEQ ID NO: 37

SEQ ID NO: 39 mature polypeptide obtained from *Aspergillus aculeatus*
SEQ ID NO: 40 DNA encoding full length polypeptide from *Aspergillus aculeatus*
SEQ ID NO: 41 polypeptide derived from SEQ ID NO: 40
SEQ ID NO: 42 mature polypeptide obtained from *Aspergillus aculeatus*
SEQ ID NO: 43 DNA encoding full length polypeptide from *Humicola insolens*
SEQ ID NO: 44 polypeptide derived from SEQ ID NO: 43
SEQ ID NO: 45 mature polypeptide obtained from *Humicola insolens*
SEQ ID NO: 46 DNA encoding full length polypeptide from *Humicola insolens*
SEQ ID NO: 47 polypeptide derived from SEQ ID NO: 46
SEQ ID NO: 48 mature polypeptide obtained from *Humicola insolens*
SEQ ID NO: 49 DNA encoding full length polypeptide from *Humicola insolens*
SEQ ID NO: 50 polypeptide derived from SEQ ID NO: 43
SEQ ID NO: 51 mature polypeptide obtained from *Humicola insolens*
SEQ ID NO: 52 DNA encoding full length polypeptide from *Humicola insolens*
SEQ ID NO: 53 polypeptide derived from SEQ ID NO: 43
SEQ ID NO: 54 mature polypeptide obtained from *Humicola insolens*
SEQ ID NO: 55 DNA encoding truncated polypeptide from Microbial community H
SEQ ID NO: 56 polypeptide derived from SEQ ID NO: 55
SEQ ID NO: 57 mature polypeptide obtained from Microbial community H
SEQ ID NO: 58 is a secretion signal
SEQ ID NO: 59 is a His tag
SEQ ID NO: 60 is a motif [YND]DD[QINLEM]
SEQ ID NO: 61 is a motif GG[ILMV]X[WS]
SEQ ID NO: 62 is a motif [GA]XX[AVL][ML]X[MA][ATV][EATV]
SEQ ID NO: 63 is a motif LA[EQ]X[VL][YF]
SEQ ID NO: 64 is a motif [RK][NLT]XXX[NTV]XP[GTLYISAVFNM]
SEQ ID NO: 65 is a motif KNTPANAPA
SEQ ID NO: 66 is a motif N[EQD][WFY][HG]E
SEQ ID NO: 67 is a beta-mannanase obtainable from *Bacillus bogoriensis*
SEQ ID NO: 68 is a beta-mannanase obtainable from *Paenibacillus* sp. (PspMan4)
SEQ ID NO: 69 is a beta-mannanase obtainable from *Bacillus hemicellulosilyticus*

Definitions

In accordance with this detailed description, the following definitions apply. Note that the singular forms "a," "an," and "the" include plural references unless the context clearly dictates otherwise.

Reference to "about" a value or parameter herein includes aspects that are directed to that value or parameter per se. For example, description referring to "about X" includes the aspect "X".

Unless defined otherwise or clearly indicated by context, all technical and scientific terms used herein have the same meaning as commonly understood by one of ordinary skill in the art to which this invention belongs.

Alpha-Mannan Degrading Enzyme: The term "alpha-mannan degrading enzyme" or "polypeptide having alpha-mannan degrading activity" means an enzyme having hydrolase activity on alpha-mannan. Relevant are enzymes having alpha-mannanase and/or alpha-mannosidase activity. In particular, the polypeptide having alpha-mannan degrading activity includes glycoside hydrolase domains GH76, GH92, or GH99, as defined in CAZY (available at cazy.org, and as described in Lombard V, et al. 2014, Nucleic Acids Res 42:D490-D495). These can include enzyme activities such as alpha-1,6-mannanase (EC 3.2.1.101), alpha-1,2-mannase; mannosyl-oligosaccharide alpha-1,2-mannosidase (EC 3.2.1.113); mannosyl-oligosaccharide alpha-1,3-mannosidase (EC 3.2.1.-); mannosyl-oligosaccharide alpha-1,6-mannosidase (EC 3.2.1.-); alpha-mannosidase (EC 3.2.1.24); alpha-1,2-mannosidase (EC 3.2.1.-); alpha-1,3-mannosidase (EC 3.2.1.-); alpha-1,4-mannosidase (EC 3.2.1.-); mannosyl-1-phosphodiester alpha-1,P-mannosidase (EC 3.2.1.-); glycoprotein endo-alpha-1,2-mannosidase (EC 3.2.1.130); and/or mannan endo-1,2-alpha-mannanase (3.2.1.-) activities.

Beta-Mannanase: The term "beta-mannanase" or "galactomannase" as used herein refers to a beta-mannanase enzyme defined as the officially named mannan endo-1,4-beta-mannosidase and having the alternative names beta-mannanase and endo-1,4-mannase. The beta-mannanase term also means a polypeptide or polypeptide domain of an enzymes that has the ability to catalyze the cleavage or hydrolysis of (1→4) beta-D-mannosidic linkages of mannans, galactomannans, glucomannans, and galactoglucmannans. Thus, it means that the beta-mannanase has beta-mannanase activity (EC 3.2.1.78). For purposes of the present invention, beta-mannanase activity is determined according to the procedure described in the Examples. In one aspect, the variants of the present invention have at least 20%, e.g., at least 40%, at least 50%, at least 60%, at least 70%, at least 80%, at least 90%, at least 95%, or at least 100% of the mannanase activity of the polypeptide of SEQ ID NO: 67.

Binding module: The term "binding module" means the region of an enzyme that mediates binding of the enzyme to amorphous regions of a cellulose substrate. The carbohydrate binding module (CBD) is typically found either at the N-terminal or at the C-terminal extremity of an alpha-mannan degrading enzyme.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide, a catalytic domain, or a carbohydrate binding module having one or more (e.g., several) amino acids absent from the amino and/or carboxyl terminus of a mature polypeptide or domain; wherein the fragment has alpha-mannan degrading activity. In some embodiments, a fragment contains at least 90% of the length of the mature polypeptide, such as at least 317 amino acid residues of SEQ ID NO: 2 or SEQ ID NO: 3, at least 314 amino acid residues of SEQ ID NO: 5 or SEQ ID NO: 6, at least 315 amino acid residues of SEQ ID NO: 8 or SEQ ID NO: 9, at least 431 amino acids of SEQ ID NO: 11 or SEQ ID NO: 12, at least 440 amino acids of SEQ ID NO: 14 or SEQ ID NO: 15, at least 313 amino acids of SEQ ID NO: 17 or SEQ ID NO: 18, at least 484 amino acids of SEQ ID NO: 20 or SEQ ID NO: 21, at least 487 amino acids of SEQ ID NO: 23 or SEQ ID NO: 24, at least 1240 amino acids of SEQ ID NO: 26 or SEQ ID NO: 27, at least 307 amino acids of SEQ ID NO: 29 or SEQ ID NO: 30, at least 332 amino acids of SEQ ID NO: 32 or SEQ ID NO: 33, at least 388 amino acids of SEQ ID NO: 35 or SEQ ID NO: 36, at least 345 amino acids of SEQ ID NO: 38 or SEQ ID NO: 39, at least 342 amino acids of SEQ ID NO: 41 or SEQ ID NO: 42, at least 352 amino acids of SEQ ID NO: 44 or SEQ ID NO: 45, at least 355 amino acids of SEQ ID NO: 47 or SEQ ID NO: 48, at least 345 amino acids of SEQ ID NO: 50 or SEQ ID NO: 51, at least 362 amino acids of SEQ ID NO: 53 or SEQ ID NO: 54, at least 450 amino acids of SEQ ID NO: 56 or SEQ ID NO: 57.

Fusion polypeptide: The term "fusion polypeptide" is a polypeptide in which one polypeptide is fused at the N-terminus or the C-terminus of a polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Heterologous: The term "heterologous" means, with respect to a host cell, that a polypeptide or nucleic acid does not naturally occur in the host cell. The term "heterologous" means, with respect to a polypeptide or nucleic acid, that a control sequence, e.g., promoter, or domain of a polypeptide or nucleic acid is not naturally associated with the polypeptide or nucleic acid, i.e., the control sequence is from a gene other than the gene encoding the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 53, SEQ ID NO: 56.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding module from one polypeptide and a catalytic domain from another polypeptide. The domains may be fused at the N-terminus or the C-terminus.

Hybridization: The term "hybridization" means the pairing of substantially complementary strands of nucleic acids, using standard Southern blotting procedures. Hybridization may be performed under medium, medium-high, high or very high stringency conditions. Medium stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 55° C. Medium-high stringency conditions means prehybridization and hybridization at 42° C. in 5×SSPE, 0.3% SDS, 200 micrograms/ml sheared and denatured salmon sperm DNA, and 35% formamide for 12 to 24 hours, followed by washing three times each for 15 minutes using 0.2×SSC, 0.2% SDS at 60° C. High stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 65° C. Very high stringency conditions means prehybridization and hybridization at 42° C. in 5×SSPE, 0.3% SDS, 200 micrograms/ml sheared and denatured salmon sperm DNA, and 50% formamide for 12 to 24 hours, followed by washing three times each for 15 minutes using 0.2×SSC, 0.2% SDS at 70° C.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc.

In some aspects, the mature polypeptide is amino acids 1 to 353 of SEQ ID NO: 2 and amino acids −32 to −1 of SEQ ID NO: 2 is a signal peptide. In some aspects, the mature polypeptide is the amino acid sequence shown in SEQ ID NO: 3. In some aspects, the mature polypeptide is amino acids 1 to 349 of SEQ ID NO: 5 and amino acids −29 to −1 of SEQ ID NO: 5 is a signal peptide. In some aspects, the mature polypeptide is the amino acid sequence shown in SEQ ID NO: 6. In some aspects, the mature polypeptide is amino acids 1 to 350 of SEQ ID NO: 8 and amino acids −30 to −1 of SEQ ID NO: 8 is a signal peptide. In some aspects, the mature polypeptide is the amino acid sequence shown in SEQ ID NO: 9. In some aspects, the mature polypeptide is amino acids 1 to 479 of SEQ ID NO: 11 and amino acids −31 to −1 of SEQ ID NO: 11 is a signal peptide. In some aspects, the mature polypeptide is the amino acid sequence shown in SEQ ID NO: 12. In some aspects, the mature polypeptide is amino acids 1 to 489 of SEQ ID NO: 14 and amino acids −31 to −1 of SEQ ID NO: 14 is a signal peptide. In some aspects, the mature polypeptide is the amino acid sequence shown in SEQ ID NO: 15. In some aspects, the mature polypeptide is amino acids 1 to 348 of SEQ ID NO: 17 and amino acids −21 to −1 of SEQ ID NO: 17 is a signal peptide. In some aspects, the mature polypeptide is the amino acid sequence shown in SEQ ID NO: 18. In some aspects, the mature polypeptide is amino acids 1 to 538 of SEQ ID NO: 20 and amino acids −35 to −1 of SEQ ID NO: 20 is a signal peptide. In some aspects, the mature polypeptide is the amino acid sequence shown in SEQ ID NO: 21. In some aspects, the mature polypeptide is amino acids 1 to 542 of SEQ ID NO: 23 and amino acids −35 to −1 of SEQ ID NO: 23 is a signal peptide. In some aspects, the mature polypeptide is the amino acid sequence shown in SEQ ID NO: 24. In some aspects, the mature polypeptide is amino acids 1 to 1378 of SEQ ID NO: 26 and amino acids −33 to −1 of SEQ ID NO: 26 is a signal peptide. In some aspects, the mature polypeptide is the amino acid sequence shown in SEQ ID NO: 27. In some aspects, the mature polypeptide is amino acids 1 to 342 of SEQ ID NO: 29 and amino acids −22 to −1 of SEQ ID NO: 29 is a signal peptide. In some aspects, the mature polypeptide is the amino acid sequence shown in SEQ ID NO: 30. In some aspects, the mature polypeptide is amino acids 1 to 369 of SEQ ID NO: 32 and amino acids −18 to −1 of SEQ ID NO: 32 is a signal peptide. In some aspects, the mature polypeptide is the amino acid sequence shown in SEQ ID NO: 33. In some aspects, the mature polypeptide is amino acids 1 to 432 of SEQ ID NO: 35 and amino acids-25 to −1 of SEQ ID NO: 35 is a signal peptide. In some aspects, the mature polypeptide is the amino acid sequence shown in SEQ ID NO: 36. In some aspects, the mature polypeptide is amino acids xx of SEQ ID NO: 38 and amino acids −24 to −1 of SEQ ID NO: 38 is a signal peptide. In some aspects, the mature polypeptide is the amino acid sequence shown in SEQ ID NO: 39. In some aspects, the mature polypeptide is amino acids 1 to 380 of SEQ ID NO: 41 and amino acids-25 to −1 of SEQ ID NO: 41 is a signal peptide. In some aspects, the mature polypeptide is the amino acid sequence shown in SEQ ID NO: 42. In some aspects, the mature polypeptide is amino acids 1 to 392 of SEQ ID NO: 44 and amino acids −23 to −1 of SEQ ID NO: 44 is a signal peptide. In some aspects, the mature polypeptide is the amino acid sequence shown in SEQ ID NO: 45. In some aspects, the mature polypeptide is amino acids 1 to 395 of SEQ ID NO: 47 and amino acids −30 to −1 of SEQ ID NO: 47 is a signal peptide. In some aspects, the mature polypeptide is the amino acid sequence shown in SEQ ID NO: 48. In some aspects, the mature polypeptide is amino acids 1 to 384 of SEQ ID NO: 50 and amino acids −21 to −1 of SEQ ID NO: 50 is a signal peptide. In some aspects, the mature polypeptide is the amino acid sequence shown in SEQ ID NO: 51. In some aspects, the mature polypeptide is amino acids 1 to 403 of SEQ ID NO: 53 and amino acids −20 to −1 of SEQ ID NO: 53 is a signal peptide. In some aspects, the mature polypeptide is the amino acid sequence shown in SEQ ID NO: 54. In some aspects, the mature polypeptide is amino acids 1 to 500 of SEQ ID NO: 56 and amino acids −35 to −1 of SEQ ID NO: 56 is a signal peptide. In some aspects, the mature polypeptide is the amino acid sequence shown in SEQ ID NO: 57.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having alpha-mannan degrading activity. In one aspect, the mature polypeptide coding sequence is nucleotides 97 to 1155 of SEQ ID NO: 1 and nucleotides 1 to 96 of SEQ ID NO: 1 encode a signal peptide. In one aspect, the mature polypeptide coding sequence is nucleotides 88 to 1134 of SEQ ID NO: 4 and nucleotides 1 to 87 encode a signal peptide. In one aspect, the mature polypeptide coding sequence is nucleotides 91 to 1140 of SEQ ID NO: 7 and nucleotides 1 to 90 encode a signal peptide. In one aspect, the mature polypeptide coding sequence is nucleotides 94 to 1530 of SEQ ID NO: 10 and nucleotides 1 to 93 encode a signal peptide. In one aspect, the mature polypeptide coding sequence is nucleotides 94 to 1560 of SEQ ID NO: 13 and nucleotides 1 to 93 encode a signal peptide. In one aspect, the mature polypeptide coding sequence is nucleotides 64 to 1107 of SEQ ID NO: 16, and nucleotides 1 to 63 encode a signal peptide. In one aspect, the mature polypeptide coding sequence is nucleotides 106 to 1719 of SEQ ID NO: 19, and nucleotides 1-105 encode a signal peptide. In one aspect, the mature polypeptide coding sequence is nucleotides 106 to 1731 of SEQ ID NO: 22, and nucleotides 1 to 105 encode a signal peptide. In one aspect, the mature polypeptide coding sequence is nucleotides 100 to 4236 of SEQ ID NO: 25, and nucleotides 1 to 99 encode a signal peptide. In one aspect, the mature polypeptide coding sequence is nucleotides 67 to 1092 of SEQ ID NO: 28, and nucleotides 1 to 66 encode a signal peptide. In one aspect, the mature polypeptide coding sequence is nucleotides 55 to 483 and 587 and 1264 of SEQ ID NO: 31, and nucleotides 1 to 54 encode a signal peptide.

In one aspect, the mature polypeptide coding sequence is nucleotides 76 to 100, 159 to 853, and 905 to 1480 of SEQ ID NO: 34, and nucleotides 1 to 75 encode a signal peptide. In one aspect, the mature polypeptide coding sequence is nucleotides 73 to 97, 163 to 857, and 921 to 1304 of SEQ ID NO: 37, and nucleotides 1 to 72 encode a signal peptide. In one aspect, the mature polypeptide coding sequence is nucleotides 76 to 100, 233 to 477, 543 to 992, and 1054 to 1473 of SEQ ID NO: 40, and nucleotides 1 to 75 encode a signal peptide. In one aspect, the mature polypeptide coding sequence is nucleotides 70 to 100, 179 to 900, 967 to 1389 of SEQ ID NO: 43, and nucleotides 1 to 69 encode a signal peptide. In one aspect, the mature polypeptide coding sequence is nucleotides 91 to 118, 180 to 1336 of SEQ ID NO: 46, and nucleotides 1 to 90 encode a signal peptide. In one aspect, the mature polypeptide coding sequence is nucleotides 64 to 85, 161 to 640, 696 to 937, and 1015 to 1422 of SEQ ID NO: 49, and nucleotides 1 to 63 encode a signal peptide. In one aspect, the mature polypeptide coding sequence is nucleotides 61 to 85 and 154 to 1337 of SEQ ID NO: 52, and nucleotides 1 to 60 encode a signal peptide. In one aspect, the mature polypeptide coding sequence is nucleotides 106 to 1605 of SEQ ID NO: 55, and nucleotides 1 to 105 encode a signal peptide.

Native: The term "native" means a nucleic acid or polypeptide naturally occurring in a host cell.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Purified: The term "purified" means a nucleic acid or polypeptide that is substantially free from other components as determined by analytical techniques well known in the art (e.g., a purified polypeptide or nucleic acid may form a discrete band in an electrophoretic gel, chromatographic eluate, and/or a media subjected to density gradient centrifugation). A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having alpha-mannan degrading activity.

Variant: The term "variant" means a polypeptide having alpha-mannan degrading activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Wild-type: The term "wild-type" in reference to an amino acid sequence or nucleic acid sequence means that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus, Staphylococcus epidermidis, Staphylococcus aureus, Pseudomonas* sp.*, Pseudomonas aeruginosa, Pseudomonas alcaliphila, Pseudomonas fluorescens, Stenotrophomonas* sp., *Paraburkholderia, Burkolderia* sp., *Candida* sp., *Bordetella pertussis, Yersinia pestis, Escherichia coli* and *Aspergillus* sp.

Cleaning component: The cleaning component e.g. a detergent adjunct ingredient is different to the polypeptides of this invention. The precise nature of these additional cleaning or adjunct components, and levels of incorporation thereof, will depend on the physical form of the composition and the nature of the operation for which it is to be used. Suitable cleaning components include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning Composition: The term cleaning composition includes "detergent composition" and refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Deep cleaning: The term "deep cleaning" means disruption, reduction or removal of organic components such as polysaccharides, proteins, DNA, soil or other components present in organic matter such as biofilm.

Delta remission value (ΔRem): The terms "Delta remission" or "Delta remission value" are defined herein as the result of a reflectance or remission measurement at a certain wavelength which typically is 460 nm. The swatch is measured with one swatch of similar colour as background, preferably a swatch from a repetition wash. A swatch representing each swatch type is measured before the wash. The Delta enzyme remission is the remission value of the swatch washed in detergent with an enzyme present minus the remission value of a similar swatch washed in a detergent without enzyme present.

Enzyme Detergency Benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

Textile care benefit: Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species.

Wash performance: The term "wash performance" is used as an enzyme's ability to remove stains present on the object to be cleaned during e.g. wash (laundry) or hard surface cleaning. The improvement in the wash performance may be quantified by calculating the so-called intensity value (Int) as described in the Examples herein. The term "improved wash performance" is defined herein as an enzyme displaying an increased wash performance in a cleaning composition relative to the wash performance of the same cleaning composition without the enzyme e.g. by increased stain removal or less re-deposition. The term "improved wash performance" includes wash performance in laundry but also e.g. in hard surface cleaning such as automated dish wash (ADW).

DETAILED DESCRIPTION OF THE INVENTION

Polypeptides Having Alpha-Mannan Degrading Activity

Polypeptides having alpha-mannan degrading activity or alpha-mannan degrading enzymes are enzymes having hydrolase activity on alpha-mannan. In particular, the polypeptide having alpha-mannan degrading activity includes enzymes from glycoside hydrolase domains GH76, GH92, and GH99, which are enzymes having alpha-mannanase and/or alpha-mannosidase activity. In an embodiment, the polypeptide belongs to GH family 76.

These can include enzyme activities such as alpha-1,6-mannanase (EC 3.2.1.101), alpha-1,2-mannase; mannosyl-oligosaccharide alpha-1,2-mannosidase (EC 3.2.1.113); mannosyl-oligosaccharide alpha-1,3-mannosidase (EC 3.2.1.-); mannosyl-oligosaccharide alpha-1,6-mannosidase (EC 3.2.1.-); alpha-mannosidase (EC 3.2.1.24); alpha-1,2-mannosidase (EC 3.2.1.-); alpha-1,3-mannosidase (EC 3.2.1.-); alpha-1,4-mannosidase (EC 3.2.1.-); mannosyl-1-phosphodiester alpha-1,P-mannosidase (EC 3.2.1.-); glycoprotein endo-alpha-1,2-mannosidase (EC 3.2.1.130); and/or mannan endo-1,2-alpha-mannanase (3.2.1.-) activities.

Also contemplated are blends of polypeptides having alpha-mannan degrading activity, including, for example, combinations of polypeptides having two or more different GH classifications according to the CAZY naming system.

In an embodiment are provided blends comprising a polypeptide belonging to GH family 76 and a polypeptide belonging to GH family 92; a polypeptide belonging to GH family 76 and a polypeptide belonging to GH family 99; a polypeptide belonging to GH family 92 and a polypeptide belonging to GH family 99; and in particular, a polypeptide belong to GH family 76 and a polypeptide belong to GH family 99.

Also contemplated are blends of three or more different GH classifications according to the CAZY naming system, including blends comprising a polypeptide belonging to GH family 76, a polypeptide belonging to GH family 92, and a polypeptide belonging to GH family 99. As also set forth in the Examples, a phylogenetic tree was constructed and various motifs have been identified. Thus, in one aspect, the polypeptide belongs to GH family 76, and comprises one or more of the motifs [YND]DD[QINLEM] (SEQ ID NO: 60) and GG[ILMV]X[WS] (SEQ ID NO: 61). Preferably, the polypeptide further comprises the motif [RK][NLT]XXX [NTV]XP[GTLYISAVFNM] (SEQ ID NO: 64). In a more preferred aspect, the polypeptide is of the KNTPA clade and is of bacterial origin.

In another aspect, the polypeptide belongs to GH family 76, and comprises one or more of the motif GA]XX[AVL][ML] X[MA][ATV][EATV] (SEQ ID NO: 62) or the motif LA[EQ]X[VL][YF] (SEQ ID NO: 63). Preferably, the polypeptide is of the AMXAAE clade and is of fungal origin.

In another aspect, the polypeptide comprises the motif N[EQD][WFY][HG]E (SEQ ID NO: 66).

In some embodiments, the present invention relates to isolated or purified polypeptides selected from the group consisting of:
  (a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3 or a fragment thereof having alpha-mannan degrading activity;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6 or a fragment thereof having alpha-mannan degrading activity;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9 or a fragment thereof having alpha-mannan degrading activity;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12 or a fragment thereof having alpha-mannan degrading activity;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15 or a fragment thereof having alpha-mannan degrading activity;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18 or a fragment thereof having alpha-mannan degrading activity;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21 or a fragment thereof having alpha-mannan degrading activity;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24 or a fragment thereof having alpha-mannan degrading activity;

(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 27 or a fragment thereof having alpha-mannan degrading activity;

(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30 or a fragment thereof having alpha-mannan degrading activity;

(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33 or a fragment thereof having alpha-mannan degrading activity;

(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36 or a fragment thereof having alpha-mannan degrading activity;

(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39 or a fragment thereof having alpha-mannan degrading activity;

(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42 or a fragment thereof having alpha-mannan degrading activity;

(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45 or a fragment thereof having alpha-mannan degrading activity;

(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48 or a fragment thereof having alpha-mannan degrading activity;

(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51 or a fragment thereof having alpha-mannan degrading activity;

(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54 or a fragment thereof having alpha-mannan degrading activity;

(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57 or a fragment thereof having alpha-mannan degrading activity.

In some embodiments, including the proviso that the isolated or purified polypeptide is not the polypeptide of geneseqp:AXR38305 as described in WO 2009/108941 A2.

In some embodiments, the present invention relates to isolated or purified polypeptides belonging to family GH76 selected from the group consisting of:

(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3 or a fragment thereof having alpha-mannan degrading activity;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6 or a fragment thereof having alpha-mannan degrading activity;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9 or a fragment thereof having alpha-mannan degrading activity;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12 or a fragment thereof having alpha-mannan degrading activity;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15 or a fragment thereof having alpha-mannan degrading activity;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18 or a fragment thereof having alpha-mannan degrading activity;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21 or a fragment thereof having alpha-mannan degrading activity;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24 or a fragment thereof having alpha-mannan degrading activity;
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33 or a fragment thereof having alpha-mannan degrading activity;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36 or a fragment thereof having alpha-mannan degrading activity;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39 or a fragment thereof having alpha-mannan degrading activity;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42 or a fragment thereof having alpha-mannan degrading activity;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45 or a fragment thereof having alpha-mannan degrading activity;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48 or a fragment thereof having alpha-mannan degrading activity;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51 or a fragment thereof having alpha-mannan degrading activity;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54 or a fragment thereof having alpha-mannan degrading activity;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57 or a fragment thereof having alpha-mannan degrading activity.

In some embodiments, the present invention relates to isolated or purified polypeptides belonging to family GH92 selected from the group consisting of:
(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 27 or a fragment thereof having alpha-mannan degrading activity.

In some embodiments, the present invention relates to isolated or purified polypeptides belonging to family GH99 selected from the group consisting of:
(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30 or a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 2, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 2.

The polypeptide preferably comprises, consists essentially of, or consists of the amino acid sequence of SEQ ID NO: 2 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 5, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 5.

The polypeptide preferably comprises, consists essentially of, or consists of the amino acid sequence of SEQ ID NO: 5 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 8, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 8.

The polypeptide preferably comprises, consists essentially of, or consists of the amino acid sequence of SEQ ID NO: 8 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 11, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 11.

The polypeptide preferably comprises, consists essentially of, or consists of the amino acid sequence of SEQ ID NO: 11 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 14, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 14.

The polypeptide preferably comprises, consists essentially of, or consists of the amino acid sequence of SEQ ID NO: 14 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 17, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 17.

The polypeptide preferably comprises, consists essentially of, or consists of the amino acid sequence of SEQ ID NO: 17 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 20, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 20.

The polypeptide preferably comprises, consists essentially of, or consists of the amino acid sequence of SEQ ID NO: 20 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 23, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 23.

The polypeptide preferably comprises, consists essentially of, or consists of the amino acid sequence of SEQ ID NO: 23 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 26, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 26.

The polypeptide preferably comprises, consists essentially of, or consists of the amino acid sequence of SEQ ID NO: 26 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 29, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 29.

The polypeptide preferably comprises, consists essentially of, or consists of the amino acid sequence of SEQ ID NO: 29 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 32, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 32.

The polypeptide preferably comprises, consists essentially of, or consists of the amino acid sequence of SEQ ID NO: 32 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 35, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 35.

The polypeptide preferably comprises, consists essentially of, or consists of the amino acid sequence of SEQ ID NO: 35 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 38, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 38.

The polypeptide preferably comprises, consists essentially of, or consists of the amino acid sequence of SEQ ID NO: 38 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 41, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 41.

The polypeptide preferably comprises, consists essentially of, or consists of the amino acid sequence of SEQ ID NO: 41 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 44, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 44.

The polypeptide preferably comprises, consists essentially of, or consists of the amino acid sequence of SEQ ID NO: 44 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 47, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 47.

The polypeptide preferably comprises, consists essentially of, or consists of the amino acid sequence of SEQ ID NO: 47 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 50, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 50.

The polypeptide preferably comprises, consists essentially of, or consists of the amino acid sequence of SEQ ID NO: 50 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 53, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 53.

The polypeptide preferably comprises, consists essentially of, or consists of the amino acid sequence of SEQ ID NO: 53 or the mature polypeptide thereof; or is a fragment thereof having alpha-mannan degrading activity.

In some embodiments, the present invention relates to isolated or purified polypeptides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide of SEQ ID NO: 56, which have alpha-mannan degrading activity. In one aspect, the polypeptides differ by up to 10 amino acids, e.g., 1, 2, 3, 4, 5, 6, 7, 8, 9, or 10, from the mature polypeptide of SEQ ID NO: 56.

The polypeptide preferably comprises, consists essentially of, or consists of the amino acid sequence of SEQ ID NO: 56 or the mature polypeptide thereof; or is a fragment thereof having alpha-mannan degrading activity.

In some embodiments, the present invention relates to isolated or purified polypeptides having alpha-mannan degrading activity encoded by polynucleotides that hybridize under medium stringency conditions, medium-high stringency conditions, high stringency conditions, or very high stringency conditions with the full-length complement of the mature polypeptide coding sequence of SEQ ID NO: 1 or the cDNA thereof (Sambrook et al., 1989, *Molecular Cloning, A Laboratory Manual*, 2d edition, Cold Spring Harbor, New York).

The polynucleotide of any of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, or a subsequence of any thereof, as well as the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56 or a fragment of any thereof, may be used to design nucleic acid probes to identify and clone DNA encoding polypeptides having alpha-mannan degrading activity from strains of different genera or species according to methods well known in the art. Such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having alpha-mannan degrading activity. Genomic or other DNA from such other strains may be separated by agarose or polyacrylamide gel electrophoresis, or other separation techniques. DNA from the libraries or the separated DNA may be transferred to and immobilized on nitrocellulose or another suitable carrier material. In order to identify a clone or DNA that hybridizes with SEQ ID NO: 1 or a subsequence thereof, the carrier material is used in a Southern blot.

For purposes of the present invention, hybridization indicates that the polynucleotides hybridize to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under medium to very high stringency conditions. Molecules to which the nucleic acid probe hybridizes under these conditions can be detected using, for example, X-ray film or any other detection means known in the art.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 1.

For purposes of the present invention, hybridization indicates that the polynucleotides hybridize to a labeled nucleic acid probe corresponding to (i) SEQ ID NO: 4; (ii) the mature polypeptide coding sequence of SEQ ID NO: 4; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 4.

For purposes of the present invention, hybridization indicates that the polynucleotides hybridize to a labeled nucleic acid probe corresponding to (i) SEQ ID NO: 7; (ii) the mature polypeptide coding sequence of SEQ ID NO: 7; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 7.

For purposes of the present invention, hybridization indicates that the polynucleotides hybridize to a labeled nucleic acid probe corresponding to (i) SEQ ID NO: 10; (ii) the mature polypeptide coding sequence of SEQ ID NO: 10; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 10.

For purposes of the present invention, hybridization indicates that the polynucleotides hybridize to a labeled nucleic acid probe corresponding to (i) SEQ ID NO: 13; (ii) the mature polypeptide coding sequence of SEQ ID NO: 13; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 13.

For purposes of the present invention, hybridization indicates that the polynucleotides hybridize to a labeled nucleic acid probe corresponding to (i) SEQ ID NO: 16; (ii) the mature polypeptide coding sequence of SEQ ID NO: 16; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 16.

For purposes of the present invention, hybridization indicates that the polynucleotides hybridize to a labeled nucleic acid probe corresponding to (i) SEQ ID NO: 19; (ii) the mature polypeptide coding sequence of SEQ ID NO: 19; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 19.

For purposes of the present invention, hybridization indicates that the polynucleotides hybridize to a labeled nucleic acid probe corresponding to (i) SEQ ID NO: 22; (ii) the mature polypeptide coding sequence of SEQ ID NO: 22; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 22.

For purposes of the present invention, hybridization indicates that the polynucleotides hybridize to a labeled nucleic acid probe corresponding to (i) SEQ ID NO: 25; (ii) the mature polypeptide coding sequence of SEQ ID NO: 25; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 25.

For purposes of the present invention, hybridization indicates that the polynucleotides hybridize to a labeled nucleic acid probe corresponding to (i) SEQ ID NO: 28; (ii) the mature polypeptide coding sequence of SEQ ID NO: 28; (iii) the full-length complement thereof; or (iv) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 28.

For purposes of the present invention, hybridization indicates that the polynucleotides hybridize to a labeled nucleic acid probe corresponding to (i) SEQ ID NO: 31; (ii) the mature polypeptide coding sequence of SEQ ID NO: 31; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 31, or the cDNA sequence thereof.

For purposes of the present invention, hybridization indicates that the polynucleotides hybridize to a labeled nucleic acid probe corresponding to (i) SEQ ID NO: 34; (ii) the mature polypeptide coding sequence of SEQ ID NO: 34; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 34, or the cDNA sequence thereof.

For purposes of the present invention, hybridization indicates that the polynucleotides hybridize to a labeled nucleic acid probe corresponding to (i) SEQ ID NO: 37; (ii) the mature polypeptide coding sequence of SEQ ID NO: 37; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 37, or the cDNA sequence thereof.

For purposes of the present invention, hybridization indicates that the polynucleotides hybridize to a labeled nucleic acid probe corresponding to (i) SEQ ID NO: 40; (ii) the mature polypeptide coding sequence of SEQ ID NO: 40; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 40, or the cDNA sequence thereof.

For purposes of the present invention, hybridization indicates that the polynucleotides hybridize to a labeled nucleic acid probe corresponding to (i) SEQ ID NO: 43; (ii) the mature polypeptide coding sequence of SEQ ID NO: 43; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 43, or the cDNA sequence thereof.

For purposes of the present invention, hybridization indicates that the polynucleotides hybridize to a labeled nucleic acid probe corresponding to (i) SEQ ID NO: 46; (ii) the mature polypeptide coding sequence of SEQ ID NO: 46; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 46, or the cDNA sequence thereof.

For purposes of the present invention, hybridization indicates that the polynucleotides hybridize to a labeled nucleic acid probe corresponding to (i) SEQ ID NO: 49; (ii) the mature polypeptide coding sequence of SEQ ID NO: 49; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 49, or the cDNA sequence thereof.

For purposes of the present invention, hybridization indicates that the polynucleotides hybridize to a labeled nucleic acid probe corresponding to (i) SEQ ID NO: 52; (ii) the mature polypeptide coding sequence of SEQ ID NO: 52; (iii) the cDNA sequence thereof; (iv) the full-length complement thereof; or (v) a subsequence thereof; under medium to very high stringency conditions.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 52, or the cDNA sequence thereof.

For purposes of the present invention, hybridization indicates that the polynucleotides hybridize to a labeled nucleic acid probe corresponding to (i) SEQ ID NO: 55; (ii) the mature polypeptide coding sequence of SEQ ID NO: 55; (iii) the full-length complement thereof; or (iv) a subsequence thereof; under medium to very high stringency conditions. Molecules to which the nucleic acid probe hybridizes under these conditions can be detected using, for example, X-ray film or any other detection means known in the art.

In some embodiments, the present invention relates to isolated polypeptides having alpha-mannan degrading activity encoded by polynucleotides having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the mature polypeptide coding sequence of SEQ ID NO: 55.

In some embodiments, the present invention relates to variants of the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, or SEQ ID NO: 56 comprising a substitution, deletion, and/or insertion at one or more (e.g., several) positions. In one aspect, the number of amino acid substitutions, deletions and/or insertions introduced into the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, or SEQ ID NO: 56 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding module.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for alpha-mannan degrading activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide.

Polypeptides Having Beta-Mannanase Activity

The beta-mannanases suitable for use according to the compositions of the present invention include polypeptides having beta-mannanase enzyme defined as the officially named mannan endo-1,4-beta-mannosidase and having the alternative names beta-mannanase and endo-1,4-mannase. The beta-mannanase term also means a polypeptide or polypeptide domain of an enzymes that has the ability to catalyze the cleavage or hydrolysis of (1→4) beta-D-mannosidic linkages of mannans, galactomannans, glucomannans, and galactoglucmannans. Thus, it means that the beta-mannanase has beta-mannanase activity (EC 3.2.1.78).

Suitable beta-mannanases include those of bacterial or fungal origin. Chemically or genetically modified mutants are included. The mannanase may be an alkaline beta-mannanase of Family 5 or 26. It may be a wild-type from *Bacillus* or *Humicola*, particularly *B. agaradhaerens, B. licheniformis, B. halodurans, B. clausii,* or *H. insolens*. Suitable GH5 beta-mannanases are described in WO 1999/064619, WO 2014/088940, WO 2014/100018, WO 2016/007929. Suitable GH26 beta-mannanases are described in WO 2012/149317, WO 2012/149325, WO 2012/149333, WO 2015/144782, WO 2016/054176, WO 2017/021514, WO 2017/021515, WO 2017/021516, WO 2017/021517, WO 2017/021518. A commercially available beta-mannanase is Mannaway (Novozymes NS).

In an embodiment, the amino acid sequence of the beta-mannanase has at least 59%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of a beta-mannanase obtainable from *Bacillus bogoriensis* shown in SEQ ID NO: 67. In one aspect, the beta-mannanase comprises, consists, or consists essentially of the amino acid sequence set forth in SEQ ID NO: 67.

In an embodiment, the amino acid sequence of the beta-mannanase has at least 59%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of a beta-mannanase obtainable from *Paenibacillus* sp. (PspMan4) shown in SEQ ID NO: 68. In one aspect, the beta-mannanase comprises, consists, or consists essentially of the amino acid sequence set forth in SEQ ID NO: 68.

In an embodiment, the amino acid sequence of the beta-mannanase has at least 59%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of a beta-mannanase obtainable from *Bacillus hemicellulosilyticus* shown in SEQ ID NO: 69. In one aspect, the beta-mannanase comprises, consists, or consists essentially of the amino acid sequence set forth in SEQ ID NO: 69.

The concentration of the beta-mannanase is preferably in the range of below 2 ppm enzyme protein, such as at from 0.01 ppm-2.0 ppm, 0.05 ppm-2.0 ppm, 0.1 ppm-2.0 ppm, 0.1 ppm-1.5 ppm, 0.1 ppm-1.0 ppm, 0.2 ppm-2.0 ppm, 0.5 ppm-2.0 ppm, 0.5 ppm-1.5 ppm or preferably at a concentration between 0.5 ppm and 1.0 ppm.

Sources of Polypeptides Having Alpha-Mannan Degrading Activity

A polypeptide having alpha-mannan degrading activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide is a *Bacillus* polypeptide, e.g., a polypeptide obtained from *Bacillus acidicola, Bacillus novalis,* or *Bacillus* sp. In another aspect, the polypeptide is a *Paenibacillus* polypeptide, e.g., a polypeptide obtained from *Paenibacillus glycanilyticus,* or *Paenibacillus* sp.

In another aspect, the polypeptide is an *Aspergillus* polypeptide, e.g., a polypeptide obtained from *Aspergillus aculeatus*. In another aspect, the polypeptide is a *Humicola* polypeptide, e.g., a polypeptide obtained from *Humicola insolens*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptides may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide, a catalytic domain, or carbohydrate binding module of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, e.g., *Bacillus acidicola*, *Bacillus novalis*, or *Bacillus* sp., a strain of *Paenibacillus*, e.g., *Paenibacillus glycanilyticus*, or *Paenibacillus* sp., or from a strain of *Aspergillus*, e.g., *Aspergillus aculeatus*, or from *Humicola*, e.g., *Humicola insolens*, or a related organism and thus, for example, may be a species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 49 or the cDNA sequence thereof, SEQ ID NO: 52 or the cDNA sequence thereof, or SEQ ID NO: 55 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, Protein Expression and Purification 2: 95-107.

Nucleic Acid Constructs

The present invention also relates to nucleic acid constructs comprising a polynucleotide of the present invention, wherein the polynucleotide is operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the polynucleotide of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the polynucleotide of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *J. Bacteriol.* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is heterologous to the coding sequence. A heterologous signal peptide coding sequence may be required where the coding sequence does not naturally contain a signal peptide coding sequence. Alternatively, a heterologous signal peptide coding sequence may simply replace the natural signal peptide coding sequence to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiol. Rev. 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola*

*insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any microbial or plant cell useful in the recombinant production of a polypeptide of the present invention, e.g., a prokaryotic cell or a fungal cell.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*. The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, Biotechniques 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, Folia Microbiol. (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, Appl. Environ. Microbiol. 71: 51-57). The introduction of DNA into a *Streptococcus* cell may be effected by natural competence (see, e.g., Perry and Kuramitsu, 1981, Infect. Immun. 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, Microbiol. Rev. 45: 409-436). However, any method known in the art for introducing DNA into a host cell can be used.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*,

*Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, Bio/Technology 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus* or *Paenibacillus* or *Aspergillus* or *Humicola* cell. In another aspect, the cell is a *Bacillus acidicola, Bacillus novalis,* or *Bacillus* sp., *Paenibacillus glycanilyticus,* or *Paenibacillus* sp., or *Aspergillus aculeatus,* or *Humicola insolens,* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid-state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

Fermentation Broth Formulations or Cell Compositions

The present invention also relates to a fermentation broth formulation or a cell composition comprising a polypeptide of the present invention. The fermentation broth formulation or the cell composition further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation or the cell composition comprises a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In some embodiments, the killed cells and/or cell debris are removed from a cell-killed whole broth to provide a composition that is free of these components.

The fermentation broth formulation or cell composition may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell composition of the present invention may be produced by a method described in WO 90/15861 or WO 2010/096673.

Enzyme Compositions

In an embodiment, the invention relates to compositions, in particular, cleaning compositions such as a detergent composition, comprising a polypeptide having alpha-mannan degrading activity in combination with one or more additional component(s). The choice of additional components is within the skill of the artisan and includes conventional ingredients, including the exemplary non-limiting components set forth below.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

In one embodiment of the present invention, the polypeptide having alpha-mannan degrading activity may be added to a cleaning composition, such as a detergent composition, in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquor.

The polypeptide having alpha-mannan degrading activity may be stabilized for inclusion in a composition using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708.

A polypeptide having alpha-mannan degrading activity may also be incorporated in the detergent formulations disclosed in WO97/07202, which is hereby incorporated by reference.

In one embodiment, the invention is directed to detergent compositions comprising an The polypeptide having alpha-mannan degrading activity in combination with one or more additional cleaning composition components. The choice of additional components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment, the invention is directed to an ADW (Automatic Dish Wash) compositions comprising an enzyme of the present invention in combination with one or more additional ADW composition components. The choice of additional components is within the skill of the artisan and includes conventional ingredients, including the exemplary non-limiting components set forth below.

Some embodiments of the invention relate to a composition comprising:
  a) at least 0.001 ppm of at least one polypeptide having alpha-mannan degrading activity, wherein the polypeptide is selected for the group consisting of: a polypeptide having at least 60%, at least 65%, at least 70%, at least 75%, at least 80%, at least 85%, at least 90%, at least 95%, at least 96%, at least 97%, at least 98%, at least 99% or 100% identity to the polypeptide of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO; 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, or SEQ ID NO: 57;
b) one or more cleaning components.

Some embodiments of the invention relate to a cleaning composition comprising:
a) at least 0.001 ppm of at least one polypeptide having alpha-mannan degrading activity, wherein the polypeptide is selected for the group consisting of: a polypeptide having at least 60%, at least 65%, at least 70%, at least 75%, at least 80%, at least 85%, at least 90%, at least 95%, at least 96%, at least 97%, at least 98%, at least 99% or 100% identity to the polypeptide of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO; 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, or SEQ ID NO: 57;
b) at least one cleaning component, preferably selected from a surfactant, a builder, a bleach component, a polymer, a dispersing agent and/or an additional enzyme.

One embodiment relates to a cleaning composition comprising:
a) at least 0.001 ppm of at least one polypeptide having alpha-mannan degrading activity e.g. a glycosyl hydrolase family 76, glycosyl hydrolase family 92, or glycosyl hydrolase family 99, preferably a glycosyl hydrolase family 76, wherein the polypeptide is selected from the group consisting of:
i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3;
ii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6;
iii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9;
iv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12;
v) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15;
vi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18;
vii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21;
viii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24;
ix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 27;
x) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30;
xi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33;
xii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36;
xiii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39;
xiv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42;
xv) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45;
xvi) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48;
xvii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51;
xviii) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54;
xix) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57, and
b) at least one cleaning component, preferably selected from a surfactant, a builder, a bleach component, a polymer, a dispersing agent and/or an additional enzyme.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

Non-limiting examples of zwitterionic surfactants include betaines such as alkyldimethylbetaines, sulfobetaines, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N,N'''-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst.

In some embodiments the bleach component may be an organic catalyst selected from the group consisting of organic catalysts having the following formulae:

(i)
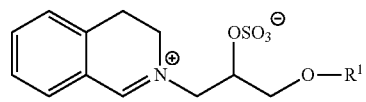

(ii)
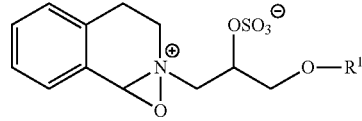

(iii) and mixtures thereof;

wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO2009/087523 (hereby incorporated by reference). Furthermore, random graft co-polymers are suitable soil release polymers. Suitable graft co-polymers are described in more detail in WO2007/138054, WO2006/108856 and WO2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl- N-2-hydroxy-ethylamino)-s-triazin-6-ylamino) stilbene-2, 2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Additional Enzymes

The detergent additive as well as the detergent composition may comprise one or more additional enzymes such as a protease, lipase, cutinase, an amylase, carbohydrase, cellulase, pectinase, beta-mannanase, arabinase, galactanase, xylanase, oxidase, e.g., a laccase, and/or peroxidase. In an embodiment, the additional enzyme is a beta-mannanase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500 (B)™ (Kao Corporation).

Beta-Mannanases

Suitable beta-mannanases include those of bacterial or fungal origin. Chemically or genetically modified mutants are included. The mannanase may be an alkaline beta-mannanase of Family 5 or 26. It may be a wild-type from *Bacillus* or *Humicola*, particularly *B. agaradhaerens, B. licheniformis, B. halodurans, B. clausii*, or *H. insolens*. Suitable GH5 beta-mannanases are described in WO 1999/064619, WO 2014/088940, WO 2014/100018, WO 2016/007929. Suitable GH26 beta-mannanases are described in WO 2012/149317, WO 2012/149325, WO 2012/149333, WO 2015/144782, WO 2016/054176, WO 2017/021514, WO 2017/021515, WO 2017/021516, WO 2017/021517, WO 2017/021518. A commercially available beta-mannanase is Mannaway (Novozymes NS).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes NS).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin *lentus*, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/ Genencor Int.) such as those derived from *Bacillus amyloliquefaciens*.

Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease shown in SEQ ID NO 1 of WO2016/001449, the *Bacillus* amylolichenifaciens protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™' Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with alpha-mannan degrading enzymes may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E, R, Q98R, S125A, N128C, T131I, T165I, K178L, T182G, M201L, F202Y, N225E, R, N272E, R, S243Q, A, E, D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K
wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I
wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus', Natalase™, Liquozyme X and BAN™ (from Novozymes NS), and Rapidase™, Purastar™/Effectenz™, Powerase, Preferenz S1000, Preferenz S100 and Preferenz S110 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as Caldariomyces, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera* hartlebii as described in WO 01/79459, *Dendryphiella salina* as described in WO 01/79458, *Phaeotrichoconis* crotalarie as described in WO 01/79461, or *Geniculosporium* sp. as described in WO 01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), ora bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, Schytalidium, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are polyethyleneglycol (PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Microorganisms

The detergent additive as well as the detergent composition may also comprise one or more microorganisms, such as one or more fungi, yeast, or bacteria.

In an embodiment, the one or more microorganisms are dehydrated (for example by lyophilization) bacteria or yeast, such as a strain of *Lactobacillus*.

In another embodiment, the microorganisms are one or more microbial spores (as opposed to vegetative cells), such as bacterial spores; or fungal spores, conidia, hypha. Preferably, the one or more spores are *Bacillus* endospores; even more preferably the one or more spores are endospores of *Bacillus subtilis*, *Bacillus licheniformis*, *Bacillus amyloliquefaciens*, or *Bacillus megaterium*.

The microorganisms may be included in the detergent composition or additive in the same way as enzymes (see above).

Adjunct Materials

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

In one aspect the detergent is a compact fluid laundry detergent composition comprising: a) at least about 10%, preferably from 20 to 80% by weight of the composition, of surfactant selected from anionic surfactants, non ionic surfactants, soap and mixtures thereof; b) from about 1% to about 30%, preferably from 5 to 30%, by weight of the composition, of water; c) from about 1% to about 15%, preferably from 3 to 10% by weight of the composition, of non-aminofunctional solvent; and d) from about 5% to about 20%, by weight of the composition, of a performance additive selected from chelants, soil release polymers, enzymes and mixtures thereof; wherein the compact fluid laundry detergent composition comprises at least one of: (i) the surfactant has a weight ratio of the anionic surfactant to the nonionic surfactant from about 1.5:1 to about 5:1, the surfactant comprises from about 15% to about 40%, by weight of the composition, of anionic surfactant and comprises from about 5% to about 40%, by weight of the composition, of the soap; (ii) from about 0.1% to about 10%, by weight of the composition, of a suds boosting agent selected from suds boosting polymers, cationic surfactants, zwitterionic surfactants, amine oxide surfactants, amphoteric surfactants, and mixtures thereof; and (ii) both (i) and (ii). All the ingredients are described in WO 2007/130562. Further polymers useful in detergent formulations are described in WO 2007/149806.

In another aspect the detergent is a compact granular (powdered) detergent comprising a) at least about 10%, preferably from 15 to 60% by weight of the composition, of surfactant selected from anionic surfactants, non-ionic surfactants, soap and mixtures thereof; b) from about 10 to 80% by weight of the composition, of a builder, preferably from 20% to 60% where the builder may be a mixture of builders selected from i) phosphate builder, preferably less than 20%, more preferably less than 10% even more preferably less than 5% of the total builder is a phosphate builder; ii) a zeolite builder, preferably less than 20%, more preferably less than 10% even more preferably less than 5% of the total builder is a zeolite builder; iii) citrate, preferably 0 to 5% of the total builder is a citrate builder; iv) polycarboxylate, preferably 0 to 5% of the total builder is a polycarboxylate builder v) carbonate, preferably 0 to 30% of the total builder is a carbonate builder and vi) sodium silicates, preferably 0 to 20% of the total builder is a sodium silicate builder; c) from about 0% to 25% by weight of the composition, of fillers such as sulphate salts, preferably from 1% to 15%, more preferably from 2% to 10%, more preferably from 3% to 5% by weight of the composition, of fillers; and d) from about 0.1% to 20% by weight of the composition, of enzymes, preferably from 1% to 15%, more preferably from 2% to 10% by weight of the composition, of enzymes.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In a preferred aspect of the present invention an alpha-mannan degrading enzyme may be combined with at least two additional enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be an alpha-mannan degrading enzyme with a stain removing enzyme, e.g., an alpha-mannan degrading enzyme and a protease, an alpha-mannan degrading enzyme and a serine protease, an alpha-mannan degrading enzyme and an amylase, an alpha-mannan degrading enzyme and a cellulase, an alpha-mannan degrading enzyme and a lipase, an alpha-mannan degrading enzyme and a cutinase, an alpha-mannan degrading enzyme and a pectinase, an alpha-mannan degrading enzyme and a beta-mannanase, or an alpha-mannan degrading enzyme and an anti-redeposition enzyme. More preferably, the an alpha-mannan degrading enzyme is combined with at least two stain removing enzymes, e.g., an alpha-mannan degrading enzyme, a lipase and an amylase; or an alpha-mannan degrading enzyme, a protease and an amylase; or an alpha-mannan degrading enzyme, a protease and a lipase; or an alpha-mannan degrading enzyme, a protease and a pectinase; or an alpha-mannan degrading enzyme, a protease and a cellulase; or an alpha-mannan degrading enzyme, a protease and a hemicellulase; or an alpha-mannan degrading enzyme, a protease and a cutinase; or an alpha-mannan degrading enzyme, an amylase and a pectinase; or an alpha-mannan degrading enzyme, an amylase and a cutinase; or an alpha-mannan degrading enzyme, an amylase and a cellulase; or an alpha-mannan degrading enzyme, an amylase and a hemicellulase; or an alpha-mannan degrading enzyme, a lipase and a pectinase; or an alpha-mannan degrading enzyme, a lipase and a cutinase; an alpha-mannan degrading enzyme, a lipase and a cellulase; or an alpha-mannan degrading enzyme, a lipase and a hemicellulase. Even more preferably, an alpha-mannan degrading enzyme may be combined with at least three stain removing enzymes, e.g., an alpha-mannan degrading enzyme, a protease, a lipase and an amylase; or an alpha-mannan degrading enzyme, a protease, an amylase and a pectinase; or an alpha-mannan degrading enzyme, a protease, an amylase and a cutinase; or an alpha-mannan degrading enzyme, a protease, an amylase and a cellulase; or an alpha-mannan degrading enzyme, a protease, an amylase and a hemicellulase; an alpha-mannan degrading enzyme, an amylase, a lipase and a pectinase; or an alpha-mannan degrading enzyme, an amylase, a lipase and a cutinase; or an alpha-mannan degrading enzyme, an amylase, a lipase and a cellulase; or an alpha-mannan degrading enzyme, an amylase, a lipase and a hemicellulase; or an alpha-mannan degrading enzyme, a protease, a lipase and a pectinase; or an alpha-mannan degrading enzyme, a protease, a lipase and a cutinase; or an alpha-mannan degrading enzyme, a protease, a lipase and a cellulase; or an alpha-mannan degrading enzyme, a protease, a lipase and a hemicellulase. An alpha-mannan degrading enzyme may be combined with any of the enzymes selected from the non-exhaustive list comprising: carbohydrases, such as an amylase, a hemicellulase, a pectinase, a cellulase, a beta-mannanase, a xanthanase or a pullulanase, a peptidase, a protease or a lipase.

In a preferred embodiment, an alpha-mannan degrading enzyme is combined with a serine protease, e.g., an S8 family protease such as Savinase®.

In another embodiment of the present invention, an alpha-mannan degrading enzyme may be combined with one or more metalloproteases, such as an M4 metalloprotease, including Neutrase® or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one mannanase of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions include various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the invention concerns the use of a composition comprising an alpha-mannan degrading enzyme, wherein said enzyme composition further comprises at least one or more of the following a surfactant, a builder, a chelator or chelating agent, bleach system or bleach component in laundry or dish wash.

In a preferred embodiment of the invention the amount of a surfactant, a builder, a chelator or chelating agent, bleach system and/or bleach component are reduced compared to amount of surfactant, builder, chelator or chelating agent, bleach system and/or bleach component used without an alpha-mannan degrading enzyme. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of an alpha-mannan degrading enzyme, such as a conventional amount of such component. In one aspect, the alpha-mannan degrading enzyme is used in detergent compositions wherein said composition is free of at least one component which is a surfactant, a builder, a chelator or chelating agent, bleach system or bleach component and/or polymer.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

Alpha-mannan degrading enzymes may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, alpha-mannan degrading enzyme, optionally one or more additional enzymes, a protease inhibitor, and a salt of a monovalent cation and an organic anion may be prepared and the mixture is then plodded. The alpha-mannan degrading enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granules

The present invention also relates to enzyme granules/particles comprising alpha-mannan degrading enzymes. In an embodiment, the granule comprises a core, and optionally one or more coatings (outer layers) surrounding the core.

The core may have a diameter, measured as equivalent spherical diameter (volume based average particle size), of 20-2000 μm, particularly 50-1500 μm, 100-1500 μm or 250-1200 μm.

In an embodiment, the core comprises one or more polypeptides having alpha-mannan degrading activity.

The core may include additional materials such as fillers, fiber materials (cellulose or synthetic fibers), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA).

The coating may be applied in an amount of at least 0.1% by weight of the core, e.g., at least 0.5%, at least 1%, at least 5%, at least 10%, or at least 15%. The amount may be at most 100%, 70%, 50%, 40% or 30%.

The coating is preferably at least 0.1 μm thick, particularly at least 0.5 μm, at least 1 μm or at least 5 μm. In some embodiments, the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should, in particular, be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

To provide acceptable protection, the salt coating is preferably at least 0.1 μm thick, e.g., at least 0.5 μm, at least 1 μm, at least 2 μm, at least 4 μm, at least 5 μm, or at least 8 μm. In a particular embodiment, the thickness of the salt coating is below 100 μm, such as below 60 μm, or below 40 μm.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular, having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminum. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}=76\%$), $Na_2CO_3$ ($CH_{20°\ C.}=92\%$), $NaNO_3$ ($CH_{20°\ C.}=73\%$), $Na_2HPO_4$ ($CH_{20°\ C.}=95\%$), $Na_3PO_4$ ($CH_{25°\ C.}=92\%$), $NH_4Cl$ ($CH_{20°\ C.}=79.5\%$), $(NH_4)_2HPO_4$ ($CH_{20°\ C.}=93.0\%$), $NH_4H_2PO_4$ ($CH_{20°\ C.}=93.1\%$), $(NH_4)_2SO_4$ ($CH_{20°\ C.}=81.1\%$), KCl ($CH_{20°\ C.}=85\%$), $K_2HPO_4$ ($CH_{20°\ C.}=92\%$), $KH_2PO_4$ ($CH_{20°\ C.}=96.5\%$), $KNO_3$ ($CH_{20°\ C.}=93.5\%$), $Na_2SO_4$ ($CH_{20°\ C.}=93\%$), $K_2SO_4$ ($CH_{20°\ C.}=98\%$), $KHSO_4$ ($CH_{20°\ C.}=86\%$), $MgSO_4$ ($CH_{20°\ C.}=90\%$), $ZnSO_4$ ($CH_{20°\ C.}=90\%$) and sodium citrate ($CH_{25°\ C.}=86\%$). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granule may optionally have one or more additional coatings. Examples of suitable coating materials are polyethylene glycol (PEG), methyl hydroxy-propyl cellulose (MHPC) and polyvinyl alcohol (PVA). Examples of enzyme granules with multiple coatings are described in WO 93/07263 and WO 97/23606.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in the Handbook of Powder Technology; Particle size enlargement by C. E. Capes; Volume 1; 1980; Elsevier. Preparation methods include known feed and granule formulation technologies, e.g., (a) Spray dried products, wherein a liquid enzyme-containing solution is atomized in a spray drying tower to form small droplets which during their way down the drying tower dry to form an enzyme-containing particulate material. Very small particles can be produced this way (Michael S. Showell (editor); Powdered detergents; Surfactant Science Series; 1998; vol. 71; page 140-142; Marcel Dekker).

(b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606.

(c) Absorbed core particles, wherein rather than coating the enzyme as a layer around the core, the enzyme is absorbed onto and/or into the surface of the core. Such a process is described in WO 97/39116.

(d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme (Michael S. Showell (editor); Powdered detergents; Surfactant Science Series; 1998; vol. 71; pages 140-142; Marcel Dekker).

(e) Prilled products, wherein an enzyme-containing powder is suspended in molten wax and the suspension is sprayed, e.g., through a rotating disk atomizer, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. U.S. Pat. Nos. 4,016,040 and 4,713,245 describe this technique.

(f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process, various high-shear mixers can be used as granulators. Granulates consisting of enzyme, fillers and binders etc. are mixed with cellulose fibers to reinforce the particles to produce a so-called T-granulate. Reinforced particles, are more robust, and release less enzymatic dust.

(g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in Martin Rhodes (editor); Principles of Powder Technology; 1990; Chapter 10; John Wiley & Sons.

(h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them to form a granule.

(i) The cores may be subjected to drying, such as in a fluid bed drier. Other known methods for drying granules in the feed or enzyme industry can be used by the skilled person. The drying preferably takes place at a product temperature of from 25 to 90° C. For some enzymes, it is important the cores comprising the enzyme contain a low amount of water before coating with the salt. If water sensitive enzymes are coated with a salt before excessive water is removed, it will be trapped within the core and may affect the activity of the enzyme negatively. After drying, the cores preferably contain 0.1-10% w/w water.

Non-dusting granulates may be produced, e.g., as disclosed in U.S. Pat. Nos. 4,106,991 and 4,661,452 and may optionally be coated by methods known in the art.

The granulate may further one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

In an embodiment, the granule further comprises one or more additional enzymes, e.g., hydrolase, isomerase, ligase, lyase, oxidoreductase, and transferase. The one or more additional enzymes are preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

Liquid Formulations

The present invention also relates to liquid compositions comprising alpha-mannan degrading enzymes. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials.

In an aspect, the present invention relates to liquid formulations comprising:
(A) 0.001% to 25% w/w of one or more polypeptides having alpha-mannan degrading activity of the present invention; and
(B) water.

In another embodiment, the liquid formulation comprises 20% to 80% w/w of polyol. In one embodiment, the liquid formulation comprises 0.001% to 2.0% w/w preservative.

In another embodiment, the invention relates to liquid formulations comprising:
(A) 0.001% to 25% w/w of one or more polypeptides having alpha-mannan degrading activity of the present invention;
(B) 20% to 80% w/w of polyol;
(C) optionally 0.001% to 2.0% w/w preservative; and
(D) water.

In another embodiment, the invention relates to liquid formulations comprising:
(A) 0.001% to 25% w/w of one or more polypeptides having alpha-mannan degrading activity of the present invention;
(B) 0.001% to 2.0% w/w preservative;
(C) optionally 20% to 80% w/w of polyol; and
(D) water.

In another embodiment, the liquid formulation comprises one or more formulating agents, such as a formulating agent selected from the group consisting of polyol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the group consisting of sodium sulfate, dextrin, cellulose, sodium thiosulfate, kaolin and calcium carbonate. In one embodiment, the polyols is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In another embodiment, the liquid formulation comprises 20%-80% polyol (i.e., total amount of polyol), e.g., 25%-75% polyol, 30%-70% polyol, 35%-65% polyol, or 40%-60% polyol. In one embodiment, the liquid formulation comprises 20%-80% polyol, e.g., 25%-75% polyol, 30%-70% polyol, 35%-65% polyol, or 40%-60% polyol, wherein the polyol is selected from the group consisting of glycerol, sorbitol, propylene glycol (MPG), ethylene glycol, diethylene glycol, triethylene glycol, 1,2-propylene glycol or 1,3- propylene glycol, dipropylene glycol, polyethylene glycol (PEG) having an average molecular weight below about 600 and polypropylene glycol (PPG) having an average molecular weight below about 600. In one embodiment, the liquid formulation comprises 20%-80% polyol (i.e., total amount of polyol), e.g., 25%-75% polyol, 30%-70% polyol, 35%-65% polyol, or 40%-60% polyol, wherein the polyol is selected from the group consisting of glycerol, sorbitol and propylene glycol (MPG).

In another embodiment, the preservative is selected from the group consisting of sodium sorbate, potassium sorbate, sodium benzoate and potassium benzoate or any combination thereof. In one embodiment, the liquid formulation comprises 0.02% to 1.5% w/w preservative, e.g., 0.05% to 1.0% w/w preservative or 0.1% to 0.5% w/w preservative. In one embodiment, the liquid formulation comprises 0.001% to 2.0% w/w preservative (i.e., total amount of preservative), e.g., 0.02% to 1.5% w/w preservative, 0.05% to 1.0% w/w preservative, or 0.1% to 0.5% w/w preservative, wherein the preservative is selected from the group consisting of sodium sorbate, potassium sorbate, sodium benzoate and potassium benzoate or any combination thereof.

In another embodiment, the liquid formulation further comprises one or more additional enzymes, e.g., hydrolase, isomerase, ligase, lyase, oxidoreductase, and transferase. The one or more additional enzymes are preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, beta-mannosidase (mannanase), phytase, phospholipase A1, phospholipase A2, phospholipase D, protease, pullulanase, pectin esterase, triacylglycerol lipase, xylanase, beta-xylosidase or any combination thereof.

Uses

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising an alpha-mannan degrading enzyme.

A preferred embodiment concerns a method of cleaning, said method comprising the steps of: contacting an object with a cleaning composition comprising an alpha-mannan degrading enzyme under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising an alpha-mannan degrading enzyme under conditions suitable for cleaning said object.

Low Temperature Uses

One embodiment of the invention concerns a method of doing laundry, dish wash or industrial cleaning comprising contacting a surface to be cleaned with an alpha-mannan degrading enzyme, and wherein said laundry, dish wash, industrial or institutional cleaning is performed at a temperature of about 40° C. or below. One embodiment of the invention relates to the use of an alpha-mannan degrading enzyme in laundry, dish wash or a cleaning process wherein the temperature in laundry, dish wash, industrial cleaning is about 40° C. or below In another embodiment, the invention concerns the use of an alpha-mannan degrading enzyme in a protein removing process, wherein the temperature in the protein removing process is about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In particular preferred embodiments the wash temperature is about 20° C., about 30° C., or about 40° C.

Preventing, Reducing or Removing a Biofilm

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms or biofilm.

In an embodiment, the present invention concerns the use of an alpha-mannan degrading enzyme for preventing, reducing or removing a biofilm from an item, wherein the polypeptide is obtained from a fungal source and wherein the item is a textile. In one embodiment, alpha-mannan degrading enzyme is used for preventing, reducing or removing the stickiness of an item.

Food Processing and Animal Feed

Accordingly, the present invention relates to an animal feed composition and/or animal feed additive composition and/or pet food comprising an alpha-mannan degrading enzyme.

The present invention further relates to a method for preparing such animal feed composition and/or animal feed additive composition and/or pet food comprising mixing an alpha-mannan degrading enzyme with one or more animal feed ingredients and/or animal feed additive ingredients and/or pet food ingredients.

Furthermore, the present invention relates to the use of an alpha-mannan degrading enzyme in the preparation of an animal feed composition and/or animal feed additive composition and/or pet food.

Degrading a Cellulosic Material and/or Producing a Fermentation Product

An alpha-mannan degrading enzyme may be used for degrading a cellulosic material, for producing a fermentation product and for fermenting a cellulosic material e.g., in a process for producing a fermentation product, comprising: (a) saccharifying a cellulosic material with an enzyme composition, wherein the enzyme composition comprises an alpha-mannan degrading enzyme; (b) fermenting the saccharified cellulosic material with one or more fermenting microorganisms to produce the fermentation product; and (c) recovering the fermentation product from the fermentation. The cellulosic material may be pretreated before saccharification. In one embodiment, the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

In another embodiment, the invention relates to a process of fermenting a cellulosic material, comprising: fermenting the cellulosic material with one or more fermenting microorganisms, wherein the cellulosic material is saccharified with an enzyme composition comprising an alpha-mannan degrading enzyme. The cellulosic material may be pretreated before saccharification. In one embodiment, the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

Use for Fermented Beverages

In one aspect, the invention relates to a method of preparing a fermented beverage, such as beer or wine, comprising mixing an alpha-mannan degrading enzyme with malt and/or adjunct.

Another aspect concerns a method of providing a fermented beverage comprising the step of contacting a mash and/or a wort with an alpha-mannan degrading enzyme.

In the context of the present invention, the term "fermented beverage" is meant to comprise any beverage such as wine or beer produced by a method comprising a fermentation process, such as a microbial, bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like may be used as a source of starch As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

Treating Coffee Extracts

An alpha-mannan degrading enzyme may also be used for hydrolyzing galactomannans present in liquid coffee extracts. In certain preferred embodiments, an alpha-mannan degrading enzyme is used to inhibit gel formation during freeze drying of liquid coffee extracts. The decreased viscosity of the extract reduces the energy consumption during drying. In certain other preferred embodiments, an alpha-mannan degrading enzyme is applied in an immobilized form in order to reduce enzyme consumption and avoid contamination of the coffee extract. This use is further disclosed in EP 676 145.

In general terms the coffee extract is incubated in the presence of an alpha-mannan degrading enzyme thereof under conditions suitable for hydrolyzing galactomannans present in liquid coffee extract.

Thus in one embodiment, then invention relates to a process for producing a coffee extract, comprising the steps:
(a) providing roast and ground coffee beans;
(b) adding to said coffee beans water and an alpha-mannan degrading enzyme;
(c) incubating to make an aqueous coffee extract; and
(d) separating the coffee extract from the extracted coffee beans.

Use in Bakery Food Products

In another aspect, the invention relates to a method of preparing baked products comprising adding an alpha-mannan degrading enzyme to a dough, followed by baking the dough.

Examples of baked products are well known to those skilled in the art and include breads, rolls, puff pastries, sweet fermented doughs, buns, cakes, crackers, cookies, biscuits, waffles, wafers, tortillas, breakfast cereals, extruded products, and the like.

An alpha-mannan degrading enzyme may be added to dough as part of a bread improver composition. Bread improvers are compositions containing a variety of ingredients, which improve dough properties and the quality of bakery products, e.g. bread and cakes. Bread improvers are often added in industrial bakery processes because of their beneficial effects e.g. the dough stability and the bread texture and volume. Bread improvers usually contain fats and oils as well as additives like emulsifiers, enzymes, antioxidants, oxidants, stabilizers and reducing agents. In addition to the mannanase of the invention, other enzymes which may also be present in the bread improver including amylases, hemicellulases, amylolytic complexes, lipases, proteases, xylanases, pectinases, pullulanases, non-starch polysaccharide degrading enzymes and redox enzymes like glucose oxidase, lipoxygenase or ascorbic acid oxidase.

In one aspect, an alpha-mannan degrading enzyme may be added to dough as part of a bread improver composition which also comprises a glucomannan and/or galactomannan source such as konjac gum, guar gum, locust bean gum (*Ceratonia siliqua*), copra meal, ivory nut mannan (*Phyteleohas macrocarpa*), seaweed mannan extract, coconut meal, and the cell wall of brewers yeast (may be dried, or used in the form of brewers yeast extract).

A further aspect of the invention relates to the use of an alpha-mannan degrading enzyme in dough to improve dough tolerance, flexibility and stickiness. Preferably the dough to which the mannanase of the invention may be added is not a pure wheat flour dough, but comprises bran or oat, rice, millet, maize, or legume flour in addition to or instead of pure wheat flour.

A yet further aspect of the invention relates to the use of an alpha-mannan degrading enzyme in dough to improve the crumb structure and retard staling in the final baked product, such as bread.

Use in Dairy Food Products

In one aspect of the current invention, an alpha-mannan degrading enzyme may be added to milk or any other dairy product, for example, to which has also been added a glucomannan and/or galactomannan.

In one aspect, the invention relates to a method of preparing milk or dairy products comprising adding to the milk or dairy product (a) glucomannan, galactomannan and/or galactoglucomannan and (b) an alpha-mannan degrading enzyme.

In one aspect an alpha-mannan degrading enzyme in combination with any glucomannan or galactomannan prior to or following addition to a dairy based foodstuff to produce a dairy based foodstuff comprising prebiotic mannan hydrolysates. In a further aspect of the invention the thus produced mannooligosacharide-containing dairy product is capable of increasing the population of beneficial human intestinal microflora, and in a yet further aspect of the current invention the dairy based foodstuff may comprise an alpha-mannan degrading enzyme together with any source of glucomannan and/or galactomannan and/or galactoglucomannan, and a dose sufficient for inoculation of at least one strain of bacteria (such as Bifidobacteria or *Lactobacillus*) known to be of benefit in the human large intestine. Preferably said dairy-based foodstuff is a yoghurt or milk drink.

Paper Pulp Bleaching

The alpha-mannan degrading enzyme may further be used in the enzyme aided bleaching of paper pulps such as chemical pulps, semi-chemical pulps, kraft pulps, mechanical pulps or pulps prepared by the sulfite method. Thus, the invention relates to a method of bleaching paper pulps comprising incubating the paper pulp with an alpha-mannan degrading enzyme.

In some embodiments, the pulps are chlorine free pulps bleached with oxygen, ozone, peroxide or peroxyacids. In some embodiments, an alpha-mannan degrading enzyme is used in enzyme aided bleaching of pulps produced by modified or continuous pulping methods that exhibit low lignin contents. In some other embodiments, an alpha-mannan degrading enzyme is applied alone or preferably in combination with xylanase and/or endoglucanase and/or alpha-galactosidase and/or cellobiohydrolase enzymes.

The invention is further defined in the following paragraphs:

Paragraph 1. A cleaning composition comprising:
  (a) at least one polypeptide having alpha-mannan degrading activity or a variant or a fragment thereof having alpha-mannan degrading activity; and
  (b) at least one cleaning component, preferably selected from a surfactant, a builder, a bleach component, a polymer, a dispersing agent and/or an additional enzyme.

Paragraph 2. The cleaning composition of paragraph 1, wherein the polypeptide has alpha-mannanase and/or alpha-mannosidase activity.

Paragraph 3. The cleaning composition of any preceding paragraph, wherein the polypeptide having alpha-mannan degrading activity belongs to glycosyl hydrolase family 76 (GH76), glycosyl hydrolase family 92 (GH92), glycosyl hydrolase family 99 (GH99), in particular to glycosyl hydrolase family 76.

Paragraph 4. The cleaning composition of any preceding paragraph, wherein the polypeptide comprises one or more of the motifs [YND]DD[QINLEM] (SEQ ID NO: 60) and GG[ILMV]X[WS] (SEQ ID NO: 61).

Paragraph 5. The cleaning composition of any preceding paragraph, wherein the polypeptide further comprises the motif [RK][NLT]XXX[NTV]XP[GTLYISAVFNM] (SEQ ID NO: 64).

Paragraph 6. The cleaning composition of any of paragraphs 1-5, wherein the polypeptide is of the KNTPA clade and is of bacterial origin.

Paragraph 7. The cleaning composition of any of paragraphs 1-4, wherein the polypeptide further comprises the motif GA]XX[AVL][ML]X[MA][ATV][EATV] (SEQ ID NO: 62) or the motif LA[EQ]X[VL][YF] (SEQ ID NO: 63).

Paragraph 8. The cleaning composition of any of paragraphs 1~4 or 7, wherein the polypeptide is of the AMXAAE clade and is of fungal origin.

Paragraph 9. The cleaning composition of any of paragraphs 1-3, wherein the polypeptide comprises the motif N[EQD][WFY][HG]E (SEQ ID NO: 66).

Paragraph 10. The cleaning composition of any preceding paragraph, comprising at least two polypeptides having alpha-mannan degrading activity.

Paragraph 11. The cleaning composition of any preceding paragraph, comprising a polypeptide belonging to GH family 76 and a polypeptide belonging to GH family 92; a polypeptide belonging to GH family 76 and a polypeptide belonging to GH family 99; a polypeptide belonging to GH family 92 and a polypeptide belonging to GH family 99; in particular, a polypeptide belong to GH family 76 and a polypeptide belonging to GH family 99.

Paragraph 12. The cleaning composition of any preceding paragraph, wherein the polypeptide having alpha-mannan degrading activity is microbial, preferably obtained from bacteria or fungi.

Paragraph 13. The cleaning composition of any preceding paragraph, wherein the polypeptide having alpha-mannan degrading activity is obtained from a strain of *Bacillus*, e.g., *Bacillus acidicola, Bacillus novalis*, or *Bacillus* sp., a strain of *Paenibacillus*, e.g., *Paenibacillus glycanilyticus*, or *Paenibacillus* sp., or from a strain of *Aspergillus*, e.g., *Aspergillus aculeatus*, or from a strain of *Humicola*, e.g., *Humicola insolens*.

Paragraph 14. The cleaning composition of any preceding paragraph, wherein the polypeptide is selected from the group consisting of:
  (a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6;
  (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9;
  (d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12;
  (e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15;
  (f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18;
  (g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21;
  (h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24;
  (i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 27;
  (j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30;
  (k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33;
  (l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36;
  (m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39;
  (n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42;
  (o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45;
  (p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48;
  (q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51;
  (r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54;
  (s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57.

Paragraph 15. The cleaning composition of any preceding paragraph, wherein the polypeptide is selected from the group consisting of:
  (a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6;
  (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24; and
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57.

Paragraph 16. The cleaning composition of any preceding paragraph, wherein the polypeptide is selected from the group consisting of:
(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54.

Paragraph 17. The cleaning composition of any preceding paragraph, comprising at least 0.001 ppm of the polypeptide having alpha-mannan degrading activity.

Paragraph 18. The cleaning composition of any preceding paragraph, comprising from 0.2 wt % to 20 wt % surfactant.

Paragraph 19. The cleaning composition of any preceding paragraph, further comprising a polypeptide having beta-mannanase activity.

Paragraph 20. The cleaning composition of paragraph 19, wherein the polypeptide having beta-mannanase activity is selected from the group consisting of:
(a) a polypeptide having at least 59%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 67;
(b) a polypeptide having at least 59%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 68;
(c) a polypeptide having at least 59%, at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 69.

Paragraph 21. The cleaning composition of paragraph 20, wherein the polypeptide having alpha-mannan degrading activity is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24.

Paragraph 22. The cleaning composition of paragraph 20, wherein the polypeptide having alpha-mannan degrading activity is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57.

Paragraph 23. The cleaning composition of paragraph 20, wherein the polypeptide having alpha-mannan degrading activity is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30.

Paragraph 24. The cleaning composition of paragraph 20, wherein the polypeptide having alpha-mannan degrading activity is a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3.

Paragraph 25. A granule comprising a core particle and one or more coatings and a polypeptide having alpha-mannan degrading activity.

Paragraph 26. A liquid composition comprising a polyol and a polypeptide having alpha-mannan degrading activity.

Paragraph 27. Use of the cleaning composition of any of paragraphs 1-24, the granule of paragraph 25 or the liquid composition of paragraph 26 for laundering, washing or cleaning a textile and/or a hard surface (such as dish wash).

Paragraph 28. Use of the cleaning composition of any of paragraphs 1-24, the granule of paragraph 25 or the liquid composition of paragraph 26 for
  (a) preventing, reducing or removing stickiness of the item;
  (b) preventing, reducing or removing biofilm or biofilm components;
  (c) preventing, reducing or removing redeposition of soil during a wash cycle;
  (d) preventing, reducing or removing adherence of soil to the item;
  (e) maintaining or improving whiteness of the item; or
  (f) preventing, reducing or removing malodor from the item,
  wherein the item is a textile.

Paragraph 29. A process for degrading alpha-mannan, comprising applying the cleaning composition of any of paragraph 1-24, the granule of paragraph 25 or the liquid composition of paragraph 26 to the alpha-mannan.

Paragraph 30. A method of cleaning an item, comprising the steps of:
  (a) contacting the item with a cleaning composition according to any of paragraphs 1-24, the granule of paragraph 25 or the liquid composition of paragraph 26; and
  (b) and optionally rinsing the item, wherein the item is preferably a textile or a hard surface.

Paragraph 31. An isolated or purified polypeptide having alpha-mannan degrading activity, wherein the polypeptide having alpha-mannan degrading activity belongs to glycosyl hydrolase family 76 (GH76), glycosyl hydrolase family 92 (GH92), glycosyl hydrolase family 99 (GH99), in particular to glycosyl hydrolase family 76.

Paragraph 32. The polypeptide of paragraph 31, which comprises one or more of the motifs

```
                              (SEQ ID NO: 60)
[YND]DD[QINLEM]
and
                              (SEQ ID NO: 61)
GG[ILMV]X[WS].
```

Paragraph 33. The polypeptide of any of paragraphs 31-32, which further comprises the motif

```
                              (SEQ ID NO: 64)
[RK][NLT]XXX[NTV]XP[GTLYISAVFNM].
```

Paragraph 34. The polypeptide of any of paragraphs 31-33, which is of the KNTPA clade and is of bacterial origin.

Paragraph 35. The polypeptide of any of paragraphs 31-32, further comprising the motif

```
                              (SEQ ID NO: 62)
GA[XX]AVL[ML]X[MA][ATV][EATV]
or the motif
                              (SEQ ID NO: 63)
LA[EQ]X[VL][YF].
```

Paragraph 36. The polypeptide of any of paragraphs 31-32 or 35, which is of the AMXAAE clade and is of fungal origin.

Paragraph 37. The polypeptide of paragraph 32, which comprises the motif N[EQD][WFY][HG]E (SEQ ID NO: 66).

Paragraph 38. The polypeptide of any preceding polypeptide paragraph, selected from the group consisting of:
  (a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3 or a fragment thereof having alpha-mannan degrading activity;
  (b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6 or a fragment thereof having alpha-mannan degrading activity;
  (c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9 or a fragment thereof having alpha-mannan degrading activity;
  (d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12 or a fragment thereof having alpha-mannan degrading activity;
  (e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15 or a fragment thereof having alpha-mannan degrading activity;
  (f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18 or a fragment thereof having alpha-mannan degrading activity;
  (g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21 or a fragment thereof having alpha-mannan degrading activity;
  (h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24 or a fragment thereof having alpha-mannan degrading activity;
  (i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 27 or a fragment thereof having alpha-mannan degrading activity;
(j) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 30 or a fragment thereof having alpha-mannan degrading activity;
(k) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33 or a fragment thereof having alpha-mannan degrading activity;
(l) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36 or a fragment thereof having alpha-mannan degrading activity;
(m) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39 or a fragment thereof having alpha-mannan degrading activity;
(n) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42 or a fragment thereof having alpha-mannan degrading activity;
(o) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45 or a fragment thereof having alpha-mannan degrading activity;
(p) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48 or a fragment thereof having alpha-mannan degrading activity;
(q) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51 or a fragment thereof having alpha-mannan degrading activity;
(r) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54 or a fragment thereof having alpha-mannan degrading activity; and
(s) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57 or a fragment thereof having alpha-mannan degrading activity. and with the proviso that the isolated or purified polypeptide is not the polypeptide of geneseqp: AXR38305.

Paragraph 39. The polypeptide of any preceding polypeptide paragraph, selected from the group consisting of:
(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3 or a fragment thereof having alpha-mannan degrading activity;
(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 6 or a fragment thereof having alpha-mannan degrading activity;
(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 9 or a fragment thereof having alpha-mannan degrading activity;
(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 12 or a fragment thereof having alpha-mannan degrading activity;
(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 15 or a fragment thereof having alpha-mannan degrading activity;
(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 18 or a fragment thereof having alpha-mannan degrading activity;
(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 21 or a fragment thereof having alpha-mannan degrading activity;
(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 24 or a fragment thereof having alpha-mannan degrading activity; and
(i) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 57 or a fragment thereof having alpha-mannan degrading activity. and with the proviso that the isolated or purified polypeptide is not the polypeptide of geneseqp: AXR38305.

Paragraph 40. The polypeptide of any preceding polypeptide paragraph, selected from the group consisting of:
(a) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 33 or a fragment thereof having alpha-mannan degrading activity;

(b) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 36 or a fragment thereof having alpha-mannan degrading activity;

(c) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 39 or a fragment thereof having alpha-mannan degrading activity;

(d) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 42 or a fragment thereof having alpha-mannan degrading activity;

(e) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 45 or a fragment thereof having alpha-mannan degrading activity;

(f) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 48 or a fragment thereof having alpha-mannan degrading activity;

(g) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 51 or a fragment thereof having alpha-mannan degrading activity;

(h) a polypeptide having at least 60%, at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 54 or a fragment thereof having alpha-mannan degrading activity.

Paragraph 41. An isolated or purified polypeptide having alpha-mannan degrading activity, selected from the group consisting of:
(a) a polypeptide having at least 60% sequence identity to the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56;
(b) a polypeptide encoded by a polynucleotide that hybridizes under medium stringency conditions with the full-length complement of the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 46 or the cDNA sequence thereof, SEQ ID NO: 49 or the cDNA sequence thereof, SEQ ID NO: 52 or the cDNA sequence thereof, or SEQ ID NO: 55;
(c) a polypeptide encoded by a polynucleotide having at least 60% sequence identity to the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 46 or the cDNA sequence thereof, SEQ ID NO: 49 or the cDNA sequence thereof, SEQ ID NO: 52 or the cDNA sequence thereof, or SEQ ID NO: 55;
(d) a fragment of the polypeptide of (a), (b), or (c), that has alpha-mannan degrading activity; and with the proviso that the isolated or purified polypeptide is not the polypeptide of geneseqp:AXR38305.

Paragraph 42. The polypeptide of paragraph 35, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56.

Paragraph 43. The polypeptide of paragraph 41 or 42, which is encoded by a polynucleotide that hybridizes under medium stringency conditions, medium-high stringency conditions, high stringency conditions, or very high stringency conditions with the full-length complement of the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 49 or the cDNA sequence thereof, SEQ ID NO: 52 or the cDNA sequence thereof, or SEQ ID NO: 55.

Paragraph 44. The polypeptide of any one of paragraphs 41-43, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31 or the cDNA sequence thereof, SEQ ID NO: 34 or the cDNA sequence thereof, SEQ ID NO: 37 or the cDNA sequence thereof, SEQ ID NO: 40 or the cDNA sequence thereof, SEQ ID NO: 43 or the cDNA sequence thereof, SEQ ID NO: 46 or the cDNA sequence thereof, SEQ ID NO: 49 or the cDNA sequence thereof, SEQ ID NO: 52 or the cDNA sequence thereof, or SEQ ID NO: 55.

Paragraph 45. The polypeptide of any one of paragraphs 41-44, which is a variant of the mature polypeptide of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50 SEQ ID NO: 53, or SEQ ID NO: 56, comprising a substitution, deletion, and/or insertion at one or more positions.

Paragraph 46. The polypeptide of any one of paragraphs 41-45, comprising, consisting essentially of, or consisting of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, or SEQ ID NO: 56, or the mature polypeptide thereof.

Paragraph 47. The polypeptide of any one of paragraphs 41-46, which is a fragment of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, or SEQ ID NO: 56 or the mature polypeptide thereof, wherein the fragment has alpha-mannan degrading activity.

Paragraph 48. A fusion polypeptide comprising the polypeptide of any one of paragraphs 41-47 and a second polypeptide.

Paragraph 49. A granule, which comprises: (a) a core comprising the polypeptide of any one of paragraphs 31-48, and, optionally (b) a coating consisting of one or more layer(s) surrounding the core.

Paragraph 50. A composition comprising the polypeptide of any one of paragraphs 31-48.

Paragraph 51. A liquid composition comprising a polyol and the polypeptide of any of paragraphs 31-48.

Paragraph 52. A whole broth formulation or cell culture composition comprising the polypeptide of any one of paragraphs 31-48.

Paragraph 53. An isolated or purified polynucleotide encoding the polypeptide of any one of paragraphs 31-48.

Paragraph 54. A nucleic acid construct or expression vector comprising the polynucleotide of paragraph 53, wherein the polynucleotide is preferably operably linked to one or more control sequences that direct the production of the polypeptide in an expression host.

Paragraph 55. A recombinant host cell comprising the polynucleotide of paragraph 53 operably linked to one or more control sequences that direct the production of the polypeptide.

Paragraph 56. The recombinant host cell of paragraph 55, wherein the polypeptide is heterologous to the recombinant host cell.

Paragraph 57. A method of producing the polypeptide of any one of paragraphs 31-48, comprising cultivating a cell, which in its wild-type form produces the polypeptide, under conditions conducive for production of the polypeptide.

Paragraph 52. The method of paragraph 51, further comprising recovering the polypeptide.

Paragraph 53. Use of the polypeptide of any one of paragraphs 31-48 for laundering, washing or cleaning a textile and/or a hard surface (such as dish wash).

Paragraph 54. Use of the polypeptide of any one of paragraphs 31-48 for
(a) preventing, reducing or removing stickiness of the item;
(b) preventing, reducing or removing biofilm or biofilm components;
(c) preventing, reducing or removing redeposition of soil during a wash cycle;
(d) preventing, reducing or removing adherence of soil to the item;
(e) maintaining or improving whiteness of the item; or
(f) preventing, reducing or removing malodor from the item,
wherein the item is a textile.

Paragraph 55. A process for degrading alpha-mannan, comprising applying the polypeptide of any one of paragraphs 31-48 to the alpha-mannan.

Paragraph 56. A method of cleaning an item, comprising the steps of:
(a) contacting the item with the polypeptide of any one of paragraphs 31-48; and
(b) and optionally rinsing the item, wherein the item is preferably a textile or a hard surface.

Paragraph 57. A process for preparing a food or feed composition and/or food or feed additive, comprising mixing the polypeptide of any of paragraphs 31-48, the granule of paragraph 49, the composition of paragraph 50, or the liquid composition of paragraph 51 with one or more food or feed and/or food or feed additive ingredients.

Paragraph 58. A process for producing a coffee extract, comprising the steps:
(a) providing roast and ground coffee beans;
(b) adding to said coffee beans water and a polypeptide of any of paragraphs 25-48, the granule of paragraph 49, the composition of paragraph 50, or the liquid composition of paragraph 51;
(c) incubating to make an aqueous coffee extract; and
(d) separating the coffee extract from the extracted coffee beans.

Paragraph 59. A process for degrading a cellulosic material, comprising: treating the cellulosic material with the polypeptide of any of paragraphs 25-48, the granule of paragraph 49, the composition of paragraph 50, or the liquid composition of paragraph 51.

Paragraph 60. A process for producing a fermentation product, comprising:
(a) saccharifying a cellulosic material with an enzyme composition in the presence of the polypeptide of any of paragraphs 25-48, the granule of paragraphs 49, the composition of paragraphs 50, or the liquid composition of paragraphs 51;
(b) fermenting the saccharified cellulosic material with one or more fermenting microorganisms to produce the fermentation product; and
(c) recovering the fermentation product from the fermentation.

The present invention is further described by the following examples that should not be construed as limiting the scope of the invention.

EXAMPLES

Materials

Chemicals used as buffers and substrates were commercial products of at least reagent grade.

Model Detergents

Model detergent A wash liquor (100%) was prepared by dissolving 3.33 g/l of model detergent A containing 12% LAS, 11% AEO Biosoft N25-7 (NI), 17.63% AEOS (SLES), 6% MPG, 3% ethanol, 3.33% TEA (triethanolamine), 2.75% cocoa soap, 2.75% soya soap, 1.7% glycerol, 1.75% sodium hydroxide, 2% sodium citrate, 1% sodium formate, 0.48% DTMPA and 0.46% PCA (all percentages are w/w (weight volume) in water with hardness 15 dH.

Triple-20 Nonionic Model Detergent (60% surfactant) was prepared by dissolving 3.33 g/l non-ionic detergent containing NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formiate 1%, Sodium Citrate 2%, DTMPA 0.2%, Ethanol (96%) 3%, adjustment of pH with NaOH or Citric acid as water to 100% (all percentages are w/w (weight volume) in water with hardness 15 dH.

Model Detergent MC: A medical cleaning model detergent (model detergent MC) was prepared containing 5% MPG (propylene glycol), 5% Pluronic PE 4300 (PO/EO block polymer; 70%/30%, approx. 1750 g/mol), 2% Plurafac LF 305 (fatty alcohol alkoxylate; C6-10+EO/PO), 1% MGDA (methyl glycine diacetic acid, 1% TEA (triethanolamine) (all percentages are w/w). The pH was adjusted to 8.7 with phosphoric acid.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines. In miniLOM, washes are performed in 50 ml test tubes placed in Stuart rotator.

Example 1: Reducing End Assay

For estimating the mannose yield after substrate hydrolysis, a reducing end assay developed by Lever (Anal. Biochem. 47: 273-279, 1972) is used. The assay is based on 4-hydroxybenzoic acid hydrazide, which under alkaline conditions reacts with the reducing ends of saccharides. The product is a strong yellow anion, which absorbs at 405 nm.

Method. The hydrolysis reaction mixture is composed of 20 μL enzyme and 180 μL substrate dissolved in buffer. The substrate is alfa-1,6-mannan prepared as described elsewhere (Cuskin, Nature, 2015, 517, 165-169) at a concentration of 2 mg/mL. The buffer is 25 mM acetate, pH5.5, 50 mM KCl, 0.01% Triton X-100, 1 mM $CaCl_2$). The reaction conditions are 30 minutes, 37° C., and 950 rpm. 4-Hydroxybenzhydrazide (PAHBAH) (Sigma, H9882) is diluted in PAHBAH buffer to a concentration of 15 mg/ml. PAHBAH buffer contains: 50 g/L K—Na-tartrate (Merck, 1.08087) and 20 g/L sodium hydroxide (Sigma, S8045). This PAHBAH mix is made just before usage. 70 μL PAHBAH mix and MiliQ water are mixed in a 96 well PCR plate (Thermo Scientific). Samples from hydrolysis experiment are added. Samples and MiliQ always reached the total volume of 150 μL, but the dilution of the sample differed. The plate is sealed with Adhesive PCR Sealing Foil Sheets (Thermo Scientific). Plates are incubated at 95° C. for 10 min, cooled down and kept at 10° C. for 1 min in PTC-200 Thermal Cycler (MJ Research). 100 μL sample is transferred to a 96 well microtiter plate, flat bottomed (Nunc™) and color development measured at 405 nm on a SpectraMax 190 Absorbance Microplate Reader (Molecular Devices). Results are compared to mannose standards, which had undergone the same treatment and dilution as the samples to which they were compared.

Example 1A: Beta-Mannanase Assay

For estimating the beta-mannanase activity, a reducing end assay developed by Lever (Anal. Biochem. 47: 273-279, 1972) is used. The assay is based on 4-hydroxybenzoic acid hydrazide, which under alkaline conditions reacts with the reducing ends of saccharides. The product is a strong yellow anion, which absorbs at 405 nm.

Method. The hydrolysis reaction mixture is composed of 20 μL enzyme and 180 μL substrate dissolved in buffer. The substrate is locust bean gum (5 g/L) and the buffer is 0.1 M Na-phosphate pH 7.5. The reaction conditions are 20 minutes, 37° C., and 950 rpm. 4-Hydroxybenzhydrazide (PAHBAH) (Sigma, $H_{9882}$) is diluted in PAHBAH buffer to a concentration of 15 mg/ml. PAHBAH buffer contains: 50 g/L K—Na-tartrate (Merck, 1.08087) and 20 g/L sodium hydroxide (Sigma, S8045). This PAHBAH mix is made just before usage. 70 μL PAHBAH mix and MiliQ water are mixed in a 96 well PCR plate (Thermo Scientific). Samples from hydrolysis experiment are added. Samples and MiliQ always reached the total volume of 150 μL, but the dilution of the sample differed. The plate is sealed with Adhesive PCR Sealing Foil Sheets (Thermo Scientific). Plates are incubated at 95° C. for 10 min, cooled down and kept at 10° C. for 1 min in PTC-200 Thermal Cycler (MJ Research). 100 μL sample is transferred to a 96 well microtiter plate, flat bottomed (Nunc™) and color development measured at 405 nm on a SpectraMax 190 Absorbance Microplate Reader (Molecular Devices). Results are compared to mannose standards, which had undergone the same treatment and dilution as the samples to which they were compared.

Example 2: Cloning and Expression of Alpha-Mannan Degrading Enzymes from Bacterial Strains The alpha-mannan degrading enzymes were derived from bacterial strains isolated from environmental sample by standard microbiological isolation techniques. The isolated pure strains were identified, and taxonomy was assigned based on DNA sequencing of the 16S ribosomal genes (Table 1). One strain was purchased from the American Type Culture Collection as *Bacillus circulans* ATCC 21590 but assigned to the species *Paenibacillus glycanilyticus* based on the results of 16S ribosomal gene sequencing.

TABLE 1

| | Strain or community | Source Country | Mature protein |
|---|---|---|---|
| 1 | Paenibacillus glycanilyticus | ATCC 21590 | SEQ ID NO: 3 |
| 2 | Bacillus acidicola | Denmark | SEQ ID NO: 6 |
| 3 | Bacillus sp. | Denmark | SEQ ID NO: 9 |
| 4 | Paenibacillus sp. A | Denmark | SEQ ID NO: 12 |
| 5 | Paenibacillus sp. B | Denmark | SEQ ID NO: 15 |
| 6 | Paenibacillus sp. C | China | SEQ ID NO: 18 |
| 7 | Microbial community B | Denmark | SEQ ID NO: 21 |
| 8 | Microbial community H | Denmark | SEQ ID NO: 24 |
| 9 | Bacillus novalis | Netherlands | SEQ ID NO: 27 |
| 10 | Chryseobacterium sp. | United States of America | SEQ ID NO: 30 |
| 11 | Microbial community H | Denmark | SEQ ID NO: 57 |

Preparation of Samples 1-6:

Chromosomal DNA was isolated from pure cultures with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) is known to the person skilled in the art and the service can be purchased commercially.

The genome sequences were analyzed for putative alpha mannanases from the CAZY database GH76 family (Lombard V, Golaconda Ramulu H, Drula E, Coutinho P M, Henrissat B (2014) The Carbohydrate-active enzymes database (CAZy) in 2013. Nucleic Acids Res 42:D490-D495). This analysis identified 6 genes encoding putative GH76 mannanases which were subsequently cloned and recombinantly expressed in Bacillus subtilis.

The linear integration constructs were SOE-PCR fusion products (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene of interest between two B. subtilis chromosomal regions along with strong promoters and a chloramphenicol resistance marker. The SOE-PCR method is also described in patent application WO 2003095658.

The mannanase genes were expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence.

The genes were fused with DNA encoding a Bacillus clausii secretion signal (encoding the following amino acid sequence: MKKPLGKIVASTALLISVAFSSSIASA (SEQ ID NO: 58)) replacing the native secretion signal. Furthermore, the expression construct results in the addition of a amino-terminal poly histidine tag consisting of the amino acid sequence HHHHHHPR (SEQ ID NO: 59)) to the mature mannanase to facilitate easy purification by immobilized metal affinity chromatography.

The SOE-PCR product was transformed into Bacillus subtilis and integrated in the chromosome by homologous recombination into the pectate lyase locus. Subsequently a recombinant Bacillus subtilis clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Purification of the Recombinant Enzyme by Immobilized Metal Affinity Chromatography The pH of the cleared supernatant was adjusted to pH 8, filtrated through a 0.2 µM filter, and the supernatant applied to a 5 ml HisTrap™ excel column. Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Preparation of Samples 7-11:

Strains are cloned and expressed according to the above protocol

Example 3: Cloning and Expression of Alpha-Mannan Degrading Enzymes from Aspergillus aculeatus The alpha mannan degrading enzyme was derived from Aspergillus aculeatus strain CBS172.66 isolated from a tropical soil sample in 1962.

Genomic DNA was isolated from Aspergillus aculeatus strain CBS172.66 using a FastDNA spin for Soil Kit (MP Biomedicals, OH, USA).

The Joint Genome Institute Aspergillus aculeatus ATCC16872 genome assembly v1 sequences were analyzed for putative alpha mannanases from the CAZY database GH76 family (Lombard V, Golaconda Ramulu H, Drula E, Coutinho PM, Henrissat B (2014) The Carbohydrate-active enzymes database (CAZy) in 2013. Nucleic Acids Res 42:D490-D495). This analysis identified a gene encoding a putative GH76 mannanase which was subsequently cloned and recombinantly expressed in Aspergillus oryzae.

The gene encoding the putative GH76 mannanase was cloned by PCR amplification from genomic DNA using gene-specific primers that also append a Kozak translation initiation sequence "TCCACC" immediately 5' of the start codon. The amplified DNA fragment was cloned into cloned into the expression vector pDAu222 as described in WO 2013024021 using BamHI and XhoI restriction sites.

The sequence of the putative GH76 mannanase encoding gene cloned in the expression vector was confirmed and the expression construct was transformed into the Aspergillus oryzae strain MT3568 (WO 11/057140) to produce the secreted mature peptide with protein sequence SEQ ID NO: 33. Transformants were selected on acetamide during regeneration from protoplasts and subsequently re-isolated under selection (Christensen et al., 1988, Biotechnology 6, 1419-1422 and WO 04/032648).

For production of the recombinant mannanase, a single Aspergillus transformant was cultured in twenty 500 ml baffled flasks each containing 150 ml of DAP-4C-1 medium (WO 12/103350). The cultures were shaken on a rotary table at 100 RPM at 30° C. for 4 days. The culture broth was subsequently separated from cellular material by passage through a 0.22 µm filter.

Purification of the Recombinant Aspergillus aculeatus Mannanase

Filtrated broth was adjusted to pH7.0 and filtrated on 0.22 µm PES filter (Nalge Nunc International, Nalgene labware cat #595-4520). Following, the filtrate was added 1.8M ammonium sulphate. The filtrate was loaded onto a Phenyl Sepharose™ 6 Fast Flow column (high sub) (GE Healthcare, Piscataway, NJ, USA) equilibrated with 1.8M ammonium sulphate, 25 mM HEPES pH7.0. The bound protein was eluted with 1.0M ammonium sulphate, 25 mM HEPES pH 7.0. Fractions were collected and analyzed by SDS-PAGE. The fractions were pooled and applied to a Sephadex™ G-25 (medium) (GE Healthcare, Piscataway, NJ, USA) column equilibrated in 25 mM HEPES pH 7.0. The fractions were applied to a SOURCE™ 15Q (GE Healthcare, Piscataway, NJ, USA) column equilibrated in 25 mM HEPES pH 7.0 and bound proteins were eluted with a linear gradient from 0-1000 mM sodium chloride over 20 CV. Fractions were collected and analyzed by SDS-PAGE.

Example 4. Cloning, Expression and Purification of Alpha-Mannan Degrading Enzymes from Fungal Strains Seven genes encoding alpha-mannanases belonging to the CAZy defined protein family GH76 (www.cazy.org, Lombard V, et al. (2014) Nucleic Acids Res 42:D490-D495) were cloned from two fungal strains that were isolated from environmental samples and are described in Table 2 below. The *Aspergillus aculeatus* isolate is available from CBS-KNAW Fungal Biodiversity Centre, Utrecht, The Netherlands, as CBS 101.43.

TABLE 2

| Strain | Source country | Mature peptide sequence SEQ ID NO: |
| --- | --- | --- |
| Aspergillus aculeatus | Unknown, isolated on or prior to 1943. | SEQ ID NO: 36 SEQ ID NO: 39 SEQ ID NO: 42 |
| Humicola insolens | Denmark | SEQ ID NO: 45 SEQ ID NO: 48 SEQ ID NO: 51 SEQ ID NO: 54 |

Chromosomal DNA was isolated and used for whole genome sequencing by standard methods known to the person skilled in the art. The whole genome sequences were assembled with either IDBA or SPAdes genome assemblers (Peng, Y., et al. Bioinformatics. (2012), 28: 1420-1428 and Bankevich, A. et al. J Comput Biol. (2012) 19(5):455-77), and genes were annotated on the genomes with the GeneMark 2.3c or GeneMark ES v4.28 gene prediction software (Ter-Hovhannisyan V. et al. Genome Res. (2008) 18(12): 1979-90).

The set of peptide sequences predicted from genes annotated on the whole genome sequences were searched for similarity to the GH76 domain. Seven peptides identified in this search are listed in the table above with SEQ ID NOs for both the nucleotide and peptide sequences. The genes encoding these peptides were cloned by PCR amplification from genomic DNA using gene-specific primers that also append a Kozak translation initiation sequence "TCACC" immediately 5' of the start codon. The predicted peptides for six of the alpha-manannases (corresponding to SEQ ID NO: 39, SEQ ID NO: 42, SEQ ID NO: 45, SEQ ID NO: 48, SEQ ID NO: 51, SEQ ID NO: 54) included a predicted GPI anchor or transmembrane domain at the C-terminus. To promote secretion of the recombinant proteins and avoid GPI or transmembrane domain mediated anchoring to the cell membrane, PCR primers were designed to amplify truncated peptides that included the full coding region for the predicted GH76 catalytic domain but did not include the C-terminal GPI or transmembrane domain. Stop codons were added in frame via the return PCR primer. The truncated nucleotide sequences amplified for expression are shown in SEQ ID NO: 39, SEQ ID NO: 42, SEQ ID NO: 45, SEQ ID NO: 48, SEQ ID NO: 51, SEQ ID NO: 54, respectively. The amplified DNA fragments were cloned into the *Aspergillus* expression vector pMStr57 (WO 04/032648) that had been digested with BamHI and XhoI.

The cloned genes were sequenced and confirmed to be identical to the corresponding genes found in the genome sequence, and transformed into the *Aspergillus oryzae* strain MT3568 (WO 11/057140) by the methods described in Christensen et al., 1988, Biotechnology 6, 1419-1422 and WO 04/032648. Transformants were selected during regeneration from protoplasts based on the ability, conferred by a selectable marker in the expression vector, to utilize acetamide as a nitrogen source, and were subsequently re-isolated twice under selection.

Production of the recombinant polypeptides was evaluated by culturing transformants in 96-well deep-well microtiter plates for 4 days at 30° C. in 0.25 ml of YPG medium (WO 05/066338) or DAP-4C-1 medium (WO 12/103350) and monitoring recombinant expression by SDS-PAGE.

Chromatographic Purification of Seven Family GH76 Alpha-Mannanases from *Aspergillus aculeatus* and *Humicola insolens*

For larger-scale production of the recombinant alpha-mannanases, a single *Aspergillus* transformant was selected for each mannanase based on recombinant yield, the transformants were cultured in 500 ml baffled flasks containing 150 ml of DAP-4C-1 medium. The cultures were shaken on a rotary table at 150 RPM at a temperature of 30° C. for 4 days. Culture broth was separated from cellular material by passage through a 0.22 um filtration unit.

To purify the samples, the pH of the filtered samples was adjusted to around pH 7.5 and 1.8M ammonium sulfate (AMS) was added. The samples were applied to a 5 ml HiTrap™ Phenyl (HS) column on an Akta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target proteins were eluted from the column into a 10 ml loop using 50 mM HEPES+20% isopropanol pH 7. From the loop, the samples were loaded onto a desalting column (HiPrep™ 26/10 Desalting), which had been equilibrated with 3 CV of 50 mM HEPES+100 mM NaCl pH 7.0. The target proteins were eluted with 50 mM HEPES+100 mM NaCl pH 7.0 and relevant fractions were selected and pooled based on the chromatograms. The flow rate was 5 ml/min.

Protein concentration in the final samples were estimated by measuring absorption at 280 nm.

Example 5: Milliscale Wash Assay (MISWA96)

Preparation of Biofilm Swatches

Biofilm swatches (10 cm×10 cm) were made by growing *Brevundimonas* sp. on polyester swatches for three days. The biofilm swatches were rinsed twice in water and dried for 2 h in a laf bench with flow and subsequently punched into round swatches circles (0.6 cm×0.6 cm) and placed into the wells of a MTP96, and stored at 4° C. for further use.

Washing Experiment

The swatches were transferred from the MTP96 to a deep-well MTP96, for the washing assay. The deep-well plate was placed in a Hamilton robot and subjected to a wash simulation program using the following conditions: shaking speed: 30 sec at 1000 rpm. Duration of wash cycle: 30 minutes with shaking; temperature 30° C.; Volume of wash liquor (total): 500 µl per well (490 µl wash liquor of Model Detergent A+10 µl sample). For screening of wash performance of alpha-mannan degrading enzymes, wash liquor Model Detergent A was prepared by dissolving 3.3 g/L in water hardness 15° dH. Soil was subsequently added to reach a concentration of 0.7 g soil/L (WFK 09V pigment soil).

A 96 deep-well plate was filled with each enzyme sample, and the program was started on the robot. Alpha-mannan degrading enzymes were tested in concentration 0.5 ppm. The blank consisted of biofilm swatches without any enzyme addition. After completion of the wash simulation cycle, the swatches were removed from the wash liquor and dried on a filter paper. The dried swatches were fixed on a sheet of white paper for scanning. The scanned picture was further used with the software color-analyzer. Each sample have an intensity measurement from the color analyzer software analysis that will be used to calculate the delta intensity by subtracting the intensity of the blank without enzyme. Values over 20 delta intensity represents a visual cleaning effect. These data are shown in Table 3.

TABLE 3

Wash performance of alpha-mannan degrading enzymes.

| SEQ ID NO: | Family | Intensity (with alpha-mannan degrading enzyme) | Intensity (without enzyme) | Delta Intensity |
|---|---|---|---|---|
| 33 | GH76 | 202 | 180 | 22 |
| 36 | GH76 | 209 | 178 | 31 |
| 45 | GH76 | 205 | 178 | 27 |
| 48 | GH76 | 228 | 180 | 48 |
| 39 | GH76 | 215 | 178 | 37 |
| 51 | GH76 | 194 | 178 | 16 |
| 21 | GH76 | 252 | 212 | 57 |
| 24 | GH76 | 228 | 228 | 40 |
| 3 | GH76 | 228 | 228 | 36 |
| 6 | GH76 | 228 | 228 | 29 |
| 9 | GH76 | 228 | 228 | 9 |
| 12 | GH76 | 228 | 228 | 19 |
| 15 | GH76 | 228 | 228 | 28 |
| 18 | GH76 | 228 | 228 | 23 |
| 27 | GH92 | 217 | 206 | 11 |
| 30 | GH99 | 290 | 260 | 31 |

The combined effect of separate different alpha-mannan degrading enzymes was also tested, as described above, but with each alpha-mannan degrading enzyme tested in concentration 0.5 ppm (total enzyme concentration 1 ppm). These data are shown in Table 4.

TABLE 4

Wash performance of alpha-mannan degrading enzymes.

| SEQ ID NO: | Family | Intensity (when combined with GH99 SEQ ID NO: 30) | Intensity (without enzyme) | Delta Intensity |
|---|---|---|---|---|
| 33 | GH76 | 284 | 179 | 105 |
| 36 | GH76 | 282 | 178 | 104 |
| 45 | GH76 | 264 | 178 | 86 |
| 48 | GH76 | 280 | 179 | 101 |
| 42 | GH76 | 285 | 178 | 107 |
| 39 | GH76 | 275 | 178 | 97 |
| 51 | GH76 | 261 | 178 | 83 |
| 54 | GH76 | 250 | 178 | 72 |
| 21 | GH76 | 327 | 181 | 146 |
| 27 | GH92 | 278.5 | 181 | 97.5 |

Example 6: Construction of Clades and Phylogenetic Trees

GH76 Phylogenetic Tree

A phylogenetic tree was constructed, of polypeptide sequences containing a GH76 domain, as defined in CAZY (GH76, Glycoside Hydrolase Family 76, CAZy database, www.cazy.org, Lombard V, et al. 2014, Nucleic Acids Res 42:D490-D495). The phylogenetic tree was constructed from a multiple alignment of mature polypeptide sequences containing at least one GH76 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, PloS one 5(3)) and visualized using iTOL (Letunic & Bork, 2007. Bioinformatics 23(1): 127-128).

The polypeptide containing a GH76 domain comprises several motifs. One example is [YND]DD[QINLEM] (SEQ ID NO: 60) situated in positions 124 to 127 in *Paenibacillus glycanilyticus* (SEQ ID NO: 3), where D at position 124 is the catalytic nucleophile of the family, and D in position 125 is the general acid/base. and fully conserved in the polypeptides of the invention. Another motif which may be comprised by the polypeptides of the invention is GG[ILMV]X[WS] (SEQ ID NO: 61) situated in positions corresponding to positions 167 to 171 in *Paenibacillus glycanilyticus* (SEQ ID NO: 3).

The polypeptides comprising a GH76 domain can be further separated into multiple distinct sub-clusters, or clades, where the denoted clades are listed below.

The AMXAAE Clade (GH76 Fungal)

The polypeptides containing a GH76 domain can be separated into distinct sub-clusters. The sub-clusters are defined by one or more short sequence motifs, as well as containing a GH76 domain as defined in CAZY (GH76, CAZy database, www.cazy.org, Lombard V, et al. 2014, Nucleic Acids Res 42:D490-D495).

We denoted one sub-cluster comprising the motif [GA]XX[AVL][ML]X[MA][ATV][EATV] (SEQ ID NO: 62) as the AMXAAE clade. It is situated at positions 99 to 107 in *Aspergillus aculeatus* (SEQ ID NO: 36). All polypeptide sequences containing a GH76 domain as well as the motif will be denoted as belonging to the AMXAAE clade. The AMXAAE clade comprises polypeptides of primarily fungal origin.

Another motif which may be comprised by members of the AMXAAE clade is LA[EQ]X[VL][YF] (SEQ ID NO: 63) situated in positions corresponding to positions 122 to 127 in *Aspergillus aculeatus* (SEQ ID NO: 36).

Examples of polypeptides of the AMXAAE clade includes SEQ ID NO: 33, SEQ ID NO: 36, SEQ ID NO: 39, SEQ ID NO: 42, SEQ ID NO: 45, SEQ ID NO: 48, SEQ ID NO: 51, and SEQ ID NO: 54.

The KNTPA Clade (GH76 Bacterial)

The polypeptides containing a GH76 domain can be separated into additional distinct sub-clusters, using the phylogenetic tree described above. One clade is denote KNTPA, which comprises polypeptides of bacterial origin.

Members of the KNTPA clade must be of bacterial origin and contain the motif [RK][NLT]XXX[NTV]XP[GTLY-ISAVFNM] (SEQ ID NO: 64), corresponding to amino acids KNTPANAPA (SEQ ID NO: 65) at positions 147 to 155 in SEQ ID NO 3 from *Paenibacillus glycanilyticus*.

Examples of polypeptides of the KNTPA clade includes SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, and SEQ ID NO: 57.

GH99 Phylogenetic Tree and the NEWHE Clade

A phylogenetic tree was constructed, of polypeptide sequences containing a GH99 domain, as defined in CAZY (GH99, Glycoside Hydrolase Family 99, CAZy database, www.cazy.org, Lombard V, et al. 2014, Nucleic Acids Res 42:D490-D495). The phylogenetic tree was constructed from a multiple alignment of mature polypeptide sequences containing at least one GH92 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

The polypeptide containing a GH99 domain comprises several motifs. One example is N[EQD][WFY][HG]E (SEQ ID NO: 66) situated in positions 296 to 300 in *Chryseobacterium* sp. (SEQ ID NO: 30), where E at position 322 is the general acid/base of the family and fully conserved in the family.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A cleaning composition comprising:
   (a) at least one polypeptide having alpha-mannan degrading activity or a variant or a fragment thereof having alpha-mannan degrading activity, wherein the at least one polypeptide, the variant or the fragment thereof is selected from the group consisting of:
   (I) a polypeptide having at least 96% sequence identity but less than 100% sequence identity to SEQ ID NO: 2 or SEQ ID NO: 3 (mature form), or a polypeptide is encoded by a polynucleotide having at least 90% sequence identity but less than 100% sequence identity to SEQ ID NO: 1;
   (II) a polypeptide having at least 70% sequence identity but less than 100% sequence identity to SEQ ID NO: 5 or SEQ ID NO: 6 (mature form), or a polypeptide is encoded by a polynucleotide having at least 60% sequence identity but less than 100% sequence identity to SEQ ID NO: 4;
   (III) a polypeptide having at least 75% sequence identity but less than 100% sequence identity to SEQ ID NO: 8 or SEQ ID NO: 9 (mature form), or a polypeptide is encoded by a polynucleotide having at least 60% sequence identity but less than 100% sequence identity to SEQ ID NO: 7;
   (IV) a polypeptide having at least 92% sequence identity but less than 100% sequence identity to SEQ ID NO: 11 or SEQ ID NO: 12 (mature form), or a polypeptide is encoded by a polynucleotide having at least 60% sequence identity but less than 100% sequence identity to SEQ ID NO: 10;
   (V) a polypeptide having at least 80% sequence identity but less than 100% sequence identity to SEQ ID NO: 14 or SEQ ID NO: 15 (mature form), or a polypeptide is encoded by a polynucleotide having at least 60% sequence identity but less than 100% sequence identity to SEQ ID NO: 13;
   (VI) a polypeptide having at least 94% sequence identity but less than 100% sequence identity to SEQ ID NO: 17, or a polypeptide is encoded by a polynucleotide having at least 90% sequence identity but less than 100% sequence identity to SEQ ID NO: 16;
   (VII) a polypeptide having at least 98% sequence identity but less than 100% sequence identity to SEQ ID NO: 20 or SEQ ID NO: 21 (mature form), or a polypeptide is encoded by a polynucleotide having at least 90% sequence identity but less than 100% sequence identity to SEQ ID NO: 19;
   (VIII) a polypeptide having at least 82% sequence identity but less than 100% sequence identity to SEQ ID NO: 23 or SEQ ID NO: 24 (mature form), or a polypeptide is encoded by a polynucleotide having at least 70% sequence identity but less than 100% sequence identity to SEQ ID NO: 22; and
   (IX) a polypeptide having at least 82% sequence identity but less than 100% sequence identity to SEQ ID NO: 56 or SEQ ID NO: 57 (mature form), or a polypeptide is encoded by a polynucleotide having at least 70% sequence identity but less than 100% sequence identity to SEQ ID NO: 55; and
   (b) at least one cleaning component selected from a surfactant, a builder, a bleach component, a polymer, a dispersing agent and/or an additional enzyme.

2. The cleaning composition of claim 1, wherein the polypeptide has alpha-mannanase and/or alpha-mannosidase activity.

3. The cleaning composition of claim 1, wherein the polypeptide having alpha-mannan degrading activity belongs to glycosyl hydrolase family 76 (GH76).

4. The cleaning composition of claim 1, wherein the polypeptide further comprises one or more of the motifs [YND]DD[QINLEM] (SEQ ID NO: 60), GG[ILMV]X[WS] (SEQ ID NO: 61) or [RK][NLT]XXX[NTV]XP[GTLY-ISAVFNM] (SEQ ID NO: 64).

5. The cleaning composition claim 1, wherein the polypeptide is of the KNTPA Clade and is of bacterial origin.

6. The cleaning composition of claim 1, comprising at least two polypeptides having alpha-mannan degrading activity.

7. The cleaning composition of claim 1, wherein the polypeptide having alpha-mannan degrading activity is obtained from a strain of Bacillus or Paenibacillus.

8. The cleaning composition of claim 1, comprising at least 0.001 ppm of the polypeptide having alpha-mannan degrading activity.

9. A process for degrading alpha-mannan, comprising applying the cleaning composition of claim 1 to the alpha-mannan.

10. A method of cleaning an item, comprising the steps of:
    (a) contacting the item with the cleaning composition of claim 1; and
    (b) optionally rinsing the item, wherein the item is a textile or a hard surface.

11. An isolated or purified polypeptide having alpha-mannan degrading activity, wherein the polypeptide is selected from the group consisting of:

(I) a polypeptide having at least 96% sequence identity but less than 100% sequence identity to SEQ ID NO: 2 or SEQ ID NO: 3 (mature form), or a polypeptide is encoded by a polynucleotide having at least 90% sequence identity but less than 100% sequence identity to SEQ ID NO: 1;

(II) a polypeptide having at least 70% sequence identity but less than 100% sequence identity to SEQ ID NO: 5 or SEQ ID NO: 6 (mature form), or a polypeptide is encoded by a polynucleotide having at least 60% sequence identity but less than 100% sequence identity to SEQ ID NO: 4;

(III) a polypeptide having at least 75% sequence identity but less than 100% sequence identity to SEQ ID NO: 8 or SEQ ID NO: 9 (mature form), or a polypeptide is encoded by a polynucleotide having at least 60% sequence identity but less than 100% sequence identity to SEQ ID NO: 7;

(IV) a polypeptide having at least 92% sequence identity but less than 100% sequence identity to SEQ ID NO: 11 or SEQ ID NO: 12 (mature form), or a polypeptide is encoded by a polynucleotide having at least 60% sequence identity but less than 100% sequence identity to SEQ ID NO: 10;

(V) a polypeptide having at least 80% sequence identity but less than 100% sequence identity to SEQ ID NO: 14 or SEQ ID NO: 15 (mature form), or a polypeptide is encoded by a polynucleotide having at least 60% sequence identity but less than 100% sequence identity to SEQ ID NO: 13;

(VI) a polypeptide having at least 94% sequence identity but less than 100% sequence identity to SEQ ID NO: 17, or a polypeptide is encoded by a polynucleotide having at least 90% sequence identity but less than 100% sequence identity to SEQ ID NO: 16;

(VII) a polypeptide having at least 98% sequence identity but less than 100% sequence identity to SEQ ID NO: 20 or SEQ ID NO: 21 (mature form), or a polypeptide is encoded by a polynucleotide having at least 90% sequence identity but less than 100% sequence identity to SEQ ID NO: 19;

(VIII) a polypeptide having at least 82% sequence identity but less than 100% sequence identity to SEQ ID NO: 23 or SEQ ID NO: 24 (mature form), or a polypeptide is encoded by a polynucleotide having at least 70% sequence identity but less than 100% sequence identity to SEQ ID NO: 22; and (IX) a polypeptide having at least 82% sequence identity but less than 100% sequence identity to SEQ ID NO: 56 or SEQ ID NO: 57 (mature form), or a polypeptide is encoded by a polynucleotide having at least 70% sequence identity but less than 100% sequence identity to SEQ ID NO: 55.

12. The polypeptide of claim 11, wherein the polypeptide having alpha-mannan degrading activity belongs to glycosyl hydrolase family 76 (GH76).

13. The polypeptide of claim 11, wherein the polypeptide further comprises one or more of the motifs [YND]DD[QINLEM] (SEQ ID NO: 60), GG[ILMV]X[WS] (SEQ ID NO: 61) or [RK][NLT]XXX[NTV]XP[GTLYISAVFNM] (SEQ ID NO: 64).

14. The polypeptide of claim 11, which is of the KNTPA Glade and is of bacterial origin.

15. A polypeptide having at least 90% sequence identity but less than 100% sequence identity to SEQ ID NO: 9.

16. A polypeptide having at least 90% sequence identity but less than 100% sequence identity to SEQ ID NO: 15.

17. A polypeptide having at least 90% sequence identity but less than 100% sequence identity to SEQ ID NO: 24.

18. A polypeptide having at least 90% sequence identity but less than 100% sequence identity to SEQ ID NO: 57.

* * * * *

SEQUENCE LISTING

```
<160> NUMBER OF SEQ ID NOS: 69

<210> SEQ ID NO 1
<211> LENGTH: 1158
<212> TYPE: DNA
<213> ORGANISM: Paenibacillus glycanilyticus
<220> FEATURE:
<221> NAME/KEY: CDS
<222> LOCATION: (1)..(1155)
<220> FEATURE:
<221> NAME/KEY: sig_peptide
<222> LOCATION: (1)..(96)
<220> FEATURE:
<221> NAME/KEY: mat_peptide
<222> LOCATION: (97)..(1155)

<400> SEQUENCE: 1 ttg aat cgc aac aaa cga tat tta tgg ctg gcc gtt gct tcg gca gtt        48
Leu Asn Arg Asn Lys Arg Tyr Leu Trp Leu Ala Val Ala Ser Ala Val
        -30                 -25                 -20 atc ctc ata gcg ttg gtc tgg tca ttg gtc tgg aag gat aaa acg gca        96
Ile Leu Ile Ala Leu Val Trp Ser Leu Val Trp Lys Asp Lys Thr Ala
    -15                 -10                  -5                  -1 gca acc tcc gtc att tgg cag gaa cgg gcg gaa gaa gcg cag ctt gaa       144
Ala Thr Ser Val Ile Trp Gln Glu Arg Ala Glu Glu Ala Gln Leu Glu
 1                5                  10                  15 ctg acc aag tcc ttc tgg gac gac aag cgc ggg ctc tac aac aat gcc       192
Leu Thr Lys Ser Phe Trp Asp Asp Lys Arg Gly Leu Tyr Asn Asn Ala
                20                  25                  30 gcg ccg tgt att gcc cag cta tgc acc gat ccg ttt aac tat tgg tgg       240
Ala Pro Cys Ile Ala Gln Leu Cys Thr Asp Pro Phe Asn Tyr Trp Trp
            35                  40                  45 ctg gcg cat gcg gtg gat gcg ctg gtc gac ggc tac gag cgc agc ggg       288
Leu Ala His Ala Val Asp Ala Leu Val Asp Gly Tyr Glu Arg Ser Gly
        50                  55                  60 gat gaa cgg tac gcg gag caa atc gcc aag ctg cat caa gga ttg ctt       336
Asp Glu Arg Tyr Ala Glu Gln Ile Ala Lys Leu His Gln Gly Leu Leu
 65                  70                  75                  80 gat cgc aac gcc ggc gtg atg atc aac gat tat tac gat gat atg gaa       384
Asp Arg Asn Ala Gly Val Met Ile Asn Asp Tyr Tyr Asp Asp Met Glu
                85                  90                  95 tgg atg gcg ctg gcc tgg ctg aga gct tac gat gcc acc aag gac gag       432
```

```
                Trp Met Ala Leu Ala Trp Leu Arg Ala Tyr Asp Ala Thr Lys Asp Glu
                                100                 105                 110 aag tat aag cag gaa gca ctt gaa ctg tgg gaa gag att aaa ggc ggc        480
Lys Tyr Lys Gln Glu Ala Leu Glu Leu Trp Glu Glu Ile Lys Gly Gly
            115                 120                 125 tgg aac gag gag atg ggc ggc ggc atc gct tgg cgc aag gag cag ctc        528
Trp Asn Glu Glu Met Gly Gly Gly Ile Ala Trp Arg Lys Glu Gln Leu
130                 135                 140 gat tac aag aat acg ccg gcg aat gct cct gcg gct att ttg gcg gca        576
Asp Tyr Lys Asn Thr Pro Ala Asn Ala Pro Ala Ala Ile Leu Ala Ala
145                 150                 155                 160 cgg ctg tac ggc cat ttc cat aac ggg gaa gat ctg gcc tgg gcg aaa        624
Arg Leu Tyr Gly His Phe His Asn Gly Glu Asp Leu Ala Trp Ala Lys
                165                 170                 175 aaa att tac gat tgg caa aaa gag acg ctt gtg gat ccg gat acc ggt        672
Lys Ile Tyr Asp Trp Gln Lys Glu Thr Leu Val Asp Pro Asp Thr Gly
            180                 185                 190 ctc gta tgg gac gga atc aac cgg acg ggc gac ggc aat atc gac aag        720
Leu Val Trp Asp Gly Ile Asn Arg Thr Gly Asp Gly Asn Ile Asp Lys
        195                 200                 205 gaa tgg cga ttc acg tat ggc caa ggc gtg ttt atc ggg gcc ggc gtt        768
Glu Trp Arg Phe Thr Tyr Gly Gln Gly Val Phe Ile Gly Ala Gly Val
210                 215                 220 gaa ctg ttc cgg gca acg gag gat aag gct tat ctg gag gat gcc cgc        816
Glu Leu Phe Arg Ala Thr Glu Asp Lys Ala Tyr Leu Glu Asp Ala Arg
225                 230                 235                 240 cgg acg gcg gct cat ctg aag gag gcg ttc ctg tct ccg gca acc ggc        864
Arg Thr Ala Ala His Leu Lys Glu Ala Phe Leu Ser Pro Ala Thr Gly
                245                 250                 255 atg ctt cca tcg gaa ggc gac ggc gac ggg ggc ttg ttc aaa ggc gta        912
Met Leu Pro Ser Glu Gly Asp Gly Asp Gly Gly Leu Phe Lys Gly Val
            260                 265                 270 tta atc cgc tat ttg gga gag ctg att gcc gct gat ccg gat gag ccg        960
Leu Ile Arg Tyr Leu Gly Glu Leu Ile Ala Ala Asp Pro Asp Glu Pro
        275                 280                 285 gag cgc aaa gaa tgg att ggc atg ctt gag acc aac gcg aac agc tta       1008
Glu Arg Lys Glu Trp Ile Gly Met Leu Glu Thr Asn Ala Asn Ser Leu
290                 295                 300 tgg caa tac gga aaa gcg gaa gat aaa gcg gta ttc agc aat tca tgg       1056
Trp Gln Tyr Gly Lys Ala Glu Asp Lys Ala Val Phe Ser Asn Ser Trp
305                 310                 315                 320 gcc gaa gcg ccg gat acg atc gtg caa tta agc acg gaa cta agc ggg       1104
Ala Glu Ala Pro Asp Thr Ile Val Gln Leu Ser Thr Glu Leu Ser Gly
                325                 330                 335 ata atg ctg ctc gag cag atg gcc gta ttg gag aaa aac gga caa tta       1152
Ile Met Leu Leu Glu Gln Met Ala Val Leu Glu Lys Asn Gly Gln Leu
            340                 345                 350 cag tag                                                                1158
Gln

<210> SEQ ID NO 2
<211> LENGTH: 385
<212> TYPE: PRT
<213> ORGANISM: Paenibacillus glycanilyticus

<400> SEQUENCE: 2

Leu Asn Arg Asn Lys Arg Tyr Leu Trp Leu Ala Val Ala Ser Ala Val
        -30                 -25                 -20

Ile Leu Ile Ala Leu Val Trp Ser Leu Val Trp Lys Asp Lys Thr Ala
        -15                 -10                 -5                  -1
```

```
Ala Thr Ser Val Ile Trp Gln Glu Arg Ala Glu Ala Gln Leu Glu
1               5                   10                  15

Leu Thr Lys Ser Phe Trp Asp Asp Lys Arg Gly Leu Tyr Asn Asn Ala
            20                  25                  30

Ala Pro Cys Ile Ala Gln Leu Cys Thr Asp Pro Phe Asn Tyr Trp Trp
            35                  40                  45

Leu Ala His Ala Val Asp Ala Leu Val Asp Gly Tyr Glu Arg Ser Gly
            50                  55                  60

Asp Glu Arg Tyr Ala Glu Gln Ile Ala Lys Leu His Gln Gly Leu Leu
65                  70                  75                  80

Asp Arg Asn Ala Gly Val Met Ile Asn Asp Tyr Tyr Asp Met Glu
                85                  90                  95

Trp Met Ala Leu Ala Trp Leu Arg Ala Tyr Asp Ala Thr Lys Asp Glu
                100                 105                 110

Lys Tyr Lys Gln Glu Ala Leu Glu Leu Trp Glu Glu Ile Lys Gly Gly
            115                 120                 125

Trp Asn Glu Glu Met Gly Gly Gly Ile Ala Trp Arg Lys Glu Gln Leu
    130                 135                 140

Asp Tyr Lys Asn Thr Pro Ala Asn Ala Pro Ala Ala Ile Leu Ala Ala
145                 150                 155                 160

Arg Leu Tyr Gly His Phe His Asn Gly Glu Asp Leu Ala Trp Ala Lys
                165                 170                 175

Lys Ile Tyr Asp Trp Gln Lys Glu Thr Leu Val Asp Pro Asp Thr Gly
                180                 185                 190

Leu Val Trp Asp Gly Ile Asn Arg Thr Gly Asp Gly Asn Ile Asp Lys
                195                 200                 205

Glu Trp Arg Phe Thr Tyr Gly Gln Gly Val Phe Ile Gly Ala Gly Val
            210                 215                 220

Glu Leu Phe Arg Ala Thr Glu Asp Lys Ala Tyr Leu Glu Asp Ala Arg
225                 230                 235                 240

Arg Thr Ala Ala His Leu Lys Glu Ala Phe Leu Ser Pro Ala Thr Gly
                245                 250                 255

Met Leu Pro Ser Glu Gly Asp Gly Asp Gly Gly Leu Phe Lys Gly Val
                260                 265                 270

Leu Ile Arg Tyr Leu Gly Glu Leu Ile Ala Ala Asp Pro Asp Glu Pro
                275                 280                 285

Glu Arg Lys Glu Trp Ile Gly Met Leu Glu Thr Asn Ala Asn Ser Leu
            290                 295                 300

Trp Gln Tyr Gly Lys Ala Glu Asp Lys Ala Val Phe Ser Asn Ser Trp
305                 310                 315                 320

Ala Glu Ala Pro Asp Thr Ile Val Gln Leu Ser Thr Glu Leu Ser Gly
                325                 330                 335

Ile Met Leu Leu Glu Gln Met Ala Val Leu Glu Lys Asn Gly Gln Leu
                340                 345                 350

Gln
```

<210> SEQ ID NO 3
<211> LENGTH: 353
<212> TYPE: PRT
<213> ORGANISM: Paenibacillus glycanilyticus

<400> SEQUENCE: 3

```
Ala Thr Ser Val Ile Trp Gln Glu Arg Ala Glu Ala Gln Leu Glu
1               5                   10                  15
```

-continued

```
Leu Thr Lys Ser Phe Trp Asp Asp Lys Arg Gly Leu Tyr Asn Asn Ala
             20                  25                  30

Ala Pro Cys Ile Ala Gln Leu Cys Thr Asp Pro Phe Asn Tyr Trp Trp
         35                  40                  45

Leu Ala His Ala Val Asp Ala Leu Val Asp Gly Tyr Glu Arg Ser Gly
     50                  55                  60

Asp Glu Arg Tyr Ala Glu Gln Ile Ala Lys Leu His Gln Gly Leu Leu
 65                  70                  75                  80

Asp Arg Asn Ala Gly Val Met Ile Asn Asp Tyr Tyr Asp Asp Met Glu
                 85                  90                  95

Trp Met Ala Leu Ala Trp Leu Arg Ala Tyr Asp Ala Thr Lys Asp Glu
            100                 105                 110

Lys Tyr Lys Gln Glu Ala Leu Glu Leu Trp Glu Glu Ile Lys Gly Gly
            115                 120                 125

Trp Asn Glu Glu Met Gly Gly Gly Ile Ala Trp Arg Lys Glu Gln Leu
130                 135                 140

Asp Tyr Lys Asn Thr Pro Ala Asn Ala Pro Ala Ala Ile Leu Ala Ala
145                 150                 155                 160

Arg Leu Tyr Gly His Phe His Asn Gly Glu Asp Leu Ala Trp Ala Lys
                165                 170                 175

Lys Ile Tyr Asp Trp Gln Lys Glu Thr Leu Val Asp Pro Asp Thr Gly
            180                 185                 190

Leu Val Trp Asp Gly Ile Asn Arg Thr Gly Asp Gly Asn Ile Asp Lys
        195                 200                 205

Glu Trp Arg Phe Thr Tyr Gly Gln Gly Val Phe Ile Gly Ala Gly Val
    210                 215                 220

Glu Leu Phe Arg Ala Thr Glu Asp Lys Ala Tyr Leu Glu Asp Ala Arg
225                 230                 235                 240

Arg Thr Ala Ala His Leu Lys Glu Ala Phe Leu Ser Pro Ala Thr Gly
                245                 250                 255

Met Leu Pro Ser Glu Gly Asp Gly Asp Gly Gly Leu Phe Lys Gly Val
            260                 265                 270

Leu Ile Arg Tyr Leu Gly Glu Leu Ile Ala Ala Asp Pro Asp Glu Pro
        275                 280                 285

Glu Arg Lys Glu Trp Ile Gly Met Leu Glu Thr Asn Ala Asn Ser Leu
    290                 295                 300

Trp Gln Tyr Gly Lys Ala Glu Asp Lys Ala Val Phe Ser Asn Ser Trp
305                 310                 315                 320

Ala Glu Ala Pro Asp Thr Ile Val Gln Leu Ser Thr Glu Leu Ser Gly
                325                 330                 335

Ile Met Leu Leu Glu Gln Met Ala Val Leu Glu Lys Asn Gly Gln Leu
            340                 345                 350

Gln

<210> SEQ ID NO 4
<211> LENGTH: 1137
<212> TYPE: DNA
<213> ORGANISM: Bacillus acidicola
<220> FEATURE:
<221> NAME/KEY: CDS
<222> LOCATION: (1)..(1134)
<220> FEATURE:
<221> NAME/KEY: sig_peptide
<222> LOCATION: (1)..(87)
<220> FEATURE:
<221> NAME/KEY: mat_peptide
```

<222> LOCATION: (88)..(1134)

<400> SEQUENCE: 4

| | | | | | | | | | | | | | | | | |
|---|---|---|---|---|---|---|---|---|---|---|---|---|---|---|---|---|
| atg | tct | aaa | ttt | ctt | aaa | cca | agt | att | gtg | ttt | act | ctg | att | gtg | atg | 48 |
| Met | Ser | Lys | Phe | Leu | Lys | Pro | Ser | Ile | Val | Phe | Thr | Leu | Ile | Val | Met | |
| | | | -25 | | | | -20 | | | | | | | -15 | | |

| | | | | | | | | | | | | | | | | |
|---|---|---|---|---|---|---|---|---|---|---|---|---|---|---|---|---|
| cta | atc | gcg | tta | gtg | gca | cct | ggc | acg | tct | aca | tat | gct | gca | tcc | tat | 96 |
| Leu | Ile | Ala | Leu | Val | Ala | Pro | Gly | Thr | Ser | Thr | Tyr | Ala | Ala | Ser | Tyr | |
| | | | -10 | | | | | -5 | | | | -1 | 1 | | | |

| | | | | | | | | | | | | | | | | |
|---|---|---|---|---|---|---|---|---|---|---|---|---|---|---|---|---|
| cat | aag | aaa | aat | gtt | gaa | aga | gcc | ctt | gcc | tct | tat | gaa | tta | atg | caa | 144 |
| His | Lys | Lys | Asn | Val | Glu | Arg | Ala | Leu | Ala | Ser | Tyr | Glu | Leu | Met | Gln | |
| | 5 | | | | 10 | | | | | 15 | | | | | | |

| | | | | | | | | | | | | | | | | |
|---|---|---|---|---|---|---|---|---|---|---|---|---|---|---|---|---|
| aag | tac | ttc | tat | cag | cct | agt | gtt | aaa | ctt | tat | act | gaa | gaa | ttt | cct | 192 |
| Lys | Tyr | Phe | Tyr | Gln | Pro | Ser | Val | Lys | Leu | Tyr | Thr | Glu | Glu | Phe | Pro | |
| 20 | | | | | 25 | | | | | 30 | | | | | 35 | |

| | | | | | | | | | | | | | | | | |
|---|---|---|---|---|---|---|---|---|---|---|---|---|---|---|---|---|
| aac | gtt | atc | ggg | aat | tca | tat | tct | tat | tta | tgg | ccg | ttt | tcc | caa | gca | 240 |
| Asn | Val | Ile | Gly | Asn | Ser | Tyr | Ser | Tyr | Leu | Trp | Pro | Phe | Ser | Gln | Ala | |
| | | | | 40 | | | | | 45 | | | | | 50 | | |

| | | | | | | | | | | | | | | | | |
|---|---|---|---|---|---|---|---|---|---|---|---|---|---|---|---|---|
| atg | gct | gca | aca | act | gat | gtg | tct | aga | ctc | cct | aaa | ata | ggt | aaa | aat | 288 |
| Met | Ala | Ala | Thr | Thr | Asp | Val | Ser | Arg | Leu | Pro | Lys | Ile | Gly | Lys | Asn | |
| | | | | 55 | | | | | 60 | | | | | 65 | | |

| | | | | | | | | | | | | | | | | |
|---|---|---|---|---|---|---|---|---|---|---|---|---|---|---|---|---|
| tat | gta | ttt | gat | aga | aat | gac | agg | ctg | gat | gga | ctg | aaa | ttg | tac | tgg | 336 |
| Tyr | Val | Phe | Asp | Arg | Asn | Asp | Arg | Leu | Asp | Gly | Leu | Lys | Leu | Tyr | Trp | |
| | | 70 | | | | | 75 | | | | | 80 | | | | |

| | | | | | | | | | | | | | | | | |
|---|---|---|---|---|---|---|---|---|---|---|---|---|---|---|---|---|
| aat | aat | gga | aca | aac | cct | gcc | ggt | tac | gat | tcc | tat | gtt | cgt | cct | cct | 384 |
| Asn | Asn | Gly | Thr | Asn | Pro | Ala | Gly | Tyr | Asp | Ser | Tyr | Val | Arg | Pro | Pro | |
| 85 | | | | | 90 | | | | | 95 | | | | | | |

| | | | | | | | | | | | | | | | | |
|---|---|---|---|---|---|---|---|---|---|---|---|---|---|---|---|---|
| ctt | ggt | cag | ggc | ggg | gat | aag | ttt | tat | gat | gat | aat | gat | tgg | att | gcc | 432 |
| Leu | Gly | Gln | Gly | Gly | Asp | Lys | Phe | Tyr | Asp | Asp | Asn | Asp | Trp | Ile | Ala | |
| 100 | | | | | 105 | | | | | 110 | | | | | 115 | |

| | | | | | | | | | | | | | | | | |
|---|---|---|---|---|---|---|---|---|---|---|---|---|---|---|---|---|
| ctt | aat | ctc | atc | aaa | ttg | tat | caa | tta | act | ggt | gat | cag | gct | gta | tta | 480 |
| Leu | Asn | Leu | Ile | Lys | Leu | Tyr | Gln | Leu | Thr | Gly | Asp | Gln | Ala | Val | Leu | |
| | | | | 120 | | | | | 125 | | | | | 130 | | |

| | | | | | | | | | | | | | | | | |
|---|---|---|---|---|---|---|---|---|---|---|---|---|---|---|---|---|
| gaa | cgg | gtc | aag | gat | att | ttc | aaa | ttg | gaa | gtg | tac | gga | tgg | gac | aat | 528 |
| Glu | Arg | Val | Lys | Asp | Ile | Phe | Lys | Leu | Glu | Val | Tyr | Gly | Trp | Asp | Asn | |
| | | | 135 | | | | | 140 | | | | | 145 | | | |

| | | | | | | | | | | | | | | | | |
|---|---|---|---|---|---|---|---|---|---|---|---|---|---|---|---|---|
| gat | cca | tca | cac | cct | tat | cga | gga | gga | ata | ttt | tgg | acg | caa | gca | tcc | 576 |
| Asp | Pro | Ser | His | Pro | Tyr | Arg | Gly | Gly | Ile | Phe | Trp | Thr | Gln | Ala | Ser | |
| | | 150 | | | | | 155 | | | | | 160 | | | | |

| | | | | | | | | | | | | | | | | |
|---|---|---|---|---|---|---|---|---|---|---|---|---|---|---|---|---|
| tgg | agt | cag | gat | cgg | aat | acg | att | tcc | aac | gca | cct | ttg | gca | caa | atc | 624 |
| Trp | Ser | Gln | Asp | Arg | Asn | Thr | Ile | Ser | Asn | Ala | Pro | Leu | Ala | Gln | Ile | |
| 165 | | | | | 170 | | | | | 175 | | | | | | |

| | | | | | | | | | | | | | | | | |
|---|---|---|---|---|---|---|---|---|---|---|---|---|---|---|---|---|
| ggg | ctt | tat | tta | tac | caa | att | acc | cga | gat | aaa | tct | tat | ttt | gac | tgg | 672 |
| Gly | Leu | Tyr | Leu | Tyr | Gln | Ile | Thr | Arg | Asp | Lys | Ser | Tyr | Phe | Asp | Trp | |
| 180 | | | | | 185 | | | | | 190 | | | | | 195 | |

| | | | | | | | | | | | | | | | | |
|---|---|---|---|---|---|---|---|---|---|---|---|---|---|---|---|---|
| gca | aaa | aaa | gcc | tac | gac | tgg | gta | aat | aat | tct | atg | ctg | gca | cca | aac | 720 |
| Ala | Lys | Lys | Ala | Tyr | Asp | Trp | Val | Asn | Asn | Ser | Met | Leu | Ala | Pro | Asn | |
| | | | 200 | | | | | 205 | | | | | 210 | | | |

| | | | | | | | | | | | | | | | | |
|---|---|---|---|---|---|---|---|---|---|---|---|---|---|---|---|---|
| ggt | tta | tat | tgg | gat | cat | gtt | gat | ctt | aaa | gga | aat | att | gat | aaa | act | 768 |
| Gly | Leu | Tyr | Trp | Asp | His | Val | Asp | Leu | Lys | Gly | Asn | Ile | Asp | Lys | Thr | |
| | | | 215 | | | | | 220 | | | | | 225 | | | |

| | | | | | | | | | | | | | | | | |
|---|---|---|---|---|---|---|---|---|---|---|---|---|---|---|---|---|
| cag | tgg | act | tac | aat | caa | gga | atg | atg | att | ggg | gca | aac | gta | ttg | ttc | 816 |
| Gln | Trp | Thr | Tyr | Asn | Gln | Gly | Met | Met | Ile | Gly | Ala | Asn | Val | Leu | Phe | |
| | | 230 | | | | | 235 | | | | | 240 | | | | |

| | | | | | | | | | | | | | | | | |
|---|---|---|---|---|---|---|---|---|---|---|---|---|---|---|---|---|
| tat | aaa | aca | aca | ggc | aat | gaa | aca | tat | tta | gat | ctt | gca | aaa | tct | att | 864 |
| Tyr | Lys | Thr | Thr | Gly | Asn | Glu | Thr | Tyr | Leu | Asp | Leu | Ala | Lys | Ser | Ile | |
| | 245 | | | | | 250 | | | | | 255 | | | | | |

| | | | | | | | | | | | | | | | | |
|---|---|---|---|---|---|---|---|---|---|---|---|---|---|---|---|---|
| gca | aat | aaa | gct | atc | caa | tat | tat | ggc | gat | gtt | ctt | ctt | tat | aat | aat | 912 |
| Ala | Asn | Lys | Ala | Ile | Gln | Tyr | Tyr | Gly | Asp | Val | Leu | Leu | Tyr | Asn | Asn | |
| 260 | | | | | 265 | | | | | 270 | | | | | 275 | |

```
cct cca gaa ttc aac gca atc ttc ttt gaa aac tta cag cta ttg gat      960
Pro Pro Glu Phe Asn Ala Ile Phe Phe Glu Asn Leu Gln Leu Leu Asp
            280                 285                 290 tcc atc aat cat aac aat ata tat cga aaa tat ata cag tcg tat gct     1008
Ser Ile Asn His Asn Asn Ile Tyr Arg Lys Tyr Ile Gln Ser Tyr Ala
            295                 300                 305 gat caa atg tgg gat aca gaa aga aat acg gaa aca ggc tta ttt cag     1056
Asp Gln Met Trp Asp Thr Glu Arg Asn Thr Glu Thr Gly Leu Phe Gln
            310                 315                 320 cgt gat aat caa aat cca gtg cct cta att gag caa gca gca ata gtt     1104
Arg Asp Asn Gln Asn Pro Val Pro Leu Ile Glu Gln Ala Ala Ile Val
            325                 330                 335 gaa att tat tct aat ttg gct tat caa aaa taa                         1137
Glu Ile Tyr Ser Asn Leu Ala Tyr Gln Lys
340             345

<210> SEQ ID NO 5
<211> LENGTH: 378
<212> TYPE: PRT
<213> ORGANISM: Bacillus acidicola

<400> SEQUENCE: 5

Met Ser Lys Phe Leu Lys Pro Ser Ile Val Phe Thr Leu Ile Val Met
                -25                 -20                 -15

Leu Ile Ala Leu Val Ala Pro Gly Thr Ser Thr Tyr Ala Ala Ser Tyr
            -10                  -5                  -1   1

His Lys Lys Asn Val Glu Arg Ala Leu Ala Ser Tyr Glu Leu Met Gln
              5                  10                  15

Lys Tyr Phe Tyr Gln Pro Ser Val Lys Leu Tyr Thr Glu Glu Phe Pro
 20                  25                  30                  35

Asn Val Ile Gly Asn Ser Tyr Ser Tyr Leu Trp Pro Phe Ser Gln Ala
                 40                  45                  50

Met Ala Thr Thr Asp Val Ser Arg Leu Pro Lys Ile Gly Lys Asn
             55                  60                  65

Tyr Val Phe Asp Arg Asn Asp Arg Leu Asp Gly Leu Lys Leu Tyr Trp
             70                  75                  80

Asn Asn Gly Thr Asn Pro Ala Gly Tyr Asp Ser Tyr Val Arg Pro Pro
 85                  90                  95

Leu Gly Gln Gly Gly Asp Lys Phe Tyr Asp Asp Asn Asp Trp Ile Ala
100                 105                 110                 115

Leu Asn Leu Ile Lys Leu Tyr Gln Leu Thr Gly Asp Gln Ala Val Leu
                 120                 125                 130

Glu Arg Val Lys Asp Ile Phe Lys Leu Glu Val Tyr Gly Trp Asp Asn
             135                 140                 145

Asp Pro Ser His Pro Tyr Arg Gly Gly Ile Phe Trp Thr Gln Ala Ser
             150                 155                 160

Trp Ser Gln Asp Arg Asn Thr Ile Ser Asn Ala Pro Leu Ala Gln Ile
             165                 170                 175

Gly Leu Tyr Leu Tyr Gln Ile Thr Arg Asp Lys Ser Tyr Phe Asp Trp
180                 185                 190                 195

Ala Lys Lys Ala Tyr Asp Trp Val Asn Asn Ser Met Leu Ala Pro Asn
                 200                 205                 210

Gly Leu Tyr Trp Asp His Val Asp Leu Lys Gly Asn Ile Asp Lys Thr
             215                 220                 225

Gln Trp Thr Tyr Asn Gln Gly Met Met Ile Gly Ala Asn Val Leu Phe
             230                 235                 240
```

```
Tyr Lys Thr Thr Gly Asn Glu Thr Tyr Leu Asp Leu Ala Lys Ser Ile
            245                 250                 255

Ala Asn Lys Ala Ile Gln Tyr Tyr Gly Asp Val Leu Leu Tyr Asn Asn
260                 265                 270                 275

Pro Pro Glu Phe Asn Ala Ile Phe Phe Glu Asn Leu Gln Leu Leu Asp
                280                 285                 290

Ser Ile Asn His Asn Asn Ile Tyr Arg Lys Tyr Ile Gln Ser Tyr Ala
            295                 300                 305

Asp Gln Met Trp Asp Thr Glu Arg Asn Thr Glu Thr Gly Leu Phe Gln
            310                 315                 320

Arg Asp Asn Gln Asn Pro Val Pro Leu Ile Glu Gln Ala Ala Ile Val
            325                 330                 335

Glu Ile Tyr Ser Asn Leu Ala Tyr Gln Lys
340                 345

<210> SEQ ID NO 6
<211> LENGTH: 349
<212> TYPE: PRT
<213> ORGANISM: Bacillus acidicola

<400> SEQUENCE: 6

Ala Ser Tyr His Lys Lys Asn Val Glu Arg Ala Leu Ala Ser Tyr Glu
1               5                   10                  15

Leu Met Gln Lys Tyr Phe Tyr Gln Pro Ser Val Lys Leu Tyr Thr Glu
            20                  25                  30

Glu Phe Pro Asn Val Ile Gly Asn Ser Tyr Ser Tyr Leu Trp Pro Phe
            35                  40                  45

Ser Gln Ala Met Ala Ala Thr Thr Asp Val Ser Arg Leu Pro Lys Ile
        50                  55                  60

Gly Lys Asn Tyr Val Phe Asp Arg Asn Asp Arg Leu Asp Gly Leu Lys
65                  70                  75                  80

Leu Tyr Trp Asn Asn Gly Thr Asn Pro Ala Gly Tyr Asp Ser Tyr Val
                85                  90                  95

Arg Pro Pro Leu Gly Gln Gly Gly Asp Lys Phe Tyr Asp Asn Asp
            100                 105                 110

Trp Ile Ala Leu Asn Leu Ile Lys Leu Tyr Gln Leu Thr Gly Asp Gln
            115                 120                 125

Ala Val Leu Glu Arg Val Lys Asp Ile Phe Lys Leu Glu Val Tyr Gly
        130                 135                 140

Trp Asp Asn Asp Pro Ser His Pro Tyr Arg Gly Gly Ile Phe Trp Thr
145                 150                 155                 160

Gln Ala Ser Trp Ser Gln Asp Arg Asn Thr Ile Ser Asn Ala Pro Leu
                165                 170                 175

Ala Gln Ile Gly Leu Tyr Leu Tyr Gln Ile Thr Arg Asp Lys Ser Tyr
            180                 185                 190

Phe Asp Trp Ala Lys Lys Ala Tyr Asp Trp Val Asn Asn Ser Met Leu
        195                 200                 205

Ala Pro Asn Gly Leu Tyr Trp Asp His Val Asp Leu Lys Gly Asn Ile
    210                 215                 220

Asp Lys Thr Gln Trp Thr Tyr Asn Gln Gly Met Met Ile Gly Ala Asn
225                 230                 235                 240

Val Leu Phe Tyr Lys Thr Thr Gly Asn Glu Thr Tyr Leu Asp Leu Ala
                245                 250                 255

Lys Ser Ile Ala Asn Lys Ala Ile Gln Tyr Tyr Gly Asp Val Leu Leu
```

```
              260                 265                 270
Tyr Asn Asn Pro Pro Glu Phe Asn Ala Ile Phe Phe Glu Asn Leu Gln
            275                 280                 285

Leu Leu Asp Ser Ile Asn His Asn Asn Ile Tyr Arg Lys Tyr Ile Gln
            290                 295                 300

Ser Tyr Ala Asp Gln Met Trp Asp Thr Glu Arg Asn Thr Glu Thr Gly
305                 310                 315                 320

Leu Phe Gln Arg Asp Asn Gln Asn Pro Val Pro Leu Ile Glu Gln Ala
            325                 330                 335

Ala Ile Val Glu Ile Tyr Ser Asn Leu Ala Tyr Gln Lys
            340                 345

<210> SEQ ID NO 7
<211> LENGTH: 1143
<212> TYPE: DNA
<213> ORGANISM: Bacillus sp.
<220> FEATURE:
<221> NAME/KEY: CDS
<222> LOCATION: (1)..(1140)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1140)

<400> SEQUENCE: 7 atg cgt aaa aaa ttt ctt aaa aca tgt ttg gta ctt act ctg gtt gtc    48
Met Arg Lys Lys Phe Leu Lys Thr Cys Leu Val Leu Thr Leu Val Val
-30                 -25                 -20                 -15 atg gca gcg tta tgg atg gtt cct ggt acg cca aca ctt gca gcg tcc    96
Met Ala Ala Leu Trp Met Val Pro Gly Thr Pro Thr Leu Ala Ala Ser
            -10                 -5                  -1  1 cat caa aag aaa aat acg ctt aga tcc ata acc act tat gaa tca ctt   144
His Gln Lys Lys Asn Thr Leu Arg Ser Ile Thr Thr Tyr Glu Ser Leu
        5                   10                  15 caa aag tac ttc tat cag cca agt gca aag ctt tat acc gaa gaa tat   192
Gln Lys Tyr Phe Tyr Gln Pro Ser Ala Lys Leu Tyr Thr Glu Glu Tyr
    20                  25                  30 ccc agg gag gga ggg aat cca tat tcc tat gtg tgg cct ttt tcc cgg   240
Pro Arg Glu Gly Gly Asn Pro Tyr Ser Tyr Val Trp Pro Phe Ser Arg
35                  40                  45                  50 gca atg gct gcc acg att gat atg aca agg att ccg aaa ata ggg aaa   288
Ala Met Ala Ala Thr Ile Asp Met Thr Arg Ile Pro Lys Ile Gly Lys
                55                  60                  65 gca tac gta tcg gat cga aac gaa cgg ctc gag gga ctg aag ctg tat   336
Ala Tyr Val Ser Asp Arg Asn Glu Arg Leu Glu Gly Leu Lys Leu Tyr
            70                  75                  80 tgg aat aat gaa acc aac cct gcc ggc tac gat tca tat gtt cgt cct   384
Trp Asn Asn Glu Thr Asn Pro Ala Gly Tyr Asp Ser Tyr Val Arg Pro
        85                  90                  95 cct gta ggc cag ggc ggg gac aaa ttc tat gat gac aat gat tgg att   432
Pro Val Gly Gln Gly Gly Asp Lys Phe Tyr Asp Asp Asn Asp Trp Ile
    100                 105                 110 gcc ctt aac ttc ctc aaa ctg tat caa tta aca ggt gac cat tcc gca   480
Ala Leu Asn Phe Leu Lys Leu Tyr Gln Leu Thr Gly Asp His Ser Ala
115                 120                 125                 130 tta aag cgg gcc aag gat atc ttt aag ctg gag gtg ctt ggg tgg gac   528
Leu Lys Arg Ala Lys Asp Ile Phe Lys Leu Glu Val Leu Gly Trp Asp
                135                 140                 145 aat gat cca tcg cat cca tat cca gga gga gta ttc tgg acg cag gca   576
```

```
Asn Asp Pro Ser His Pro Tyr Pro Gly Gly Val Phe Trp Thr Gln Ala
            150                 155                 160 ccg tgg agc cag gac cgg aat acc att tcc aat gcg cct gtg gca cag      624
Pro Trp Ser Gln Asp Arg Asn Thr Ile Ser Asn Ala Pro Val Ala Gln
        165                 170                 175 att ggg tta tat cta tac caa atc act ggt gat aaa tac tat ttt gac      672
Ile Gly Leu Tyr Leu Tyr Gln Ile Thr Gly Asp Lys Tyr Tyr Phe Asp
180                 185                 190 tgg gca aag aaa acc tat gac tgg gta aac aat tct atg ctc gcg cca      720
Trp Ala Lys Lys Thr Tyr Asp Trp Val Asn Asn Ser Met Leu Ala Pro
195                 200                 205                 210 aac ggc ttg tat tgg gac cat gtc gat cta aaa ggg aat ata gag aaa      768
Asn Gly Leu Tyr Trp Asp His Val Asp Leu Lys Gly Asn Ile Glu Lys
            215                 220                 225 act cag tgg acc tat aac cag gga atg atg atc ggg gca aac gtt ctt      816
Thr Gln Trp Thr Tyr Asn Gln Gly Met Met Ile Gly Ala Asn Val Leu
        230                 235                 240 ttc tat aaa aca aca ggt gac aaa atg tat ctt gaa cgt gca gag tcc      864
Phe Tyr Lys Thr Thr Gly Asp Lys Met Tyr Leu Glu Arg Ala Glu Ser
    245                 250                 255 ctt gca gaa aag tct atc caa tat tat ggc gac acc cag ctg tat aaa      912
Leu Ala Glu Lys Ser Ile Gln Tyr Tyr Gly Asp Thr Gln Leu Tyr Lys
260                 265                 270 aat cct cca gaa ttc aac gcc atc ttc ttc gaa aac ctg cag cta ttg      960
Asn Pro Pro Glu Phe Asn Ala Ile Phe Phe Glu Asn Leu Gln Leu Leu
275                 280                 285                 290 tac tca gtc aaa cat aat aat gaa tat aga aaa tat act caa gcc tat     1008
Tyr Ser Val Lys His Asn Asn Glu Tyr Arg Lys Tyr Thr Gln Ala Tyr
            295                 300                 305 gcg gat aaa atg tgg gat acg gtg cga aat ccg aaa acg ggc tta ttc     1056
Ala Asp Lys Met Trp Asp Thr Val Arg Asn Pro Lys Thr Gly Leu Phe
        310                 315                 320 caa cgt gat cct caa aag ccg gtg ccg ctt ata gag cag gct gcg atg     1104
Gln Arg Asp Pro Gln Lys Pro Val Pro Leu Ile Glu Gln Ala Ala Met
    325                 330                 335 gtt gag att tat gcg aat cta gca tat aaa aaa caa taa                 1143
Val Glu Ile Tyr Ala Asn Leu Ala Tyr Lys Lys Gln
340                 345                 350

<210> SEQ ID NO 8
<211> LENGTH: 380
<212> TYPE: PRT
<213> ORGANISM: Bacillus sp.

<400> SEQUENCE: 8

Met Arg Lys Lys Phe Leu Lys Thr Cys Leu Val Thr Leu Val Val
-30                 -25                 -20                 -15

Met Ala Ala Leu Trp Met Val Pro Gly Thr Pro Thr Leu Ala Ala Ser
                -10                 -5                  -1   1

His Gln Lys Lys Asn Thr Leu Arg Ser Ile Thr Thr Tyr Glu Ser Leu
        5                   10                  15

Gln Lys Tyr Phe Tyr Gln Pro Ser Ala Lys Leu Tyr Thr Glu Glu Tyr
    20                  25                  30

Pro Arg Glu Gly Gly Asn Pro Tyr Ser Tyr Val Trp Pro Phe Ser Arg
35                  40                  45                  50

Ala Met Ala Ala Thr Ile Asp Met Thr Arg Ile Pro Lys Ile Gly Lys
                55                  60                  65

Ala Tyr Val Ser Asp Arg Asn Glu Arg Leu Glu Gly Leu Lys Leu Tyr
            70                  75                  80
```

```
Trp Asn Asn Glu Thr Asn Pro Ala Gly Tyr Asp Ser Tyr Val Arg Pro
            85                  90                  95

Pro Val Gly Gln Gly Gly Asp Lys Phe Tyr Asp Asp Asn Asp Trp Ile
100                 105                 110

Ala Leu Asn Phe Leu Lys Leu Tyr Gln Leu Thr Gly Asp His Ser Ala
115                 120                 125                 130

Leu Lys Arg Ala Lys Asp Ile Phe Lys Leu Glu Val Leu Gly Trp Asp
                135                 140                 145

Asn Asp Pro Ser His Pro Tyr Pro Gly Gly Val Phe Trp Thr Gln Ala
                150                 155                 160

Pro Trp Ser Gln Asp Arg Asn Thr Ile Ser Asn Ala Pro Val Ala Gln
                165                 170                 175

Ile Gly Leu Tyr Leu Tyr Gln Ile Thr Gly Asp Lys Tyr Tyr Phe Asp
                180                 185                 190

Trp Ala Lys Lys Thr Tyr Asp Trp Val Asn Asn Ser Met Leu Ala Pro
195                 200                 205                 210

Asn Gly Leu Tyr Trp Asp His Val Asp Leu Lys Gly Asn Ile Glu Lys
                215                 220                 225

Thr Gln Trp Thr Tyr Asn Gln Gly Met Met Ile Gly Ala Asn Val Leu
                230                 235                 240

Phe Tyr Lys Thr Thr Gly Asp Lys Met Tyr Leu Glu Arg Ala Glu Ser
            245                 250                 255

Leu Ala Glu Lys Ser Ile Gln Tyr Tyr Gly Asp Thr Gln Leu Tyr Lys
            260                 265                 270

Asn Pro Pro Glu Phe Asn Ala Ile Phe Phe Glu Asn Leu Gln Leu Leu
275                 280                 285                 290

Tyr Ser Val Lys His Asn Asn Glu Tyr Arg Lys Tyr Thr Gln Ala Tyr
                295                 300                 305

Ala Asp Lys Met Trp Asp Thr Val Arg Asn Pro Lys Thr Gly Leu Phe
                310                 315                 320

Gln Arg Asp Pro Gln Lys Pro Val Pro Leu Ile Glu Gln Ala Ala Met
            325                 330                 335

Val Glu Ile Tyr Ala Asn Leu Ala Tyr Lys Lys Gln
            340                 345                 350

<210> SEQ ID NO 9
<211> LENGTH: 350
<212> TYPE: PRT
<213> ORGANISM: Bacillus sp.

<400> SEQUENCE: 9

Ala Ser His Gln Lys Lys Asn Thr Leu Arg Ser Ile Thr Thr Tyr Glu
1               5                   10                  15

Ser Leu Gln Lys Tyr Phe Tyr Gln Pro Ser Ala Lys Leu Tyr Thr Glu
                20                  25                  30

Glu Tyr Pro Arg Glu Gly Gly Asn Pro Tyr Ser Tyr Val Trp Pro Phe
            35                  40                  45

Ser Arg Ala Met Ala Ala Thr Ile Asp Met Thr Arg Ile Pro Lys Ile
50                  55                  60

Gly Lys Ala Tyr Val Ser Asp Arg Asn Glu Leu Glu Gly Leu Lys
65                  70                  75                  80

Leu Tyr Trp Asn Asn Glu Thr Asn Pro Ala Gly Tyr Asp Ser Tyr Val
                85                  90                  95

Arg Pro Pro Val Gly Gln Gly Gly Asp Lys Phe Tyr Asp Asp Asn Asp
```

```
                100             105                 110
Trp Ile Ala Leu Asn Phe Leu Lys Leu Tyr Gln Leu Thr Gly Asp His
            115                 120                 125

Ser Ala Leu Lys Arg Ala Lys Asp Ile Phe Lys Leu Glu Val Leu Gly
            130                 135             140

Trp Asp Asn Asp Pro Ser His Pro Tyr Pro Gly Val Phe Trp Thr
145                 150                 155                 160

Gln Ala Pro Trp Ser Gln Asp Arg Asn Thr Ile Ser Asn Ala Pro Val
                165                 170                 175

Ala Gln Ile Gly Leu Tyr Leu Tyr Gln Ile Thr Gly Asp Lys Tyr Tyr
            180                 185                 190

Phe Asp Trp Ala Lys Lys Thr Tyr Asp Trp Val Asn Asn Ser Met Leu
            195                 200                 205

Ala Pro Asn Gly Leu Tyr Trp Asp His Val Asp Leu Lys Gly Asn Ile
            210                 215                 220

Glu Lys Thr Gln Trp Thr Tyr Asn Gln Gly Met Met Ile Gly Ala Asn
225                 230                 235                 240

Val Leu Phe Tyr Lys Thr Thr Gly Asp Lys Met Tyr Leu Glu Arg Ala
                245                 250                 255

Glu Ser Leu Ala Glu Lys Ser Ile Gln Tyr Tyr Gly Asp Thr Gln Leu
            260                 265                 270

Tyr Lys Asn Pro Pro Glu Phe Asn Ala Ile Phe Phe Glu Asn Leu Gln
            275                 280                 285

Leu Leu Tyr Ser Val Lys His Asn Asn Glu Tyr Arg Lys Tyr Thr Gln
            290                 295                 300

Ala Tyr Ala Asp Lys Met Trp Asp Thr Val Arg Asn Pro Lys Thr Gly
305                 310                 315                 320

Leu Phe Gln Arg Asp Pro Gln Lys Pro Val Pro Leu Ile Glu Gln Ala
                325                 330                 335

Ala Met Val Glu Ile Tyr Ala Asn Leu Ala Tyr Lys Lys Gln
            340                 345                 350

<210> SEQ ID NO 10
<211> LENGTH: 1533
<212> TYPE: DNA
<213> ORGANISM: Paenibacillus sp.
<220> FEATURE:
<221> NAME/KEY: CDS
<222> LOCATION: (1)..(1530)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1530)

<400> SEQUENCE: 10 atg gca aag ttc ggc aag aaa gca tct gct atc gcc agt ggt att ttg     48
Met Ala Lys Phe Gly Lys Lys Ala Ser Ala Ile Ala Ser Gly Ile Leu
    -30                 -25                 -20 gct gct gca ctt ctg att gca ccc ttt ggg gga gaa caa cgt gca gct     96
Ala Ala Ala Leu Leu Ile Ala Pro Phe Gly Gly Glu Gln Arg Ala Ala
-15                 -10                 -5                  -1  1 gcg ttt acc gca gcg aat gcc gac acg gcg atg aac agt ttt gtc agt    144
Ala Phe Thr Ala Ala Asn Ala Asp Thr Ala Met Asn Ser Phe Val Ser
                5                  10                  15 acc ttt tat gat cct gta gcg aaa tat ttc tat acc aac agc gac cat    192
Thr Phe Tyr Asp Pro Val Ala Lys Tyr Phe Tyr Thr Asn Ser Asp His
        20                  25                  30
```

| | | | | | | | | | | | | | | | |
|---|---|---|---|---|---|---|---|---|---|---|---|---|---|---|---|
| ctg | att | cat | tcc | gag | cat | gcg | cat | gga | cct | gac | ggt | ggt | ctg | tat | acc | 240 |
| Leu | Ile | His | Ser | Glu | His | Ala | His | Gly | Pro | Asp | Gly | Gly | Leu | Tyr | Thr | |
| | 35 | | | | 40 | | | | | 45 | | | | | | |

| gac | ttc | tgg | tgg | gag | gcc | cag | ctc | tgg | gag | acg | gtg | atg | gat | gcg | tat | 288 |
| Asp | Phe | Trp | Trp | Glu | Ala | Gln | Leu | Trp | Glu | Thr | Val | Met | Asp | Ala | Tyr | |
| 50 | | | | | 55 | | | | | 60 | | | | | 65 | |

| gag | cgg | act | ggc | agc | agc | acc | tac | cgt | gcc | atg | atc | gat | gat | gtt | tat | 336 |
| Glu | Arg | Thr | Gly | Ser | Ser | Thr | Tyr | Arg | Ala | Met | Ile | Asp | Asp | Val | Tyr | |
| | | | | | 70 | | | | | 75 | | | | | 80 | |

| acc | gga | ttt | aat | gcg | aaa | tac | ccg | gat | atg | atg | gcc | aat | gat | ttt | aat | 384 |
| Thr | Gly | Phe | Asn | Ala | Lys | Tyr | Pro | Asp | Met | Met | Ala | Asn | Asp | Phe | Asn | |
| | | | 85 | | | | | 90 | | | | | 95 | | | |

| gat | gat | ctc | ggc | tgg | tgg | gcg | ctc | gcc | tgt | atg | cgg | gct | tat | gaa | ctg | 432 |
| Asp | Asp | Leu | Gly | Trp | Trp | Ala | Leu | Ala | Cys | Met | Arg | Ala | Tyr | Glu | Leu | |
| | | | 100 | | | | | 105 | | | | | 110 | | | |

| act | ggc | acc | gat | gag | tac | cgc | aac | cgt | gcg | tcg | ttc | ctg | ttc | gac | cag | 480 |
| Thr | Gly | Thr | Asp | Glu | Tyr | Arg | Asn | Arg | Ala | Ser | Phe | Leu | Phe | Asp | Gln | |
| | | | 115 | | | | | 120 | | | | | 125 | | | |

| atc | tgg | ggc | gat | tgg | gac | agt | acg | tat | ggc | ggc | ggt | atc | tgg | tgg | aag | 528 |
| Ile | Trp | Gly | Asp | Trp | Asp | Ser | Thr | Tyr | Gly | Gly | Gly | Ile | Trp | Trp | Lys | |
| 130 | | | | | 135 | | | | | 140 | | | | | 145 | |

| cgg | gat | ggc | act | tcg | ccg | cag | aag | aat | atg | gcg | acc | aat | gcg | ccg | atg | 576 |
| Arg | Asp | Gly | Thr | Ser | Pro | Gln | Lys | Asn | Met | Ala | Thr | Asn | Ala | Pro | Met | |
| | | | | 150 | | | | | 155 | | | | | 160 | | |

| gtt | atg | acg | gct | att | aag | ctg | aag | aat | gcc | acg | ggc | aac | aac | gat | tat | 624 |
| Val | Met | Thr | Ala | Ile | Lys | Leu | Lys | Asn | Ala | Thr | Gly | Asn | Asn | Asp | Tyr | |
| | | | 165 | | | | | 170 | | | | | 175 | | | |

| ttg | aca | aaa | gcg | cag | agt | atc | tac | agc | tgg | att | cag | agc | aga | ctg | gtc | 672 |
| Leu | Thr | Lys | Ala | Gln | Ser | Ile | Tyr | Ser | Trp | Ile | Gln | Ser | Arg | Leu | Val | |
| | | 180 | | | | | 185 | | | | | 190 | | | | |

| tcc | ggc | agc | aaa | atc | aat | gac | cac | gtc | gaa | ggc | tcc | ggc | tcc | ggg | acg | 720 |
| Ser | Gly | Ser | Lys | Ile | Asn | Asp | His | Val | Glu | Gly | Ser | Gly | Ser | Gly | Thr | |
| | 195 | | | | | 200 | | | | | 205 | | | | | |

| gtg | gta | gat | tgg | gac | ttt | acc | tat | aat | tac | ggc | acg | tat | ctc | ggc | gca | 768 |
| Val | Val | Asp | Trp | Asp | Phe | Thr | Tyr | Asn | Tyr | Gly | Thr | Tyr | Leu | Gly | Ala | |
| 210 | | | | | 215 | | | | | 220 | | | | | 225 | |

| gca | ctg | gcc | ctg | aat | caa | gct | acg | ggg | aat | gca | tcc | tat | ctc | acg | gat | 816 |
| Ala | Leu | Ala | Leu | Asn | Gln | Ala | Thr | Gly | Asn | Ala | Ser | Tyr | Leu | Thr | Asp | |
| | | | | 230 | | | | | 235 | | | | | 240 | | |

| gcg | aac | aca | gcc | gca | gct | tat | gtc | atg | gat | aaa | atg | acg | ctc | tcc | tat | 864 |
| Ala | Asn | Thr | Ala | Ala | Ala | Tyr | Val | Met | Asp | Lys | Met | Thr | Leu | Ser | Tyr | |
| | | | 245 | | | | | 250 | | | | | 255 | | | |

| tcg | ctt | atg | tac | gaa | gga | gag | aat | gat | tcg | cct | ggc | ttc | cgc | atg | gtg | 912 |
| Ser | Leu | Met | Tyr | Glu | Gly | Glu | Asn | Asp | Ser | Pro | Gly | Phe | Arg | Met | Val | |
| | | 260 | | | | | 265 | | | | | 270 | | | | |

| ttc | gcc | cgc | aat | ttg | aac | cag | ctg | cgg | aag | gcg | aca | ggg | aac | gct | tcc | 960 |
| Phe | Ala | Arg | Asn | Leu | Asn | Gln | Leu | Arg | Lys | Ala | Thr | Gly | Asn | Ala | Ser | |
| | 275 | | | | | 280 | | | | | 285 | | | | | |

| tac | ttg | aat | ttc | ttg | caa | cag | aat | gct | acg | caa | gcc | ttt | aac | cac | cgc | 1008 |
| Tyr | Leu | Asn | Phe | Leu | Gln | Gln | Asn | Ala | Thr | Gln | Ala | Phe | Asn | His | Arg | |
| 290 | | | | | 295 | | | | | 300 | | | | | 305 | |

| cgt | gcg | tct | gac | ggg | att | att | gac | agc | gac | tgg | aca | gcg | cct | gcc | aga | 1056 |
| Arg | Ala | Ser | Asp | Gly | Ile | Ile | Asp | Ser | Asp | Trp | Thr | Ala | Pro | Ala | Arg | |
| | | | | 310 | | | | | 315 | | | | | 320 | | |

| agc | ggc | tat | atc | cag | tct | atc | gcc | gca | gcc | gca | ggt | gct | tcg | atc | ctg | 1104 |
| Ser | Gly | Tyr | Ile | Gln | Ser | Ile | Ala | Ala | Ala | Ala | Gly | Ala | Ser | Ile | Leu | |
| | | | 325 | | | | | 330 | | | | | 335 | | | |

| caa | ctg | gtc | cct | gcg | gac | aat | tac | acc | gga | ccg | att | gcc | ggc | aac | ggt | 1152 |
| Gln | Leu | Val | Pro | Ala | Asp | Asn | Tyr | Thr | Gly | Pro | Ile | Ala | Gly | Asn | Gly | |

```
                340                 345                 350
acc tat gag gct gag aac gcc cgc cgc tac ggc atc aac aat gaa tcc      1200
Thr Tyr Glu Ala Glu Asn Ala Arg Arg Tyr Gly Ile Asn Asn Glu Ser
    355                 360                 365 tcg cag cca ggc ttc tcg gga cgg ggt tat aca gca ggc tgg aac acc      1248
Ser Gln Pro Gly Phe Ser Gly Arg Gly Tyr Thr Ala Gly Trp Asn Thr
370                 375                 380                 385 gat aat acg aaa att gtg ttc cat gtt aat cag aac agt gcc agt aca      1296
Asp Asn Thr Lys Ile Val Phe His Val Asn Gln Asn Ser Ala Ser Thr
                390                 395                 400 agg acc att agc ttt cgt tat acc gct gcg ggg ggg aat gct gga cgg      1344
Arg Thr Ile Ser Phe Arg Tyr Thr Ala Ala Gly Gly Asn Ala Gly Arg
            405                 410                 415 tac gtc aaa gtg aac ggt acg gtg gtc agc aat aat ttg att ttt aac      1392
Tyr Val Lys Val Asn Gly Thr Val Val Ser Asn Asn Leu Ile Phe Asn
        420                 425                 430 ggt acc agc agt tgg tct gcc tgg aac acg gtg acg cta aac gta ccg      1440
Gly Thr Ser Ser Trp Ser Ala Trp Asn Thr Val Thr Leu Asn Val Pro
    435                 440                 445 ctt aat gca ggc tac aac tcg att gag ctc gga ttt gat agc acc aag      1488
Leu Asn Ala Gly Tyr Asn Ser Ile Glu Leu Gly Phe Asp Ser Thr Lys
450                 455                 460                 465 ggc aac agc aat tat ctg aat gta gac aaa atg acg gga ctt taa          1533
Gly Asn Ser Asn Tyr Leu Asn Val Asp Lys Met Thr Gly Leu
                470                 475

<210> SEQ ID NO 11
<211> LENGTH: 510
<212> TYPE: PRT
<213> ORGANISM: Paenibacillus sp.

<400> SEQUENCE: 11

Met Ala Lys Phe Gly Lys Lys Ala Ser Ala Ile Ala Ser Gly Ile Leu
        -30                 -25                 -20

Ala Ala Ala Leu Leu Ile Ala Pro Phe Gly Gly Glu Gln Arg Ala Ala
    -15                 -10                  -5              -1   1

Ala Phe Thr Ala Ala Asn Ala Asp Thr Ala Met Asn Ser Phe Val Ser
                5                   10                  15

Thr Phe Tyr Asp Pro Val Ala Lys Tyr Phe Tyr Thr Asn Ser Asp His
            20                  25                  30

Leu Ile His Ser Glu His Ala His Gly Pro Asp Gly Gly Leu Tyr Thr
        35                  40                  45

Asp Phe Trp Trp Glu Ala Gln Leu Trp Glu Thr Val Met Asp Ala Tyr
50                  55                  60                  65

Glu Arg Thr Gly Ser Ser Thr Tyr Arg Ala Met Ile Asp Asp Val Tyr
                70                  75                  80

Thr Gly Phe Asn Ala Lys Tyr Pro Asp Met Met Ala Asn Asp Phe Asn
            85                  90                  95

Asp Asp Leu Gly Trp Trp Ala Leu Ala Cys Met Arg Ala Tyr Glu Leu
        100                 105                 110

Thr Gly Thr Asp Glu Tyr Arg Asn Arg Ala Ser Phe Leu Phe Asp Gln
    115                 120                 125

Ile Trp Gly Asp Trp Asp Ser Thr Tyr Gly Gly Ile Trp Trp Lys
130                 135                 140                 145

Arg Asp Gly Thr Ser Pro Gln Lys Asn Met Ala Thr Asn Ala Pro Met
                150                 155                 160

Val Met Thr Ala Ile Lys Leu Lys Asn Ala Thr Gly Asn Asn Asp Tyr
```

165                 170                 175
Leu Thr Lys Ala Gln Ser Ile Tyr Ser Trp Ile Gln Ser Arg Leu Val
            180                 185                 190

Ser Gly Ser Lys Ile Asn Asp His Val Glu Gly Ser Gly Ser Gly Thr
195                 200                 205

Val Val Asp Trp Asp Phe Thr Tyr Asn Tyr Gly Thr Tyr Leu Gly Ala
210                 215                 220                 225

Ala Leu Ala Leu Asn Gln Ala Thr Gly Asn Ala Ser Tyr Leu Thr Asp
            230                 235                 240

Ala Asn Thr Ala Ala Ala Tyr Val Met Asp Lys Met Thr Leu Ser Tyr
            245                 250                 255

Ser Leu Met Tyr Glu Gly Glu Asn Asp Ser Pro Gly Phe Arg Met Val
            260                 265                 270

Phe Ala Arg Asn Leu Asn Gln Leu Arg Lys Ala Thr Gly Asn Ala Ser
            275                 280                 285

Tyr Leu Asn Phe Leu Gln Gln Asn Ala Thr Gln Ala Phe Asn His Arg
290                 295                 300                 305

Arg Ala Ser Asp Gly Ile Ile Asp Ser Asp Trp Thr Ala Pro Ala Arg
            310                 315                 320

Ser Gly Tyr Ile Gln Ser Ile Ala Ala Ala Gly Ala Ser Ile Leu
            325                 330                 335

Gln Leu Val Pro Ala Asp Asn Tyr Thr Gly Pro Ile Ala Gly Asn Gly
            340                 345                 350

Thr Tyr Glu Ala Glu Asn Ala Arg Arg Tyr Gly Ile Asn Asn Glu Ser
            355                 360                 365

Ser Gln Pro Gly Phe Ser Gly Arg Gly Tyr Thr Ala Gly Trp Asn Thr
370                 375                 380                 385

Asp Asn Thr Lys Ile Val Phe His Val Asn Gln Asn Ser Ala Ser Thr
            390                 395                 400

Arg Thr Ile Ser Phe Arg Tyr Thr Ala Ala Gly Gly Asn Ala Gly Arg
            405                 410                 415

Tyr Val Lys Val Asn Gly Thr Val Ser Asn Asn Leu Ile Phe Asn
            420                 425                 430

Gly Thr Ser Ser Trp Ser Ala Trp Asn Thr Val Thr Leu Asn Val Pro
            435                 440                 445

Leu Asn Ala Gly Tyr Asn Ser Ile Glu Leu Gly Phe Asp Ser Thr Lys
450                 455                 460                 465

Gly Asn Ser Asn Tyr Leu Asn Val Asp Lys Met Thr Gly Leu
            470                 475

<210> SEQ ID NO 12
<211> LENGTH: 479
<212> TYPE: PRT
<213> ORGANISM: Paenibacillus sp. A

<400> SEQUENCE: 12

Ala Ala Phe Thr Ala Ala Asn Ala Asp Thr Ala Met Asn Ser Phe Val
1               5                   10                  15

Ser Thr Phe Tyr Asp Pro Val Ala Lys Tyr Phe Tyr Thr Asn Ser Asp
            20                  25                  30

His Leu Ile His Ser Glu His Ala His Gly Pro Asp Gly Gly Leu Tyr
            35                  40                  45

Thr Asp Phe Trp Trp Glu Ala Gln Leu Trp Glu Thr Val Met Asp Ala
            50                  55                  60

```
Tyr Glu Arg Thr Gly Ser Ser Thr Tyr Arg Ala Met Ile Asp Asp Val
 65                  70                  75                  80

Tyr Thr Gly Phe Asn Ala Lys Tyr Pro Asp Met Met Ala Asn Asp Phe
                 85                  90                  95

Asn Asp Asp Leu Gly Trp Trp Ala Leu Ala Cys Met Arg Ala Tyr Glu
            100                 105                 110

Leu Thr Gly Thr Asp Glu Tyr Arg Asn Arg Ala Ser Phe Leu Phe Asp
        115                 120                 125

Gln Ile Trp Gly Asp Trp Asp Ser Thr Tyr Gly Gly Ile Trp Trp
    130                 135                 140

Lys Arg Asp Gly Thr Ser Pro Gln Lys Asn Met Ala Thr Asn Ala Pro
145                 150                 155                 160

Met Val Met Thr Ala Ile Lys Leu Lys Asn Ala Thr Gly Asn Asn Asp
                165                 170                 175

Tyr Leu Thr Lys Ala Gln Ser Ile Tyr Ser Trp Ile Gln Ser Arg Leu
            180                 185                 190

Val Ser Gly Ser Lys Ile Asn Asp His Val Glu Gly Ser Gly Ser Gly
        195                 200                 205

Thr Val Val Asp Trp Asp Phe Thr Tyr Asn Tyr Gly Thr Tyr Leu Gly
    210                 215                 220

Ala Ala Leu Ala Leu Asn Gln Ala Thr Gly Asn Ala Ser Tyr Leu Thr
225                 230                 235                 240

Asp Ala Asn Thr Ala Ala Tyr Val Met Asp Lys Met Thr Leu Ser
                245                 250                 255

Tyr Ser Leu Met Tyr Glu Gly Glu Asn Asp Ser Pro Gly Phe Arg Met
            260                 265                 270

Val Phe Ala Arg Asn Leu Asn Gln Leu Arg Lys Ala Thr Gly Asn Ala
        275                 280                 285

Ser Tyr Leu Asn Phe Leu Gln Gln Asn Ala Thr Gln Ala Phe Asn His
    290                 295                 300

Arg Arg Ala Ser Asp Gly Ile Ile Asp Ser Asp Trp Thr Ala Pro Ala
305                 310                 315                 320

Arg Ser Gly Tyr Ile Gln Ser Ile Ala Ala Ala Gly Ala Ser Ile
                325                 330                 335

Leu Gln Leu Val Pro Ala Asp Asn Tyr Thr Gly Pro Ile Ala Gly Asn
            340                 345                 350

Gly Thr Tyr Glu Ala Glu Asn Ala Arg Arg Tyr Gly Ile Asn Asn Glu
        355                 360                 365

Ser Ser Gln Pro Gly Phe Ser Gly Arg Gly Tyr Thr Ala Gly Trp Asn
    370                 375                 380

Thr Asp Asn Thr Lys Ile Val Phe His Val Asn Gln Asn Ser Ala Ser
385                 390                 395                 400

Thr Arg Thr Ile Ser Phe Arg Tyr Thr Ala Gly Gly Asn Ala Gly
                405                 410                 415

Arg Tyr Val Lys Val Asn Gly Thr Val Val Ser Asn Asn Leu Ile Phe
            420                 425                 430

Asn Gly Thr Ser Ser Trp Ser Ala Trp Asn Thr Val Thr Leu Asn Val
        435                 440                 445

Pro Leu Asn Ala Gly Tyr Asn Ser Ile Glu Leu Gly Phe Asp Ser Thr
    450                 455                 460

Lys Gly Asn Ser Asn Tyr Leu Asn Val Asp Lys Met Thr Gly Leu
465                 470                 475
```

```
<210> SEQ ID NO 13
<211> LENGTH: 1563
<212> TYPE: DNA
<213> ORGANISM: Paenibacillus sp. B
<220> FEATURE:
<221> NAME/KEY: CDS
<222> LOCATION: (1)..(1560)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1560)

<400> SEQUENCE: 13 atg att gtc tgg aaa aaa cgt gtg acc ctc gct atg gct ttt ctg ctt        48
Met Ile Val Trp Lys Lys Arg Val Thr Leu Ala Met Ala Phe Leu Leu
    -30                 -25                 -20 gtc ttg tcc ctg ctg ggc ccg acc ggc agc cga aaa gcg gaa gcg ttc        96
Val Leu Ser Leu Leu Gly Pro Thr Gly Ser Arg Lys Ala Glu Ala Phe
-15                 -10                  -5                  -1   1 acc gca gcc aat gcc aat gat gct atg caa gcc ttc att aac gtt ttc       144
Thr Ala Ala Asn Ala Asn Asp Ala Met Gln Ala Phe Ile Asn Val Phe
                5                  10                  15 tat gac ccg acg gcc aag tat ttc tac acg aac agt gac cac cag att       192
Tyr Asp Pro Thr Ala Lys Tyr Phe Tyr Thr Asn Ser Asp His Gln Ile
         20                  25                  30 cac acg cac gcg cat ggt ccg aac ggg ggg ctg tat acc gac ttc tgg       240
His Thr His Ala His Gly Pro Asn Gly Gly Leu Tyr Thr Asp Phe Trp
     35                  40                  45 tgg gag gct cag ttg tgg gag acg gta atg gat gcc tat gag cga aca       288
Trp Glu Ala Gln Leu Trp Glu Thr Val Met Asp Ala Tyr Glu Arg Thr
 50                  55                  60                  65 ggc aac gcc act tac cgc acc atg att gat gat att tac acc ggc ttc       336
Gly Asn Ala Thr Tyr Arg Thr Met Ile Asp Asp Ile Tyr Thr Gly Phe
                 70                  75                  80 aat gcc aag tac ccg gat atg atg cag aat gtg ttc aac gac gac ctc       384
Asn Ala Lys Tyr Pro Asp Met Met Gln Asn Val Phe Asn Asp Asp Leu
             85                  90                  95 ggc tgg tgg gcg cag gct gcc ctg cgg gcc tat gag ctg acg ggg aca       432
Gly Trp Trp Ala Gln Ala Ala Leu Arg Ala Tyr Glu Leu Thr Gly Thr
        100                 105                 110 gcg gag tat cgc aac cgg ggc tca ttt ctc ttc gac aag atc tat gag       480
Ala Glu Tyr Arg Asn Arg Gly Ser Phe Leu Phe Asp Lys Ile Tyr Glu
    115                 120                 125 gaa tgg gac acg agc tac tac ggc ggc ggc atc tgg tgg cgg aga gat       528
Glu Trp Asp Thr Ser Tyr Tyr Gly Gly Gly Ile Trp Trp Arg Arg Asp
130                 135                 140                 145 gct cat aac ccg aat gtc tcg tcc aat gcc cag aag aac gta gct acg       576
Ala His Asn Pro Asn Val Ser Ser Asn Ala Gln Lys Asn Val Ala Thr
                150                 155                 160 aac gca cca atg gtc att aca gct gtg aag ctg tac cag gcg acg ggc       624
Asn Ala Pro Met Val Ile Thr Ala Val Lys Leu Tyr Gln Ala Thr Gly
            165                 170                 175 gac agc gct tat ctg acg aag gcg acg cag atc tac aac tgg gtc aaa       672
Asp Ser Ala Tyr Leu Thr Lys Ala Thr Gln Ile Tyr Asn Trp Val Lys
        180                 185                 190 acc aag ctc gtc ggg tca ggc ggc aag atc aat gac cat ctg gaa ggt       720
Thr Lys Leu Val Gly Ser Gly Gly Lys Ile Asn Asp His Leu Glu Gly
    195                 200                 205 ccg ggg gca ggc acg ctc atc gac tgg gac ttc tcg tac aac tac ggc       768
Pro Gly Ala Gly Thr Leu Ile Asp Trp Asp Phe Ser Tyr Asn Tyr Gly
210                 215                 220                 225
```

```
aac tac ctg ggc gcg gcg gtg tcg ctg tat cag gca acg ggc aac agt      816
Asn Tyr Leu Gly Ala Ala Val Ser Leu Tyr Gln Ala Thr Gly Asn Ser
            230                 235                 240 gcc tac atc acc gat gcc aac aca gcc gcg acc tat gcc att aat aac      864
Ala Tyr Ile Thr Asp Ala Asn Thr Ala Ala Thr Tyr Ala Ile Asn Asn
            245                 250                 255 ctg gtg tcg gcg cag acc ctt atg tat gag ggt gag aat gat gcc gcc      912
Leu Val Ser Ala Gln Thr Leu Met Tyr Glu Gly Glu Asn Asp Ala Ala
            260                 265                 270 ggc ttc aaa atg atc ttc gct cgc aac ctg aac cgc ctg cgc gtc atc      960
Gly Phe Lys Met Ile Phe Ala Arg Asn Leu Asn Arg Leu Arg Val Ile
275                 280                 285 ggt ggc cag tcg cag tat ctg aac ttc ttg cag cag aac gcg aca cag     1008
Gly Gly Gln Ser Gln Tyr Leu Asn Phe Leu Gln Gln Asn Ala Thr Gln
290                 295                 300                 305 gcc tgg aat cac cgc cgc acc agc gat aat atc atc ggc agc gac tgg     1056
Ala Trp Asn His Arg Arg Thr Ser Asp Asn Ile Ile Gly Ser Asp Trp
                310                 315                 320 ctc cgg cct acc ggc tcc ggt tat atc cag agt cta gcc gca gcg gcg     1104
Leu Arg Pro Thr Gly Ser Gly Tyr Ile Gln Ser Leu Ala Ala Ala Ala
            325                 330                 335 ggt gtc tcg atc ctg cag ctg acg ccg cca gac aac tat acg ggt tac     1152
Gly Val Ser Ile Leu Gln Leu Thr Pro Pro Asp Asn Tyr Thr Gly Tyr
            340                 345                 350 atc gcc ggc aac ggt gcc tac gag gct gag aac gcc cag cgg acg ctg     1200
Ile Ala Gly Asn Gly Ala Tyr Glu Ala Glu Asn Ala Gln Arg Thr Leu
            355                 360                 365 gtg agc ggc ggg ggc atg atc aac gag agc acg cag ggc gga tat acg     1248
Val Ser Gly Gly Gly Met Ile Asn Glu Ser Thr Gln Gly Gly Tyr Thr
370                 375                 380                 385 ggc cgc ggc tat gtc gcg ggc tgg aat acg acc ggc act tcg ctc aac     1296
Gly Arg Gly Tyr Val Ala Gly Trp Asn Thr Thr Gly Thr Ser Leu Asn
            390                 395                 400 ttc tac gtg aac cag aac acc gcc ggc aat cgc acc atc acc ttc cgc     1344
Phe Tyr Val Asn Gln Asn Thr Ala Gly Asn Arg Thr Ile Thr Phe Arg
            405                 410                 415 tat gcg gcg ggt gcg ggc aac gcc tcg cgg tat gta cgt gtg aac ggc     1392
Tyr Ala Ala Gly Ala Gly Asn Ala Ser Arg Tyr Val Arg Val Asn Gly
            420                 425                 430 gtc tat gtg gcc aac aat ctg agc ttc agc ggc acc tca ggc tgg ggc     1440
Val Tyr Val Ala Asn Asn Leu Ser Phe Ser Gly Thr Ser Gly Trp Gly
            435                 440                 445 agc tgg aac acc gtc tcc gtc aca gtc ccg ctg aac gcc ggc tcg aac     1488
Ser Trp Asn Thr Val Ser Val Thr Val Pro Leu Asn Ala Gly Ser Asn
450                 455                 460                 465 acg atc cag ctc ggc tac gac agt tcc cga ggc aat agt aac ttc ttg     1536
Thr Ile Gln Leu Gly Tyr Asp Ser Ser Arg Gly Asn Ser Asn Phe Leu
            470                 475                 480 aac gta gat att ctg agc ggt ttg taa                                 1563
Asn Val Asp Ile Leu Ser Gly Leu
            485

<210> SEQ ID NO 14
<211> LENGTH: 520
<212> TYPE: PRT
<213> ORGANISM: Paenibacillus sp. B

<400> SEQUENCE: 14

Met Ile Val Trp Lys Lys Arg Val Thr Leu Ala Met Ala Phe Leu Leu
        -30                 -25                 -20
```

```
Val Leu Ser Leu Leu Gly Pro Thr Gly Ser Arg Lys Ala Glu Ala Phe
-15              -10                 -5                  -1   1

Thr Ala Ala Asn Ala Asn Asp Ala Met Gln Ala Phe Ile Asn Val Phe
         5                   10                  15

Tyr Asp Pro Thr Ala Lys Tyr Phe Tyr Thr Asn Ser Asp His Gln Ile
        20                  25                  30

His Thr His Ala His Gly Pro Asn Gly Gly Leu Tyr Thr Asp Phe Trp
        35                  40                  45

Trp Glu Ala Gln Leu Trp Glu Thr Val Met Asp Ala Tyr Glu Arg Thr
50                  55                  60                  65

Gly Asn Ala Thr Tyr Arg Thr Met Ile Asp Asp Ile Tyr Thr Gly Phe
                70                  75                  80

Asn Ala Lys Tyr Pro Asp Met Met Gln Asn Val Phe Asn Asp Asp Leu
                85                  90                  95

Gly Trp Trp Ala Gln Ala Ala Leu Arg Ala Tyr Glu Leu Thr Gly Thr
                100                 105                 110

Ala Glu Tyr Arg Asn Arg Gly Ser Phe Leu Phe Asp Lys Ile Tyr Glu
        115                 120                 125

Glu Trp Asp Thr Ser Tyr Tyr Gly Gly Ile Trp Trp Arg Arg Asp
130             135                 140                 145

Ala His Asn Pro Asn Val Ser Ser Asn Ala Gln Lys Asn Val Ala Thr
                150                 155                 160

Asn Ala Pro Met Val Ile Thr Ala Val Lys Leu Tyr Gln Ala Thr Gly
                165                 170                 175

Asp Ser Ala Tyr Leu Thr Lys Ala Thr Gln Ile Tyr Asn Trp Val Lys
        180                 185                 190

Thr Lys Leu Val Gly Ser Gly Lys Ile Asn Asp His Leu Glu Gly
        195                 200                 205

Pro Gly Ala Gly Thr Leu Ile Asp Trp Asp Phe Ser Tyr Asn Tyr Gly
210                 215                 220                 225

Asn Tyr Leu Gly Ala Ala Val Ser Leu Tyr Gln Ala Thr Gly Asn Ser
            230                 235                 240

Ala Tyr Ile Thr Asp Ala Asn Thr Ala Ala Thr Tyr Ala Ile Asn Asn
            245                 250                 255

Leu Val Ser Ala Gln Thr Leu Met Tyr Glu Gly Glu Asn Asp Ala Ala
            260                 265                 270

Gly Phe Lys Met Ile Phe Ala Arg Asn Leu Asn Arg Leu Arg Val Ile
            275                 280                 285

Gly Gly Gln Ser Gln Tyr Leu Asn Phe Leu Gln Asn Ala Thr Gln
290                 295                 300                 305

Ala Trp Asn His Arg Arg Thr Ser Asp Asn Ile Ile Gly Ser Asp Trp
                310                 315                 320

Leu Arg Pro Thr Gly Ser Gly Tyr Ile Gln Ser Leu Ala Ala Ala Ala
            325                 330                 335

Gly Val Ser Ile Leu Gln Leu Thr Pro Pro Asp Asn Tyr Thr Gly Tyr
            340                 345                 350

Ile Ala Gly Asn Gly Ala Tyr Glu Ala Glu Asn Ala Gln Arg Thr Leu
            355                 360                 365

Val Ser Gly Gly Met Ile Asn Glu Ser Thr Gln Gly Gly Tyr Thr
370                 375                 380                 385

Gly Arg Gly Tyr Val Ala Gly Trp Asn Thr Thr Gly Thr Ser Leu Asn
                390                 395                 400
```

-continued

```
Phe Tyr Val Asn Gln Asn Thr Ala Gly Asn Arg Thr Ile Thr Phe Arg
            405                 410                 415

Tyr Ala Ala Gly Ala Gly Asn Ala Ser Arg Tyr Val Arg Val Asn Gly
        420                 425                 430

Val Tyr Val Ala Asn Asn Leu Ser Phe Ser Gly Thr Ser Gly Trp Gly
    435                 440                 445

Ser Trp Asn Thr Val Ser Val Thr Val Pro Leu Asn Ala Gly Ser Asn
450                 455                 460                 465

Thr Ile Gln Leu Gly Tyr Asp Ser Ser Arg Gly Asn Ser Asn Phe Leu
            470                 475                 480

Asn Val Asp Ile Leu Ser Gly Leu
            485

<210> SEQ ID NO 15
<211> LENGTH: 489
<212> TYPE: PRT
<213> ORGANISM: Paenibacillus sp. B

<400> SEQUENCE: 15

Phe Thr Ala Ala Asn Ala Asn Asp Ala Met Gln Ala Phe Ile Asn Val
1               5                   10                  15

Phe Tyr Asp Pro Thr Ala Lys Tyr Phe Tyr Thr Asn Ser Asp His Gln
            20                  25                  30

Ile His Thr His Ala His Gly Pro Asn Gly Gly Leu Tyr Thr Asp Phe
        35                  40                  45

Trp Trp Glu Ala Gln Leu Trp Glu Thr Val Met Asp Ala Tyr Glu Arg
    50                  55                  60

Thr Gly Asn Ala Thr Tyr Arg Thr Met Ile Asp Asp Ile Tyr Thr Gly
65                  70                  75                  80

Phe Asn Ala Lys Tyr Pro Asp Met Met Gln Asn Val Phe Asn Asp Asp
            85                  90                  95

Leu Gly Trp Trp Ala Gln Ala Ala Leu Arg Ala Tyr Glu Leu Thr Gly
        100                 105                 110

Thr Ala Glu Tyr Arg Asn Arg Gly Ser Phe Leu Phe Asp Lys Ile Tyr
    115                 120                 125

Glu Glu Trp Asp Thr Ser Tyr Tyr Gly Gly Ile Trp Trp Arg Arg
130                 135                 140

Asp Ala His Asn Pro Asn Val Ser Ser Asn Ala Gln Lys Asn Val Ala
145                 150                 155                 160

Thr Asn Ala Pro Met Val Ile Thr Ala Val Lys Leu Tyr Gln Ala Thr
            165                 170                 175

Gly Asp Ser Ala Tyr Leu Thr Lys Ala Thr Gln Ile Tyr Asn Trp Val
        180                 185                 190

Lys Thr Lys Leu Val Gly Ser Gly Lys Ile Asn Asp His Leu Glu
    195                 200                 205

Gly Pro Gly Ala Gly Thr Leu Ile Asp Trp Asp Phe Ser Tyr Asn Tyr
    210                 215                 220

Gly Asn Tyr Leu Gly Ala Ala Val Ser Leu Tyr Gln Ala Thr Gly Asn
225                 230                 235                 240

Ser Ala Tyr Ile Thr Asp Ala Asn Thr Ala Thr Tyr Ala Ile Asn
            245                 250                 255

Asn Leu Val Ser Ala Gln Thr Leu Met Tyr Glu Gly Glu Asn Asp Ala
        260                 265                 270

Ala Gly Phe Lys Met Ile Phe Ala Arg Asn Leu Asn Arg Leu Arg Val
    275                 280                 285
```

-continued

```
Ile Gly Gly Gln Ser Gln Tyr Leu Asn Phe Leu Gln Gln Asn Ala Thr
    290                 295                 300

Gln Ala Trp Asn His Arg Arg Thr Ser Asp Asn Ile Ile Gly Ser Asp
305                 310                 315                 320

Trp Leu Arg Pro Thr Gly Ser Gly Tyr Ile Gln Ser Leu Ala Ala Ala
                325                 330                 335

Ala Gly Val Ser Ile Leu Gln Leu Thr Pro Pro Asp Asn Tyr Thr Gly
            340                 345                 350

Tyr Ile Ala Gly Asn Gly Ala Tyr Glu Ala Glu Asn Ala Gln Arg Thr
        355                 360                 365

Leu Val Ser Gly Gly Met Ile Asn Glu Ser Thr Gln Gly Gly Tyr
    370                 375                 380

Thr Gly Arg Gly Tyr Val Ala Gly Trp Asn Thr Thr Gly Thr Ser Leu
385                 390                 395                 400

Asn Phe Tyr Val Asn Gln Asn Thr Ala Gly Asn Arg Thr Ile Thr Phe
                405                 410                 415

Arg Tyr Ala Ala Gly Ala Gly Asn Ala Ser Arg Tyr Val Arg Val Asn
            420                 425                 430

Gly Val Tyr Val Ala Asn Asn Leu Ser Phe Ser Gly Thr Ser Gly Trp
        435                 440                 445

Gly Ser Trp Asn Thr Val Ser Val Thr Val Pro Leu Asn Ala Gly Ser
    450                 455                 460

Asn Thr Ile Gln Leu Gly Tyr Asp Ser Ser Arg Gly Asn Ser Asn Phe
465                 470                 475                 480

Leu Asn Val Asp Ile Leu Ser Gly Leu
                485
```

```
<210> SEQ ID NO 16
<211> LENGTH: 1110
<212> TYPE: DNA
<213> ORGANISM: Paenibacillus sp. C
<220> FEATURE:
<221> NAME/KEY: CDS
<222> LOCATION: (1)..(1107)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1107)

<400> SEQUENCE: 16
```

```
atg aaa agc ata tgc atg ctg ctt gtc ggc agt ttt ttc ttg aca ggc      48
Met Lys Ser Ile Cys Met Leu Leu Val Gly Ser Phe Phe Leu Thr Gly
    -20                 -15                 -10 tgc aat gga aat gag gag cgc ttg gaa aat tac aat aat cat gcg gaa      96
Cys Asn Gly Asn Glu Glu Arg Leu Glu Asn Tyr Asn Asn His Ala Glu
 -5              -1   1               5                  10 tgg gca gaa gag aag ctc atc gag cat tat tgg aat gag aat ggg aag     144
Trp Ala Glu Glu Lys Leu Ile Glu His Tyr Trp Asn Glu Asn Gly Lys
                15                  20                  25 ctg atg aac aac gct tat cct tat agc aaa gaa cgc gag gag agc cta     192
Leu Met Asn Asn Ala Tyr Pro Tyr Ser Lys Glu Arg Glu Glu Ser Leu
            30                  35                  40 aac tat tgg tgg aag gcg cat gcc gtg gat gcc atg atg gat ggg tat     240
Asn Tyr Trp Trp Lys Ala His Ala Val Asp Ala Met Met Asp Gly Tyr
        45                  50                  55 gag aga acg ggt gat gct gct tat acg gat agg gca gag ggg atc gtc     288
Glu Arg Thr Gly Asp Ala Ala Tyr Thr Asp Arg Ala Glu Gly Ile Val
```

```
                60                  65                  70                  75
aaa agc att att aaa aaa aat ggg tca ttg ttt aat gaa ttt tat gat       336
Lys Ser Ile Ile Lys Lys Asn Gly Ser Leu Phe Asn Glu Phe Tyr Asp
                    80                  85                  90 gat atg gaa tgg ctc gct ctt gca gcg ctg agg cta tat gat gca acc       384
Asp Met Glu Trp Leu Ala Leu Ala Ala Leu Arg Leu Tyr Asp Ala Thr
            95                  100                 105 aaa agc gag acg gtt aaa ggt tat gtt tta aag ctg tgg aat gat att       432
Lys Ser Glu Thr Val Lys Gly Tyr Val Leu Lys Leu Trp Asn Asp Ile
        110                 115                 120 aag acc gct tgg tgg gaa gat gag ctg ggc ggc atg gct tgg aag aag       480
Lys Thr Ala Trp Trp Glu Asp Glu Leu Gly Gly Met Ala Trp Lys Lys
    125                 130                 135 gat caa cga gac agc cgg aat gca tgc tcg aac ggg ccg gca gct att       528
Asp Gln Arg Asp Ser Arg Asn Ala Cys Ser Asn Gly Pro Ala Ala Ile
140                 145                 150                 155 ttg gct gcc agg atg tat gag tat ttt ggc gat aag gaa gat ctg gaa       576
Leu Ala Ala Arg Met Tyr Glu Tyr Phe Gly Asp Lys Glu Asp Leu Glu
                160                 165                 170 tgg gcc aaa aaa ata tat gat tgg cag aag aaa aat ttg gtt gat cct       624
Trp Ala Lys Lys Ile Tyr Asp Trp Gln Lys Lys Asn Leu Val Asp Pro
            175                 180                 185 gaa agc ggt ctt gtg tat gat ggc ctt aag ctg gaa gag aat ggt gat       672
Glu Ser Gly Leu Val Tyr Asp Gly Leu Lys Leu Glu Glu Asn Gly Asp
        190                 195                 200 ctt aat gtt aat aaa aat tgg ata ttc acc tat aac caa ggc act tat       720
Leu Asn Val Asn Lys Asn Trp Ile Phe Thr Tyr Asn Gln Gly Thr Tyr
    205                 210                 215 ata ggc gca gca gtt gag ctt tat aag cat aca aat gac aag acg tat       768
Ile Gly Ala Ala Val Glu Leu Tyr Lys His Thr Asn Asp Lys Thr Tyr
220                 225                 230                 235 ttg gca gat gcg gag aaa acc gct gcc tcg gct atg aaa tat cat acg       816
Leu Ala Asp Ala Glu Lys Thr Ala Ala Ser Ala Met Lys Tyr His Thr
                240                 245                 250 gtt gct gag acc gga atg atg aag gaa gaa gga acc gga gac ggt gga       864
Val Ala Glu Thr Gly Met Met Lys Glu Glu Gly Thr Gly Asp Gly Gly
            255                 260                 265 ctg ttc aaa ggc ata ttc att cgt tat ctg atc cat ttg tat gaa gtc       912
Leu Phe Lys Gly Ile Phe Ile Arg Tyr Leu Ile His Leu Tyr Glu Val
        270                 275                 280 aac gaa agc gtc caa att aaa gaa atg atc ttt cat aat gcg gat aca       960
Asn Glu Ser Val Gln Ile Lys Glu Met Ile Phe His Asn Ala Asp Thr
    285                 290                 295 ctg ctc tcg aaa ggc agc acg aag gaa att ggc ttg ttt ggt cct gct      1008
Leu Leu Ser Lys Gly Ser Thr Lys Glu Ile Gly Leu Phe Gly Pro Ala
300                 305                 310                 315 tgg gat atg cct cat cag gag cct ctg gat ata tcc gtg caa ttg agc      1056
Trp Asp Met Pro His Gln Glu Pro Leu Asp Ile Ser Val Gln Leu Ser
                320                 325                 330 gga gtt ttc tta ata gaa gcc gca gcc aaa ata gaa aga cta gat tcg      1104
Gly Val Phe Leu Ile Glu Ala Ala Ala Lys Ile Glu Arg Leu Asp Ser
            335                 340                 345 gaa taa                                                              1110
Glu

<210> SEQ ID NO 17
<211> LENGTH: 369
<212> TYPE: PRT
<213> ORGANISM: Paenibacillus sp. C
```

```
<400> SEQUENCE: 17

Met Lys Ser Ile Cys Met Leu Leu Val Gly Ser Phe Phe Leu Thr Gly
    -20                 -15                 -10

Cys Asn Gly Asn Glu Glu Arg Leu Glu Asn Tyr Asn Asn His Ala Glu
 -5              -1   1               5                    10

Trp Ala Glu Glu Lys Leu Ile Glu His Tyr Trp Asn Glu Asn Gly Lys
                 15                 20                  25

Leu Met Asn Asn Ala Tyr Pro Tyr Ser Lys Glu Arg Glu Glu Ser Leu
             30              35                  40

Asn Tyr Trp Trp Lys Ala His Ala Val Asp Ala Met Met Asp Gly Tyr
         45                  50                  55

Glu Arg Thr Gly Asp Ala Ala Tyr Thr Asp Arg Ala Glu Gly Ile Val
60                   65                  70                  75

Lys Ser Ile Ile Lys Lys Asn Gly Ser Leu Phe Asn Glu Phe Tyr Asp
             80                  85                  90

Asp Met Glu Trp Leu Ala Leu Ala Ala Leu Arg Leu Tyr Asp Ala Thr
             95                 100                 105

Lys Ser Glu Thr Val Lys Gly Tyr Val Leu Lys Leu Trp Asn Asp Ile
         110                 115                 120

Lys Thr Ala Trp Trp Glu Asp Glu Leu Gly Gly Met Ala Trp Lys Lys
         125                 130                 135

Asp Gln Arg Asp Ser Arg Asn Ala Cys Ser Asn Gly Pro Ala Ala Ile
140                 145                 150                 155

Leu Ala Ala Arg Met Tyr Glu Tyr Phe Gly Asp Lys Glu Asp Leu Glu
                 160                 165                 170

Trp Ala Lys Lys Ile Tyr Asp Trp Gln Lys Lys Asn Leu Val Asp Pro
             175                 180                 185

Glu Ser Gly Leu Val Tyr Asp Gly Leu Lys Leu Glu Glu Asn Gly Asp
         190                 195                 200

Leu Asn Val Asn Lys Asn Trp Ile Phe Thr Tyr Asn Gln Gly Thr Tyr
         205                 210                 215

Ile Gly Ala Ala Val Glu Leu Tyr Lys His Thr Asn Asp Lys Thr Tyr
220                 225                 230                 235

Leu Ala Asp Ala Glu Lys Thr Ala Ala Ser Ala Met Lys Tyr His Thr
                 240                 245                 250

Val Ala Glu Thr Gly Met Met Lys Glu Glu Gly Thr Gly Asp Gly Gly
             255                 260                 265

Leu Phe Lys Gly Ile Phe Ile Arg Tyr Leu Ile His Leu Tyr Glu Val
         270                 275                 280

Asn Glu Ser Val Gln Ile Lys Glu Met Ile Phe His Asn Ala Asp Thr
         285                 290                 295

Leu Leu Ser Lys Gly Ser Thr Lys Glu Ile Gly Leu Phe Gly Pro Ala
300                 305                 310                 315

Trp Asp Met Pro His Gln Glu Pro Leu Asp Ile Ser Val Gln Leu Ser
                 320                 325                 330

Gly Val Phe Leu Ile Glu Ala Ala Lys Ile Glu Arg Leu Asp Ser
             335                 340                 345

Glu

<210> SEQ ID NO 18
<211> LENGTH: 348
<212> TYPE: PRT
<213> ORGANISM: Paenibacillus sp. C
```

<400> SEQUENCE: 18

| | | | | | | | | | | | | | | |
|---|---|---|---|---|---|---|---|---|---|---|---|---|---|---|
|Glu|Arg|Leu|Glu|Asn|Tyr|Asn|Asn|His|Ala|Glu|Trp|Ala|Glu|Lys|
|1| | |  |5| | | | |10| | | | |15|
|Leu|Ile|Glu|His|Tyr|Trp|Asn|Glu|Asn|Gly|Lys|Leu|Met|Asn|Asn|Ala|
| | | |20| | | |25| | | |30| | | |
|Tyr|Pro|Tyr|Ser|Lys|Glu|Arg|Glu|Ser|Leu|Asn|Tyr|Trp|Trp|Lys|
| | |35| | | |40| | | |45| | | | |
|Ala|His|Ala|Val|Asp|Ala|Met|Met|Asp|Gly|Tyr|Glu|Arg|Thr|Gly|Asp|
| |50| | | |55| | | |60| | | | | |
|Ala|Ala|Tyr|Thr|Asp|Arg|Ala|Glu|Gly|Ile|Val|Lys|Ser|Ile|Ile|Lys|
|65| | | |70| | | |75| | | | | |80|
|Lys|Asn|Gly|Ser|Leu|Phe|Asn|Glu|Phe|Tyr|Asp|Met|Glu|Trp|Leu|
| | | |85| | | |90| | | |95| | | |
|Ala|Leu|Ala|Ala|Leu|Arg|Leu|Tyr|Asp|Ala|Thr|Lys|Ser|Glu|Thr|Val|
| | | |100| | | |105| | | |110| | | |
|Lys|Gly|Tyr|Val|Leu|Lys|Leu|Trp|Asn|Asp|Ile|Lys|Thr|Ala|Trp|Trp|
| | |115| | | |120| | | |125| | | | |
|Glu|Asp|Glu|Leu|Gly|Gly|Met|Ala|Trp|Lys|Lys|Asp|Gln|Arg|Asp|Ser|
| |130| | | |135| | | |140| | | | | |
|Arg|Asn|Ala|Cys|Ser|Asn|Gly|Pro|Ala|Ala|Ile|Leu|Ala|Ala|Arg|Met|
|145| | | |150| | | |155| | | | | |160|
|Tyr|Glu|Tyr|Phe|Gly|Asp|Lys|Glu|Asp|Leu|Glu|Trp|Ala|Lys|Lys|Ile|
| | | |165| | | |170| | | |175| | | |
|Tyr|Asp|Trp|Gln|Lys|Lys|Asn|Leu|Val|Asp|Pro|Glu|Ser|Gly|Leu|Val|
| | |180| | | |185| | | |190| | | | |
|Tyr|Asp|Gly|Leu|Lys|Leu|Glu|Glu|Asn|Gly|Asp|Leu|Asn|Val|Asn|Lys|
| |195| | | |200| | | |205| | | | | |
|Asn|Trp|Ile|Phe|Thr|Tyr|Asn|Gln|Gly|Thr|Tyr|Ile|Gly|Ala|Ala|Val|
| |210| | | |215| | | |220| | | | | |
|Glu|Leu|Tyr|Lys|His|Thr|Asn|Asp|Lys|Thr|Tyr|Leu|Ala|Asp|Ala|Glu|
|225| | | |230| | | |235| | | | | |240|
|Lys|Thr|Ala|Ala|Ser|Ala|Met|Lys|Tyr|His|Thr|Val|Ala|Glu|Thr|Gly|
| | | |245| | | |250| | | |255| | | |
|Met|Met|Lys|Glu|Glu|Gly|Thr|Gly|Asp|Gly|Gly|Leu|Phe|Lys|Gly|Ile|
| | | |260| | | |265| | | |270| | | |
|Phe|Ile|Arg|Tyr|Leu|Ile|His|Leu|Tyr|Glu|Val|Asn|Glu|Ser|Val|Gln|
| | |275| | | |280| | | |285| | | | |
|Ile|Lys|Glu|Met|Ile|Phe|His|Asn|Ala|Asp|Thr|Leu|Leu|Ser|Lys|Gly|
| |290| | | |295| | | |300| | | | | |
|Ser|Thr|Lys|Glu|Ile|Gly|Leu|Phe|Gly|Pro|Ala|Trp|Asp|Met|Pro|His|
|305| | | |310| | | |315| | | | | |320|
|Gln|Glu|Pro|Leu|Asp|Ile|Ser|Val|Gln|Leu|Ser|Gly|Val|Phe|Leu|Ile|
| | | |325| | | |330| | | |335| | | |
|Glu|Ala|Ala|Ala|Lys|Ile|Glu|Arg|Leu|Asp|Ser|Glu|
| | | |340| | | |345| | | | | | | |

```
<210> SEQ ID NO 19
<211> LENGTH: 1719
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1719)
<220> FEATURE:
```

```
<221> NAME/KEY: sig_peptide
<222> LOCATION: (1)..(105)
<220> FEATURE:
<221> NAME/KEY: mat_peptide
<222> LOCATION: (106)..(1719)

<400> SEQUENCE: 19
```

| | | | | | | | | | | | | | | | | |
|---|---|---|---|---|---|---|---|---|---|---|---|---|---|---|---|---|
| atg | tca | ctt | aga | tca | ggt | caa | ctt | ttc | agg | ctt | ctg | gcg | gtg | cct | ctg | 48 |
| Met | Ser | Leu | Arg | Ser | Gly | Gln | Leu | Phe | Arg | Leu | Leu | Ala | Val | Pro | Leu | |
| -35 | | | | -30 | | | | | -25 | | | | | -20 | | |
| gct | atc | gca | ctt | atg | ctc | ggt | tcc | atg | ccg | ggc | atc | gga | tcg | tcc | aaa | 96 |
| Ala | Ile | Ala | Leu | Met | Leu | Gly | Ser | Met | Pro | Gly | Ile | Gly | Ser | Ser | Lys | |
| | | | | -15 | | | | | -10 | | | | | -5 | | |
| gcc | tac | gcc | tat | acc | gca | tcg | gac | ggg | gat | act | gcg | atg | aga | gct | ttt | 144 |
| Ala | Tyr | Ala | Tyr | Thr | Ala | Ser | Asp | Gly | Asp | Thr | Ala | Met | Arg | Ala | Phe | |
| | | | -1 | 1 | | | | | 5 | | | | | 10 | | |
| aac | gat | aca | ttc | tgg | gac | ccg | aac | gcc | aag | atg | ttc | tgg | aag | gac | tcg | 192 |
| Asn | Asp | Thr | Phe | Trp | Asp | Pro | Asn | Ala | Lys | Met | Phe | Trp | Lys | Asp | Ser | |
| | 15 | | | | | 20 | | | | | 25 | | | | | |
| aag | cga | gaa | aag | cat | caa | gac | ttc | tgg | gtg | gag | gca | gag | ctg | tgg | gaa | 240 |
| Lys | Arg | Glu | Lys | His | Gln | Asp | Phe | Trp | Val | Glu | Ala | Glu | Leu | Trp | Glu | |
| 30 | | | | | 35 | | | | | 40 | | | | | 45 | |
| ttg | gtc | atg | gat | gca | tat | cag | cat | acc | tcc | gat | cct | gcc | ttg | aaa | gcc | 288 |
| Leu | Val | Met | Asp | Ala | Tyr | Gln | His | Thr | Ser | Asp | Pro | Ala | Leu | Lys | Ala | |
| | | | | 50 | | | | | 55 | | | | | 60 | | |
| gag | ctt | aaa | acg | cag | atc | gac | gat | gta | tat | gac | ggc | acc | gtc | gcc | aag | 336 |
| Glu | Leu | Lys | Thr | Gln | Ile | Asp | Asp | Val | Tyr | Asp | Gly | Thr | Val | Ala | Lys | |
| | | | | 65 | | | | | 70 | | | | | 75 | | |
| tac | ggc | caa | gat | tgg | acg | aat | aat | ccc | ttc | aat | gac | gat | att | atg | tgg | 384 |
| Tyr | Gly | Gln | Asp | Trp | Thr | Asn | Asn | Pro | Phe | Asn | Asp | Asp | Ile | Met | Trp | |
| | | | 80 | | | | | 85 | | | | | 90 | | | |
| tgg | gcg | atg | gga | agc | gcc | aga | gcc | tat | caa | atc | acc | ggg | aat | cca | aga | 432 |
| Trp | Ala | Met | Gly | Ser | Ala | Arg | Ala | Tyr | Gln | Ile | Thr | Gly | Asn | Pro | Arg | |
| | 95 | | | | | 100 | | | | | 105 | | | | | |
| tat | ttg | aag | gcc | gca | aag | gat | cat | ttc | gat | ttt | gtg | tac | gat | acg | cag | 480 |
| Tyr | Leu | Lys | Ala | Ala | Lys | Asp | His | Phe | Asp | Phe | Val | Tyr | Asp | Thr | Gln | |
| 110 | | | | | 115 | | | | | 120 | | | | | 125 | |
| tgg | gat | gaa | gag | ttc | gcg | agc | ggc | ggc | att | tgg | tgg | ctg | aac | agc | gac | 528 |
| Trp | Asp | Glu | Glu | Phe | Ala | Ser | Gly | Gly | Ile | Trp | Trp | Leu | Asn | Ser | Asp | |
| | | | | 130 | | | | | 135 | | | | | 140 | | |
| cat | aat | acc | aag | aat | gcg | tgc | att | aac | ttc | ccg | gcg | gcg | gaa | gct | gca | 576 |
| His | Asn | Thr | Lys | Asn | Ala | Cys | Ile | Asn | Phe | Pro | Ala | Ala | Glu | Ala | Ala | |
| | | | 145 | | | | | 150 | | | | | 155 | | | |
| ctt | tat | ctt | tac | gat | att | aca | aaa | gat | gag | cat | tat | ttg | aac | acg | gca | 624 |
| Leu | Tyr | Leu | Tyr | Asp | Ile | Thr | Lys | Asp | Glu | His | Tyr | Leu | Asn | Thr | Ala | |
| | 160 | | | | | 165 | | | | | 170 | | | | | |
| acc | aaa | ata | ttc | aga | tgg | ggc | aaa | acg | atg | ctt | acg | gac | gga | aac | gga | 672 |
| Thr | Lys | Ile | Phe | Arg | Trp | Gly | Lys | Thr | Met | Leu | Thr | Asp | Gly | Asn | Gly | |
| | 175 | | | | | 180 | | | | | 185 | | | | | |
| aaa | gtg | ttc | gac | cgt | atc | gaa | gtt | gaa | cat | ggc | gcg | gtt | ccg | gat | gcc | 720 |
| Lys | Val | Phe | Asp | Arg | Ile | Glu | Val | Glu | His | Gly | Ala | Val | Pro | Asp | Ala | |
| 190 | | | | | 195 | | | | | 200 | | | | | 205 | |
| act | cac | tac | aac | cag | ggt | aca | tac | atc | gga | gcg | gcc | gtc | gga | ttg | tat | 768 |
| Thr | His | Tyr | Asn | Gln | Gly | Thr | Tyr | Ile | Gly | Ala | Ala | Val | Gly | Leu | Tyr | |
| | | | | 210 | | | | | 215 | | | | | 220 | | |
| gaa | gcg | acc | gga | aat | gcc | gtt | tac | ctc | gat | gac | gcg | gtc | aag | gcc | gct | 816 |
| Glu | Ala | Thr | Gly | Asn | Ala | Val | Tyr | Leu | Asp | Asp | Ala | Val | Lys | Ala | Ala | |
| | | | 225 | | | | | 230 | | | | | 235 | | | |
| aaa | ttc | acc | aag | aat | cac | ctg | gtg | gat | tca | aac | ggg | gta | ttg | aat | tac | 864 |
| Lys | Phe | Thr | Lys | Asn | His | Leu | Val | Asp | Ser | Asn | Gly | Val | Leu | Asn | Tyr | |
| | 240 | | | | | 245 | | | | | 250 | | | | | |

```
gaa ggc ccc aac gga gat ctg aaa ggc ggc aaa acg atc ctg atg cgc      912
Glu Gly Pro Asn Gly Asp Leu Lys Gly Gly Lys Thr Ile Leu Met Arg
        255                 260                 265 aat ctg gcc tat ctg caa aag aca ctg gat gaa acc ggc cag cac ccc      960
Asn Leu Ala Tyr Leu Gln Lys Thr Leu Asp Glu Thr Gly Gln His Pro
270                 275                 280                 285 gaa ttc agc gct gaa ttc gac gaa tgg ctt gca ttc aat gtc gaa atg     1008
Glu Phe Ser Ala Glu Phe Asp Glu Trp Leu Ala Phe Asn Val Glu Met
                    290                 295                 300 gcc tgg agc cac cgc aat ccg gat cat atc gtg gat gga aac tgg gca     1056
Ala Trp Ser His Arg Asn Pro Asp His Ile Val Asp Gly Asn Trp Ala
                305                 310                 315 gga cag ctg ctg tcc ggg acc tat gaa tcc tgg tcc tcg gcc gct gcc     1104
Gly Gln Leu Leu Ser Gly Thr Tyr Glu Ser Trp Ser Ser Ala Ala Ala
            320                 325                 330 gtt caa gct tta aac gtt atc aag ccg atg gaa gcg gag ctt cgt tat     1152
Val Gln Ala Leu Asn Val Ile Lys Pro Met Glu Ala Glu Leu Arg Tyr
        335                 340                 345 gcc gtc aaa aac ccc ttt gag aaa atc gaa gcg gaa cgc tac aac att     1200
Ala Val Lys Asn Pro Phe Glu Lys Ile Glu Ala Glu Arg Tyr Asn Ile
350                 355                 360                 365 ggg gcc gga ttc gtg ctg gag ggt tca ttt gaa ggt tca ctg caa tta     1248
Gly Ala Gly Phe Val Leu Glu Gly Ser Phe Glu Gly Ser Leu Gln Leu
                    370                 375                 380 ggc gga atc cag cat ggc tct tat gcc gct tac aaa aat gtg gat ttc     1296
Gly Gly Ile Gln His Gly Ser Tyr Ala Ala Tyr Lys Asn Val Asp Phe
                385                 390                 395 gga tca gac ggc gcg atc ggc ttc att gcc aga gcg tct agc gga acg     1344
Gly Ser Asp Gly Ala Ile Gly Phe Ile Ala Arg Ala Ser Ser Gly Thr
            400                 405                 410 ggc gga ggc caa att gag atc cgg ctt gat tcc aag gat ggc ccc aaa     1392
Gly Gly Gly Gln Ile Glu Ile Arg Leu Asp Ser Lys Asp Gly Pro Lys
        415                 420                 425 gtc ggg acc ttg aac gta gag gga acg ggc gat tgg aat cat tat atc     1440
Val Gly Thr Leu Asn Val Glu Gly Thr Gly Asp Trp Asn His Tyr Ile
430                 435                 440                 445 gat gcc gtc acc ctc ctt aaa gat gac cag gga gcg cca agc acc ata     1488
Asp Ala Val Thr Leu Leu Lys Asp Asp Gln Gly Ala Pro Ser Thr Ile
                    450                 455                 460 acc ggc gtc cat gat gtg tat ctt gtc ttc acc aag aca aat gac gat     1536
Thr Gly Val His Asp Val Tyr Leu Val Phe Thr Lys Thr Asn Asp Asp
                465                 470                 475 tat tta ttc aat tta aac tgg gtt caa ttt acg acg acg gac ccg acc     1584
Tyr Leu Phe Asn Leu Asn Trp Val Gln Phe Thr Thr Thr Asp Pro Thr
            480                 485                 490 gaa acc gac gcc tat gcc aag ctg aag gcc gga aac tat gac agc agc     1632
Glu Thr Asp Ala Tyr Ala Lys Leu Lys Ala Gly Asn Tyr Asp Ser Ser
        495                 500                 505 gaa gga ctt agt aaa cat gcc gag ttc gga tat ttg gac gga atc cat     1680
Glu Gly Leu Ser Lys His Ala Glu Phe Gly Tyr Leu Asp Gly Ile His
510                 515                 520                 525 cac aat gcc tat gcc tct tat gaa gga att gat ttt gga               1719
His Asn Ala Tyr Ala Ser Tyr Glu Gly Ile Asp Phe Gly
                530                 535

<210> SEQ ID NO 20
<211> LENGTH: 573
<212> TYPE: PRT
<213> ORGANISM: Artificial Sequence
<220> FEATURE:
```

<223> OTHER INFORMATION: Synthetic Construct

<400> SEQUENCE: 20

```
Met Ser Leu Arg Ser Gly Gln Leu Phe Arg Leu Ala Val Pro Leu
-35                 -30                 -25                 -20

Ala Ile Ala Leu Met Leu Gly Ser Met Pro Gly Ile Gly Ser Ser Lys
            -15                 -10                  -5

Ala Tyr Ala Tyr Thr Ala Ser Asp Gly Asp Thr Ala Met Arg Ala Phe
         -1   1               5                  10

Asn Asp Thr Phe Trp Asp Pro Asn Ala Lys Met Phe Trp Lys Asp Ser
         15                  20                  25

Lys Arg Glu Lys His Gln Asp Phe Trp Val Glu Ala Glu Leu Trp Glu
 30                  35                  40                  45

Leu Val Met Asp Ala Tyr Gln His Thr Ser Asp Pro Ala Leu Lys Ala
                 50                  55                  60

Glu Leu Lys Thr Gln Ile Asp Asp Val Tyr Asp Gly Thr Val Ala Lys
             65                  70                  75

Tyr Gly Gln Asp Trp Thr Asn Asn Pro Phe Asn Asp Ile Met Trp
         80                  85                  90

Trp Ala Met Gly Ser Ala Arg Ala Tyr Gln Ile Thr Gly Asn Pro Arg
 95                 100                 105

Tyr Leu Lys Ala Ala Lys Asp His Phe Asp Phe Val Tyr Asp Thr Gln
110                 115                 120                 125

Trp Asp Glu Glu Phe Ala Ser Gly Gly Ile Trp Trp Leu Asn Ser Asp
                130                 135                 140

His Asn Thr Lys Asn Ala Cys Ile Asn Phe Pro Ala Ala Glu Ala Ala
             145                 150                 155

Leu Tyr Leu Tyr Asp Ile Thr Lys Asp Glu His Tyr Leu Asn Thr Ala
                160                 165                 170

Thr Lys Ile Phe Arg Trp Gly Lys Thr Met Leu Thr Asp Gly Asn Gly
175                 180                 185

Lys Val Phe Asp Arg Ile Glu Val Glu His Gly Ala Val Pro Asp Ala
190                 195                 200                 205

Thr His Tyr Asn Gln Gly Thr Tyr Ile Gly Ala Ala Val Gly Leu Tyr
                210                 215                 220

Glu Ala Thr Gly Asn Ala Val Tyr Leu Asp Asp Ala Val Lys Ala Ala
                225                 230                 235

Lys Phe Thr Lys Asn His Leu Val Asp Ser Asn Gly Val Leu Asn Tyr
                240                 245                 250

Glu Gly Pro Asn Gly Asp Leu Lys Gly Gly Lys Thr Ile Leu Met Arg
                255                 260                 265

Asn Leu Ala Tyr Leu Gln Lys Thr Leu Asp Glu Thr Gly Gln His Pro
270                 275                 280                 285

Glu Phe Ser Ala Glu Phe Asp Glu Trp Leu Ala Phe Asn Val Glu Met
                290                 295                 300

Ala Trp Ser His Arg Asn Pro Asp His Ile Val Asp Gly Asn Trp Ala
                305                 310                 315

Gly Gln Leu Leu Ser Gly Thr Tyr Glu Ser Trp Ser Ser Ala Ala Ala
                320                 325                 330

Val Gln Ala Leu Asn Val Ile Lys Pro Met Glu Ala Glu Leu Arg Tyr
                335                 340                 345

Ala Val Lys Asn Pro Phe Glu Lys Ile Glu Ala Glu Arg Tyr Asn Ile
350                 355                 360                 365
```

```
Gly Ala Gly Phe Val Leu Glu Gly Ser Phe Glu Gly Ser Leu Gln Leu
                370                 375                 380
Gly Gly Ile Gln His Gly Ser Tyr Ala Ala Tyr Lys Asn Val Asp Phe
            385                 390                 395
Gly Ser Asp Gly Ala Ile Gly Phe Ile Ala Arg Ala Ser Ser Gly Thr
        400                 405                 410
Gly Gly Gly Gln Ile Glu Ile Arg Leu Asp Ser Lys Asp Gly Pro Lys
    415                 420                 425
Val Gly Thr Leu Asn Val Glu Gly Thr Gly Asp Trp Asn His Tyr Ile
430                 435                 440                 445
Asp Ala Val Thr Leu Leu Lys Asp Asp Gln Gly Ala Pro Ser Thr Ile
                450                 455                 460
Thr Gly Val His Asp Val Tyr Leu Val Phe Thr Lys Thr Asn Asp Asp
            465                 470                 475
Tyr Leu Phe Asn Leu Asn Trp Val Gln Phe Thr Thr Thr Asp Pro Thr
        480                 485                 490
Glu Thr Asp Ala Tyr Ala Lys Leu Lys Ala Gly Asn Tyr Asp Ser Ser
    495                 500                 505
Glu Gly Leu Ser Lys His Ala Glu Phe Gly Tyr Leu Asp Gly Ile His
510                 515                 520                 525
His Asn Ala Tyr Ala Ser Tyr Glu Gly Ile Asp Phe Gly
                530                 535

<210> SEQ ID NO 21
<211> LENGTH: 538
<212> TYPE: PRT
<213> ORGANISM: Artificial Sequence
<220> FEATURE:
<223> OTHER INFORMATION: Synthetic construct

<400> SEQUENCE: 21

Tyr Thr Ala Ser Asp Gly Asp Thr Ala Met Arg Ala Phe Asn Asp Thr
1               5                   10                  15
Phe Trp Asp Pro Asn Ala Lys Met Phe Trp Lys Asp Ser Lys Arg Glu
                20                  25                  30
Lys His Gln Asp Phe Trp Val Glu Ala Glu Leu Trp Glu Leu Val Met
            35                  40                  45
Asp Ala Tyr Gln His Thr Ser Asp Pro Ala Leu Lys Ala Glu Leu Lys
        50                  55                  60
Thr Gln Ile Asp Asp Val Tyr Asp Gly Thr Val Ala Lys Tyr Gly Gln
65                  70                  75                  80
Asp Trp Thr Asn Asn Pro Phe Asn Asp Ile Met Trp Trp Ala Met
                85                  90                  95
Gly Ser Ala Arg Ala Tyr Gln Ile Thr Gly Asn Pro Arg Tyr Leu Lys
            100                 105                 110
Ala Ala Lys Asp His Phe Asp Phe Val Tyr Asp Thr Gln Trp Asp Glu
        115                 120                 125
Glu Phe Ala Ser Gly Gly Ile Trp Trp Leu Asn Ser Asp His Asn Thr
    130                 135                 140
Lys Asn Ala Cys Ile Asn Phe Pro Ala Ala Glu Ala Ala Leu Tyr Leu
145                 150                 155                 160
Tyr Asp Ile Thr Lys Asp Glu His Tyr Leu Asn Thr Ala Thr Lys Ile
                165                 170                 175
Phe Arg Trp Gly Lys Thr Met Leu Thr Asp Gly Asn Gly Lys Val Phe
            180                 185                 190
```

Asp Arg Ile Glu Val Glu His Gly Ala Val Pro Asp Ala Thr His Tyr
            195                 200                 205

Asn Gln Gly Thr Tyr Ile Gly Ala Ala Val Gly Leu Tyr Glu Ala Thr
        210                 215                 220

Gly Asn Ala Val Tyr Leu Asp Asp Ala Val Lys Ala Ala Lys Phe Thr
225                 230                 235                 240

Lys Asn His Leu Val Asp Ser Asn Gly Val Leu Asn Tyr Glu Gly Pro
                245                 250                 255

Asn Gly Asp Leu Lys Gly Gly Lys Thr Ile Leu Met Arg Asn Leu Ala
            260                 265                 270

Tyr Leu Gln Lys Thr Leu Asp Glu Thr Gly Gln His Pro Glu Phe Ser
        275                 280                 285

Ala Glu Phe Asp Glu Trp Leu Ala Phe Asn Val Glu Met Ala Trp Ser
290                 295                 300

His Arg Asn Pro Asp His Ile Val Asp Gly Asn Trp Ala Gly Gln Leu
305                 310                 315                 320

Leu Ser Gly Thr Tyr Glu Ser Trp Ser Ser Ala Ala Val Gln Ala
                325                 330                 335

Leu Asn Val Ile Lys Pro Met Glu Ala Glu Leu Arg Tyr Ala Val Lys
            340                 345                 350

Asn Pro Phe Glu Lys Ile Glu Ala Glu Arg Tyr Asn Ile Gly Ala Gly
        355                 360                 365

Phe Val Leu Glu Gly Ser Phe Glu Gly Ser Leu Gln Leu Gly Gly Ile
370                 375                 380

Gln His Gly Ser Tyr Ala Ala Tyr Lys Asn Val Asp Phe Gly Ser Asp
385                 390                 395                 400

Gly Ala Ile Gly Phe Ile Ala Arg Ala Ser Ser Gly Thr Gly Gly Gly
                405                 410                 415

Gln Ile Glu Ile Arg Leu Asp Ser Lys Asp Gly Pro Lys Val Gly Thr
            420                 425                 430

Leu Asn Val Glu Gly Thr Gly Asp Trp Asn His Tyr Ile Asp Ala Val
        435                 440                 445

Thr Leu Leu Lys Asp Asp Gln Gly Ala Pro Ser Thr Ile Thr Gly Val
450                 455                 460

His Asp Val Tyr Leu Val Phe Thr Lys Thr Asn Asp Asp Tyr Leu Phe
465                 470                 475                 480

Asn Leu Asn Trp Val Gln Phe Thr Thr Thr Asp Pro Thr Glu Thr Asp
                485                 490                 495

Ala Tyr Ala Lys Leu Lys Ala Gly Asn Tyr Asp Ser Ser Glu Gly Leu
            500                 505                 510

Ser Lys His Ala Glu Phe Gly Tyr Leu Asp Gly Ile His His Asn Ala
        515                 520                 525

Tyr Ala Ser Tyr Glu Gly Ile Asp Phe Gly
530                 535

<210> SEQ ID NO 22
<211> LENGTH: 1731
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1731)
<220> FEATURE:
<221> NAME/KEY: sig_peptide
<222> LOCATION: (1)..(105)

-continued

```
<220> FEATURE:
<221> NAME/KEY: mat_peptide
<222> LOCATION: (106)..(1731)

<400> SEQUENCE: 22 ttg gcc agt aag gtt aga aga aga ttc aag ctt atc gta ttg ctt gtt      48
Leu Ala Ser Lys Val Arg Arg Arg Phe Lys Leu Ile Val Leu Leu Val
-35                 -30                 -25                 -20 gtt ctt gca ctc tcg atc agt acc cta tct cca agc gga atg cct cgc      96
Val Leu Ala Leu Ser Ile Ser Thr Leu Ser Pro Ser Gly Met Pro Arg
            -15                 -10                  -5 gcc cat gct ttt gaa gcg gag gat gcg aag acg gca atc gtt gcc tac     144
Ala His Ala Phe Glu Ala Glu Asp Ala Lys Thr Ala Ile Val Ala Tyr
        -1   1                   5                  10 aat gat gca ttc tgg gat gca aac gcg aaa tac ttc tgg aaa tcc acc     192
Asn Asp Ala Phe Trp Asp Ala Asn Ala Lys Tyr Phe Trp Lys Ser Thr
         15                  20                  25 aat cgt acc gat tat cag gac ttt tgg ata gag gcc gag ctt tgg gag     240
Asn Arg Thr Asp Tyr Gln Asp Phe Trp Ile Glu Ala Glu Leu Trp Glu
 30                  35                  40                  45 ctc gtt atg gat gcc tat ctg cat aca tcg gac ccg gag ctc aag gcg     288
Leu Val Met Asp Ala Tyr Leu His Thr Ser Asp Pro Glu Leu Lys Ala
                 50                  55                  60 cag ctg cgg acc cag att gac gat gtg ttc gat gga gcc gta acg agg     336
Gln Leu Arg Thr Gln Ile Asp Asp Val Phe Asp Gly Ala Val Thr Arg
             65                  70                  75 tac ggc gag gac tgg aca tat aat ccg tat aac gat gac atc atg tgg     384
Tyr Gly Glu Asp Trp Thr Tyr Asn Pro Tyr Asn Asp Asp Ile Met Trp
         80                  85                  90 tgg gca atg gca agt gca aga gcc tat cag att acg aat gac gaa cgg     432
Trp Ala Met Ala Ser Ala Arg Ala Tyr Gln Ile Thr Asn Asp Glu Arg
 95                 100                 105 tat ttg gaa caa gcg gaa tat tat ttc aat tat gtc tat gat aat gaa     480
Tyr Leu Glu Gln Ala Glu Tyr Tyr Phe Asn Tyr Val Tyr Asp Asn Glu
110                 115                 120                 125 tgg gat act gaa ttt gcc gga ggc ggc att tgg tgg aaa agc gat gat     528
Trp Asp Thr Glu Phe Ala Gly Gly Gly Ile Trp Trp Lys Ser Asp Asp
                130                 135                 140 cgc acg aca aaa aat gca tgc atc aac ttt cct gcc gct caa acc gct     576
Arg Thr Thr Lys Asn Ala Cys Ile Asn Phe Pro Ala Ala Gln Thr Ala
            145                 150                 155 gtc ttt ttg tat aac gtt acc caa gac gaa caa tac ctg gat gca gcc     624
Val Phe Leu Tyr Asn Val Thr Gln Asp Glu Gln Tyr Leu Asp Ala Ala
        160                 165                 170 gaa acc atc tac cat tgg gga aaa aca ata ctg act gac ggc aac ggc     672
Glu Thr Ile Tyr His Trp Gly Lys Thr Ile Leu Thr Asp Gly Asn Gly
    175                 180                 185 aaa gta ttc gat cga att gaa acg caa aat gga gct att caa ggc gcg     720
Lys Val Phe Asp Arg Ile Glu Thr Gln Asn Gly Ala Ile Gln Gly Ala
190                 195                 200                 205 act cac tat aat caa ggt gcg ttt att ggg tca gcc gca ggt ctc tac     768
Thr His Tyr Asn Gln Gly Ala Phe Ile Gly Ser Ala Ala Gly Leu Tyr
                210                 215                 220 gag att acg gga gac acg gat tat ctg gac gat gcg atc aaa gcg gcc     816
Glu Ile Thr Gly Asp Thr Asp Tyr Leu Asp Asp Ala Ile Lys Ala Ala
            225                 230                 235 acg tat acg aag gag cat atg gtt gac gtc aac gga ctg ctg cga tat     864
Thr Tyr Thr Lys Glu His Met Val Asp Val Asn Gly Leu Leu Arg Tyr
        240                 245                 250 gag ggc cct aac gga gat ttg aag ggc ggc aaa acg att ctg ctg cgc     912
```

```
                Glu Gly Pro Asn Gly Asp Leu Lys Gly Gly Lys Thr Ile Leu Leu Arg
                    255                 260                 265 aac ctc ggc tat ttt caa gcg gcg ata gac gct cgc cag gaa gaa aat          960
Asn Leu Gly Tyr Phe Gln Ala Ala Ile Asp Ala Arg Gln Glu Glu Asn
270                 275                 280                 285 tac caa tcc ttc gcc gaa agc tac aat gag tgg ctg gct ttt aat gcc         1008
Tyr Gln Ser Phe Ala Glu Ser Tyr Asn Glu Trp Leu Ala Phe Asn Ala
                290                 295                 300 gat atg gca tgg aac aat cgc aat gcg gcc aat ctc gtc gac ggc aac         1056
Asp Met Ala Trp Asn Asn Arg Asn Ala Ala Asn Leu Val Asp Gly Asn
            305                 310                 315 tgg gcg gga caa cag tta tcc ggc gcc atc gag tca tgg agc gcg gca         1104
Trp Ala Gly Gln Gln Leu Ser Gly Ala Ile Glu Ser Trp Ser Ala Ala
        320                 325                 330 gcg gcc gta caa gct ttg ata tcc cta aag ccg cag aac gcg gta cag         1152
Ala Ala Val Gln Ala Leu Ile Ser Leu Lys Pro Gln Asn Ala Val Gln
    335                 340                 345 ctg gga tat gcc gtt aag aac cct tat aac agg atc gaa gcg gaa agt         1200
Leu Gly Tyr Ala Val Lys Asn Pro Tyr Asn Arg Ile Glu Ala Glu Ser
350                 355                 360                 365 tac aat att ata aac ggc cct ggc ctg gag gac agc aat gaa ggc tcg         1248
Tyr Asn Ile Ile Asn Gly Pro Gly Leu Glu Asp Ser Asn Glu Gly Ser
                370                 375                 380 caa caa ctg gcc ggt att cag gac agt cat tat gcg gca tat aaa aat         1296
Gln Gln Leu Ala Gly Ile Gln Asp Ser His Tyr Ala Ala Tyr Lys Asn
            385                 390                 395 gtc gat ttt ggt tcg gaa gat ggt gca agc ggt ttc att gcg cga gca         1344
Val Asp Phe Gly Ser Glu Asp Gly Ala Ser Gly Phe Ile Ala Arg Ala
        400                 405                 410 tcg agc gga acg ggc ggc ggc cag atc gaa atc aga ctg gat gct ttg         1392
Ser Ser Gly Thr Gly Gly Gly Gln Ile Glu Ile Arg Leu Asp Ala Leu
    415                 420                 425 gac gga cca aag gca ggt acg cta aat gta aat ggt acc gga ggc tgg         1440
Asp Gly Pro Lys Ala Gly Thr Leu Asn Val Asn Gly Thr Gly Gly Trp
430                 435                 440                 445 aac aac tac atc gac gcg gct gta ctg ctg aag gat gag caa ggg aat         1488
Asn Asn Tyr Ile Asp Ala Ala Val Leu Leu Lys Asp Glu Gln Gly Asn
                450                 455                 460 ccg agt cct gtg acc ggc gta cac gat gtg tat ctg gtg ttt aag agg         1536
Pro Ser Pro Val Thr Gly Val His Asp Val Tyr Leu Val Phe Lys Arg
            465                 470                 475 aca aat gac aca tat cta ttc aat ctc aat tgg ttc caa ttt acg aag         1584
Thr Asn Asp Thr Tyr Leu Phe Asn Leu Asn Trp Phe Gln Phe Thr Lys
        480                 485                 490 gtc gat ccg acc ctg att tct gct tat acg ata ttg cag gcc gag cat         1632
Val Asp Pro Thr Leu Ile Ser Ala Tyr Thr Ile Leu Gln Ala Glu His
    495                 500                 505 ttt gca agc agt gac ggg ctg agt att aac tca aca ggg caa tat gca         1680
Phe Ala Ser Ser Asp Gly Leu Ser Ile Asn Ser Thr Gly Gln Tyr Ala
510                 515                 520                 525 gac ggc att caa aat acc gca tat gct tcc tac gaa aat att gat ttt         1728
Asp Gly Ile Gln Asn Thr Ala Tyr Ala Ser Tyr Glu Asn Ile Asp Phe
                530                 535                 540 ggc                                                                     1731
Gly <210> SEQ ID NO 23
<211> LENGTH: 577
<212> TYPE: PRT
<213> ORGANISM: Artificial Sequence
```

<220> FEATURE:
<223> OTHER INFORMATION: Synthetic Construct

<400> SEQUENCE: 23

```
Leu Ala Ser Lys Val Arg Arg Phe Lys Leu Ile Val Leu Val
-35             -30                 -25                 -20

Val Leu Ala Leu Ser Ile Ser Thr Leu Ser Pro Ser Gly Met Pro Arg
                -15                 -10                     -5

Ala His Ala Phe Glu Ala Glu Asp Ala Lys Thr Ala Ile Val Ala Tyr
        -1  1             5                     10

Asn Asp Ala Phe Trp Asp Ala Asn Ala Lys Tyr Phe Trp Lys Ser Thr
    15              20                  25

Asn Arg Thr Asp Tyr Gln Asp Phe Trp Ile Glu Ala Glu Leu Trp Glu
30              35                  40                  45

Leu Val Met Asp Ala Tyr Leu His Thr Ser Asp Pro Glu Leu Lys Ala
            50              55                  60

Gln Leu Arg Thr Gln Ile Asp Asp Val Phe Asp Gly Ala Val Thr Arg
                65              70                  75

Tyr Gly Glu Asp Trp Thr Tyr Asn Pro Tyr Asn Asp Asp Ile Met Trp
        80              85                  90

Trp Ala Met Ala Ser Ala Arg Ala Tyr Gln Ile Thr Asn Asp Glu Arg
95              100                 105

Tyr Leu Glu Gln Ala Glu Tyr Tyr Phe Asn Tyr Val Tyr Asp Asn Glu
110             115                 120                 125

Trp Asp Thr Glu Phe Ala Gly Gly Ile Trp Trp Lys Ser Asp Asp
            130                 135                 140

Arg Thr Thr Lys Asn Ala Cys Ile Asn Phe Pro Ala Ala Gln Thr Ala
                145                 150                 155

Val Phe Leu Tyr Asn Val Thr Gln Asp Glu Gln Tyr Leu Asp Ala Ala
                160                 165                 170

Glu Thr Ile Tyr His Trp Gly Lys Thr Ile Leu Thr Asp Gly Asn Gly
            175                 180                 185

Lys Val Phe Asp Arg Ile Glu Thr Gln Asn Gly Ala Ile Gln Gly Ala
190                 195                 200                 205

Thr His Tyr Asn Gln Gly Ala Phe Ile Gly Ser Ala Ala Gly Leu Tyr
                210                 215                 220

Glu Ile Thr Gly Asp Thr Asp Tyr Leu Asp Asp Ala Ile Lys Ala Ala
            225                 230                 235

Thr Tyr Thr Lys Glu His Met Val Asp Val Asn Gly Leu Leu Arg Tyr
            240                 245                 250

Glu Gly Pro Asn Gly Asp Leu Lys Gly Gly Lys Thr Ile Leu Leu Arg
            255                 260                 265

Asn Leu Gly Tyr Phe Gln Ala Ala Ile Asp Ala Arg Gln Glu Glu Asn
270                 275                 280                 285

Tyr Gln Ser Phe Ala Glu Ser Tyr Asn Glu Trp Leu Ala Phe Asn Ala
                290                 295                 300

Asp Met Ala Trp Asn Asn Arg Asn Ala Ala Asn Leu Val Asp Gly Asn
            305                 310                 315

Trp Ala Gly Gln Gln Leu Ser Gly Ala Ile Glu Ser Trp Ser Ala Ala
            320                 325                 330

Ala Ala Val Gln Ala Leu Ile Ser Leu Lys Pro Gln Asn Ala Val Gln
            335                 340                 345

Leu Gly Tyr Ala Val Lys Asn Pro Tyr Asn Arg Ile Glu Ala Glu Ser
350                 355                 360                 365
```

```
Tyr Asn Ile Ile Asn Gly Pro Gly Leu Glu Asp Ser Asn Glu Gly Ser
                370                 375                 380

Gln Gln Leu Ala Gly Ile Gln Asp Ser His Tyr Ala Ala Tyr Lys Asn
            385                 390                 395

Val Asp Phe Gly Ser Glu Asp Gly Ala Ser Gly Phe Ile Ala Arg Ala
        400                 405                 410

Ser Ser Gly Thr Gly Gly Gln Ile Glu Ile Arg Leu Asp Ala Leu
415                 420                 425

Asp Gly Pro Lys Ala Gly Thr Leu Asn Val Asn Gly Thr Gly Gly Trp
430                 435                 440                 445

Asn Asn Tyr Ile Asp Ala Ala Val Leu Leu Lys Asp Glu Gln Gly Asn
                450                 455                 460

Pro Ser Pro Val Thr Gly Val His Asp Val Tyr Leu Val Phe Lys Arg
            465                 470                 475

Thr Asn Asp Thr Tyr Leu Phe Asn Leu Asn Trp Phe Gln Phe Thr Lys
        480                 485                 490

Val Asp Pro Thr Leu Ile Ser Ala Tyr Thr Ile Leu Gln Ala Glu His
    495                 500                 505

Phe Ala Ser Ser Asp Gly Leu Ser Ile Asn Ser Thr Gly Gln Tyr Ala
510                 515                 520                 525

Asp Gly Ile Gln Asn Thr Ala Tyr Ala Ser Tyr Glu Asn Ile Asp Phe
                530                 535                 540

Gly

<210> SEQ ID NO 24
<211> LENGTH: 542
<212> TYPE: PRT
<213> ORGANISM: Artificial Sequence
<220> FEATURE:
<223> OTHER INFORMATION: Synthetic construct

<400> SEQUENCE: 24

Phe Glu Ala Glu Asp Ala Lys Thr Ala Ile Val Ala Tyr Asn Asp Ala
1               5                   10                  15

Phe Trp Asp Ala Asn Ala Lys Tyr Phe Trp Lys Ser Thr Asn Arg Thr
            20                  25                  30

Asp Tyr Gln Asp Phe Trp Ile Glu Ala Glu Leu Trp Glu Leu Val Met
        35                  40                  45

Asp Ala Tyr Leu His Thr Ser Asp Pro Glu Leu Lys Ala Gln Leu Arg
    50                  55                  60

Thr Gln Ile Asp Asp Val Phe Asp Gly Ala Val Thr Arg Tyr Gly Glu
65                  70                  75                  80

Asp Trp Thr Tyr Asn Pro Tyr Asn Asp Ile Met Trp Trp Ala Met
                85                  90                  95

Ala Ser Ala Arg Ala Tyr Gln Ile Thr Asn Asp Glu Arg Tyr Leu Glu
            100                 105                 110

Gln Ala Glu Tyr Tyr Phe Asn Tyr Val Tyr Asp Asn Glu Trp Asp Thr
        115                 120                 125

Glu Phe Ala Gly Gly Gly Ile Trp Trp Lys Ser Asp Asp Arg Thr Thr
    130                 135                 140

Lys Asn Ala Cys Ile Asn Phe Pro Ala Ala Gln Thr Ala Val Phe Leu
145                 150                 155                 160

Tyr Asn Val Thr Gln Asp Glu Gln Tyr Leu Asp Ala Ala Glu Thr Ile
                165                 170                 175
```

-continued

```
Tyr His Trp Gly Lys Thr Ile Leu Thr Asp Gly Asn Gly Lys Val Phe
                180                 185                 190

Asp Arg Ile Glu Thr Gln Asn Gly Ala Ile Gln Gly Ala Thr His Tyr
            195                 200                 205

Asn Gln Gly Ala Phe Ile Gly Ser Ala Ala Gly Leu Tyr Glu Ile Thr
        210                 215                 220

Gly Asp Thr Asp Tyr Leu Asp Asp Ala Ile Lys Ala Thr Tyr Thr
225                 230                 235                 240

Lys Glu His Met Val Asp Val Asn Gly Leu Leu Arg Tyr Glu Gly Pro
                245                 250                 255

Asn Gly Asp Leu Lys Gly Gly Lys Thr Ile Leu Leu Arg Asn Leu Gly
            260                 265                 270

Tyr Phe Gln Ala Ala Ile Asp Ala Arg Gln Glu Glu Asn Tyr Gln Ser
        275                 280                 285

Phe Ala Glu Ser Tyr Asn Glu Trp Leu Ala Phe Asn Ala Asp Met Ala
    290                 295                 300

Trp Asn Asn Arg Asn Ala Ala Asn Leu Val Asp Gly Asn Trp Ala Gly
305                 310                 315                 320

Gln Gln Leu Ser Gly Ala Ile Glu Ser Trp Ser Ala Ala Ala Val
                325                 330                 335

Gln Ala Leu Ile Ser Leu Lys Pro Gln Asn Ala Val Gln Leu Gly Tyr
            340                 345                 350

Ala Val Lys Asn Pro Tyr Asn Arg Ile Glu Ala Glu Ser Tyr Asn Ile
        355                 360                 365

Ile Asn Gly Pro Gly Leu Glu Asp Ser Asn Gly Ser Gln Gln Leu
    370                 375                 380

Ala Gly Ile Gln Asp Ser His Tyr Ala Ala Tyr Lys Asn Val Asp Phe
385                 390                 395                 400

Gly Ser Glu Asp Gly Ala Ser Gly Phe Ile Ala Arg Ala Ser Ser Gly
                405                 410                 415

Thr Gly Gly Gly Gln Ile Glu Ile Arg Leu Asp Ala Leu Asp Gly Pro
            420                 425                 430

Lys Ala Gly Thr Leu Asn Val Asn Gly Thr Gly Gly Trp Asn Asn Tyr
        435                 440                 445

Ile Asp Ala Ala Val Leu Leu Lys Asp Glu Gln Gly Asn Pro Ser Pro
    450                 455                 460

Val Thr Gly Val His Asp Val Tyr Leu Val Phe Lys Arg Thr Asn Asp
465                 470                 475                 480

Thr Tyr Leu Phe Asn Leu Asn Trp Phe Gln Phe Thr Lys Val Asp Pro
                485                 490                 495

Thr Leu Ile Ser Ala Tyr Thr Ile Leu Gln Ala Glu His Phe Ala Ser
            500                 505                 510

Ser Asp Gly Leu Ser Ile Asn Ser Thr Gly Gln Tyr Ala Asp Gly Ile
        515                 520                 525

Gln Asn Thr Ala Tyr Ala Ser Tyr Glu Asn Ile Asp Phe Gly
    530                 535                 540

<210> SEQ ID NO 25
<211> LENGTH: 4236
<212> TYPE: DNA
<213> ORGANISM: Bacillus novalis
<220> FEATURE:
<221> NAME/KEY: CDS
<222> LOCATION: (1)..(4233)
<220> FEATURE:
<221> NAME/KEY: sig_peptide
```

```
<222> LOCATION: (1)..(99)
<220> FEATURE:
<221> NAME/KEY: mat_peptide
<222> LOCATION: (100)..(4233)

<400> SEQUENCE: 25 atg aaa aaa aga gcg atc caa aag atc att tcg agt att gta tcc ctc        48
Met Lys Lys Arg Ala Ile Gln Lys Ile Ile Ser Ser Ile Val Ser Leu
            -30                 -25                 -20 gca gtt ctg acc agt gtc cct gtt atg caa aaa cca tct gta ttg gca        96
Ala Val Leu Thr Ser Val Pro Val Met Gln Lys Pro Ser Val Leu Ala
        -15                 -10                  -5 gca tcg tct gat tcc act tca gca tcg aaa acg gat ttc ttt agc tcg       144
Ala Ser Ser Asp Ser Thr Ser Ala Ser Lys Thr Asp Phe Phe Ser Ser
 -1   1              5                  10                  15 ttt gaa aaa tcc gat ctg caa ctc act tgg act aat aca gtg gag aca       192
Phe Glu Lys Ser Asp Leu Gln Leu Thr Trp Thr Asn Thr Val Glu Thr
             20                  25                  30 gat gct aac gga aag aaa atg tcc tca gga att gat ggg aat gtt aag       240
Asp Ala Asn Gly Lys Lys Met Ser Ser Gly Ile Asp Gly Asn Val Lys
             35                  40                  45 cgg gat tta atc ctt ggc gat att acc gat aaa gtt gtt caa gta aca       288
Arg Asp Leu Ile Leu Gly Asp Ile Thr Asp Lys Val Val Gln Val Thr
             50                  55                  60 gcg agt gca aac aat ccc ccg aat gaa atc gat tct aag ttg atc gat       336
Ala Ser Ala Asn Asn Pro Pro Asn Glu Ile Asp Ser Lys Leu Ile Asp
         65                  70                  75 ggg gac ccg aca aca aaa tgg tta gca ttt gaa ccg act gct aac atc       384
Gly Asp Pro Thr Thr Lys Trp Leu Ala Phe Glu Pro Thr Ala Asn Ile
 80                  85                  90                  95 gtc ctt aag ctg gct gaa cca gtg gcc gtt gtc aaa tat gcc tta aca       432
Val Leu Lys Leu Ala Glu Pro Val Ala Val Val Lys Tyr Ala Leu Thr
                100                 105                 110 tct gct aat gac gct aaa gga agg gat cca aaa aac tgg aca tta tac       480
Ser Ala Asn Asp Ala Lys Gly Arg Asp Pro Lys Asn Trp Thr Leu Tyr
            115                 120                 125 ggt tcc tta gat gga acg aat tgg aca gcc gtc gat aca cga gaa ggg       528
Gly Ser Leu Asp Gly Thr Asn Trp Thr Ala Val Asp Thr Arg Glu Gly
            130                 135                 140 gaa gat ttt aaa gat cgc ttc caa cga aat atg tat gat tta aaa aat       576
Glu Asp Phe Lys Asp Arg Phe Gln Arg Asn Met Tyr Asp Leu Lys Asn
145                 150                 155 act aca aag tac ttg tat tac aaa ttg gac att acg aaa aat gct ggt       624
Thr Thr Lys Tyr Leu Tyr Tyr Lys Leu Asp Ile Thr Lys Asn Ala Gly
160                 165                 170                 175 gac agt att acc cag tta gcg gaa att tct tta tca gac gga att gaa       672
Asp Ser Ile Thr Gln Leu Ala Glu Ile Ser Leu Ser Asp Gly Ile Glu
                180                 185                 190 gtt cca gca cca ccg ccg gga gat atg aag tcg cta ata gga aaa ggc       720
Val Pro Ala Pro Pro Pro Gly Asp Met Lys Ser Leu Ile Gly Lys Gly
            195                 200                 205 cca act agt tct tat acc gct aaa aca aat gtg ggc tgg acc gga tta       768
Pro Thr Ser Ser Tyr Thr Ala Lys Thr Asn Val Gly Trp Thr Gly Leu
            210                 215                 220 ggt gcc ctt aat tat tca ggt aca cat ctt tca gac gga agg gct tat       816
Gly Ala Leu Asn Tyr Ser Gly Thr His Leu Ser Asp Gly Arg Ala Tyr
            225                 230                 235 tct tac aac aag ctt tat gat gtc gac atc ctt gtt acc cca gca aca       864
Ser Tyr Asn Lys Leu Tyr Asp Val Asp Ile Leu Val Thr Pro Ala Thr
240                 245                 250                 255
```

```
gag ctt tcg tat ttt att gcc cca gaa ttt aca gat aaa aat cat aat    912
Glu Leu Ser Tyr Phe Ile Ala Pro Glu Phe Thr Asp Lys Asn His Asn
                260                 265                 270 gac tat tca agc aca tat gtc tct gtg gac ctt gcc ttt tca gat gga    960
Asp Tyr Ser Ser Thr Tyr Val Ser Val Asp Leu Ala Phe Ser Asp Gly
            275                 280                 285 acc tac ctt cat gat ctt aaa gca gta gac cag tat ggt gta gga ctt   1008
Thr Tyr Leu His Asp Leu Lys Ala Val Asp Gln Tyr Gly Val Gly Leu
        290                 295                 300 aat ccg aaa gac caa ggt gat tca aaa tac tta tac gta aac caa tgg   1056
Asn Pro Lys Asp Gln Gly Asp Ser Lys Tyr Leu Tyr Val Asn Gln Trp
    305                 310                 315 aac aca att aaa tct act att ggt tct gtt gcg gca ggt aaa acc ata   1104
Asn Thr Ile Lys Ser Thr Ile Gly Ser Val Ala Ala Gly Lys Thr Ile
320                 325                 330                 335 aaa agg att cta gta gcc tac gat aat cca aaa ggc cct gga gcc ttt   1152
Lys Arg Ile Leu Val Ala Tyr Asp Asn Pro Lys Gly Pro Gly Ala Phe
                340                 345                 350 aga gga agc atc gat gat att aaa att gat gga aaa cct gtt cag aaa   1200
Arg Gly Ser Ile Asp Asp Ile Lys Ile Asp Gly Lys Pro Val Gln Lys
            355                 360                 365 gca ttt ggt tct cca att gac tat gta aat atc ctt cgc ggg aca caa   1248
Ala Phe Gly Ser Pro Ile Asp Tyr Val Asn Ile Leu Arg Gly Thr Gln
        370                 375                 380 tcg aac gga tca ttt tct cgt gga aat aac ttc cca gcc gtg gcg att   1296
Ser Asn Gly Ser Phe Ser Arg Gly Asn Asn Phe Pro Ala Val Ala Ile
    385                 390                 395 ccg cat gga ttt aac ttt tgg aca cca act act aat gca gga tct agt   1344
Pro His Gly Phe Asn Phe Trp Thr Pro Thr Thr Asn Ala Gly Ser Ser
400                 405                 410                 415 tgg att tat caa tat cat gaa agc aac agt gtc aat aat ctc cca caa   1392
Trp Ile Tyr Gln Tyr His Glu Ser Asn Ser Val Asn Asn Leu Pro Gln
                420                 425                 430 atc caa gct ttt tct gtc agc cat gaa cca agc cct tgg atg ggg gat   1440
Ile Gln Ala Phe Ser Val Ser His Glu Pro Ser Pro Trp Met Gly Asp
            435                 440                 445 cgt cag aca ttc caa gtg atg cca tcc gct tcg acg gca gct aca cca   1488
Arg Gln Thr Phe Gln Val Met Pro Ser Ala Ser Thr Ala Ala Thr Pro
        450                 455                 460 aat gca aat cgt gat tca cgt gca tta gaa ttt aac cat gcg aat gaa   1536
Asn Ala Asn Arg Asp Ser Arg Ala Leu Glu Phe Asn His Ala Asn Glu
    465                 470                 475 att gcc cag cca cac tat tac agc gtg aaa ttt gaa aat ggg att cgt   1584
Ile Ala Gln Pro His Tyr Tyr Ser Val Lys Phe Glu Asn Gly Ile Arg
480                 485                 490                 495 acg gaa atg act cca aca gac cat gca gct atg ttt aag ttt act ttt   1632
Thr Glu Met Thr Pro Thr Asp His Ala Ala Met Phe Lys Phe Thr Phe
                500                 505                 510 aca ggt gcc aca tct aac ctc att ttt gat aat gtt aac aat aat gga   1680
Thr Gly Ala Thr Ser Asn Leu Ile Phe Asp Asn Val Asn Asn Asn Gly
            515                 520                 525 ggc ctt aca atc gat gct aaa tca gga gag atc acc ggc tat tct gat   1728
Gly Leu Thr Ile Asp Ala Lys Ser Gly Glu Ile Thr Gly Tyr Ser Asp
        530                 535                 540 gtg aaa agc ggc ctc tct aca gga gca acg cgc ttg ttc gtc tac gca   1776
Val Lys Ser Gly Leu Ser Thr Gly Ala Thr Arg Leu Phe Val Tyr Ala
    545                 550                 555 gca ttt gat aag cct gtt att aaa agt ggc aaa tta aca ggt gaa agt   1824
Ala Phe Asp Lys Pro Val Ile Lys Ser Gly Lys Leu Thr Gly Glu Ser
560                 565                 570                 575
```

```
aga aac aat gtc aca gga tat gtc cga ttc gat act tct aaa gat gaa    1872
Arg Asn Asn Val Thr Gly Tyr Val Arg Phe Asp Thr Ser Lys Asp Glu
                580                 585                 590 gac aaa gtt gtc act atg aaa att gca aca tcc tta att agt gtc gag    1920
Asp Lys Val Val Thr Met Lys Ile Ala Thr Ser Leu Ile Ser Val Glu
            595                 600                 605 caa gca aag aaa aat ctc gaa cag gaa atc gga ttg aat gat acg ttt    1968
Gln Ala Lys Lys Asn Leu Glu Gln Glu Ile Gly Leu Asn Asp Thr Phe
        610                 615                 620 gag gga cta aaa gaa aaa gcg aaa aca gag tgg aat aaa aag ttg ggc    2016
Glu Gly Leu Lys Glu Lys Ala Lys Thr Glu Trp Asn Lys Lys Leu Gly
    625                 630                 635 atc atc gaa gta gaa gga gca tcg gag gat cag ctc gtt acg ctt tat    2064
Ile Ile Glu Val Glu Gly Ala Ser Glu Asp Gln Leu Val Thr Leu Tyr
640                 645                 650                 655 tct aat tta tac cgc ttg ttc ttg tat ccg aat tct gcc ttt gaa aat    2112
Ser Asn Leu Tyr Arg Leu Phe Leu Tyr Pro Asn Ser Ala Phe Glu Asn
                660                 665                 670 gtc gga acg aca act gac cca gtc tat aaa tat gca agt ccg tat tca    2160
Val Gly Thr Thr Thr Asp Pro Val Tyr Lys Tyr Ala Ser Pro Tyr Ser
            675                 680                 685 gcg gca act ggc caa gat aca gcg aca aca act ggt gca aaa atc gtc    2208
Ala Ala Thr Gly Gln Asp Thr Ala Thr Thr Thr Gly Ala Lys Ile Val
        690                 695                 700 gac gga aaa acg tat gtc aat aac ggc ttc tgg gac act tac aga aca    2256
Asp Gly Lys Thr Tyr Val Asn Asn Gly Phe Trp Asp Thr Tyr Arg Thr
    705                 710                 715 gca tgg ccc gcc tat tct tta tta aca cca aca ttt gct ggt gaa ctg    2304
Ala Trp Pro Ala Tyr Ser Leu Leu Thr Pro Thr Phe Ala Gly Glu Leu
720                 725                 730                 735 att gat gga ttt gtc cag caa tac aga gat ggc ggc tgg ata gca cgg    2352
Ile Asp Gly Phe Val Gln Gln Tyr Arg Asp Gly Gly Trp Ile Ala Arg
                740                 745                 750 tgg tct tca cca gga ttt gca aac tta atg ccg ggt acg agt tcg gat    2400
Trp Ser Ser Pro Gly Phe Ala Asn Leu Met Pro Gly Thr Ser Ser Asp
            755                 760                 765 gtc gcc ttt gcg gat gct tat ctt aaa ggg gta acg aat ttt gat gtc    2448
Val Ala Phe Ala Asp Ala Tyr Leu Lys Gly Val Thr Asn Phe Asp Val
        770                 775                 780 cag agc ttt tac caa tcg gcg att cga aat gca gag gct gtc agt cct    2496
Gln Ser Phe Tyr Gln Ser Ala Ile Arg Asn Ala Glu Ala Val Ser Pro
    785                 790                 795 aat gcc ggc aca ggc cga aaa ggg cta aca act tcg ata ttt gat gga    2544
Asn Ala Gly Thr Gly Arg Lys Gly Leu Thr Thr Ser Ile Phe Asp Gly
800                 805                 810                 815 tat acc aat act tca acg ggt gaa gga tta gca tgg gca atg gat ggc    2592
Tyr Thr Asn Thr Ser Thr Gly Glu Gly Leu Ala Trp Ala Met Asp Gly
                820                 825                 830 tat att aac gac ttc ggt atc gct aat ttg gca aag gct cta aaa gaa    2640
Tyr Ile Asn Asp Phe Gly Ile Ala Asn Leu Ala Lys Ala Leu Lys Glu
            835                 840                 845 aag ggc gac aag agt gat ccc tac tat gct aac tat gct gca gat tat    2688
Lys Gly Asp Lys Ser Asp Pro Tyr Tyr Ala Asn Tyr Ala Ala Asp Tyr
        850                 855                 860 cag tac ttc ctg aat cgt gcg caa aac tat gtg cat atg ttc aat cca    2736
Gln Tyr Phe Leu Asn Arg Ala Gln Asn Tyr Val His Met Phe Asn Pro
    865                 870                 875 tcc att gaa ttt ttt aat ggc aga aca gca aat ggg gca tgg aga tca    2784
Ser Ile Glu Phe Phe Asn Gly Arg Thr Ala Asn Gly Ala Trp Arg Ser
```

-continued

| | | | | | | | | | | | | | | |
|---|---|---|---|---|---|---|---|---|---|---|---|---|---|---|
|880| |  |885| |  |  |890| |  |  |895| |  |  |

```
aca  ccg  gat  aac  ttc  aat  cct  gcc  gtt  tgg  ggg  tcc  gat  tat  aca  gaa    2832
Thr  Pro  Asp  Asn  Phe  Asn  Pro  Ala  Val  Trp  Gly  Ser  Asp  Tyr  Thr  Glu
                         900                      905                      910 aca  aat  ggc  tgg  aat  atg  gcg  ttc  cat  gta  cca  caa  gac  ggt  cag  ggg    2880
Thr  Asn  Gly  Trp  Asn  Met  Ala  Phe  His  Val  Pro  Gln  Asp  Gly  Gln  Gly
                         915                      920                      925 cta  gcc  aat  ctc  tac  ggt  gga  aaa  gag  ggg  ctg  gcg  act  aag  ctt  gat    2928
Leu  Ala  Asn  Leu  Tyr  Gly  Gly  Lys  Glu  Gly  Leu  Ala  Thr  Lys  Leu  Asp
                         930                      935                      940 caa  ttc  ttt  agc  aca  tca  gaa  aca  gga  ttg  ttt  cct  ggc  tca  tat  ggc    2976
Gln  Phe  Phe  Ser  Thr  Ser  Glu  Thr  Gly  Leu  Phe  Pro  Gly  Ser  Tyr  Gly
               945                      950                      955 ggg  aca  atc  cat  gaa  atg  aga  gag  gca  aga  gat  gtc  aga  atg  ggg  atg    3024
Gly  Thr  Ile  His  Glu  Met  Arg  Glu  Ala  Arg  Asp  Val  Arg  Met  Gly  Met
960                      965                      970                      975 tat  ggc  cat  agc  aat  cag  ccg  tcc  cat  cat  atc  gcc  tac  atg  tat  gat    3072
Tyr  Gly  His  Ser  Asn  Gln  Pro  Ser  His  His  Ile  Ala  Tyr  Met  Tyr  Asp
                         980                      985                      990 tac  gct  gga  cag  cca  tgg  aag  aca  cag  gaa  aaa  gtc  cgt  gaa  gcc  ctt    3120
Tyr  Ala  Gly  Gln  Pro  Trp  Lys  Thr  Gln  Glu  Lys  Val  Arg  Glu  Ala  Leu
               995                      1000                     1005 aat  cga  ctt  tac  att  ggc  agt  gca  atc  ggc  caa  gga  tat  tcc  ggg         3165
Asn  Arg  Leu  Tyr  Ile  Gly  Ser  Ala  Ile  Gly  Gln  Gly  Tyr  Ser  Gly
               1010                     1015                     1020 gat  gag  gat  aac  ggt  gaa  atg  tcc  gcc  tgg  tat  atc  tta  agc  gca         3210
Asp  Glu  Asp  Asn  Gly  Glu  Met  Ser  Ala  Trp  Tyr  Ile  Leu  Ser  Ala
               1025                     1030                     1035 atg  gga  ttc  tat  ccg  ctt  aaa  atg  ggt  aca  cct  gaa  tat  gcg  att         3255
Met  Gly  Phe  Tyr  Pro  Leu  Lys  Met  Gly  Thr  Pro  Glu  Tyr  Ala  Ile
               1040                     1045                     1050 ggt  gca  ccg  tta  ttt  aag  aag  gca  acc  atc  cat  ttg  gaa  aat  gga         3300
Gly  Ala  Pro  Leu  Phe  Lys  Lys  Ala  Thr  Ile  His  Leu  Glu  Asn  Gly
               1055                     1060                     1065 aaa  tca  att  gtt  ata  aac  gct  cct  aac  aat  agc  aag  gaa  aac  aaa         3345
Lys  Ser  Ile  Val  Ile  Asn  Ala  Pro  Asn  Asn  Ser  Lys  Glu  Asn  Lys
               1070                     1075                     1080 tat  gtg  caa  agt  atg  aaa  gta  aat  gga  aaa  gcc  tat  gct  aaa  acc         3390
Tyr  Val  Gln  Ser  Met  Lys  Val  Asn  Gly  Lys  Ala  Tyr  Ala  Lys  Thr
               1085                     1090                     1095 tcc  ata  tta  cat  gcg  gat  atc  gcc  aat  ggt  gcc  gta  att  gat  ttt         3435
Ser  Ile  Leu  His  Ala  Asp  Ile  Ala  Asn  Gly  Ala  Val  Ile  Asp  Phe
               1100                     1105                     1110 gaa  atg  gga  tcc  aag  cca  tcc  aaa  tgg  ggc  agc  gga  gat  cag  gat         3480
Glu  Met  Gly  Ser  Lys  Pro  Ser  Lys  Trp  Gly  Ser  Gly  Asp  Gln  Asp
               1115                     1120                     1125 att  tta  caa  tcg  att  act  ccg  ggg  tct  aca  gat  ggg  aca  tca  ttg         3525
Ile  Leu  Gln  Ser  Ile  Thr  Pro  Gly  Ser  Thr  Asp  Gly  Thr  Ser  Leu
               1130                     1135                     1140 tct  cca  ctg  cca  tta  cgt  gat  gta  aca  gat  cgt  tta  att  gca  gcg         3570
Ser  Pro  Leu  Pro  Leu  Arg  Asp  Val  Thr  Asp  Arg  Leu  Ile  Ala  Ala
               1145                     1150                     1155 gaa  aaa  gga  gct  gta  act  gta  agt  gat  gag  gga  aat  gga  caa  tta         3615
Glu  Lys  Gly  Ala  Val  Thr  Val  Ser  Asp  Glu  Gly  Asn  Gly  Gln  Leu
               1160                     1165                     1170 ttg  ttt  gat  aac  aca  tca  aac  act  caa  tta  tct  atg  aag  agt  aaa         3660
Leu  Phe  Asp  Asn  Thr  Ser  Asn  Thr  Gln  Leu  Ser  Met  Lys  Ser  Lys
               1175                     1180                     1185 acc  cca  tcg  att  gtg  tat  caa  ttt  aag  gaa  ggc  aaa  caa  aac  gta         3705
```

```
Thr Pro Ser Ile Val Tyr Gln Phe Lys Glu Gly Lys Gln Asn Val
        1190            1195            1200 aaa atg tat acg ttg act tct tca aaa gct tca cag aat gag gat      3750
Lys Met Tyr Thr Leu Thr Ser Ser Lys Ala Ser Gln Asn Glu Asp
        1205            1210            1215 cca aaa tct tgg gta tta aaa ggt tca aat gat ggg aag agt tgg      3795
Pro Lys Ser Trp Val Leu Lys Gly Ser Asn Asp Gly Lys Ser Trp
        1220            1225            1230 agc gtc ctt gat caa aga aaa aat gaa acg ttc caa tgg cgt caa      3840
Ser Val Leu Asp Gln Arg Lys Asn Glu Thr Phe Gln Trp Arg Gln
        1235            1240            1245 tat acg agg gcc ttt acg att caa cat cca ggg aag tat tca cag      3885
Tyr Thr Arg Ala Phe Thr Ile Gln His Pro Gly Lys Tyr Ser Gln
        1250            1255            1260 tat aag ctc gaa ata aca gaa aat gct gga gcg gag gtt act act      3930
Tyr Lys Leu Glu Ile Thr Glu Asn Ala Gly Ala Glu Val Thr Thr
        1265            1270            1275 tta gca gag ctt gag ctc cta ggc tat gat gat gta acc aat agc      3975
Leu Ala Glu Leu Glu Leu Leu Gly Tyr Asp Asp Val Thr Asn Ser
        1280            1285            1290 tat cag gct gtg tat gag cta atg gaa caa ttt aaa cag tcc aaa      4020
Tyr Gln Ala Val Tyr Glu Leu Met Glu Gln Phe Lys Gln Ser Lys
        1295            1300            1305 gac tta aca gga cca atg gct gta caa ttg aac aac agt tta acc      4065
Asp Leu Thr Gly Pro Met Ala Val Gln Leu Asn Asn Ser Leu Thr
        1310            1315            1320 aca tcg cta gat cat ttc aaa aag gat cat aag gat cag gca atc      4110
Thr Ser Leu Asp His Phe Lys Lys Asp His Lys Asp Gln Ala Ile
        1325            1330            1335 aag cat ctg gaa gat ttc tta aag cac ctt aat aat aaa ggt tta      4155
Lys His Leu Glu Asp Phe Leu Lys His Leu Asn Asn Lys Gly Leu
        1340            1345            1350 cag gac cgg att tct tct aag gca aaa ggg gtc ctc tct gcc gat      4200
Gln Asp Arg Ile Ser Ser Lys Ala Lys Gly Val Leu Ser Ala Asp
        1355            1360            1365 gcg aat caa ctg att gta tta cta gca aga gat taa                  4236
Ala Asn Gln Leu Ile Val Leu Leu Ala Arg Asp
        1370            1375

<210> SEQ ID NO 26
<211> LENGTH: 1411
<212> TYPE: PRT
<213> ORGANISM: Bacillus novalis

<400> SEQUENCE: 26

Met Lys Lys Arg Ala Ile Gln Lys Ile Ile Ser Ser Ile Val Ser Leu
            -30                 -25                 -20

Ala Val Leu Thr Ser Val Pro Val Met Gln Lys Pro Ser Val Leu Ala
        -15                 -10                 -5

Ala Ser Ser Asp Ser Thr Ser Ala Ser Lys Thr Asp Phe Phe Ser Ser
 -1  1               5                  10                  15

Phe Glu Lys Ser Asp Leu Gln Leu Thr Trp Thr Asn Thr Val Glu Thr
                20                  25                  30

Asp Ala Asn Gly Lys Lys Met Ser Ser Gly Ile Asp Gly Asn Val Lys
            35                  40                  45

Arg Asp Leu Ile Leu Gly Asp Ile Thr Asp Lys Val Val Gln Val Thr
        50                  55                  60

Ala Ser Ala Asn Asn Pro Pro Asn Glu Ile Asp Ser Lys Leu Ile Asp
 65                  70                  75
```

```
Gly Asp Pro Thr Thr Lys Trp Leu Ala Phe Glu Pro Thr Ala Asn Ile
 80              85                  90                  95

Val Leu Lys Leu Ala Glu Pro Val Ala Val Lys Tyr Ala Leu Thr
            100                 105                 110

Ser Ala Asn Asp Ala Lys Gly Arg Asp Pro Lys Asn Trp Thr Leu Tyr
            115                 120                 125

Gly Ser Leu Asp Gly Thr Asn Trp Thr Ala Val Asp Thr Arg Glu Gly
            130                 135                 140

Glu Asp Phe Lys Asp Arg Phe Gln Arg Asn Met Tyr Asp Leu Lys Asn
            145                 150                 155

Thr Thr Lys Tyr Leu Tyr Tyr Lys Leu Asp Ile Thr Lys Asn Ala Gly
160             165                 170                 175

Asp Ser Ile Thr Gln Leu Ala Glu Ile Ser Leu Ser Asp Gly Ile Glu
                180                 185                 190

Val Pro Ala Pro Pro Gly Asp Met Lys Ser Leu Ile Gly Lys Gly
            195                 200                 205

Pro Thr Ser Ser Tyr Thr Ala Lys Thr Asn Val Gly Trp Thr Gly Leu
            210                 215                 220

Gly Ala Leu Asn Tyr Ser Gly Thr His Leu Ser Asp Gly Arg Ala Tyr
225             230                 235

Ser Tyr Asn Lys Leu Tyr Asp Val Asp Ile Leu Val Thr Pro Ala Thr
240             245                 250                 255

Glu Leu Ser Tyr Phe Ile Ala Pro Glu Phe Thr Asp Lys Asn His Asn
                260                 265                 270

Asp Tyr Ser Ser Thr Tyr Val Ser Val Asp Leu Ala Phe Ser Asp Gly
            275                 280                 285

Thr Tyr Leu His Asp Leu Lys Ala Val Asp Gln Tyr Gly Val Gly Leu
            290                 295                 300

Asn Pro Lys Asp Gln Gly Asp Ser Lys Tyr Leu Tyr Val Asn Gln Trp
305             310                 315

Asn Thr Ile Lys Ser Thr Ile Gly Ser Val Ala Ala Gly Lys Thr Ile
320             325                 330                 335

Lys Arg Ile Leu Val Ala Tyr Asp Asn Pro Lys Gly Pro Gly Ala Phe
                340                 345                 350

Arg Gly Ser Ile Asp Asp Ile Lys Ile Asp Gly Lys Pro Val Gln Lys
            355                 360                 365

Ala Phe Gly Ser Pro Ile Asp Tyr Val Asn Ile Leu Arg Gly Thr Gln
            370                 375                 380

Ser Asn Gly Ser Phe Ser Arg Gly Asn Asn Phe Pro Ala Val Ala Ile
385             390                 395

Pro His Gly Phe Asn Phe Trp Thr Pro Thr Thr Asn Ala Gly Ser Ser
400             405                 410                 415

Trp Ile Tyr Gln Tyr His Glu Ser Asn Ser Val Asn Asn Leu Pro Gln
                420                 425                 430

Ile Gln Ala Phe Ser Val Ser His Glu Pro Ser Pro Trp Met Gly Asp
            435                 440                 445

Arg Gln Thr Phe Gln Val Met Pro Ser Ala Ser Thr Ala Ala Thr Pro
            450                 455                 460

Asn Ala Asn Arg Asp Ser Arg Ala Leu Glu Phe Asn His Ala Asn Glu
            465                 470                 475

Ile Ala Gln Pro His Tyr Tyr Ser Val Lys Phe Glu Asn Gly Ile Arg
480             485                 490                 495
```

-continued

```
Thr Glu Met Thr Pro Thr Asp His Ala Ala Met Phe Lys Phe Thr Phe
                500                 505                 510

Thr Gly Ala Thr Ser Asn Leu Ile Phe Asp Asn Val Asn Asn Asn Gly
            515                 520                 525

Gly Leu Thr Ile Asp Ala Lys Ser Gly Glu Ile Thr Gly Tyr Ser Asp
        530                 535                 540

Val Lys Ser Gly Leu Ser Thr Gly Ala Thr Arg Leu Phe Val Tyr Ala
545                 550                 555

Ala Phe Asp Lys Pro Val Ile Lys Ser Gly Lys Leu Thr Gly Glu Ser
560                 565                 570                 575

Arg Asn Asn Val Thr Gly Tyr Val Arg Phe Asp Thr Ser Lys Asp Glu
                580                 585                 590

Asp Lys Val Val Thr Met Lys Ile Ala Thr Ser Leu Ile Ser Val Glu
            595                 600                 605

Gln Ala Lys Lys Asn Leu Glu Gln Glu Ile Gly Leu Asn Asp Thr Phe
        610                 615                 620

Glu Gly Leu Lys Glu Lys Ala Lys Thr Glu Trp Asn Lys Lys Leu Gly
625                 630                 635

Ile Ile Glu Val Glu Gly Ala Ser Glu Asp Gln Leu Val Thr Leu Tyr
640                 645                 650                 655

Ser Asn Leu Tyr Arg Leu Phe Leu Tyr Pro Asn Ser Ala Phe Glu Asn
                660                 665                 670

Val Gly Thr Thr Thr Asp Pro Val Tyr Lys Tyr Ala Ser Pro Tyr Ser
            675                 680                 685

Ala Ala Thr Gly Gln Asp Thr Ala Thr Thr Gly Ala Lys Ile Val
        690                 695                 700

Asp Gly Lys Thr Tyr Val Asn Asn Gly Phe Trp Asp Thr Tyr Arg Thr
705                 710                 715

Ala Trp Pro Ala Tyr Ser Leu Leu Thr Pro Thr Phe Ala Gly Glu Leu
720                 725                 730                 735

Ile Asp Gly Phe Val Gln Gln Tyr Arg Asp Gly Gly Trp Ile Ala Arg
                740                 745                 750

Trp Ser Ser Pro Gly Phe Ala Asn Leu Met Pro Gly Thr Ser Ser Asp
            755                 760                 765

Val Ala Phe Ala Asp Ala Tyr Leu Lys Gly Val Thr Asn Phe Asp Val
        770                 775                 780

Gln Ser Phe Tyr Gln Ser Ala Ile Arg Asn Ala Glu Ala Val Ser Pro
785                 790                 795

Asn Ala Gly Thr Gly Arg Lys Gly Leu Thr Thr Ser Ile Phe Asp Gly
800                 805                 810                 815

Tyr Thr Asn Thr Ser Thr Gly Glu Gly Leu Ala Trp Ala Met Asp Gly
                820                 825                 830

Tyr Ile Asn Asp Phe Gly Ile Ala Asn Leu Ala Lys Ala Leu Lys Glu
            835                 840                 845

Lys Gly Asp Lys Ser Asp Pro Tyr Tyr Ala Asn Tyr Ala Ala Asp Tyr
        850                 855                 860

Gln Tyr Phe Leu Asn Arg Ala Gln Asn Tyr Val His Met Phe Asn Pro
865                 870                 875

Ser Ile Glu Phe Phe Asn Gly Arg Thr Ala Asn Gly Ala Trp Arg Ser
880                 885                 890                 895

Thr Pro Asp Asn Phe Asn Pro Ala Val Trp Gly Ser Asp Tyr Thr Glu
                900                 905                 910

Thr Asn Gly Trp Asn Met Ala Phe His Val Pro Gln Asp Gly Gln Gly
```

```
                915                 920                 925
Leu Ala Asn Leu Tyr Gly Gly Lys Glu Gly Leu Ala Thr Lys Leu Asp
            930                 935                 940

Gln Phe Phe Ser Thr Ser Glu Thr Gly Leu Phe Pro Gly Ser Tyr Gly
        945                 950                 955

Gly Thr Ile His Glu Met Arg Glu Ala Arg Asp Val Arg Met Gly Met
960                 965                 970                 975

Tyr Gly His Ser Asn Gln Pro Ser His His Ile Ala Tyr Met Tyr Asp
                980                 985                 990

Tyr Ala Gly Gln Pro Trp Lys Thr Gln Glu Lys Val Arg Glu Ala Leu
            995                 1000                1005

Asn Arg Leu Tyr Ile Gly Ser Ala Ile Gly Gln Gly Tyr Ser Gly
        1010                1015                1020

Asp Glu Asp Asn Gly Glu Met Ser Ala Trp Tyr Ile Leu Ser Ala
        1025                1030                1035

Met Gly Phe Tyr Pro Leu Lys Met Gly Thr Pro Glu Tyr Ala Ile
        1040                1045                1050

Gly Ala Pro Leu Phe Lys Lys Ala Thr Ile His Leu Glu Asn Gly
        1055                1060                1065

Lys Ser Ile Val Ile Asn Ala Pro Asn Asn Ser Lys Glu Asn Lys
        1070                1075                1080

Tyr Val Gln Ser Met Lys Val Asn Gly Lys Ala Tyr Ala Lys Thr
        1085                1090                1095

Ser Ile Leu His Ala Asp Ile Ala Asn Gly Ala Val Ile Asp Phe
        1100                1105                1110

Glu Met Gly Ser Lys Pro Ser Lys Trp Gly Ser Gly Asp Gln Asp
        1115                1120                1125

Ile Leu Gln Ser Ile Thr Pro Gly Ser Thr Asp Gly Thr Ser Leu
        1130                1135                1140

Ser Pro Leu Pro Leu Arg Asp Val Thr Asp Arg Leu Ile Ala Ala
        1145                1150                1155

Glu Lys Gly Ala Val Thr Val Ser Asp Glu Gly Asn Gly Gln Leu
        1160                1165                1170

Leu Phe Asp Asn Thr Ser Asn Thr Gln Leu Ser Met Lys Ser Lys
        1175                1180                1185

Thr Pro Ser Ile Val Tyr Gln Phe Lys Glu Gly Lys Gln Asn Val
        1190                1195                1200

Lys Met Tyr Thr Leu Thr Ser Ser Lys Ala Ser Gln Asn Glu Asp
        1205                1210                1215

Pro Lys Ser Trp Val Leu Lys Gly Ser Asn Asp Gly Lys Ser Trp
        1220                1225                1230

Ser Val Leu Asp Gln Arg Lys Asn Glu Thr Phe Gln Trp Arg Gln
        1235                1240                1245

Tyr Thr Arg Ala Phe Thr Ile Gln His Pro Gly Lys Tyr Ser Gln
        1250                1255                1260

Tyr Lys Leu Glu Ile Thr Glu Asn Ala Gly Ala Glu Val Thr Thr
        1265                1270                1275

Leu Ala Glu Leu Glu Leu Gly Tyr Asp Asp Val Thr Asn Ser
        1280                1285                1290

Tyr Gln Ala Val Tyr Glu Leu Met Glu Gln Phe Lys Gln Ser Lys
        1295                1300                1305

Asp Leu Thr Gly Pro Met Ala Val Gln Leu Asn Asn Ser Leu Thr
        1310                1315                1320
```

```
Thr Ser Leu Asp His Phe Lys Lys Asp His Lys Asp Gln Ala Ile
        1325                1330                1335

Lys His Leu Glu Asp Phe Leu Lys His Leu Asn Asn Lys Gly Leu
        1340                1345                1350

Gln Asp Arg Ile Ser Ser Lys Ala Lys Gly Val Leu Ser Ala Asp
        1355                1360                1365

Ala Asn Gln Leu Ile Val Leu Leu Ala Arg Asp
        1370                1375

<210> SEQ ID NO 27
<211> LENGTH: 1378
<212> TYPE: PRT
<213> ORGANISM: Bacillus novalis

<400> SEQUENCE: 27

Ser Ser Asp Ser Thr Ser Ala Ser Lys Thr Asp Phe Phe Ser Ser Phe
1               5                   10                  15

Glu Lys Ser Asp Leu Gln Leu Thr Trp Thr Asn Thr Val Glu Thr Asp
                20                  25                  30

Ala Asn Gly Lys Lys Met Ser Ser Gly Ile Asp Gly Asn Val Lys Arg
            35                  40                  45

Asp Leu Ile Leu Gly Asp Ile Thr Asp Lys Val Val Gln Val Thr Ala
        50                  55                  60

Ser Ala Asn Asn Pro Pro Asn Glu Ile Asp Ser Lys Leu Ile Asp Gly
65                  70                  75                  80

Asp Pro Thr Thr Lys Trp Leu Ala Phe Glu Pro Thr Ala Asn Ile Val
                85                  90                  95

Leu Lys Leu Ala Glu Pro Val Ala Val Val Lys Tyr Ala Leu Thr Ser
            100                 105                 110

Ala Asn Asp Ala Lys Gly Arg Asp Pro Lys Asn Trp Thr Leu Tyr Gly
        115                 120                 125

Ser Leu Asp Gly Thr Asn Trp Thr Ala Val Asp Thr Arg Glu Gly Glu
    130                 135                 140

Asp Phe Lys Asp Arg Phe Gln Arg Asn Met Tyr Asp Leu Lys Asn Thr
145                 150                 155                 160

Thr Lys Tyr Leu Tyr Tyr Lys Leu Asp Ile Thr Lys Asn Ala Gly Asp
                165                 170                 175

Ser Ile Thr Gln Leu Ala Glu Ile Ser Leu Ser Asp Gly Ile Glu Val
            180                 185                 190

Pro Ala Pro Pro Gly Asp Met Lys Ser Leu Ile Gly Lys Gly Pro
        195                 200                 205

Thr Ser Ser Tyr Thr Ala Lys Thr Asn Val Gly Trp Thr Gly Leu Gly
    210                 215                 220

Ala Leu Asn Tyr Ser Gly Thr His Leu Ser Asp Gly Arg Ala Tyr Ser
225                 230                 235                 240

Tyr Asn Lys Leu Tyr Asp Val Asp Ile Leu Val Thr Pro Ala Thr Glu
                245                 250                 255

Leu Ser Tyr Phe Ile Ala Pro Glu Phe Thr Asp Lys Asn His Asn Asp
            260                 265                 270

Tyr Ser Ser Thr Tyr Val Ser Val Asp Leu Ala Phe Ser Asp Gly Thr
        275                 280                 285

Tyr Leu His Asp Leu Lys Ala Val Asp Gln Tyr Gly Val Gly Leu Asn
    290                 295                 300

Pro Lys Asp Gln Gly Asp Ser Lys Tyr Leu Tyr Val Asn Gln Trp Asn
```

```
        305                 310                 315                 320
        Thr Ile Lys Ser Thr Ile Gly Ser Val Ala Ala Gly Lys Thr Ile Lys
                        325                 330                 335

Arg Ile Leu Val Ala Tyr Asp Asn Pro Lys Gly Pro Gly Ala Phe Arg
                        340                 345                 350

Gly Ser Ile Asp Asp Ile Lys Ile Asp Gly Lys Pro Val Gln Lys Ala
                        355                 360                 365

Phe Gly Ser Pro Ile Asp Tyr Val Asn Ile Leu Arg Gly Thr Gln Ser
                370                 375                 380

Asn Gly Ser Phe Ser Arg Gly Asn Asn Phe Pro Ala Val Ala Ile Pro
        385                 390                 395                 400

His Gly Phe Asn Phe Trp Thr Pro Thr Thr Asn Ala Gly Ser Ser Trp
                        405                 410                 415

Ile Tyr Gln Tyr His Glu Ser Asn Ser Val Asn Asn Leu Pro Gln Ile
                        420                 425                 430

Gln Ala Phe Ser Val Ser His Glu Pro Ser Pro Trp Met Gly Asp Arg
                        435                 440                 445

Gln Thr Phe Gln Val Met Pro Ser Ala Ser Thr Ala Ala Thr Pro Asn
                        450                 455                 460

Ala Asn Arg Asp Ser Arg Ala Leu Glu Phe Asn His Ala Asn Glu Ile
        465                 470                 475                 480

Ala Gln Pro His Tyr Tyr Ser Val Lys Phe Glu Asn Gly Ile Arg Thr
                        485                 490                 495

Glu Met Thr Pro Thr Asp His Ala Ala Met Phe Lys Phe Thr Phe Thr
                        500                 505                 510

Gly Ala Thr Ser Asn Leu Ile Phe Asp Asn Val Asn Asn Asn Gly Gly
                        515                 520                 525

Leu Thr Ile Asp Ala Lys Ser Gly Glu Ile Thr Gly Tyr Ser Asp Val
                        530                 535                 540

Lys Ser Gly Leu Ser Thr Gly Ala Thr Arg Leu Phe Val Tyr Ala Ala
        545                 550                 555                 560

Phe Asp Lys Pro Val Ile Lys Ser Gly Lys Leu Thr Gly Glu Ser Arg
                        565                 570                 575

Asn Asn Val Thr Gly Tyr Val Arg Phe Asp Thr Ser Lys Asp Glu Asp
                        580                 585                 590

Lys Val Val Thr Met Lys Ile Ala Thr Ser Leu Ile Ser Val Glu Gln
                        595                 600                 605

Ala Lys Lys Asn Leu Glu Gln Glu Ile Gly Leu Asn Asp Thr Phe Glu
                        610                 615                 620

Gly Leu Lys Glu Lys Ala Lys Thr Glu Trp Asn Lys Lys Leu Gly Ile
        625                 630                 635                 640

Ile Glu Val Glu Gly Ala Ser Glu Asp Gln Leu Val Thr Leu Tyr Ser
                        645                 650                 655

Asn Leu Tyr Arg Leu Phe Leu Tyr Pro Asn Ser Ala Phe Glu Asn Val
                        660                 665                 670

Gly Thr Thr Thr Asp Pro Val Tyr Lys Tyr Ala Ser Pro Tyr Ser Ala
                        675                 680                 685

Ala Thr Gly Gln Asp Thr Ala Thr Thr Gly Ala Lys Ile Val Asp
                        690                 695                 700

Gly Lys Thr Tyr Val Asn Asn Gly Phe Trp Asp Thr Tyr Arg Thr Ala
        705                 710                 715                 720

Trp Pro Ala Tyr Ser Leu Leu Thr Pro Thr Phe Ala Gly Glu Leu Ile
                        725                 730                 735
```

```
Asp Gly Phe Val Gln Gln Tyr Arg Asp Gly Gly Trp Ile Ala Arg Trp
            740                 745                 750

Ser Ser Pro Gly Phe Ala Asn Leu Met Pro Gly Thr Ser Ser Asp Val
            755                 760                 765

Ala Phe Ala Asp Ala Tyr Leu Lys Gly Val Thr Asn Phe Asp Val Gln
770                 775                 780

Ser Phe Tyr Gln Ser Ala Ile Arg Asn Ala Glu Ala Val Ser Pro Asn
785                 790                 795                 800

Ala Gly Thr Gly Arg Lys Gly Leu Thr Thr Ser Ile Phe Asp Gly Tyr
                805                 810                 815

Thr Asn Thr Ser Thr Gly Glu Gly Leu Ala Trp Ala Met Asp Gly Tyr
            820                 825                 830

Ile Asn Asp Phe Gly Ile Ala Asn Leu Ala Lys Ala Leu Lys Glu Lys
            835                 840                 845

Gly Asp Lys Ser Asp Pro Tyr Tyr Ala Asn Tyr Ala Ala Asp Tyr Gln
        850                 855                 860

Tyr Phe Leu Asn Arg Ala Gln Asn Tyr Val His Met Phe Asn Pro Ser
865                 870                 875                 880

Ile Glu Phe Phe Asn Gly Arg Thr Ala Asn Gly Ala Trp Arg Ser Thr
                885                 890                 895

Pro Asp Asn Phe Asn Pro Ala Val Trp Gly Ser Asp Tyr Thr Glu Thr
                900                 905                 910

Asn Gly Trp Asn Met Ala Phe His Val Pro Gln Asp Gly Gln Gly Leu
            915                 920                 925

Ala Asn Leu Tyr Gly Gly Lys Glu Gly Leu Ala Thr Lys Leu Asp Gln
            930                 935                 940

Phe Phe Ser Thr Ser Glu Thr Gly Leu Phe Pro Gly Ser Tyr Gly Gly
945                 950                 955                 960

Thr Ile His Glu Met Arg Glu Ala Arg Asp Val Arg Met Gly Met Tyr
                965                 970                 975

Gly His Ser Asn Gln Pro Ser His His Ile Ala Tyr Met Tyr Asp Tyr
            980                 985                 990

Ala Gly Gln Pro Trp Lys Thr Gln  Glu Lys Val Arg Glu  Ala Leu Asn
            995                 1000                1005

Arg Leu Tyr Ile Gly Ser Ala  Ile Gly Gln Gly Tyr  Ser Gly Asp
    1010                1015                1020

Glu Asp Asn Gly Glu Met Ser  Ala Trp Tyr Ile Leu  Ser Ala Met
    1025                1030                1035

Gly Phe Tyr Pro Leu Lys Met  Gly Thr Pro Glu Tyr  Ala Ile Gly
    1040                1045                1050

Ala Pro Leu Phe Lys Lys Ala  Thr Ile His Leu Glu  Asn Gly Lys
    1055                1060                1065

Ser Ile Val Ile Asn Ala Pro  Asn Asn Ser Lys Glu  Asn Lys Tyr
    1070                1075                1080

Val Gln Ser Met Lys Val Asn  Gly Lys Ala Tyr Ala  Lys Thr Ser
    1085                1090                1095

Ile Leu His Ala Asp Ile Ala  Asn Gly Ala Val Ile  Asp Phe Glu
    1100                1105                1110

Met Gly Ser Lys Pro Ser Lys  Trp Gly Ser Gly Asp  Gln Asp Ile
    1115                1120                1125

Leu Gln Ser Ile Thr Pro Gly  Ser Thr Asp Gly Thr  Ser Leu Ser
    1130                1135                1140
```

```
Pro Leu Pro Leu Arg Asp Val Thr Asp Arg Leu Ile Ala Ala Glu
    1145            1150                1155

Lys Gly Ala Val Thr Val Ser Asp Glu Gly Asn Gly Gln Leu Leu
1160            1165                1170

Phe Asp Asn Thr Ser Asn Thr Gln Leu Ser Met Lys Ser Lys Thr
    1175            1180                1185

Pro Ser Ile Val Tyr Gln Phe Lys Glu Gly Lys Gln Asn Val Lys
    1190            1195                1200

Met Tyr Thr Leu Thr Ser Ser Lys Ala Ser Gln Asn Glu Asp Pro
    1205            1210                1215

Lys Ser Trp Val Leu Lys Gly Ser Asn Asp Gly Lys Ser Trp Ser
    1220            1225                1230

Val Leu Asp Gln Arg Lys Asn Glu Thr Phe Gln Trp Arg Gln Tyr
    1235            1240                1245

Thr Arg Ala Phe Thr Ile Gln His Pro Gly Lys Tyr Ser Gln Tyr
    1250            1255                1260

Lys Leu Glu Ile Thr Glu Asn Ala Gly Ala Glu Val Thr Thr Leu
    1265            1270                1275

Ala Glu Leu Glu Leu Leu Gly Tyr Asp Asp Val Thr Asn Ser Tyr
    1280            1285                1290

Gln Ala Val Tyr Glu Leu Met Glu Gln Phe Lys Gln Ser Lys Asp
    1295            1300                1305

Leu Thr Gly Pro Met Ala Val Gln Leu Asn Asn Ser Leu Thr Thr
    1310            1315                1320

Ser Leu Asp His Phe Lys Lys Asp His Lys Asp Gln Ala Ile Lys
    1325            1330                1335

His Leu Glu Asp Phe Leu Lys His Leu Asn Asn Lys Gly Leu Gln
    1340            1345                1350

Asp Arg Ile Ser Ser Lys Ala Lys Gly Val Leu Ser Ala Asp Ala
    1355            1360                1365

Asn Gln Leu Ile Val Leu Leu Ala Arg Asp
    1370            1375

<210> SEQ ID NO 28
<211> LENGTH: 1095
<212> TYPE: DNA
<213> ORGANISM: Chryseobacterium sp.
<220> FEATURE:
<221> NAME/KEY: CDS
<222> LOCATION: (1)..(1092)
<220> FEATURE:
<221> NAME/KEY: sig_peptide
<222> LOCATION: (1)..(66)
<220> FEATURE:
<221> NAME/KEY: mat_peptide
<222> LOCATION: (67)..(1092)

<400> SEQUENCE: 28 atg aaa cat tta aag aac ttt ctg tta ata ctg gta tgt ata ttt tct    48
Met Lys His Leu Lys Asn Phe Leu Leu Ile Leu Val Cys Ile Phe Ser
        -20                 -15                 -10 ttt tca aaa acc ttt gct caa aag gag act gct tta aga gat aaa gtt    96
Phe Ser Lys Thr Phe Ala Gln Lys Glu Thr Ala Leu Arg Asp Lys Val
    -5                  -1   1               5                  10 cag ata ttc tat tat gga tgg tat gga aac caa caa aca gat gga agt   144
Gln Ile Phe Tyr Tyr Gly Trp Tyr Gly Asn Gln Gln Thr Asp Gly Ser
                15                  20                  25 ctg cag cat tgg aac cat gag atc att ccg cat tgg agc aat ccg aaa   192
Leu Gln His Trp Asn His Glu Ile Ile Pro His Trp Ser Asn Pro Lys
```

|  |  |  |  |  |  |  |  |  |  |  |  |  |  |
|---|---|---|---|---|---|---|---|---|---|---|---|---|---|
| tgg | aat | aat | ctt | gga | cat | tat | aaa | gga | ggg | aat | gat | att | ggc | gct | aat | 240 |
| Trp | Asn | Asn | Leu | Gly | His | Tyr | Lys | Gly | Gly | Asn | Asp | Ile | Gly | Ala | Asn |  |
|  |  | 45 |  |  |  | 50 |  |  |  | 55 |  |  |  |  |  |
| ttt | tat | ccg | gga | tta | gga | aat | tat | agt | tcc | aat | gac | aaa | aag | att | ata | 288 |
| Phe | Tyr | Pro | Gly | Leu | Gly | Asn | Tyr | Ser | Ser | Asn | Asp | Lys | Lys | Ile | Ile |  |
| 60 |  |  |  |  | 65 |  |  |  |  | 70 |  |  |  |  |  |
| aag | aaa | cac | atg | cag | atg | atg | aag | gat | tca | gga | gtg | ggt | gtt | gtg | gtg | 336 |
| Lys | Lys | His | Met | Gln | Met | Met | Lys | Asp | Ser | Gly | Val | Gly | Val | Val | Val |  |
| 75 |  |  |  |  | 80 |  |  |  |  | 85 |  |  |  |  | 90 |  |
| ata | agc | tgg | ttg | gga | aaa | gat | tct | ttt | aca | gat | aaa | agt | gtg | atg | cag | 384 |
| Ile | Ser | Trp | Leu | Gly | Lys | Asp | Ser | Phe | Thr | Asp | Lys | Ser | Val | Met | Gln |  |
|  |  |  |  | 95 |  |  |  |  | 100 |  |  |  |  | 105 |  |  |
| tac | ctg | gat | att | gca | caa | cag | ttt | aat | ttg | aaa | ata | gca | ttt | cac | ata | 432 |
| Tyr | Leu | Asp | Ile | Ala | Gln | Gln | Phe | Asn | Leu | Lys | Ile | Ala | Phe | His | Ile |  |
|  |  |  | 110 |  |  |  |  | 115 |  |  |  |  | 120 |  |  |  |
| gaa | cct | ttc | tat | aaa | aca | att | act | gaa | ctt | aga | gat | cag | ctt | tct | tat | 480 |
| Glu | Pro | Phe | Tyr | Lys | Thr | Ile | Thr | Glu | Leu | Arg | Asp | Gln | Leu | Ser | Tyr |  |
|  |  |  |  | 125 |  |  |  |  | 130 |  |  |  |  | 135 |  |  |
| ctt | gtt | gaa | aaa | tat | tct | cag | cat | ccg | gca | ttt | tac | aaa | aaa | gac | gga | 528 |
| Leu | Val | Glu | Lys | Tyr | Ser | Gln | His | Pro | Ala | Phe | Tyr | Lys | Lys | Asp | Gly |  |
|  | 140 |  |  |  |  | 145 |  |  |  |  | 150 |  |  |  |  |  |
| aag | cct | atg | tat | tat | gta | tat | gac | agt | tat | aaa | atc | gct | ccg | gaa | gaa | 576 |
| Lys | Pro | Met | Tyr | Tyr | Val | Tyr | Asp | Ser | Tyr | Lys | Ile | Ala | Pro | Glu | Glu |  |
| 155 |  |  |  |  | 160 |  |  |  |  | 165 |  |  |  |  | 170 |  |
| tgg | tca | aaa | cta | ctt | tcc | gaa | aac | ggt | gaa | aaa | aca | gta | cgt | aat | acg | 624 |
| Trp | Ser | Lys | Leu | Leu | Ser | Glu | Asn | Gly | Glu | Lys | Thr | Val | Arg | Asn | Thr |  |
|  |  |  |  | 175 |  |  |  |  | 180 |  |  |  |  | 185 |  |  |
| aaa | ctt | gat | gca | ttg | tat | atc | ggg | cta | tgg | gta | gaa | aaa | aat | gat | tca | 672 |
| Lys | Leu | Asp | Ala | Leu | Tyr | Ile | Gly | Leu | Trp | Val | Glu | Lys | Asn | Asp | Ser |  |
|  |  |  | 190 |  |  |  |  | 195 |  |  |  |  | 200 |  |  |  |
| gag | ttt | ttt | aat | aag | tca | gga | ttc | gat | ggt | ttt | tac | act | tac | ttt | gcc | 720 |
| Glu | Phe | Phe | Asn | Lys | Ser | Gly | Phe | Asp | Gly | Phe | Tyr | Thr | Tyr | Phe | Ala |  |
|  |  | 205 |  |  |  |  | 210 |  |  |  |  | 215 |  |  |  |  |
| agt | gaa | ggt | ttt | gtg | ttc | ggg | agt | aca | act | tcc | aac | tgg | aag | gat | atg | 768 |
| Ser | Glu | Gly | Phe | Val | Phe | Gly | Ser | Thr | Thr | Ser | Asn | Trp | Lys | Asp | Met |  |
| 220 |  |  |  |  | 225 |  |  |  |  | 230 |  |  |  |  |  |  |
| gct | caa | tat | gca | aaa | gat | cat | cat | ctt | att | ttt | att | cct | tgc | gtg | ggt | 816 |
| Ala | Gln | Tyr | Ala | Lys | Asp | His | His | Leu | Ile | Phe | Ile | Pro | Cys | Val | Gly |  |
| 235 |  |  |  |  | 240 |  |  |  |  | 245 |  |  |  |  | 250 |  |
| cct | ggg | tat | tca | gat | acg | agg | atc | aga | cct | tgg | aat | gag | gct | aat | ttt | 864 |
| Pro | Gly | Tyr | Ser | Asp | Thr | Arg | Ile | Arg | Pro | Trp | Asn | Glu | Ala | Asn | Phe |  |
|  |  |  |  | 255 |  |  |  |  | 260 |  |  |  |  | 265 |  |  |
| aaa | agc | aga | gac | aat | ggt | aaa | tat | tac | gaa | aaa | atg | ttt | gat | gct | gcc | 912 |
| Lys | Ser | Arg | Asp | Asn | Gly | Lys | Tyr | Tyr | Glu | Lys | Met | Phe | Asp | Ala | Ala |  |
|  |  |  | 270 |  |  |  |  | 275 |  |  |  |  | 280 |  |  |  |
| act | aaa | gtg | aat | ccg | gaa | ttt | ata | gga | att | act | tca | ttt | aat | gaa | tgg | 960 |
| Thr | Lys | Val | Asn | Pro | Glu | Phe | Ile | Gly | Ile | Thr | Ser | Phe | Asn | Glu | Trp |  |
|  |  | 285 |  |  |  |  | 290 |  |  |  |  | 295 |  |  |  |  |
| cat | gaa | ggt | acg | cag | ata | gag | ccc | gca | att | cct | aag | aaa | ata | gac | aat | 1008 |
| His | Glu | Gly | Thr | Gln | Ile | Glu | Pro | Ala | Ile | Pro | Lys | Lys | Ile | Asp | Asn |  |
| 300 |  |  |  |  | 305 |  |  |  |  | 310 |  |  |  |  |  |  |
| ttc | atc | tac | gaa | gat | tac | gga | aaa | gat | cca | tgg | atg | tat | atc | aaa | gaa | 1056 |
| Phe | Ile | Tyr | Glu | Asp | Tyr | Gly | Lys | Asp | Pro | Trp | Met | Tyr | Ile | Lys | Glu |  |
| 315 |  |  |  |  | 320 |  |  |  |  | 325 |  |  |  |  | 330 |  |
| aca | aaa | cgc | ttg | acg | gat | aag | ttt | ctg | aaa | gga | aag | tga |  |  |  | 1095 |
| Thr | Lys | Arg | Leu | Thr | Asp | Lys | Phe | Leu | Lys | Gly | Lys |  |  |  |  |  |
|  |  |  | 335 |  |  |  |  | 340 |  |  |  |  |  |  |  |  |

<210> SEQ ID NO 29
<211> LENGTH: 364
<212> TYPE: PRT
<213> ORGANISM: Chryseobacterium sp.

<400> SEQUENCE: 29

```
Met Lys His Leu Lys Asn Phe Leu Leu Ile Leu Val Cys Ile Phe Ser
        -20                 -15                 -10

Phe Ser Lys Thr Phe Ala Gln Lys Glu Thr Ala Leu Arg Asp Lys Val
        -5              -1   1               5                  10

Gln Ile Phe Tyr Tyr Gly Trp Tyr Gly Asn Gln Gln Thr Asp Gly Ser
                    15                  20                  25

Leu Gln His Trp Asn His Glu Ile Ile Pro His Trp Ser Asn Pro Lys
                30                  35                  40

Trp Asn Asn Leu Gly His Tyr Lys Gly Gly Asn Asp Ile Gly Ala Asn
                45                  50                  55

Phe Tyr Pro Gly Leu Gly Asn Tyr Ser Ser Asn Asp Lys Lys Ile Ile
        60                  65                  70

Lys Lys His Met Gln Met Met Lys Asp Ser Gly Val Gly Val Val Val
75                  80                  85                  90

Ile Ser Trp Leu Gly Lys Asp Ser Phe Thr Asp Lys Ser Val Met Gln
                    95                 100                 105

Tyr Leu Asp Ile Ala Gln Gln Phe Asn Leu Lys Ile Ala Phe His Ile
                110                 115                 120

Glu Pro Phe Tyr Lys Thr Ile Thr Glu Leu Arg Asp Gln Leu Ser Tyr
                125                 130                 135

Leu Val Glu Lys Tyr Ser Gln His Pro Ala Phe Tyr Lys Lys Asp Gly
            140                 145                 150

Lys Pro Met Tyr Tyr Val Tyr Asp Ser Tyr Lys Ile Ala Pro Glu Glu
155                 160                 165                 170

Trp Ser Lys Leu Leu Ser Glu Asn Gly Glu Lys Thr Val Arg Asn Thr
                175                 180                 185

Lys Leu Asp Ala Leu Tyr Ile Gly Leu Trp Val Glu Lys Asn Asp Ser
                190                 195                 200

Glu Phe Phe Asn Lys Ser Gly Phe Asp Gly Phe Tyr Thr Tyr Phe Ala
                205                 210                 215

Ser Glu Gly Phe Val Phe Gly Ser Thr Thr Ser Asn Trp Lys Asp Met
220                 225                 230

Ala Gln Tyr Ala Lys Asp His His Leu Ile Phe Ile Pro Cys Val Gly
235                 240                 245                 250

Pro Gly Tyr Ser Asp Thr Arg Ile Arg Pro Trp Asn Glu Ala Asn Phe
                255                 260                 265

Lys Ser Arg Asp Asn Gly Lys Tyr Tyr Glu Lys Met Phe Asp Ala Ala
                270                 275                 280

Thr Lys Val Asn Pro Glu Phe Ile Gly Ile Thr Ser Phe Asn Glu Trp
                285                 290                 295

His Glu Gly Thr Gln Ile Glu Pro Ala Ile Pro Lys Lys Ile Asp Asn
                300                 305                 310

Phe Ile Tyr Glu Asp Tyr Gly Lys Asp Pro Trp Met Tyr Ile Lys Glu
315                 320                 325                 330

Thr Lys Arg Leu Thr Asp Lys Phe Leu Lys Gly Lys
                335                 340
```

<210> SEQ ID NO 30
<211> LENGTH: 342

<212> TYPE: PRT
<213> ORGANISM: Chryseobacterium sp.

<400> SEQUENCE: 30

```
Gln Lys Glu Thr Ala Leu Arg Asp Lys Val Gln Ile Phe Tyr Tyr Gly
1               5                   10                  15
Trp Tyr Gly Asn Gln Gln Thr Asp Gly Ser Leu Gln His Trp Asn His
                20                  25                  30
Glu Ile Ile Pro His Trp Ser Asn Pro Lys Trp Asn Asn Leu Gly His
            35                  40                  45
Tyr Lys Gly Gly Asn Asp Ile Gly Ala Asn Phe Tyr Pro Gly Leu Gly
    50                  55                  60
Asn Tyr Ser Ser Asn Asp Lys Lys Ile Ile Lys His Met Gln Met
65                  70                  75                  80
Met Lys Asp Ser Gly Val Gly Val Val Ile Ser Trp Leu Gly Lys
                85                  90                  95
Asp Ser Phe Thr Asp Lys Ser Val Met Gln Tyr Leu Asp Ile Ala Gln
            100                 105                 110
Gln Phe Asn Leu Lys Ile Ala Phe His Ile Glu Pro Phe Tyr Lys Thr
    115                 120                 125
Ile Thr Glu Leu Arg Asp Gln Leu Ser Tyr Leu Val Glu Lys Tyr Ser
130                 135                 140
Gln His Pro Ala Phe Tyr Lys Lys Asp Gly Lys Pro Met Tyr Tyr Val
145                 150                 155                 160
Tyr Asp Ser Tyr Lys Ile Ala Pro Glu Glu Trp Ser Lys Leu Leu Ser
                165                 170                 175
Glu Asn Gly Glu Lys Thr Val Arg Asn Thr Lys Leu Asp Ala Leu Tyr
            180                 185                 190
Ile Gly Leu Trp Val Glu Lys Asn Asp Ser Glu Phe Phe Asn Lys Ser
    195                 200                 205
Gly Phe Asp Gly Phe Tyr Thr Tyr Phe Ala Ser Glu Gly Phe Val Phe
210                 215                 220
Gly Ser Thr Thr Ser Asn Trp Lys Asp Met Ala Gln Tyr Ala Lys Asp
225                 230                 235                 240
His His Leu Ile Phe Ile Pro Cys Val Gly Pro Gly Tyr Ser Asp Thr
                245                 250                 255
Arg Ile Arg Pro Trp Asn Glu Ala Asn Phe Lys Ser Arg Asp Asn Gly
            260                 265                 270
Lys Tyr Tyr Glu Lys Met Phe Asp Ala Ala Thr Lys Val Asn Pro Glu
    275                 280                 285
Phe Ile Gly Ile Thr Ser Phe Asn Glu Trp His Glu Gly Thr Gln Ile
290                 295                 300
Glu Pro Ala Ile Pro Lys Lys Ile Asp Asn Phe Ile Tyr Glu Asp Tyr
305                 310                 315                 320
Gly Lys Asp Pro Trp Met Tyr Ile Lys Glu Thr Lys Arg Leu Thr Asp
                325                 330                 335
Lys Phe Leu Lys Gly Lys
            340
```

<210> SEQ ID NO 31
<211> LENGTH: 1267
<212> TYPE: DNA
<213> ORGANISM: Aspergillus aculeatus
<220> FEATURE:
<221> NAME/KEY: CDS
<222> LOCATION: (1)..(483)

```
<220> FEATURE:
<221> NAME/KEY: sig_peptide
<222> LOCATION: (1)..(54)
<220> FEATURE:
<221> NAME/KEY: mat_peptide
<222> LOCATION: (55)..(1264)
<220> FEATURE:
<221> NAME/KEY: CDS
<222> LOCATION: (587)..(1264)

<400> SEQUENCE: 31
```

| | | | | | | | | | | | | | | | | |
|---|---|---|---|---|---|---|---|---|---|---|---|---|---|---|---|---|
| atg | cac | acc | aca | aca | cta | gcc | ctg | gcc | ctc | gcc | ctc | gcc | agc | ggc | act | 48 |
| Met | His | Thr | Thr | Thr | Leu | Ala | Leu | Ala | Leu | Ala | Leu | Ala | Ser | Gly | Thr | |
| | | | | -15 | | | | -10 | | | | | -5 | | | |

| tct | gcg | aca | aac | tac | acg | gcc | atg | acc | cgc | gcc | gtg | acc | gcg | ctc | aac | 96 |
|---|---|---|---|---|---|---|---|---|---|---|---|---|---|---|---|---|
| Ser | Ala | Thr | Asn | Tyr | Thr | Ala | Met | Thr | Arg | Ala | Val | Thr | Ala | Leu | Asn | |
| -1 | 1 | | | | 5 | | | | | 10 | | | | | | |

| acc | ctc | cag | acc | tac | tac | aac | ccc | acg | acc | ggg | atc | tgg | aac | acc | tgc | 144 |
|---|---|---|---|---|---|---|---|---|---|---|---|---|---|---|---|---|
| Thr | Leu | Gln | Thr | Tyr | Tyr | Asn | Pro | Thr | Thr | Gly | Ile | Trp | Asn | Thr | Cys | |
| 15 | | | | 20 | | | | | 25 | | | | | 30 | | |

| ggc | tgg | tgg | aat | ggc | gcc | aac | tgc | cta | acc | acg | ctg | gcg | aat | ttg | tcc | 192 |
|---|---|---|---|---|---|---|---|---|---|---|---|---|---|---|---|---|
| Gly | Trp | Trp | Asn | Gly | Ala | Asn | Cys | Leu | Thr | Thr | Leu | Ala | Asn | Leu | Ser | |
| | | | 35 | | | | | 40 | | | | | 45 | | | |

| ctc | aag | aac | agc | act | gtc | aac | gac | acc | gcc | acc | ggg | gtg | ttc | gag | aac | 240 |
|---|---|---|---|---|---|---|---|---|---|---|---|---|---|---|---|---|
| Leu | Lys | Asn | Ser | Thr | Val | Asn | Asp | Thr | Ala | Thr | Gly | Val | Phe | Glu | Asn | |
| | 50 | | | | | 55 | | | | | | 60 | | | | |

| acc | ttc | cgg | gtg | gcc | acg | aac | acg | aac | ccg | tac | ccg | gcg | cgc | ggg | atc | 288 |
|---|---|---|---|---|---|---|---|---|---|---|---|---|---|---|---|---|
| Thr | Phe | Arg | Val | Ala | Thr | Asn | Thr | Asn | Pro | Tyr | Pro | Ala | Arg | Gly | Ile | |
| | 65 | | | | | 70 | | | | | 75 | | | | | |

| gac | gcc | gac | tac | acc | gcc | gcc | aac | ggc | acc | gcg | tac | acc | atc | tcg | ggc | 336 |
|---|---|---|---|---|---|---|---|---|---|---|---|---|---|---|---|---|
| Asp | Ala | Asp | Tyr | Thr | Ala | Ala | Asn | Gly | Thr | Ala | Tyr | Thr | Ile | Ser | Gly | |
| 80 | | | | | 85 | | | | | 90 | | | | | | |

| cag | cct | acg | ggg | gcc | gcc | aac | gcc | tcg | ctg | tgg | ctg | gac | ggg | agc | tac | 384 |
|---|---|---|---|---|---|---|---|---|---|---|---|---|---|---|---|---|
| Gln | Pro | Thr | Gly | Ala | Ala | Asn | Ala | Ser | Leu | Trp | Leu | Asp | Gly | Ser | Tyr | |
| 95 | | | | 100 | | | | | 105 | | | | | 110 | | |

| gac | gac | gac | atg | tgg | tgg | ggg | atg | gcc | tgg | gtg | gcc | gcg | tat | gat | gtg | 432 |
|---|---|---|---|---|---|---|---|---|---|---|---|---|---|---|---|---|
| Asp | Asp | Asp | Met | Trp | Trp | Gly | Met | Ala | Trp | Val | Ala | Ala | Tyr | Asp | Val | |
| | | | | 115 | | | | | 120 | | | | | 125 | | |

| acg | ggg | gtg | acg | gat | tat | ctc | gat | ctc | gcg | gag | ggg | gta | ttt | tac | cat | 480 |
|---|---|---|---|---|---|---|---|---|---|---|---|---|---|---|---|---|
| Thr | Gly | Val | Thr | Asp | Tyr | Leu | Asp | Leu | Ala | Glu | Gly | Val | Phe | Tyr | His | |
| | | 130 | | | | | 135 | | | | | 140 | | | | |

| ctt | gtacgttctc | tatccccgt | tcattccact | acagggtgtc | attcccctt | | | | | | | | | | | 533 |
|---|---|---|---|---|---|---|---|---|---|---|---|---|---|---|---|---|
| Leu | | | | | | | | | | | | | | | | |

| cgatttgagt | tagggctgtg | ttgtgtcgga | atgcatgcta | atggaaacga | tag | agc | | | | | | | | | | 589 |
|---|---|---|---|---|---|---|---|---|---|---|---|---|---|---|---|---|
| | | | | | | Ser | | | | | | | | | | |

| cgc | gct | tgg | ccc | tcc | ctc | tgc | ggc | aac | ggc | ggt | ctc | gac | tcg | gac | tac | 637 |
|---|---|---|---|---|---|---|---|---|---|---|---|---|---|---|---|---|
| Arg | Ala | Trp | Pro | Ser | Leu | Cys | Gly | Asn | Gly | Gly | Leu | Asp | Ser | Asp | Tyr | |
| 145 | | | | | 150 | | | | | 155 | | | | | 160 | |

| acg | cac | gtg | tac | gtc | ggc | gcg | atc | agc | aac | gag | ctc | ttc | ctg | gcg | ctg | 685 |
|---|---|---|---|---|---|---|---|---|---|---|---|---|---|---|---|---|
| Thr | His | Val | Tyr | Val | Gly | Ala | Ile | Ser | Asn | Glu | Leu | Phe | Leu | Ala | Leu | |
| | | | | 165 | | | | | 170 | | | | | 175 | | |

| ggc | gcc | tca | ctc | gcc | aac | cgc | gtc | gcg | acc | aac | agc | agc | cgc | gag | tac | 733 |
|---|---|---|---|---|---|---|---|---|---|---|---|---|---|---|---|---|
| Gly | Ala | Ser | Leu | Ala | Asn | Arg | Val | Ala | Thr | Asn | Ser | Ser | Arg | Glu | Tyr | |
| | | | 180 | | | | | 185 | | | | | 190 | | | |

| tac | ctg | gac | tgg | gcg | aag | cgg | caa | tgg | gcg | tgg | ttt | gag | agc | agc | ggc | 781 |
|---|---|---|---|---|---|---|---|---|---|---|---|---|---|---|---|---|
| Tyr | Leu | Asp | Trp | Ala | Lys | Arg | Gln | Trp | Ala | Trp | Phe | Glu | Ser | Ser | Gly | |
| | | 195 | | | | | 200 | | | | | 205 | | | | |

| ctc | atc | aac | gct | aac | cac | acc | atc | aac | gac | ggg | ctg | acg | ggg | gcg | tgc | 829 |
|---|---|---|---|---|---|---|---|---|---|---|---|---|---|---|---|---|
| Leu | Ile | Asn | Ala | Asn | His | Thr | Ile | Asn | Asp | Gly | Leu | Thr | Gly | Ala | Cys | |
| | 210 | | | | | 215 | | | | | 220 | | | | | |

| acc | aac | aac | gga | atg | acc | gtg | tgg | tcg | tac | aac | cag | ggc | gtc | atc | ctg | 877 |
|---|---|---|---|---|---|---|---|---|---|---|---|---|---|---|---|---|

```
Thr Asn Asn Gly Met Thr Val Trp Ser Tyr Asn Gln Gly Val Ile Leu
225                 230                 235                 240 ggg gga ctg gtg gag ctg cac cgc gcc acg ggc agc cac gcc tcc aac    925
Gly Gly Leu Val Glu Leu His Arg Ala Thr Gly Ser His Ala Ser Asn
                    245                 250                 255 tcc acg tac ctg act gct gcg ggc aag atc gcg cag ggg gcg atc gcc    973
Ser Thr Tyr Leu Thr Ala Ala Gly Lys Ile Ala Gln Gly Ala Ile Ala
            260                 265                 270 gcg ctc gcc gac gag gac gac gtc atc cat gaa tcg tgc gag ccg gac    1021
Ala Leu Ala Asp Glu Asp Asp Val Ile His Glu Ser Cys Glu Pro Asp
        275                 280                 285 gcc tgt gac tcg aac gag acg cag ttc aag ggg atc ttc atc cgc aac    1069
Ala Cys Asp Ser Asn Glu Thr Gln Phe Lys Gly Ile Phe Ile Arg Asn
    290                 295                 300 ctc aag gtg ttg cag ggc gtc gcg ccg aat gag acc tac gcc cgg gtg    1117
Leu Lys Val Leu Gln Gly Val Ala Pro Asn Glu Thr Tyr Ala Arg Val
305                 310                 315                 320 atc aat gcg tcg gcg gcg agt ctg tgg gcg aat gat cgc act gac gct    1165
Ile Asn Ala Ser Ala Ala Ser Leu Trp Ala Asn Asp Arg Thr Asp Ala
                325                 330                 335 acg ggg ttc ggg atc gat tgg tcg ggg ccc gtc gat gcg gcc acg gtc    1213
Thr Gly Phe Gly Ile Asp Trp Ser Gly Pro Val Asp Ala Ala Thr Val
            340                 345                 350 aac gcc tcg acg cag agt tcg gcg ctg gat gcg ctg gtc gcg gcg att    1261
Asn Ala Ser Thr Gln Ser Ser Ala Leu Asp Ala Leu Val Ala Ala Ile
        355                 360                 365 tgg tag                                                            1267
Trp

<210> SEQ ID NO 32
<211> LENGTH: 387
<212> TYPE: PRT
<213> ORGANISM: Aspergillus aculeatus

<400> SEQUENCE: 32

Met His Thr Thr Thr Leu Ala Leu Ala Leu Ala Ser Gly Thr
            -15                 -10                 -5

Ser Ala Thr Asn Tyr Thr Ala Met Thr Arg Ala Val Thr Ala Leu Asn
    -1  1               5                   10

Thr Leu Gln Thr Tyr Tyr Asn Pro Thr Gly Ile Trp Asn Thr Cys
15                  20                  25                  30

Gly Trp Trp Asn Gly Ala Asn Cys Leu Thr Thr Leu Ala Asn Leu Ser
                35                  40                  45

Leu Lys Asn Ser Thr Val Asn Asp Thr Ala Thr Gly Val Phe Glu Asn
                50                  55                  60

Thr Phe Arg Val Ala Thr Asn Thr Asn Pro Tyr Pro Ala Arg Gly Ile
            65                  70                  75

Asp Ala Asp Tyr Thr Ala Ala Asn Gly Thr Ala Tyr Thr Ile Ser Gly
        80                  85                  90

Gln Pro Thr Gly Ala Ala Asn Ala Ser Leu Trp Leu Asp Gly Ser Tyr
95                  100                 105                 110

Asp Asp Asp Met Trp Trp Gly Met Ala Trp Val Ala Ala Tyr Asp Val
                115                 120                 125

Thr Gly Val Thr Asp Tyr Leu Asp Leu Ala Glu Gly Val Phe Tyr His
            130                 135                 140

Leu Ser Arg Ala Trp Pro Ser Leu Cys Gly Asn Gly Gly Leu Asp Ser
        145                 150                 155
```

```
Asp Tyr Thr His Val Tyr Val Gly Ala Ile Ser Asn Glu Leu Phe Leu
    160                 165                 170

Ala Leu Gly Ala Ser Leu Ala Asn Arg Val Ala Thr Asn Ser Ser Arg
175                 180                 185                 190

Glu Tyr Tyr Leu Asp Trp Ala Lys Arg Gln Trp Ala Trp Phe Glu Ser
                195                 200                 205

Ser Gly Leu Ile Asn Ala Asn His Thr Ile Asn Asp Gly Leu Thr Gly
            210                 215                 220

Ala Cys Thr Asn Asn Gly Met Thr Val Trp Ser Tyr Asn Gln Gly Val
            225                 230                 235

Ile Leu Gly Gly Leu Val Glu Leu His Arg Ala Thr Gly Ser His Ala
240                 245                 250

Ser Asn Ser Thr Tyr Leu Thr Ala Ala Gly Lys Ile Ala Gln Gly Ala
255                 260                 265                 270

Ile Ala Ala Leu Ala Asp Glu Asp Val Ile His Glu Ser Cys Glu
                275                 280                 285

Pro Asp Ala Cys Asp Ser Asn Glu Thr Gln Phe Lys Gly Ile Phe Ile
                290                 295                 300

Arg Asn Leu Lys Val Leu Gln Gly Val Ala Pro Asn Glu Thr Tyr Ala
                305                 310                 315

Arg Val Ile Asn Ala Ser Ala Ala Ser Leu Trp Ala Asn Asp Arg Thr
320                 325                 330

Asp Ala Thr Gly Phe Gly Ile Asp Trp Ser Gly Pro Val Asp Ala Ala
335                 340                 345                 350

Thr Val Asn Ala Ser Thr Gln Ser Ser Ala Leu Asp Ala Leu Val Ala
                355                 360                 365

Ala Ile Trp

<210> SEQ ID NO 33
<211> LENGTH: 369
<212> TYPE: PRT
<213> ORGANISM: Aspergillus aculeatus

<400> SEQUENCE: 33

Thr Asn Tyr Thr Ala Met Thr Arg Ala Val Thr Ala Leu Asn Thr Leu
1               5                   10                  15

Gln Thr Tyr Tyr Asn Pro Thr Thr Gly Ile Trp Asn Thr Cys Gly Trp
                20                  25                  30

Trp Asn Gly Ala Asn Cys Leu Thr Thr Leu Ala Asn Leu Ser Leu Lys
            35                  40                  45

Asn Ser Thr Val Asn Asp Thr Ala Thr Gly Val Phe Glu Asn Thr Phe
50                  55                  60

Arg Val Ala Thr Asn Thr Asn Pro Tyr Pro Ala Arg Gly Ile Asp Ala
65                  70                  75                  80

Asp Tyr Thr Ala Ala Asn Gly Thr Ala Tyr Thr Ile Ser Gly Gln Pro
                85                  90                  95

Thr Gly Ala Ala Asn Ala Ser Leu Trp Leu Asp Gly Ser Tyr Asp Asp
                100                 105                 110

Asp Met Trp Trp Gly Met Ala Trp Val Ala Ala Tyr Asp Val Thr Gly
                115                 120                 125

Val Thr Asp Tyr Leu Asp Leu Ala Glu Gly Val Phe Tyr His Leu Ser
            130                 135                 140

Arg Ala Trp Pro Ser Leu Cys Gly Asn Gly Gly Leu Asp Ser Asp Tyr
145                 150                 155                 160
```

```
Thr His Val Tyr Val Gly Ala Ile Ser Asn Glu Leu Phe Leu Ala Leu
            165                 170                 175
Gly Ala Ser Leu Ala Asn Arg Val Ala Thr Asn Ser Ser Arg Glu Tyr
        180                 185                 190
Tyr Leu Asp Trp Ala Lys Arg Gln Trp Ala Trp Phe Glu Ser Ser Gly
        195                 200                 205
Leu Ile Asn Ala Asn His Thr Ile Asn Asp Gly Leu Thr Gly Ala Cys
        210                 215                 220
Thr Asn Asn Gly Met Thr Val Trp Ser Tyr Asn Gln Gly Val Ile Leu
225                 230                 235                 240
Gly Gly Leu Val Glu Leu His Arg Ala Thr Gly Ser His Ala Ser Asn
            245                 250                 255
Ser Thr Tyr Leu Thr Ala Ala Gly Lys Ile Ala Gln Gly Ala Ile Ala
            260                 265                 270
Ala Leu Ala Asp Glu Asp Val Ile His Glu Ser Cys Glu Pro Asp
        275                 280                 285
Ala Cys Asp Ser Asn Glu Thr Gln Phe Lys Gly Ile Phe Ile Arg Asn
        290                 295                 300
Leu Lys Val Leu Gln Gly Val Ala Pro Asn Glu Thr Tyr Ala Arg Val
305                 310                 315                 320
Ile Asn Ala Ser Ala Ala Ser Leu Trp Ala Asn Asp Arg Thr Asp Ala
            325                 330                 335
Thr Gly Phe Gly Ile Asp Trp Ser Gly Pro Val Asp Ala Ala Thr Val
            340                 345                 350
Asn Ala Ser Thr Gln Ser Ser Ala Leu Asp Ala Leu Val Ala Ala Ile
            355                 360                 365
Trp

<210> SEQ ID NO 34
<211> LENGTH: 1483
<212> TYPE: DNA
<213> ORGANISM: Aspergillus aculeatus
<220> FEATURE:
<221> NAME/KEY: CDS
<222> LOCATION: (1)..(100)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1480)
<220> FEATURE:
<221> NAME/KEY: CDS
<222> LOCATION: (159)..(853)
<220> FEATURE:
<221> NAME/KEY: CDS
<222> LOCATION: (905)..(1480)

<400> SEQUENCE: 34 atg gcg aga act acc ttc cag aac ctc ctg aaa gtg gct tat gcc gct    48
Met Ala Arg Thr Thr Phe Gln Asn Leu Leu Lys Val Ala Tyr Ala Ala
-25                 -20                 -15                 -10 gcc ctt gtg gcg ggc acc gtg tct gcc atc gat ttg gac atc aac aat    96
Ala Leu Val Ala Gly Thr Val Ser Ala Ile Asp Leu Asp Ile Asn Asn
                -5              -1  1               5 gaa c gtatgatttc aatgaactct actcctcttg tctcctgctg aaatcatccc       150
Glu atctgcag ag tcc att aaa gat gca gcc gcc acc gcc gcg ttc aac acc   199
         Gln Ser Ile Lys Asp Ala Ala Ala Thr Ala Ala Phe Asn Thr
               10                  15                  20
```

-continued

| | |
|---|---|
| atg cag cac tac aac ggt aac aag acc gga gag att cca ggt gtc atc<br>Met Gln His Tyr Asn Gly Asn Lys Thr Gly Glu Ile Pro Gly Val Ile<br>         25                      30                  35 | 247 |
| ccc agc ctc tgg ggt gag ggc ggc gtt ctc ttc aat ctc atg atc caa<br>Pro Ser Leu Trp Gly Glu Gly Gly Val Leu Phe Asn Leu Met Ile Gln<br>    40                      45                      50 | 295 |
| tac tgg tac ttc acc ggc gac gcc tcc tac aac ccc gcc gtc agc cag<br>Tyr Trp Tyr Phe Thr Gly Asp Ala Ser Tyr Asn Pro Ala Val Ser Gln<br>55                      60                      65                      70 | 343 |
| ggc atg tac tgg cag atc ggc gac gac gat tac atg ccg tcg aac tgg<br>Gly Met Tyr Trp Gln Ile Gly Asp Asp Asp Tyr Met Pro Ser Asn Trp<br>                      75                      80                      85 | 391 |
| agc tcg cag ata ggc aat gac gac cag atg gcc tgg ggc ctt gcc gcg<br>Ser Ser Gln Ile Gly Asn Asp Asp Gln Met Ala Trp Gly Leu Ala Ala<br>              90                      95                      100 | 439 |
| atg aca gcc gca gag ctg gac tac cct cag gac gtt aat cag aca tcg<br>Met Thr Ala Ala Glu Leu Asp Tyr Pro Gln Asp Val Asn Gln Thr Ser<br>        105                      110                      115 | 487 |
| tgg ttg act ctg gcc gaa ggc gtt ttc aac acc cag gtt gca cgg tgg<br>Trp Leu Thr Leu Ala Glu Gly Val Phe Asn Thr Gln Val Ala Arg Trp<br>120                      125                      130 | 535 |
| gac acg agc aac tgc ggg ggc gga ctg cgc tgg cag atc tgg ccc ttt<br>Asp Thr Ser Asn Cys Gly Gly Gly Leu Arg Trp Gln Ile Trp Pro Phe<br>135                      140                      145                      150 | 583 |
| gag tcc gga tac acc cag aag aat gcc atc agc aac ggt ggt ctc ttc<br>Glu Ser Gly Tyr Thr Gln Lys Asn Ala Ile Ser Asn Gly Gly Leu Phe<br>                      155                      160                      165 | 631 |
| cag ctc tct gcg cgg ctg gct cgg tac acc cac aac cag acg tac gca<br>Gln Leu Ser Ala Arg Leu Ala Arg Tyr Thr His Asn Gln Thr Tyr Ala<br>                  170                      175                      180 | 679 |
| gac tgg gcg gat aag atc tgg gac tgg agt gcc agc gtg ccg ctc ttg<br>Asp Trp Ala Asp Lys Ile Trp Asp Trp Ser Ala Ser Val Pro Leu Leu<br>              185                      190                      195 | 727 |
| aac aac aaa acc tgg agt atc gcc gac agc acg aat gtg gac aat ggt<br>Asn Asn Lys Thr Trp Ser Ile Ala Asp Ser Thr Asn Val Asp Asn Gly<br>200                      205                      210 | 775 |
| tgc acg acc cag gga aac aac cag tgg acg gcc aat tac ggg ccg tac<br>Cys Thr Thr Gln Gly Asn Asn Gln Trp Thr Ala Asn Tyr Gly Pro Tyr<br>215                      220                      225                      230 | 823 |
| atc agc ggt gca gcc tat atg tac aac tac gtaagtcatt tgcaagccag<br>Ile Ser Gly Ala Ala Tyr Met Tyr Asn Tyr<br>                235                      240 | 873 |
| cttagagcaa caacgactaa cgagaacgaa g acc aac ggt caa aac agc aaa<br>                                                        Thr Asn Gly Gln Asn Ser Lys<br>                                                                              245 | 925 |
| tgg aag tcc ggc ctc gac ggc ttg ctc aac gtc tcg ttc gaa acc ttc<br>Trp Lys Ser Gly Leu Asp Gly Leu Leu Asn Val Ser Phe Glu Thr Phe<br>        250                      255                      260 | 973 |
| ttc ccc gag aag tac ggc ggt ctg atc ctg tcg gaa atc ctt tgt gag<br>Phe Pro Glu Lys Tyr Gly Gly Leu Ile Leu Ser Glu Ile Leu Cys Glu<br>              265                      270                      275 | 1021 |
| ccc gca gag gtt tgc aac tcg ctc gaa gac acg tac aag ggg act ttt<br>Pro Ala Glu Val Cys Asn Ser Leu Glu Asp Thr Tyr Lys Gly Thr Phe<br>280                      285                      290                      295 | 1069 |
| gtc tcg gat ttg gcg ctg gca agt ctc gtc gct ccg tac atc tcg tct<br>Val Ser Asp Leu Ala Leu Ala Ser Leu Val Ala Pro Tyr Ile Ser Ser<br>                  300                      305                      310 | 1117 |
| gag gtg tct tcg cgt ctg cag gcg tcg gct gtc gga gcg gcg aag caa<br>Glu Val Ser Ser Arg Leu Gln Ala Ser Ala Val Gly Ala Ala Lys Gln<br>              315                      320                      325 | 1165 |

```
tgc acg ggt ggc aac aat cag aca ctc tgc ggt cgt cgc tgg tat tcg         1213
Cys Thr Gly Gly Asn Asn Gln Thr Leu Cys Gly Arg Arg Trp Tyr Ser
        330                 335                 340 gac gaa tgg gac ggg act gat ggg aga gag gaa cag ctc agt gca acc         1261
Asp Glu Trp Asp Gly Thr Asp Gly Arg Glu Glu Gln Leu Ser Ala Thr
    345                 350                 355 agc atc ttt ttc gcg aat atg gct ggc ttc act ggg aag ggc gtt gcc         1309
Ser Ile Phe Phe Ala Asn Met Ala Gly Phe Thr Gly Lys Gly Val Ala
360                 365                 370                 375 act gct gcc gcg gct gtt gat cag acg acc ggg tct gcc ggc acg aat         1357
Thr Ala Ala Ala Ala Val Asp Gln Thr Thr Gly Ser Ala Gly Thr Asn
            380                 385                 390 ggg act tcc aca aac ggc act ggt gtt cct gtt gcc ttg aat ggt gct         1405
Gly Thr Ser Thr Asn Gly Thr Gly Val Pro Val Ala Leu Asn Gly Ala
        395                 400                 405 ggc aga tcg tct cag gga caa ttt ggt gtt gcc act gct ggc gtt tta         1453
Gly Arg Ser Ser Gln Gly Gln Phe Gly Val Ala Thr Ala Gly Val Leu
    410                 415                 420 gca ggt ctt gta ttg ctt ctt gtg ctt tga                                 1483
Ala Gly Leu Val Leu Leu Leu Val Leu
425                 430

<210> SEQ ID NO 35
<211> LENGTH: 457
<212> TYPE: PRT
<213> ORGANISM: Aspergillus aculeatus

<400> SEQUENCE: 35

Met Ala Arg Thr Thr Phe Gln Asn Leu Leu Lys Val Ala Tyr Ala Ala
-25                 -20                 -15                 -10

Ala Leu Val Ala Gly Thr Val Ser Ala Ile Asp Leu Asp Ile Asn Asn
            -5                  -1  1               5

Glu Gln Ser Ile Lys Asp Ala Ala Thr Ala Ala Phe Asn Thr Met
        10                  15                  20

Gln His Tyr Asn Gly Asn Lys Thr Gly Glu Ile Pro Gly Val Ile Pro
    25                  30                  35

Ser Leu Trp Gly Glu Gly Val Leu Phe Asn Leu Met Ile Gln Tyr
40                  45                  50                  55

Trp Tyr Phe Thr Gly Asp Ala Ser Tyr Asn Pro Ala Val Ser Gln Gly
                60                  65                  70

Met Tyr Trp Gln Ile Gly Asp Asp Tyr Met Pro Ser Asn Trp Ser
            75                  80                  85

Ser Gln Ile Gly Asn Asp Asp Gln Met Ala Trp Gly Leu Ala Ala Met
        90                  95                  100

Thr Ala Ala Glu Leu Asp Tyr Pro Gln Asp Val Asn Gln Thr Ser Trp
105                 110                 115

Leu Thr Leu Ala Glu Gly Val Phe Asn Thr Gln Val Ala Arg Trp Asp
120                 125                 130                 135

Thr Ser Asn Cys Gly Gly Gly Leu Arg Trp Gln Ile Trp Pro Phe Glu
                140                 145                 150

Ser Gly Tyr Thr Gln Lys Asn Ala Ile Ser Asn Gly Gly Leu Phe Gln
            155                 160                 165

Leu Ser Ala Arg Leu Ala Arg Tyr Thr His Asn Gln Thr Tyr Ala Asp
        170                 175                 180

Trp Ala Asp Lys Ile Trp Asp Trp Ser Ala Ser Val Pro Leu Leu Asn
    185                 190                 195
```

Asn Lys Thr Trp Ser Ile Ala Asp Ser Thr Asn Val Asp Asn Gly Cys
200                 205                 210                 215

Thr Thr Gln Gly Asn Asn Gln Trp Thr Ala Asn Tyr Gly Pro Tyr Ile
            220                 225                 230

Ser Gly Ala Ala Tyr Met Tyr Asn Tyr Thr Asn Gly Gln Asn Ser Lys
                235                 240                 245

Trp Lys Ser Gly Leu Asp Gly Leu Leu Asn Val Ser Phe Glu Thr Phe
            250                 255                 260

Phe Pro Glu Lys Tyr Gly Gly Leu Ile Leu Ser Glu Ile Leu Cys Glu
            265                 270                 275

Pro Ala Glu Val Cys Asn Ser Leu Glu Asp Thr Tyr Lys Gly Thr Phe
280                 285                 290                 295

Val Ser Asp Leu Ala Leu Ala Ser Leu Val Ala Pro Tyr Ile Ser Ser
                300                 305                 310

Glu Val Ser Ser Arg Leu Gln Ala Ser Ala Val Gly Ala Ala Lys Gln
                315                 320                 325

Cys Thr Gly Gly Asn Asn Gln Thr Leu Cys Gly Arg Arg Trp Tyr Ser
            330                 335                 340

Asp Glu Trp Asp Gly Thr Asp Gly Arg Glu Glu Gln Leu Ser Ala Thr
345                 350                 355

Ser Ile Phe Phe Ala Asn Met Ala Gly Phe Thr Gly Lys Gly Val Ala
360                 365                 370                 375

Thr Ala Ala Ala Val Asp Gln Thr Thr Gly Ser Ala Gly Thr Asn
                380                 385                 390

Gly Thr Ser Thr Asn Gly Thr Gly Val Pro Val Ala Leu Asn Gly Ala
            395                 400                 405

Gly Arg Ser Ser Gln Gly Gln Phe Gly Val Ala Thr Ala Gly Val Leu
            410                 415                 420

Ala Gly Leu Val Leu Leu Leu Val Leu
            425                 430

<210> SEQ ID NO 36
<211> LENGTH: 432
<212> TYPE: PRT
<213> ORGANISM: Aspergillus aculeatus

<400> SEQUENCE: 36

Ile Asp Leu Asp Ile Asn Asn Glu Gln Ser Ile Lys Asp Ala Ala Ala
1               5                   10                  15

Thr Ala Ala Phe Asn Thr Met Gln His Tyr Asn Gly Asn Lys Thr Gly
            20                  25                  30

Glu Ile Pro Gly Val Ile Pro Ser Leu Trp Gly Glu Gly Gly Val Leu
        35                  40                  45

Phe Asn Leu Met Ile Gln Tyr Trp Tyr Phe Thr Gly Asp Ala Ser Tyr
    50                  55                  60

Asn Pro Ala Val Ser Gln Gly Met Tyr Trp Gln Ile Gly Asp Asp
65                  70                  75                  80

Tyr Met Pro Ser Asn Trp Ser Gln Ile Gly Asn Asp Asp Gln Met
                85                  90                  95

Ala Trp Gly Leu Ala Ala Met Thr Ala Ala Glu Leu Asp Tyr Pro Gln
            100                 105                 110

Asp Val Asn Gln Thr Ser Trp Leu Thr Leu Ala Glu Gly Val Phe Asn
            115                 120                 125

Thr Gln Val Ala Arg Trp Asp Ser Asn Cys Gly Gly Gly Leu Arg
130                 135                 140

-continued

```
Trp Gln Ile Trp Pro Phe Glu Ser Gly Tyr Thr Gln Lys Asn Ala Ile
145                 150                 155                 160

Ser Asn Gly Gly Leu Phe Gln Leu Ser Ala Arg Leu Ala Arg Tyr Thr
                165                 170                 175

His Asn Gln Thr Tyr Ala Asp Trp Ala Asp Lys Ile Trp Asp Trp Ser
            180                 185                 190

Ala Ser Val Pro Leu Leu Asn Asn Lys Thr Trp Ser Ile Ala Asp Ser
        195                 200                 205

Thr Asn Val Asp Asn Gly Cys Thr Thr Gln Gly Asn Asn Gln Trp Thr
    210                 215                 220

Ala Asn Tyr Gly Pro Tyr Ile Ser Gly Ala Ala Tyr Met Tyr Asn Tyr
225                 230                 235                 240

Thr Asn Gly Gln Asn Ser Lys Trp Lys Ser Gly Leu Asp Gly Leu Leu
                245                 250                 255

Asn Val Ser Phe Glu Thr Phe Phe Pro Glu Lys Tyr Gly Gly Leu Ile
                260                 265                 270

Leu Ser Glu Ile Leu Cys Glu Pro Ala Glu Val Cys Asn Ser Leu Glu
            275                 280                 285

Asp Thr Tyr Lys Gly Thr Phe Val Ser Asp Leu Ala Leu Ala Ser Leu
        290                 295                 300

Val Ala Pro Tyr Ile Ser Ser Glu Val Ser Ser Arg Leu Gln Ala Ser
305                 310                 315                 320

Ala Val Gly Ala Ala Lys Gln Cys Thr Gly Gly Asn Asn Gln Thr Leu
                325                 330                 335

Cys Gly Arg Arg Trp Tyr Ser Asp Glu Trp Asp Gly Thr Asp Gly Arg
                340                 345                 350

Glu Glu Gln Leu Ser Ala Thr Ser Ile Phe Phe Ala Asn Met Ala Gly
            355                 360                 365

Phe Thr Gly Lys Gly Val Ala Thr Ala Ala Ala Val Asp Gln Thr
        370                 375                 380

Thr Gly Ser Ala Gly Thr Asn Gly Thr Ser Thr Asn Gly Thr Gly Val
385                 390                 395                 400

Pro Val Ala Leu Asn Gly Ala Gly Arg Ser Ser Gln Gly Gln Phe Gly
                405                 410                 415

Val Ala Thr Ala Gly Val Leu Ala Gly Leu Val Leu Leu Val Leu
                420                 425                 430
```

<210> SEQ ID NO 37
<211> LENGTH: 1352
<212> TYPE: DNA
<213> ORGANISM: Aspergillus aculeatus
<220> FEATURE:
<221> NAME/KEY: CDS
<222> LOCATION: (1)..(97)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1304)
<220> FEATURE:
<221> NAME/KEY: CDS
<222> LOCATION: (163)..(857)
<220> FEATURE:
<221> NAME/KEY: CDS
<222> LOCATION: (921)..(1352)

<400> SEQUENCE: 37

```
atg atc ttg tcc ccg cgc tgg tgg acg gct ctg ctg gcc gtc ctc acc        48
```

```
Met Ile Leu Ser Pro Arg Trp Trp Thr Ala Leu Leu Ala Val Leu Thr
            -20                 -15                    -10 gtc ggg cag cac aca gtc aga gcc tta cag tta gat ctc aat gat gag c    97
Val Gly Gln His Thr Val Arg Ala Leu Gln Leu Asp Leu Asn Asp Glu
         -5              -1  1               5 gtaagcgcat acttcctgtt cacgagtatg attcatgcgc caagcactga ccttcttcta    157 catag aa  tcg atc aag aat gcg gcc gcg acg gca gcc tac aac atg atg   206
          Gln Ser Ile Lys Asn Ala Ala Ala Thr Ala Ala Tyr Asn Met Met
                 10              15                  20 agc tac tac cac ggc aac gaa tct ggg cag atc ccg ggc aaa ttg gta     254
Ser Tyr Tyr His Gly Asn Glu Ser Gly Gln Ile Pro Gly Lys Leu Val
     25              30                  35 gat aca tgg tgg gaa gga ggc gcc atg ttt atg acg ctg att caa tat     302
Asp Thr Trp Trp Glu Gly Gly Ala Met Phe Met Thr Leu Ile Gln Tyr
40                  45                  50                  55 tgg tat tgg acc ggc gac aca tcc tac aac gcc gtc acc acc gag ggt     350
Trp Tyr Trp Thr Gly Asp Thr Ser Tyr Asn Ala Val Thr Thr Glu Gly
                 60                  65                  70 atg ctc tgg cag aag ggc cag aac gat tat ttc ccc gcc aat tac agt     398
Met Leu Trp Gln Lys Gly Gln Asn Asp Tyr Phe Pro Ala Asn Tyr Ser
             75                  80                  85 aac tac ctc gga aac gat gac cag gtg ttc tgg ggg ctg gcc gca atg     446
Asn Tyr Leu Gly Asn Asp Asp Gln Val Phe Trp Gly Leu Ala Ala Met
         90                  95                 100 acg gcc gcc gag ttg aat tac cca gag gag gac ggc caa ccg tct tgg     494
Thr Ala Ala Glu Leu Asn Tyr Pro Glu Glu Asp Gly Gln Pro Ser Trp
    105                 110                 115 ctg tcg ctt gcg cag ggg gtc ttc aac act caa gta ccc cgc tgg gac     542
Leu Ser Leu Ala Gln Gly Val Phe Asn Thr Gln Val Pro Arg Trp Asp
120                 125                 130                 135 acg acc agt tgt caa ggt ggt ttg cgc tgg cag ctg tgg ccc tac cag     590
Thr Thr Ser Cys Gln Gly Gly Leu Arg Trp Gln Leu Trp Pro Tyr Gln
                140                 145                 150 gct gga tac acc acc aag aat gcg atc tcc aac ggg ggt ctc ttc caa     638
Ala Gly Tyr Thr Thr Lys Asn Ala Ile Ser Asn Gly Gly Leu Phe Gln
            155                 160                 165 tta gcg gcg cga ctg ggg cgc tac acc aac aat gag acg tac agc aac     686
Leu Ala Ala Arg Leu Gly Arg Tyr Thr Asn Asn Glu Thr Tyr Ser Asn
        170                 175                 180 tgg gcg gag aag atc tac gac tgg atg gcg acc acc ccg ctc ctg agg     734
Trp Ala Glu Lys Ile Tyr Asp Trp Met Ala Thr Thr Pro Leu Leu Arg
    185                 190                 195 gag gac cag tgg tcc att gct gat acg acc acg cag acg gag tgt         782
Glu Asp Gln Trp Ser Ile Ala Asp Thr Thr Thr Gln Thr Glu Cys
200                 205                 210                 215 aaa gac cat ggc gat ctc cag tgg acg tac aac tac gga acg tac atc     830
Lys Asp His Gly Asp Leu Gln Trp Thr Tyr Asn Tyr Gly Thr Tyr Ile
                220                 225                 230 agt gga gcc gcc tat atg tat aac cac gtatgacacc gtccttacca           877
Ser Gly Ala Ala Tyr Met Tyr Asn His
            235                 240 taggatctcc ctcaagtgac tgcaggaagc taactagact tag acc aac ggg gga     932
                                                Thr Asn Gly Gly gac aag tgg aag aag gcg tta gac ggc ttg ctc gga act acc ttg cag     980
Asp Lys Trp Lys Lys Ala Leu Asp Gly Leu Leu Gly Thr Thr Leu Gln
245                 250                 255                 260 aag ttc ttc cct caa gag ttc ggc ggc aac atc atg tcc gag atc tcc     1028
Lys Phe Phe Pro Gln Glu Phe Gly Gly Asn Ile Met Ser Glu Ile Ser
                265                 270                 275
```

-continued

| | | | | | | | | | | | | | | | | |
|---|---|---|---|---|---|---|---|---|---|---|---|---|---|---|---|---|
| tgc | gaa | ccg | aac | atg | atg | tgc | gat | cgc | aat | caa | gac | tgc | ttc | aag | ggg | 1076 |
| Cys | Glu | Pro | Asn | Met | Met | Cys | Asp | Arg | Asn | Gln | Asp | Cys | Phe | Lys | Gly | |
| | | | 280 | | | | | 285 | | | | | 290 | | | |
| ttt | ctg | tca | tcc | tgg | ttg | acc | ttc | acc | acc | acc | att | gcg | cct | cac | acc | 1124 |
| Phe | Leu | Ser | Ser | Trp | Leu | Thr | Phe | Thr | Thr | Thr | Ile | Ala | Pro | His | Thr | |
| | | | 295 | | | | | 300 | | | | | 305 | | | |
| gcg | ggc | gag | atc | atc | ccc | aaa | atc | cag | caa | tcg | gcc | ctg | gca | gcg | gcc | 1172 |
| Ala | Gly | Glu | Ile | Ile | Pro | Lys | Ile | Gln | Gln | Ser | Ala | Leu | Ala | Ala | Ala | |
| | | | 310 | | | | | 315 | | | | | 320 | | | |
| aag | caa | tgc | tct | ggc | ggc | aaa | tcg | ggc | act | gaa | tgc | ggc | cgc | cgc | tgg | 1220 |
| Lys | Gln | Cys | Ser | Gly | Gly | Lys | Ser | Gly | Thr | Glu | Cys | Gly | Arg | Arg | Trp | |
| 325 | | | | 330 | | | | | 335 | | | | | 340 | | |
| cac | cag | gcg | act | tgg | gat | ggg | gag | act | tcg | ctg | gag | tct | gat | atg | agt | 1268 |
| His | Gln | Ala | Thr | Trp | Asp | Gly | Glu | Thr | Ser | Leu | Glu | Ser | Asp | Met | Ser | |
| | | | | 345 | | | | | 350 | | | | | 355 | | |
| gcg | ctg | agc | gtc | ttt | tct | tcc | act | atg | att | gcc | cac | aag | ggc | caa | gaa | 1316 |
| Ala | Leu | Ser | Val | Phe | Ser | Ser | Thr | Met | Ile | Ala | His | Lys | Gly | Gln | Glu | |
| | | | 360 | | | | | 365 | | | | | 370 | | | |
| cag | agt | cac | caa | gga | ccg | ctg | act | tcg | gag | act | ggg | | | | | 1352 |
| Gln | Ser | His | Gln | Gly | Pro | Leu | Thr | Ser | Glu | Thr | Gly | | | | | |
| | | | 375 | | | | | 380 | | | | | | | | |

<210> SEQ ID NO 38
<211> LENGTH: 408
<212> TYPE: PRT
<213> ORGANISM: Aspergillus aculeatus

<400> SEQUENCE: 38

Met Ile Leu Ser Pro Arg Trp Trp Thr Ala Leu Leu Ala Val Leu Thr
               -20                  -15                -10

Val Gly Gln His Thr Val Arg Ala Leu Gln Leu Asp Leu Asn Asp Glu
          -5               -1  1                  5

Gln Ser Ile Lys Asn Ala Ala Ala Thr Ala Ala Tyr Asn Met Met Ser
       10                15              20

Tyr Tyr His Gly Asn Glu Ser Gly Gln Ile Pro Gly Lys Leu Val Asp
25               30                35              40

Thr Trp Trp Glu Gly Gly Ala Met Phe Met Thr Leu Ile Gln Tyr Trp
         45                50              55

Tyr Trp Thr Gly Asp Thr Ser Tyr Asn Ala Val Thr Thr Glu Gly Met
       60                65              70

Leu Trp Gln Lys Gly Gln Asn Asp Tyr Phe Pro Ala Asn Tyr Ser Asn
         75                80              85

Tyr Leu Gly Asn Asp Asp Gln Val Phe Trp Gly Leu Ala Ala Met Thr
     90                95              100

Ala Ala Glu Leu Asn Tyr Pro Glu Glu Asp Gly Gln Pro Ser Trp Leu
105              110              115            120

Ser Leu Ala Gln Gly Val Phe Asn Thr Gln Val Pro Arg Trp Asp Thr
         125              130              135

Thr Ser Cys Gln Gly Gly Leu Arg Trp Gln Leu Trp Pro Tyr Gln Ala
       140               145             150

Gly Tyr Thr Thr Lys Asn Ala Ile Ser Asn Gly Gly Leu Phe Gln Leu
         155              160            165

Ala Ala Arg Leu Gly Arg Tyr Thr Asn Asn Glu Thr Tyr Ser Asn Trp
    170              175              180

Ala Glu Lys Ile Tyr Asp Trp Met Ala Thr Thr Pro Leu Leu Arg Glu
185              190              195            200

-continued

```
Asp Gln Trp Ser Ile Ala Asp Thr Thr Thr Gln Thr Glu Cys Lys
                205                 210                 215

Asp His Gly Asp Leu Gln Trp Thr Tyr Asn Tyr Gly Tyr Ile Ser
            220                 225                 230

Gly Ala Ala Tyr Met Tyr Asn His Thr Asn Gly Gly Asp Lys Trp Lys
        235                 240                 245

Lys Ala Leu Asp Gly Leu Leu Gly Thr Thr Leu Gln Lys Phe Phe Pro
250                 255                 260

Gln Glu Phe Gly Gly Asn Ile Met Ser Glu Ile Ser Cys Glu Pro Asn
265                 270                 275                 280

Met Met Cys Asp Arg Asn Gln Asp Cys Phe Lys Gly Phe Leu Ser Ser
                285                 290                 295

Trp Leu Thr Phe Thr Thr Thr Ile Ala Pro His Thr Ala Gly Glu Ile
            300                 305                 310

Ile Pro Lys Ile Gln Gln Ser Ala Leu Ala Ala Lys Gln Cys Ser
        315                 320                 325

Gly Gly Lys Ser Gly Thr Glu Cys Gly Arg Arg Trp His Gln Ala Thr
        330                 335                 340

Trp Asp Gly Glu Thr Ser Leu Glu Ser Asp Met Ser Ala Leu Ser Val
345                 350                 355                 360

Phe Ser Ser Thr Met Ile Ala His Lys Gly Gln Gln Ser His Gln
                365                 370                 375

Gly Pro Leu Thr Ser Glu Thr Gly
            380

<210> SEQ ID NO 39
<211> LENGTH: 384
<212> TYPE: PRT
<213> ORGANISM: Aspergillus aculeatus

<400> SEQUENCE: 39

Leu Gln Leu Asp Leu Asn Asp Glu Gln Ser Ile Lys Asn Ala Ala Ala
1               5                   10                  15

Thr Ala Ala Tyr Asn Met Met Ser Tyr Tyr His Gly Asn Glu Ser Gly
            20                  25                  30

Gln Ile Pro Gly Lys Leu Val Asp Thr Trp Trp Glu Gly Gly Ala Met
        35                  40                  45

Phe Met Thr Leu Ile Gln Tyr Trp Tyr Trp Thr Gly Asp Thr Ser Tyr
    50                  55                  60

Asn Ala Val Thr Thr Glu Gly Met Leu Trp Gln Lys Gly Gln Asn Asp
65                  70                  75                  80

Tyr Phe Pro Ala Asn Tyr Ser Asn Tyr Leu Gly Asn Asp Asp Gln Val
                85                  90                  95

Phe Trp Gly Leu Ala Ala Met Thr Ala Ala Glu Leu Asn Tyr Pro Glu
            100                 105                 110

Glu Asp Gly Gln Pro Ser Trp Leu Ser Leu Ala Gln Gly Val Phe Asn
        115                 120                 125

Thr Gln Val Pro Arg Trp Asp Thr Thr Ser Cys Gln Gly Gly Leu Arg
    130                 135                 140

Trp Gln Leu Trp Pro Tyr Gln Ala Gly Tyr Thr Thr Lys Asn Ala Ile
145                 150                 155                 160

Ser Asn Gly Gly Leu Phe Gln Leu Ala Ala Arg Leu Gly Arg Tyr Thr
                165                 170                 175

Asn Asn Glu Thr Tyr Ser Asn Trp Ala Glu Lys Ile Tyr Asp Trp Met
            180                 185                 190
```

```
Ala Thr Thr Pro Leu Leu Arg Glu Asp Gln Trp Ser Ile Ala Asp Thr
        195                 200                 205

Thr Thr Thr Gln Thr Glu Cys Lys Asp His Gly Asp Leu Gln Trp Thr
    210                 215                 220

Tyr Asn Tyr Gly Thr Tyr Ile Ser Gly Ala Ala Tyr Met Tyr Asn His
225                 230                 235                 240

Thr Asn Gly Gly Asp Lys Trp Lys Lys Ala Leu Asp Gly Leu Leu Gly
                245                 250                 255

Thr Thr Leu Gln Lys Phe Phe Pro Gln Glu Phe Gly Gly Asn Ile Met
        260                 265                 270

Ser Glu Ile Ser Cys Glu Pro Asn Met Met Cys Asp Arg Asn Gln Asp
        275                 280                 285

Cys Phe Lys Gly Phe Leu Ser Ser Trp Leu Thr Phe Thr Thr Thr Ile
290                 295                 300

Ala Pro His Thr Ala Gly Glu Ile Ile Pro Lys Ile Gln Gln Ser Ala
305                 310                 315                 320

Leu Ala Ala Ala Lys Gln Cys Ser Gly Gly Lys Ser Gly Thr Glu Cys
                325                 330                 335

Gly Arg Arg Trp His Gln Ala Thr Trp Asp Gly Glu Thr Ser Leu Glu
                340                 345                 350

Ser Asp Met Ser Ala Leu Ser Val Phe Ser Ser Thr Met Ile Ala His
        355                 360                 365

Lys Gly Gln Glu Gln Ser His Gln Gly Pro Leu Thr Ser Glu Thr Gly
        370                 375                 380

<210> SEQ ID NO 40
<211> LENGTH: 1473
<212> TYPE: DNA
<213> ORGANISM: Aspergillus aculeatus
<220> FEATURE:
<221> NAME/KEY: CDS
<222> LOCATION: (1)..(100)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1473)
<220> FEATURE:
<221> NAME/KEY: CDS
<222> LOCATION: (233)..(477)
<220> FEATURE:
<221> NAME/KEY: CDS
<222> LOCATION: (543)..(992)
<220> FEATURE:
<221> NAME/KEY: CDS
<222> LOCATION: (1054)..(1473)

<400> SEQUENCE: 40 atg cgc ttc ctc cat ggt gct ctc cat gga ggg ctg ctt tta aat gcc      48
Met Arg Phe Leu His Gly Ala Leu His Gly Gly Leu Leu Leu Asn Ala
-25             -20                 -15                 -10 gct ctc ttc ggc cat gtt gct cat gcc att gat att gat atc agc agt      96
Ala Leu Phe Gly His Val Ala His Ala Ile Asp Ile Asp Ile Ser Ser
            -5                  -1  1               5 gaa t gtatgccttc cgctctttga ttctatcgcg tcctccagcc tgccgtctac        150
Glu ctttccatac caatcgggga taacttgtgg cattctcgga taagctgtca cacagaacac   210
tgaccatcgt ctatcgcaac ag ca  tct ata aag gct gcg gca agc aaa aca   261
                           Ser Ser Ile Lys Ala Ala Ala Ser Lys Thr
                                10                  15
```

| | | |
|---|---|---|
| gca tac ggg tca atg acc tgg tac cac ggc aat gag acc ggc caa att<br>Ala Tyr Gly Ser Met Thr Trp Tyr His Gly Asn Glu Thr Gly Gln Ile<br>   20                        25                       30 | 309 | |
| cct ggt gca ttc ccc acc aag tgg tgg gaa ggc agt gcg ctg ttc atg<br>Pro Gly Ala Phe Pro Thr Lys Trp Trp Glu Gly Ser Ala Leu Phe Met<br>35                   40                   45                   50 | 357 | |
| agt ttg ctt ctc tac tat tat tat acc gga gac agc acc tac aac gat<br>Ser Leu Leu Leu Tyr Tyr Tyr Tyr Thr Gly Asp Ser Thr Tyr Asn Asp<br>                 55                    60                  65 | 405 | |
| gaa gtt cgc caa ggt atg caa tgg caa gca ggt gat tgc gac tac atg<br>Glu Val Arg Gln Gly Met Gln Trp Gln Ala Gly Asp Cys Asp Tyr Met<br>          70                    75                   80 | 453 | |
| ccg agc aac tac agt agt tat ctg gtatgtaatc cggctcgcgt gggatcagac<br>Pro Ser Asn Tyr Ser Ser Tyr Leu<br>         85                    90 | 507 | |
| tttcggacgg aatctcacat aaggcatctg ggtag ggt aac gac gat caa atg<br>                                                             Gly Asn Asp Asp Gln Met<br>                                                                            95 | 560 | |
| ttc tgg ggc ctt gcg gcg atg acc gcg gcg gag atc gac ttc gcc gat<br>Phe Trp Gly Leu Ala Ala Met Thr Ala Ala Glu Ile Asp Phe Ala Asp<br>                 100                   105                   110 | 608 | |
| tcg acc gac gga tat tcc tgg ctc gct ctt gct cag ggc gtg tac aac<br>Ser Thr Asp Gly Tyr Ser Trp Leu Ala Leu Ala Gln Gly Val Tyr Asn<br>              115                    120                   125 | 656 | |
| acc caa gtc gca cgc tgg gac tcg tcg aac tgt gga ggc ggc ctg cgc<br>Thr Gln Val Ala Arg Trp Asp Ser Ser Asn Cys Gly Gly Gly Leu Arg<br>          130                   135                   140 | 704 | |
| tgg cag atc tgg ccg tac gag gct ggt tac gat atg aag aac tca atc<br>Trp Gln Ile Trp Pro Tyr Glu Ala Gly Tyr Asp Met Lys Asn Ser Ile<br>145                 150                   155                   160 | 752 | |
| tcg aac gga ggc ttg ttt cag ctg gct gcc cgt ctc gcc cgt tac acg<br>Ser Asn Gly Gly Leu Phe Gln Leu Ala Ala Arg Leu Ala Arg Tyr Thr<br>                 165                   170                   175 | 800 | |
| aac aac gat acg tac gcc gac tgg gcc gag aag atc ttc gat tgg tcg<br>Asn Asn Asp Thr Tyr Ala Asp Trp Ala Glu Lys Ile Phe Asp Trp Ser<br>                 180                   185                   190 | 848 | |
| gca tct gtt cct ctg ttg aat aac gaa acg tgg aac gtt gca gac tct<br>Ala Ser Val Pro Leu Leu Asn Asn Glu Thr Trp Asn Val Ala Asp Ser<br>          195                   200                   205 | 896 | |
| acc gac atc gat aac ggc tgc aca acg cag ggc aac aac caa tgg tct<br>Thr Asp Ile Asp Asn Gly Cys Thr Thr Gln Gly Asn Asn Gln Trp Ser<br>          210                   215                   220 | 944 | |
| tac aac tat gga aca tat ctg atg ggt gcc gca tac atg tac aac tac<br>Tyr Asn Tyr Gly Thr Tyr Leu Met Gly Ala Ala Tyr Met Tyr Asn Tyr<br>225                 230                   235                   240 | 992 | |
| gtaaggacga aacccgactg acctttggtt gtgtggacgc tgacctgaga caaaatcgca | 1052 | |
| g acg ggc aag gcc aaa tgg aag acc gcc gtg gat ggt ctt ttg aac gtc<br>   Thr Gly Lys Ala Lys Trp Lys Thr Ala Val Asp Gly Leu Leu Asn Val<br>                        245                          250                   255 | 1101 | |
| act ctg acc aca ttc ttc ccg tcc aag tac ggc ggc aac atc atg tct<br>Thr Leu Thr Thr Phe Phe Pro Ser Lys Tyr Gly Gly Asn Ile Met Ser<br>          260                   265                   270 | 1149 | |
| gag gaa cta tgt gaa ccc ctg gag gtt tgc aac gac aac gaa atc ctc<br>Glu Glu Leu Cys Glu Pro Leu Glu Val Cys Asn Asp Asn Glu Ile Leu<br>          275                   280                   285 | 1197 | |
| ttc aag ggc ctg ctt agc gga tgg ctc ggg ttt gtg gcg ttg gtg gtt<br>Phe Lys Gly Leu Leu Ser Gly Trp Leu Gly Phe Val Ala Leu Val Val<br>          290                   295                   300 | 1245 | |

| | | | | | | | | | | | | | | | |
|---|---|---|---|---|---|---|---|---|---|---|---|---|---|---|---|
| ccc | tcg | aca | tat | gac | cag | atc | ttg | ccg | aag | ctg | cag | ggc | tcc | gcc | gag | 1293 |
| Pro | Ser | Thr | Tyr | Asp | Gln | Ile | Leu | Pro | Lys | Leu | Gln | Gly | Ser | Ala | Glu | |
| 305 | | | | 310 | | | | | 315 | | | | | 320 | | |
| gcc | gct | gcc | gcg | tct | tgc | agc | gga | atg | agc | aac | aac | acg | tgt | ggt | gta | 1341 |
| Ala | Ala | Ala | Ala | Ser | Cys | Ser | Gly | Met | Ser | Asn | Asn | Thr | Cys | Gly | Val | |
| | | | | 325 | | | | | 330 | | | | | 335 | | |
| cgg | tgg | tac | ccg | aag | tcg | tgg | gat | gga | tgg | aac | ggc | atg | gag | gaa | gaa | 1389 |
| Arg | Trp | Tyr | Pro | Lys | Ser | Trp | Asp | Gly | Trp | Asn | Gly | Met | Glu | Glu | Glu | |
| | | | | 340 | | | | | 345 | | | | | 350 | | |
| atc | gcc | gtc | acc | aat | gtt | ctt | tca | tct | gtc | ctc | att | acg | acg | aag | aag | 1437 |
| Ile | Ala | Val | Thr | Asn | Val | Leu | Ser | Ser | Val | Leu | Ile | Thr | Thr | Lys | Lys | |
| | | | 355 | | | | | 360 | | | | | 365 | | | |
| tcc | ggt | cca | gtg | acc | tcc | act | acc | ggc | ggt | aac | agt | | | | | 1473 |
| Ser | Gly | Pro | Val | Thr | Ser | Thr | Thr | Gly | Gly | Asn | Ser | | | | | |
| | 370 | | | | | 375 | | | | | 380 | | | | | |

<210> SEQ ID NO 41
<211> LENGTH: 405
<212> TYPE: PRT
<213> ORGANISM: Aspergillus aculeatus

<400> SEQUENCE: 41

Met Arg Phe Leu His Gly Ala Leu His Gly Gly Leu Leu Asn Ala
-25              -20              -15                   -10

Ala Leu Phe Gly His Val Ala His Ala Ile Asp Ile Asp Ile Ser Ser
              -5               -1  1                  5

Glu Ser Ser Ile Lys Ala Ala Ala Ser Lys Thr Ala Tyr Gly Ser Met
             10                   15                    20

Thr Trp Tyr His Gly Asn Glu Thr Gly Gln Ile Pro Gly Ala Phe Pro
25                   30                   35

Thr Lys Trp Trp Glu Gly Ser Ala Leu Phe Met Ser Leu Leu Leu Tyr
40                   45                   50                   55

Tyr Tyr Tyr Thr Gly Asp Ser Thr Tyr Asn Asp Glu Val Arg Gln Gly
              60                   65                   70

Met Gln Trp Gln Ala Gly Asp Cys Asp Tyr Met Pro Ser Asn Tyr Ser
              75                   80                   85

Ser Tyr Leu Gly Asn Asp Asp Gln Met Phe Trp Gly Leu Ala Ala Met
              90                   95                   100

Thr Ala Ala Glu Ile Asp Phe Ala Asp Ser Thr Asp Gly Tyr Ser Trp
              105                   110                   115

Leu Ala Leu Ala Gln Gly Val Tyr Asn Thr Gln Val Ala Arg Trp Asp
120                   125                   130                   135

Ser Ser Asn Cys Gly Gly Gly Leu Arg Trp Gln Ile Trp Pro Tyr Glu
              140                   145                   150

Ala Gly Tyr Asp Met Lys Asn Ser Ile Ser Asn Gly Gly Leu Phe Gln
              155                   160                   165

Leu Ala Ala Arg Leu Ala Arg Tyr Thr Asn Asn Asp Thr Tyr Ala Asp
              170                   175                   180

Trp Ala Glu Lys Ile Phe Asp Trp Ser Ala Ser Val Pro Leu Leu Asn
185                   190                   195

Asn Glu Thr Trp Asn Val Ala Asp Ser Thr Asp Ile Asp Asn Gly Cys
200                   205                   210                   215

Thr Thr Gln Gly Asn Asn Gln Trp Ser Tyr Asn Tyr Gly Thr Tyr Leu
              220                   225                   230

Met Gly Ala Ala Tyr Met Tyr Asn Tyr Thr Gly Lys Ala Lys Trp Lys
              235                   240                   245

```
Thr Ala Val Asp Gly Leu Leu Asn Val Thr Leu Thr Thr Phe Phe Pro
            250                 255                 260

Ser Lys Tyr Gly Gly Asn Ile Met Ser Glu Glu Leu Cys Glu Pro Leu
        265                 270                 275

Glu Val Cys Asn Asp Asn Glu Ile Leu Phe Lys Gly Leu Leu Ser Gly
280                 285                 290                 295

Trp Leu Gly Phe Val Ala Leu Val Val Pro Ser Thr Tyr Asp Gln Ile
                300                 305                 310

Leu Pro Lys Leu Gln Gly Ser Ala Glu Ala Ala Ala Ser Cys Ser
                315                 320                 325

Gly Met Ser Asn Asn Thr Cys Gly Val Arg Trp Tyr Pro Lys Ser Trp
            330                 335                 340

Asp Gly Trp Asn Gly Met Glu Glu Glu Ile Ala Val Thr Asn Val Leu
            345                 350                 355

Ser Ser Val Leu Ile Thr Thr Lys Lys Ser Gly Pro Val Thr Ser Thr
360                 365                 370                 375

Thr Gly Gly Asn Ser
            380

<210> SEQ ID NO 42
<211> LENGTH: 380
<212> TYPE: PRT
<213> ORGANISM: Aspergillus aculeatus

<400> SEQUENCE: 42

Ile Asp Ile Asp Ile Ser Ser Glu Ser Ser Ile Lys Ala Ala Ala Ser
1               5                   10                  15

Lys Thr Ala Tyr Gly Ser Met Thr Trp Tyr His Gly Asn Glu Thr Gly
            20                  25                  30

Gln Ile Pro Gly Ala Phe Pro Thr Lys Trp Trp Glu Gly Ser Ala Leu
        35                  40                  45

Phe Met Ser Leu Leu Tyr Tyr Tyr Tyr Thr Gly Asp Ser Thr Tyr
    50                  55                  60

Asn Asp Glu Val Arg Gln Gly Met Gln Trp Gln Ala Gly Asp Cys Asp
65                  70                  75                  80

Tyr Met Pro Ser Asn Tyr Ser Ser Tyr Leu Gly Asn Asp Asp Gln Met
                85                  90                  95

Phe Trp Gly Leu Ala Ala Met Thr Ala Ala Glu Ile Asp Phe Ala Asp
            100                 105                 110

Ser Thr Asp Gly Tyr Ser Trp Leu Ala Leu Ala Gln Gly Val Tyr Asn
        115                 120                 125

Thr Gln Val Ala Arg Trp Asp Ser Ser Asn Cys Gly Gly Gly Leu Arg
130                 135                 140

Trp Gln Ile Trp Pro Tyr Glu Ala Gly Tyr Asp Met Lys Asn Ser Ile
145                 150                 155                 160

Ser Asn Gly Gly Leu Phe Gln Leu Ala Ala Arg Leu Ala Arg Tyr Thr
                165                 170                 175

Asn Asn Asp Thr Tyr Ala Asp Trp Ala Glu Lys Ile Phe Asp Trp Ser
            180                 185                 190

Ala Ser Val Pro Leu Leu Asn Asn Glu Thr Trp Asn Val Ala Asp Ser
        195                 200                 205

Thr Asp Ile Asp Asn Gly Cys Thr Thr Gln Gly Asn Asn Gln Trp Ser
210                 215                 220

Tyr Asn Tyr Gly Thr Tyr Leu Met Gly Ala Ala Tyr Met Tyr Asn Tyr
225                 230                 235                 240
```

```
Thr Gly Lys Ala Lys Trp Lys Thr Ala Val Asp Gly Leu Leu Asn Val
            245                 250                 255
Thr Leu Thr Thr Phe Phe Pro Ser Lys Tyr Gly Gly Asn Ile Met Ser
            260                 265                 270
Glu Glu Leu Cys Glu Pro Leu Glu Val Cys Asn Asp Asn Glu Ile Leu
            275                 280                 285
Phe Lys Gly Leu Leu Ser Gly Trp Leu Gly Phe Val Ala Leu Val Val
            290                 295                 300
Pro Ser Thr Tyr Asp Gln Ile Leu Pro Lys Leu Gln Gly Ser Ala Glu
305                 310                 315                 320
Ala Ala Ala Ala Ser Cys Ser Gly Met Ser Asn Asn Thr Cys Gly Val
            325                 330                 335
Arg Trp Tyr Pro Lys Ser Trp Asp Gly Trp Asn Gly Met Glu Glu Glu
            340                 345                 350
Ile Ala Val Thr Asn Val Leu Ser Ser Val Leu Ile Thr Thr Lys Lys
            355                 360                 365
Ser Gly Pro Val Thr Ser Thr Thr Gly Gly Asn Ser
            370                 375                 380

<210> SEQ ID NO 43
<211> LENGTH: 1389
<212> TYPE: DNA
<213> ORGANISM: Humicola insolens
<220> FEATURE:
<221> NAME/KEY: CDS
<222> LOCATION: (1)..(100)
<220> FEATURE:
<221> NAME/KEY: sig_peptide
<222> LOCATION: (1)..(69)
<220> FEATURE:
<221> NAME/KEY: mat_peptide
<222> LOCATION: (70)..(1389)
<220> FEATURE:
<221> NAME/KEY: CDS
<222> LOCATION: (179)..(900)
<220> FEATURE:
<221> NAME/KEY: CDS
<222> LOCATION: (967)..(1389)

<400> SEQUENCE: 43 atg ctc ccc aag cca gcg gcg ctc ctt cgc gcc atg ctg ctt gcg gcc    48
Met Leu Pro Lys Pro Ala Ala Leu Leu Arg Ala Met Leu Leu Ala Ala
        -20                 -15                 -10 atc gcc gcc gat gcc cag tcc gac aag ctc caa gtc gac ctc aac tct    96
Ile Ala Ala Asp Ala Gln Ser Asp Lys Leu Gln Val Asp Leu Asn Ser
        -5                  -1  1                   5 cca g gtgcgtcttt gacacggtag ttcgcctccg ttgcttcgag gataattctc        150
Pro
10 gctgacccaa gcgcctctgc atctccag cc tcg atc aag aaa gcc gca aaa       201
                                 Ala Ser Ile Lys Lys Ala Ala Lys
                                                         15 ctg gtc gct gcc aac ctc atg tcc cac tac cat ggc gac gaa ccc ggt    249
Leu Val Ala Ala Asn Leu Met Ser His Tyr His Gly Asp Glu Pro Gly
        20                  25                  30 gct act cct ggt atc ctc cca ggc ccg cct cct gct ggt cca tac tac    297
Ala Thr Pro Gly Ile Leu Pro Gly Pro Pro Pro Ala Gly Pro Tyr Tyr
35                  40                  45                  50 tgg tgg caa gcc ggt gct atg tgg ggg acc ata gtc gac tac tgg cac    345
Trp Trp Gln Ala Gly Ala Met Trp Gly Thr Ile Val Asp Tyr Trp His
                55                  60                  65
```

```
                                                 -continued tac acg gga gac gaa aca tac aac gcc gaa gcg ctg cgg tcc atg gtc      393
Tyr Thr Gly Asp Glu Thr Tyr Asn Ala Glu Ala Leu Arg Ser Met Val
             70                  75                  80 ttc cag gct gaa cct ccc gcc aac gcc tac atg ccc cgc aac tgg acc      441
Phe Gln Ala Glu Pro Pro Ala Asn Ala Tyr Met Pro Arg Asn Trp Thr
         85                  90                  95 gcg tcc cta ggt aac gac gat caa ggt ttc tgg ggt atg gcc gcc atg      489
Ala Ser Leu Gly Asn Asp Asp Gln Gly Phe Trp Gly Met Ala Ala Met
        100                 105                 110 ctc gcc gcc gag acg aac ttc acc aac cca cca gaa gac cag cct caa      537
Leu Ala Ala Glu Thr Asn Phe Thr Asn Pro Pro Glu Asp Gln Pro Gln
115             120                 125                 130 tgg cta gcc ctt gcc cag gcc gtc ttc aac acc cag gtc ccg cgt tgg      585
Trp Leu Ala Leu Ala Gln Ala Val Phe Asn Thr Gln Val Pro Arg Trp
                135                 140                 145 gag atg gac tac tgc aac ggt ggt ctg cga tgg caa atc gtg cag gcc      633
Glu Met Asp Tyr Cys Asn Gly Gly Leu Arg Trp Gln Ile Val Gln Ala
            150                 155                 160 aac aac ggc tac aac tac aag aac acc atc gct gct gcc gtc ttc ctc      681
Asn Asn Gly Tyr Asn Tyr Lys Asn Thr Ile Ala Ala Ala Val Phe Leu
        165                 170                 175 aac att gct tcc cgt ctg gcc cga tac acc ggc aac gac tcg tac gcg      729
Asn Ile Ala Ser Arg Leu Ala Arg Tyr Thr Gly Asn Asp Ser Tyr Ala
    180                 185                 190 gaa tgg gct gaa agg gct tgg gac tgg atg gag ggt gtc gga tac atc      777
Glu Trp Ala Glu Arg Ala Trp Asp Trp Met Glu Gly Val Gly Tyr Ile
195                 200                 205                 210 acc gag gac ttc aat gtt aag gat ggt gcc cac gtc gaa tcc aac tgc      825
Thr Glu Asp Phe Asn Val Lys Asp Gly Ala His Val Glu Ser Asn Cys
                215                 220                 225 acc gac atc aac ccc gtc cag ttc tct gcc aac gct gcc atc ctg atc      873
Thr Asp Ile Asn Pro Val Gln Phe Ser Ala Asn Ala Ala Ile Leu Ile
            230                 235                 240 cac ggc gtt tcc gtc atg tac aac tac gtatgttcac tacctgcttg            920
His Gly Val Ser Val Met Tyr Asn Tyr
        245                 250 acttgctcca ttatctcccg acctattcct tgctaaccca actcag aca tcc ggg       975
                                                  Thr Ser Gly agc gcc cgc gat aaa tgg cgt tac cgc gtc gtt ggc ctt gtc aac cgc     1023
Ser Ala Arg Asp Lys Trp Arg Tyr Arg Val Val Gly Leu Val Asn Arg
255                 260                 265                 270 acc ctc gaa cac ttt ttc ccc gac ggc atc atg gtc gaa cgc ccc tgc     1071
Thr Leu Glu His Phe Phe Pro Asp Gly Ile Met Val Glu Arg Pro Cys
                275                 280                 285 gaa ctc gaa gac cgc atg caa tgc aac aca gac cag cac tcc ttc aaa     1119
Glu Leu Glu Asp Arg Met Gln Cys Asn Thr Asp Gln His Ser Phe Lys
            290                 295                 300 ggg tac atg cac cgc gcc ctc gcc aca gcc gcc gtc gtc gcc ccc ttc     1167
Gly Tyr Met His Arg Ala Leu Ala Thr Ala Ala Val Val Ala Pro Phe
        305                 310                 315 atg cgc gat acc atc gtc ccc gtc ctc cgc tct tcc acc gaa ggc tgc     1215
Met Arg Asp Thr Ile Val Pro Val Leu Arg Ser Ser Thr Glu Gly Cys
    320                 325                 330 gtc tcc tcc tgc ctc gcc gac gga acc tgc ggt ttc cgt tgg aac att     1263
Val Ser Ser Cys Leu Ala Asp Gly Thr Cys Gly Phe Arg Trp Asn Ile
335                 340                 345                 350 ggc cgc tac gac ggc gac gtc gac cac ggt ccc gcc ggt cag cag atg     1311
Gly Arg Tyr Asp Gly Asp Val Asp His Gly Pro Ala Gly Gln Gln Met
                355                 360                 365
```

```
agc gcc ctc gcc gcg ctg tcg acc ttg ctg atc gat cag gat cgg gtt      1359
Ser Ala Leu Ala Ala Leu Ser Thr Leu Leu Ile Asp Gln Asp Arg Val
            370                 375                 380 ctg cgc ggg ccg ttg acg aac gcg acc ggc                              1389
Leu Arg Gly Pro Leu Thr Asn Ala Thr Gly
        385                 390
```

<210> SEQ ID NO 44
<211> LENGTH: 415
<212> TYPE: PRT
<213> ORGANISM: Humicola insolens

<400> SEQUENCE: 44

```
Met Leu Pro Lys Pro Ala Leu Leu Arg Ala Met Leu Leu Ala Ala
            -20                 -15                 -10

Ile Ala Ala Asp Ala Gln Ser Asp Lys Leu Gln Val Asp Leu Asn Ser
             -5              -1  1               5

Pro Ala Ser Ile Lys Lys Ala Ala Lys Leu Val Ala Ala Asn Leu Met
 10              15                  20                  25

Ser His Tyr His Gly Asp Glu Pro Gly Ala Thr Pro Gly Ile Leu Pro
                 30                  35                  40

Gly Pro Pro Pro Ala Gly Pro Tyr Tyr Trp Trp Gln Ala Gly Ala Met
             45                  50                  55

Trp Gly Thr Ile Val Asp Tyr Trp His Tyr Thr Gly Asp Glu Thr Tyr
             60                  65                  70

Asn Ala Glu Ala Leu Arg Ser Met Val Phe Gln Ala Glu Pro Pro Ala
 75                  80                  85

Asn Ala Tyr Met Pro Arg Asn Trp Thr Ala Ser Leu Gly Asn Asp Asp
 90                  95                 100                 105

Gln Gly Phe Trp Gly Met Ala Ala Met Leu Ala Ala Glu Thr Asn Phe
                110                 115                 120

Thr Asn Pro Pro Glu Asp Gln Pro Gln Trp Leu Ala Leu Ala Gln Ala
                125                 130                 135

Val Phe Asn Thr Gln Val Pro Arg Trp Glu Met Asp Tyr Cys Asn Gly
            140                 145                 150

Gly Leu Arg Trp Gln Ile Val Gln Ala Asn Asn Gly Tyr Asn Tyr Lys
    155                 160                 165

Asn Thr Ile Ala Ala Ala Val Phe Leu Asn Ile Ala Ser Arg Leu Ala
170                 175                 180                 185

Arg Tyr Thr Gly Asn Asp Ser Tyr Ala Glu Trp Ala Glu Arg Ala Trp
                190                 195                 200

Asp Trp Met Glu Gly Val Gly Tyr Ile Thr Glu Asp Phe Asn Val Lys
                205                 210                 215

Asp Gly Ala His Val Glu Ser Asn Cys Thr Asp Ile Asn Pro Val Gln
                220                 225                 230

Phe Ser Ala Asn Ala Ala Ile Leu Ile His Gly Val Ser Val Met Tyr
    235                 240                 245

Asn Tyr Thr Ser Gly Ser Ala Arg Asp Lys Trp Arg Tyr Arg Val Val
250                 255                 260                 265

Gly Leu Val Asn Arg Thr Leu Glu His Phe Phe Pro Asp Gly Ile Met
                270                 275                 280

Val Glu Arg Pro Cys Glu Leu Glu Asp Arg Met Gln Cys Asn Thr Asp
            285                 290                 295

Gln His Ser Phe Lys Gly Tyr Met His Arg Ala Leu Ala Thr Ala Ala
    300                 305                 310
```

```
Val Val Ala Pro Phe Met Arg Asp Thr Ile Val Pro Val Leu Arg Ser
    315                 320                 325

Ser Thr Glu Gly Cys Val Ser Ser Cys Leu Ala Asp Gly Thr Cys Gly
330                 335                 340                 345

Phe Arg Trp Asn Ile Gly Arg Tyr Asp Gly Asp Val Asp His Gly Pro
                350                 355                 360

Ala Gly Gln Gln Met Ser Ala Leu Ala Ala Leu Ser Thr Leu Leu Ile
                365                 370                 375

Asp Gln Asp Arg Val Leu Arg Gly Pro Leu Thr Asn Ala Thr Gly
                380                 385                 390

<210> SEQ ID NO 45
<211> LENGTH: 392
<212> TYPE: PRT
<213> ORGANISM: Humicola insolens

<400> SEQUENCE: 45

Asp Lys Leu Gln Val Asp Leu Asn Ser Pro Ala Ser Ile Lys Lys Ala
1               5                   10                  15

Ala Lys Leu Val Ala Ala Asn Leu Met Ser His Tyr His Gly Asp Glu
                20                  25                  30

Pro Gly Ala Thr Pro Gly Ile Leu Pro Gly Pro Pro Ala Gly Pro
                35                  40                  45

Tyr Tyr Trp Trp Gln Ala Gly Ala Met Trp Gly Thr Ile Val Asp Tyr
50                  55                  60

Trp His Tyr Thr Gly Asp Glu Thr Tyr Asn Ala Glu Ala Leu Arg Ser
65                  70                  75                  80

Met Val Phe Gln Ala Glu Pro Pro Ala Asn Ala Tyr Met Pro Arg Asn
                85                  90                  95

Trp Thr Ala Ser Leu Gly Asn Asp Gln Gly Phe Trp Gly Met Ala
                100                 105                 110

Ala Met Leu Ala Ala Glu Thr Asn Phe Thr Asn Pro Pro Glu Asp Gln
                115                 120                 125

Pro Gln Trp Leu Ala Leu Ala Gln Ala Val Phe Asn Thr Gln Val Pro
    130                 135                 140

Arg Trp Glu Met Asp Tyr Cys Asn Gly Gly Leu Arg Trp Gln Ile Val
145                 150                 155                 160

Gln Ala Asn Asn Gly Tyr Asn Tyr Lys Asn Thr Ile Ala Ala Ala Val
                165                 170                 175

Phe Leu Asn Ile Ala Ser Arg Leu Ala Arg Tyr Thr Gly Asn Asp Ser
                180                 185                 190

Tyr Ala Glu Trp Ala Glu Arg Ala Trp Asp Trp Met Glu Gly Val Gly
                195                 200                 205

Tyr Ile Thr Glu Asp Phe Asn Val Lys Asp Gly Ala His Val Glu Ser
    210                 215                 220

Asn Cys Thr Asp Ile Asn Pro Val Gln Phe Ser Ala Asn Ala Ala Ile
225                 230                 235                 240

Leu Ile His Gly Val Ser Val Met Tyr Asn Tyr Thr Ser Gly Ser Ala
                245                 250                 255

Arg Asp Lys Trp Arg Tyr Arg Val Gly Leu Val Asn Arg Thr Leu
                260                 265                 270

Glu His Phe Phe Pro Asp Gly Ile Met Val Glu Arg Pro Cys Glu Leu
            275                 280                 285

Glu Asp Arg Met Gln Cys Asn Thr Asp Gln His Ser Phe Lys Gly Tyr
            290                 295                 300
```

```
Met His Arg Ala Leu Ala Thr Ala Ala Val Val Ala Pro Phe Met Arg
305                 310                 315                 320

Asp Thr Ile Val Pro Val Leu Arg Ser Ser Thr Glu Gly Cys Val Ser
                325                 330                 335

Ser Cys Leu Ala Asp Gly Thr Cys Gly Phe Arg Trp Asn Ile Gly Arg
                340                 345                 350

Tyr Asp Gly Asp Val Asp His Gly Pro Ala Gly Gln Gln Met Ser Ala
                355                 360                 365

Leu Ala Ala Leu Ser Thr Leu Leu Ile Asp Gln Asp Arg Val Leu Arg
                370                 375                 380

Gly Pro Leu Thr Asn Ala Thr Gly
385                 390

<210> SEQ ID NO 46
<211> LENGTH: 1336
<212> TYPE: DNA
<213> ORGANISM: Humicola insolens
<220> FEATURE:
<221> NAME/KEY: CDS
<222> LOCATION: (1)..(118)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1336)
<220> FEATURE:
<221> NAME/KEY: CDS
<222> LOCATION: (180)..(1336)

<400> SEQUENCE: 46
```

| | | | | | | | | | | | | | | | | |
|---|---|---|---|---|---|---|---|---|---|---|---|---|---|---|---|---|
| atg tcg cca tca gcc aga caa cgg ggc ccg gcg cga tgg ctg gct gcc | | | | | | | | | | | | | | | | 48 |
| Met Ser Pro Ser Ala Arg Gln Arg Gly Pro Ala Arg Trp Leu Ala Ala | | | | | | | | | | | | | | | | |
| -30 | | | | -25 | | | | -20 | | | | | | -15 | | |
| gcc ctc gcg aca agc agt gtg ctg ttt tcg acg aca cgg gcg caa cag | | | | | | | | | | | | | | | | 96 |
| Ala Leu Ala Thr Ser Ser Val Leu Phe Ser Thr Thr Arg Ala Gln Gln | | | | | | | | | | | | | | | | |
| | | | | -10 | | | | -5 | | | | -1 1 | | | | |
| tat tat aag atc gac aca ata g gtagcgaagc tgatgccctc gtatgctttg | | | | | | | | | | | | | | | | 148 |
| Tyr Tyr Lys Ile Asp Thr Ile | | | | | | | | | | | | | | | | |
| | | 5 | | | | | | | | | | | | | | |
| cgcggtgggc tcgagactaa caggtgacca g ag  gag atc aag gag tcg gcg | | | | | | | | | | | | | | | | 199 |
| | | | | | | | | Glu Glu Ile Lys Glu Ser Ala | | | | | | | | |
| | | | | | | | | 10 | | | | 15 | | | | |
| cgc act ctt gca tac gac ttg atg ctc tat tac aag ggc aac cag tct | | | | | | | | | | | | | | | | 247 |
| Arg Thr Leu Ala Tyr Asp Leu Met Leu Tyr Tyr Lys Gly Asn Gln Ser | | | | | | | | | | | | | | | | |
| | | | 20 | | | | 25 | | | | 30 | | | | | |
| ggc gaa atc ccc ggt atc ttg cca ggt ccc ccg acc gaa cac aaa ggc | | | | | | | | | | | | | | | | 295 |
| Gly Glu Ile Pro Gly Ile Leu Pro Gly Pro Pro Thr Glu His Lys Gly | | | | | | | | | | | | | | | | |
| | | | 35 | | | 40 | | | | 45 | | | | | | |
| gac tac tac tgg tgg gaa ggc ggc gcg atg atg ggt aca tac gtc gac | | | | | | | | | | | | | | | | 343 |
| Asp Tyr Tyr Trp Trp Glu Gly Gly Ala Met Met Gly Thr Tyr Val Asp | | | | | | | | | | | | | | | | |
| | | | 50 | | | 55 | | | | 60 | | | | | | |
| tac tgg ttt ttg acc cgc gac cca agc tac aac cac gtc gtc atg gaa | | | | | | | | | | | | | | | | 391 |
| Tyr Trp Phe Leu Thr Arg Asp Pro Ser Tyr Asn His Val Val Met Glu | | | | | | | | | | | | | | | | |
| 65 | | | | 70 | | | | 75 | | | | 80 | | | | |
| ggc atg ctt cac caa gtc ggt ccc aac gct gat tac atg cca ccc aac | | | | | | | | | | | | | | | | 439 |
| Gly Met Leu His Gln Val Gly Pro Asn Ala Asp Tyr Met Pro Pro Asn | | | | | | | | | | | | | | | | |
| | | | | 85 | | | | 90 | | | | 95 | | | | |
| cat acc gct tct ctc ggt aac gac gac caa gga ttc tgg ggc atg tcg | | | | | | | | | | | | | | | | 487 |
| His Thr Ala Ser Leu Gly Asn Asp Asp Gln Gly Phe Trp Gly Met Ser | | | | | | | | | | | | | | | | |
| | | | | 100 | | | | 105 | | | | 110 | | | | |

```
gct atg ctc gcc gcc gag aac aag ttt ccc aac cca ccc gaa gac cag      535
Ala Met Leu Ala Ala Glu Asn Lys Phe Pro Asn Pro Pro Glu Asp Gln
        115                 120                 125 cca cag tgg ttg gcc ctt gcc cag gcc gtc ttc aac acg cag gct gcc      583
Pro Gln Trp Leu Ala Leu Ala Gln Ala Val Phe Asn Thr Gln Ala Ala
    130                 135                 140 ccg gag cgg cac gac ggc acc tgc aac ggc ggt ctc cgt tgg cag gtt      631
Pro Glu Arg His Asp Gly Thr Cys Asn Gly Gly Leu Arg Trp Gln Val
145                 150                 155                 160 ccc ccc acg aat gcc ggg tac aac tac aaa aac acc atc gcc aac gcc      679
Pro Pro Thr Asn Ala Gly Tyr Asn Tyr Lys Asn Thr Ile Ala Asn Ala
                165                 170                 175 tgt ttc ttc gac ctc gga gcc cgc ctg gcc cgt tac acc aag aac gag      727
Cys Phe Phe Asp Leu Gly Ala Arg Leu Ala Arg Tyr Thr Lys Asn Glu
            180                 185                 190 acg tac gcc aat tgg gcc aac aac att ttc gat tgg ttg atg ggc gtc      775
Thr Tyr Ala Asn Trp Ala Asn Asn Ile Phe Asp Trp Leu Met Gly Val
        195                 200                 205 gga tac atc gac acc agg gaa ccc ggc tgg cga gtt tat gac ggc gcc      823
Gly Tyr Ile Asp Thr Arg Glu Pro Gly Trp Arg Val Tyr Asp Gly Ala
210                 215                 220 cat gtc gag cat aac tgc acc gat atc aac aaa gcc cag ttc agc tac      871
His Val Glu His Asn Cys Thr Asp Ile Asn Lys Ala Gln Phe Ser Tyr
225                 230                 235                 240 aac gct gcc ctt ctc ttg cac ggc gcg gcc ttc atg tac aac tac acc      919
Asn Ala Ala Leu Leu Leu His Gly Ala Ala Phe Met Tyr Asn Tyr Thr
                245                 250                 255 aac ggc gag gag aaa tgg aag acg cgc atc gat ggc ctg atc gag ggt      967
Asn Gly Glu Glu Lys Trp Lys Thr Arg Ile Asp Gly Leu Ile Glu Gly
            260                 265                 270 atc ttg cgc gac ttt ttc aag gac ggc gct gcc tat gag ttg ccg tgc     1015
Ile Leu Arg Asp Phe Phe Lys Asp Gly Ala Ala Tyr Glu Leu Pro Cys
        275                 280                 285 gag ggt cgt cag ggt gcg tgt acc acg gac atg ttg agc ttc aag ggt     1063
Glu Gly Arg Gln Gly Ala Cys Thr Thr Asp Met Leu Ser Phe Lys Gly
    290                 295                 300 tac atg cac cgc tgg atg gcg gtc gtg acc aag gtg gct cct tat acg     1111
Tyr Met His Arg Trp Met Ala Val Val Thr Lys Val Ala Pro Tyr Thr
305                 310                 315                 320 gcg gaa aag atc ctc cct gcg ctt cgc acg tcc acc gag gcc gcg gtg     1159
Ala Glu Lys Ile Leu Pro Ala Leu Arg Thr Ser Thr Glu Ala Ala Val
                325                 330                 335 gct caa tgc acg ggt ccg ccg acg ggc cgt cgt tgc ggc ttc tac tgg     1207
Ala Gln Cys Thr Gly Pro Pro Thr Gly Arg Arg Cys Gly Phe Tyr Trp
            340                 345                 350 tcc acc cgt caa tat gtc gat acc gcc gtc gac aag acc agc ggc gcc     1255
Ser Thr Arg Gln Tyr Val Asp Thr Ala Val Asp Lys Thr Ser Gly Ala
        355                 360                 365 gga gag gcc atg aat gtc ctt gct gca gtc tcg agc ttg ctc att gag     1303
Gly Glu Ala Met Asn Val Leu Ala Ala Val Ser Ser Leu Leu Ile Glu
    370                 375                 380 tac gcg gat cca cca gcg acc aac gag acg ggc                          1336
Tyr Ala Asp Pro Pro Ala Thr Asn Glu Thr Gly
385                 390                 395
```

<210> SEQ ID NO 47
<211> LENGTH: 425
<212> TYPE: PRT
<213> ORGANISM: Humicola insolens

<400> SEQUENCE: 47

```
Met Ser Pro Ser Ala Arg Gln Arg Gly Pro Ala Arg Trp Leu Ala Ala
-30             -25                 -20                 -15

Ala Leu Ala Thr Ser Ser Val Leu Phe Ser Thr Thr Arg Ala Gln Gln
                -10                 -5              -1  1

Tyr Tyr Lys Ile Asp Thr Ile Glu Glu Ile Lys Glu Ser Ala Arg Thr
        5                   10                  15

Leu Ala Tyr Asp Leu Met Leu Tyr Tyr Lys Gly Asn Gln Ser Gly Glu
    20                  25                  30

Ile Pro Gly Ile Leu Pro Gly Pro Pro Thr Glu His Lys Gly Asp Tyr
35              40                  45                      50

Tyr Trp Trp Glu Gly Gly Ala Met Met Gly Thr Tyr Val Asp Tyr Trp
                55                  60                  65

Phe Leu Thr Arg Asp Pro Ser Tyr Asn His Val Val Met Glu Gly Met
            70                  75                  80

Leu His Gln Val Gly Pro Asn Ala Asp Tyr Met Pro Pro Asn His Thr
        85                  90                  95

Ala Ser Leu Gly Asn Asp Asp Gln Gly Phe Trp Gly Met Ser Ala Met
        100                 105                 110

Leu Ala Ala Glu Asn Lys Phe Pro Asn Pro Pro Glu Asp Gln Pro Gln
115                 120                 125                 130

Trp Leu Ala Leu Ala Gln Ala Val Phe Asn Thr Gln Ala Ala Pro Glu
                135                 140                 145

Arg His Asp Gly Thr Cys Asn Gly Gly Leu Arg Trp Gln Val Pro Pro
                150                 155                 160

Thr Asn Ala Gly Tyr Asn Tyr Lys Asn Thr Ile Ala Asn Ala Cys Phe
            165                 170                 175

Phe Asp Leu Gly Ala Arg Leu Ala Arg Tyr Thr Lys Asn Glu Thr Tyr
            180                 185                 190

Ala Asn Trp Ala Asn Asn Ile Phe Asp Trp Leu Met Gly Val Gly Tyr
195                 200                 205                 210

Ile Asp Thr Arg Glu Pro Gly Trp Arg Val Tyr Asp Gly Ala His Val
                215                 220                 225

Glu His Asn Cys Thr Asp Ile Asn Lys Ala Gln Phe Ser Tyr Asn Ala
                230                 235                 240

Ala Leu Leu Leu His Gly Ala Ala Phe Met Tyr Asn Tyr Thr Asn Gly
                245                 250                 255

Glu Glu Lys Trp Lys Thr Arg Ile Asp Gly Leu Ile Glu Gly Ile Leu
            260                 265                 270

Arg Asp Phe Phe Lys Asp Gly Ala Ala Tyr Glu Leu Pro Cys Glu Gly
275                 280                 285                 290

Arg Gln Gly Ala Cys Thr Thr Asp Met Leu Ser Phe Lys Gly Tyr Met
                295                 300                 305

His Arg Trp Met Ala Val Val Thr Lys Val Ala Pro Tyr Thr Ala Glu
            310                 315                 320

Lys Ile Leu Pro Ala Leu Arg Thr Ser Thr Glu Ala Ala Val Ala Gln
            325                 330                 335

Cys Thr Gly Pro Pro Thr Gly Arg Arg Cys Gly Phe Tyr Trp Ser Thr
            340                 345                 350

Arg Gln Tyr Val Asp Thr Ala Val Asp Lys Thr Ser Gly Ala Gly Glu
355                 360                 365                 370

Ala Met Asn Val Leu Ala Ala Val Ser Ser Leu Leu Ile Glu Tyr Ala
                375                 380                 385
```

```
Asp Pro Pro Ala Thr Asn Glu Thr Gly
        390                 395

<210> SEQ ID NO 48
<211> LENGTH: 395
<212> TYPE: PRT
<213> ORGANISM: Humicola insolens

<400> SEQUENCE: 48

Gln Gln Tyr Tyr Lys Ile Asp Thr Ile Glu Glu Ile Lys Ser Ala
1               5                   10                  15

Arg Thr Leu Ala Tyr Asp Leu Met Leu Tyr Tyr Lys Gly Asn Gln Ser
                20                  25                  30

Gly Glu Ile Pro Gly Ile Leu Pro Gly Pro Thr Glu His Lys Gly
            35                  40                  45

Asp Tyr Tyr Trp Trp Glu Gly Ala Met Met Gly Thr Tyr Val Asp
    50                  55                  60

Tyr Trp Phe Leu Thr Arg Asp Pro Ser Tyr Asn His Val Val Met Glu
65                  70                  75                  80

Gly Met Leu His Gln Val Gly Pro Asn Ala Asp Tyr Met Pro Pro Asn
                85                  90                  95

His Thr Ala Ser Leu Gly Asn Asp Asp Gln Gly Phe Trp Gly Met Ser
                100                 105                 110

Ala Met Leu Ala Ala Glu Asn Lys Phe Pro Asn Pro Glu Asp Gln
                115                 120                 125

Pro Gln Trp Leu Ala Leu Ala Gln Ala Val Phe Asn Thr Gln Ala Ala
    130                 135                 140

Pro Glu Arg His Asp Gly Thr Cys Asn Gly Gly Leu Arg Trp Gln Val
145                 150                 155                 160

Pro Pro Thr Asn Ala Gly Tyr Asn Tyr Lys Asn Thr Ile Ala Asn Ala
                165                 170                 175

Cys Phe Phe Asp Leu Gly Ala Arg Leu Ala Arg Tyr Thr Lys Asn Glu
                180                 185                 190

Thr Tyr Ala Asn Trp Ala Asn Asn Ile Phe Asp Trp Leu Met Gly Val
        195                 200                 205

Gly Tyr Ile Asp Thr Arg Glu Pro Gly Trp Arg Val Tyr Asp Gly Ala
    210                 215                 220

His Val Glu His Asn Cys Thr Asp Ile Asn Lys Ala Gln Phe Ser Tyr
225                 230                 235                 240

Asn Ala Ala Leu Leu Leu His Gly Ala Ala Phe Met Tyr Asn Tyr Thr
                245                 250                 255

Asn Gly Glu Glu Lys Trp Lys Thr Arg Ile Asp Gly Leu Ile Glu Gly
                260                 265                 270

Ile Leu Arg Asp Phe Phe Lys Asp Gly Ala Ala Tyr Glu Leu Pro Cys
            275                 280                 285

Glu Gly Arg Gln Gly Ala Cys Thr Thr Asp Met Leu Ser Phe Lys Gly
    290                 295                 300

Tyr Met His Arg Trp Met Ala Val Val Thr Lys Val Ala Pro Tyr Thr
305                 310                 315                 320

Ala Glu Lys Ile Leu Pro Ala Leu Arg Thr Ser Thr Glu Ala Ala Val
                325                 330                 335

Ala Gln Cys Thr Gly Pro Pro Thr Gly Arg Arg Cys Gly Phe Tyr Trp
            340                 345                 350

Ser Thr Arg Gln Tyr Val Asp Thr Ala Val Asp Lys Thr Ser Gly Ala
        355                 360                 365
```

```
Gly Glu Ala Met Asn Val Leu Ala Ala Val Ser Ser Leu Leu Ile Glu
    370                 375                 380

Tyr Ala Asp Pro Pro Ala Thr Asn Glu Thr Gly
385                 390                 395

<210> SEQ ID NO 49
<211> LENGTH: 1422
<212> TYPE: DNA
<213> ORGANISM: Humicola insolens
<220> FEATURE:
<221> NAME/KEY: CDS
<222> LOCATION: (1)..(85)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1422)
<220> FEATURE:
<221> NAME/KEY: CDS
<222> LOCATION: (161)..(640)
<220> FEATURE:
<221> NAME/KEY: CDS
<222> LOCATION: (696)..(937)
<220> FEATURE:
<221> NAME/KEY: CDS
<222> LOCATION: (1015)..(1422)

<400> SEQUENCE: 49 atg tac acc aca agc tcc gta gta gcg gcg gcc gcc ctc ctc ggg gcc      48
Met Tyr Thr Thr Ser Ser Val Val Ala Ala Ala Leu Leu Gly Ala
    -20                 -15                 -10 ggc gct gcg aat gcc gcc tac agc atc gac act gtc g gtacgtatat         95
Gly Ala Ala Asn Ala Ala Tyr Ser Ile Asp Thr Val
-5              -1  1               5 ttcctacctc agttctttga tgcgccgcct tctaagtacc tagatatcta actccgcttt   155 cccag cc  gac ata aaa aag acc gcc gcc acc gtc gcc tgg gac ctg atg   204
          Asp Ile Lys Lys Thr Ala Ala Thr Val Ala Trp Asp Leu Met
              10                  15                  20 cag tac tac cac ggc aac gag acg ggc caa acc ccc ggc atc ctc ccc     252
Gln Tyr Tyr His Gly Asn Glu Thr Gly Gln Thr Pro Gly Ile Leu Pro
        25                  30                  35 ggc ccc cct ccc gcg ggg gac tac tac tgg tgg gag gcc ggc gcc atg     300
Gly Pro Pro Pro Ala Gly Asp Tyr Tyr Trp Trp Glu Ala Gly Ala Met
40                  45                  50 tgg ggg acg ctg atc gac tac tgg aag tac acg ggc gac gac tcg tac     348
Trp Gly Thr Leu Ile Asp Tyr Trp Lys Tyr Thr Gly Asp Asp Ser Tyr
55                  60                  65                  70 aac gcc gtc atc acc cag gcc atg gtg cac cag gcc ggc ccc aac cgc     396
Asn Ala Val Ile Thr Gln Ala Met Val His Gln Ala Gly Pro Asn Arg
                75                  80                  85 gac tac atg cct ccc aac gtg acc ctc tct ctg ggc aac gac gac caa     444
Asp Tyr Met Pro Pro Asn Val Thr Leu Ser Leu Gly Asn Asp Asp Gln
            90                  95                  100 ggc ttc tgg ggc atg tcg gcc atg ctg gcc gcc gag ctc cgc ttc ccc     492
Gly Phe Trp Gly Met Ser Ala Met Leu Ala Ala Glu Leu Arg Phe Pro
        105                 110                 115 gat ccg ccg ccg gac cag ccc cag tgg ctg gct ttg gcg cag gcc gtg     540
Asp Pro Pro Pro Asp Gln Pro Gln Trp Leu Ala Leu Ala Gln Ala Val
    120                 125                 130 ttt aat acg cag gcg agc cca gac cgc cat gac gag acg tgc aac ggc     588
Phe Asn Thr Gln Ala Ser Pro Asp Arg His Asp Glu Thr Cys Asn Gly
135                 140                 145                 150
```

```
ggg ttg agg tgg cag atc ccg tgg tcg aat ccc ggt tat gac tac aag      636
Gly Leu Arg Trp Gln Ile Pro Trp Ser Asn Pro Gly Tyr Asp Tyr Lys
            155                 160                 165 aac a gtgagttggt ctgtatcgga acaggaccg agacagagtt gctgacgggg           690
Asn accag ct  atc gcc aac ggc tgc ttc ttc aac ctc ggc gcc cgt ctg gcc    739
      Thr Ile Ala Asn Gly Cys Phe Phe Asn Leu Gly Ala Arg Leu Ala
              170                 175                 180 cgc tac acc aga aac aag acg tat gcc gag tgg gct gag aag acg tgg      787
Arg Tyr Thr Arg Asn Lys Thr Tyr Ala Glu Trp Ala Glu Lys Thr Trp
            185                 190                 195 gac tgg gtc gag ggc gtc ggg tat atc acc aag gac tac caa gtg tat      835
Asp Trp Val Glu Gly Val Gly Tyr Ile Thr Lys Asp Tyr Gln Val Tyr
200                 205                 210 gac ggc gcc cat gtg gac cat aac tgc acc gac ctc aac cgg gcc cag      883
Asp Gly Ala His Val Asp His Asn Cys Thr Asp Leu Asn Arg Ala Gln
215                 220                 225                 230 ttc tcc tac aac aac gcc atc ttt ctc ctc ggc gcg gcc ttc atg tac      931
Phe Ser Tyr Asn Asn Ala Ile Phe Leu Leu Gly Ala Ala Phe Met Tyr
            235                 240                 245 aac tat gtaagcccgt ccatttcccc cggttcctgc gcgcatttac ctcctctgac       987
Asn Tyr ttgctaacct ccacttcctc cacccag acc gac ggc agc ccc aaa tgg cgc gac   1041
                           Thr Asp Gly Ser Pro Lys Trp Arg Asp
                                   250                 255 cgc gtc gaa ggc ctc gtc gac ggc gcc atc cgc gat ttc ttc ccg gac     1089
Arg Val Glu Gly Leu Val Asp Gly Ala Ile Arg Asp Phe Phe Pro Asp
            260                 265                 270 ggc gtc gcc ttc gag gtg ccc tgt gag acc aac atg act tgc acg acc     1137
Gly Val Ala Phe Glu Val Pro Cys Glu Thr Asn Met Thr Cys Thr Thr
275                 280                 285 gac atg ctc agc ttc aag ggg tac ctg cac cgc tgg ctg gcg gcg gcc     1185
Asp Met Leu Ser Phe Lys Gly Tyr Leu His Arg Trp Leu Ala Ala Ala
290                 295                 300                 305 acc acg gtg gcg ccc ttc atc gcg ccc aag gtg ctg ccc gtg ctg cgc     1233
Thr Thr Val Ala Pro Phe Ile Ala Pro Lys Val Leu Pro Val Leu Arg
            310                 315                 320 agc tcg gcc gag gcg gcc atc tcg acc tgc acg ggc gag gcc gac ggc     1281
Ser Ser Ala Glu Ala Ala Ile Ser Thr Cys Thr Gly Glu Ala Asp Gly
            325                 330                 335 cgc acg tgc ggc ttc cag tgg gcc aag cgc cag tat gac ggc agc aag     1329
Arg Thr Cys Gly Phe Gln Trp Ala Lys Arg Gln Tyr Asp Gly Ser Lys
            340                 345                 350 ggc gcc ggg cag cag atg aac gtc ctg ggc gcc gtg tcg gcg ctg atg     1377
Gly Ala Gly Gln Gln Met Asn Val Leu Gly Ala Val Ser Ala Leu Met
355                 360                 365 gtg gag cat aat ccg gat tat gtg atg gtg acg gcg gac tcg ggc         1422
Val Glu His Asn Pro Asp Tyr Val Met Val Thr Ala Asp Ser Gly
370                 375                 380

<210> SEQ ID NO 50
<211> LENGTH: 405
<212> TYPE: PRT
<213> ORGANISM: Humicola insolens

<400> SEQUENCE: 50

Met Tyr Thr Thr Ser Ser Val Val Ala Ala Ala Ala Leu Leu Gly Ala
    -20                 -15                 -10

Gly Ala Ala Asn Ala Ala Tyr Ser Ile Asp Thr Val Ala Asp Ile Lys
-5              -1   1               5                   10
```

Lys Thr Ala Ala Thr Val Ala Trp Asp Leu Met Gln Tyr Tyr His Gly
                15                  20                  25

Asn Glu Thr Gly Gln Thr Pro Gly Ile Leu Pro Gly Pro Pro Pro Ala
                30                  35                  40

Gly Asp Tyr Tyr Trp Trp Glu Ala Gly Ala Met Trp Gly Thr Leu Ile
 45                  50                  55

Asp Tyr Trp Lys Tyr Thr Gly Asp Asp Ser Tyr Asn Ala Val Ile Thr
 60                  65                  70                  75

Gln Ala Met Val His Gln Ala Gly Pro Asn Arg Asp Tyr Met Pro Pro
                80                  85                  90

Asn Val Thr Leu Ser Leu Gly Asn Asp Asp Gln Gly Phe Trp Gly Met
                95                  100                 105

Ser Ala Met Leu Ala Ala Glu Leu Arg Phe Pro Asp Pro Pro Pro Asp
                110                 115                 120

Gln Pro Gln Trp Leu Ala Leu Ala Gln Ala Val Phe Asn Thr Gln Ala
 125                 130                 135

Ser Pro Asp Arg His Asp Glu Thr Cys Asn Gly Gly Leu Arg Trp Gln
 140                 145                 150                 155

Ile Pro Trp Ser Asn Pro Gly Tyr Asp Tyr Lys Asn Thr Ile Ala Asn
                160                 165                 170

Gly Cys Phe Phe Asn Leu Gly Ala Arg Leu Ala Arg Tyr Thr Arg Asn
                175                 180                 185

Lys Thr Tyr Ala Glu Trp Ala Glu Lys Thr Trp Asp Trp Val Glu Gly
                190                 195                 200

Val Gly Tyr Ile Thr Lys Asp Tyr Gln Val Tyr Asp Gly Ala His Val
 205                 210                 215

Asp His Asn Cys Thr Asp Leu Asn Arg Ala Gln Phe Ser Tyr Asn Asn
220                  225                 230                 235

Ala Ile Phe Leu Leu Gly Ala Ala Phe Met Tyr Asn Tyr Thr Asp Gly
                240                 245                 250

Ser Pro Lys Trp Arg Asp Arg Val Glu Gly Leu Val Asp Gly Ala Ile
                255                 260                 265

Arg Asp Phe Phe Pro Asp Gly Val Ala Phe Glu Val Pro Cys Glu Thr
                270                 275                 280

Asn Met Thr Cys Thr Thr Asp Met Leu Ser Phe Lys Gly Tyr Leu His
                285                 290                 295

Arg Trp Leu Ala Ala Thr Thr Val Ala Pro Phe Ile Ala Pro Lys
300                  305                 310                 315

Val Leu Pro Val Leu Arg Ser Ser Ala Glu Ala Ile Ser Thr Cys
                320                 325                 330

Thr Gly Glu Ala Asp Gly Arg Thr Cys Gly Phe Gln Trp Ala Lys Arg
                335                 340                 345

Gln Tyr Asp Gly Ser Lys Gly Ala Gly Gln Gln Met Asn Val Leu Gly
                350                 355                 360

Ala Val Ser Ala Leu Met Val Glu His Asn Pro Asp Tyr Val Met Val
                365                 370                 375

Thr Ala Asp Ser Gly
380

<210> SEQ ID NO 51
<211> LENGTH: 384
<212> TYPE: PRT
<213> ORGANISM: Humicola insolens

```
<400> SEQUENCE: 51

Ala Tyr Ser Ile Asp Thr Val Ala Asp Ile Lys Lys Thr Ala Ala Thr
1               5                   10                  15

Val Ala Trp Asp Leu Met Gln Tyr Tyr His Gly Asn Glu Thr Gly Gln
            20                  25                  30

Thr Pro Gly Ile Leu Pro Gly Pro Pro Ala Gly Asp Tyr Tyr Trp
        35                  40                  45

Trp Glu Ala Gly Ala Met Trp Gly Thr Leu Ile Asp Tyr Trp Lys Tyr
    50                  55                  60

Thr Gly Asp Asp Ser Tyr Asn Ala Val Ile Thr Gln Ala Met Val His
65                  70                  75                  80

Gln Ala Gly Pro Asn Arg Asp Tyr Met Pro Asn Val Thr Leu Ser
                85                  90                  95

Leu Gly Asn Asp Asp Gln Gly Phe Trp Gly Met Ser Ala Met Leu Ala
                100                 105                 110

Ala Glu Leu Arg Phe Pro Asp Pro Pro Asp Gln Pro Gln Trp Leu
            115                 120                 125

Ala Leu Ala Gln Ala Val Phe Asn Thr Gln Ala Ser Pro Asp Arg His
130                 135                 140

Asp Glu Thr Cys Asn Gly Gly Leu Arg Trp Gln Ile Pro Trp Ser Asn
145                 150                 155                 160

Pro Gly Tyr Asp Tyr Lys Asn Thr Ile Ala Asn Gly Cys Phe Phe Asn
                165                 170                 175

Leu Gly Ala Arg Leu Ala Arg Tyr Thr Arg Asn Lys Thr Tyr Ala Glu
                180                 185                 190

Trp Ala Glu Lys Thr Trp Asp Trp Val Glu Gly Val Gly Tyr Ile Thr
            195                 200                 205

Lys Asp Tyr Gln Val Tyr Asp Gly Ala His Val Asp His Asn Cys Thr
        210                 215                 220

Asp Leu Asn Arg Ala Gln Phe Ser Tyr Asn Asn Ala Ile Phe Leu Leu
225                 230                 235                 240

Gly Ala Ala Phe Met Tyr Asn Tyr Thr Asp Gly Ser Pro Lys Trp Arg
                245                 250                 255

Asp Arg Val Glu Gly Leu Val Asp Gly Ala Ile Arg Asp Phe Phe Pro
                260                 265                 270

Asp Gly Val Ala Phe Glu Val Pro Cys Glu Thr Asn Met Thr Cys Thr
            275                 280                 285

Thr Asp Met Leu Ser Phe Lys Gly Tyr Leu His Arg Trp Leu Ala Ala
        290                 295                 300

Ala Thr Thr Val Ala Pro Phe Ile Ala Pro Lys Val Leu Pro Val Leu
305                 310                 315                 320

Arg Ser Ser Ala Glu Ala Ala Ile Ser Thr Cys Thr Gly Glu Ala Asp
                325                 330                 335

Gly Arg Thr Cys Gly Phe Gln Trp Ala Lys Arg Gln Tyr Asp Gly Ser
                340                 345                 350

Lys Gly Ala Gly Gln Gln Met Asn Val Leu Gly Ala Val Ser Ala Leu
            355                 360                 365

Met Val Glu His Asn Pro Asp Tyr Val Met Val Thr Ala Asp Ser Gly
        370                 375                 380

<210> SEQ ID NO 52
<211> LENGTH: 1337
<212> TYPE: DNA
<213> ORGANISM: Humicola insolens
```

```
<220> FEATURE:
<221> NAME/KEY: CDS
<222> LOCATION: (1)..(85)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1337)
<220> FEATURE:
<221> NAME/KEY: CDS
<222> LOCATION: (154)..(1337)

<400> SEQUENCE: 52
```

| | | | | | | | | | | | | | | | |
|---|---|---|---|---|---|---|---|---|---|---|---|---|---|---|---|
| atg | agg | tta | cta | cct | tgg | ttg | acg | gcg | tct | ctt | ggt | gtg | ctg | gtg | agg | 48 |
| Met | Arg | Leu | Leu | Pro | Trp | Leu | Thr | Ala | Ser | Leu | Gly | Val | Leu | Val | Arg |
| -20 | | | | | -15 | | | | | -10 | | | | | -5 |

| | | | | | | | | | | |
|---|---|---|---|---|---|---|---|---|---|---|
| tcg | gcg | gcg | gct | atc | gag | ttg | gat | ttg | gac | aat | gaa | g gtgaggaggc | 95 |
| Ser | Ala | Ala | Ala | Ile | Glu | Leu | Asp | Leu | Asp | Asn | Glu |
| | -1 | 1 | | | | 5 | acttgtccaa ggactgtctt tgatattcat gtctttcaga agctgacacc cccctcag 153

| | | | | | | | | | | | | | |
|---|---|---|---|---|---|---|---|---|---|---|---|---|---|
| aa | tcc | atc | aag | gcc | gcc | gcg | agc | acc | atc | gcc | ttc | ggc | ctg | gtc | cgc | 200 |
| Glu | Ser | Ile | Lys | Ala | Ala | Ala | Ser | Thr | Ile | Ala | Phe | Gly | Leu | Val | Arg |
| | 10 | | | | | 15 | | | | | 20 |

| tac | tac | acc | ggc | aac | tac | acc | ggc | gac | act | ccc | ggc | aac | ctg | ccg | gac | 248 |
|---|---|---|---|---|---|---|---|---|---|---|---|---|---|---|---|---|
| Tyr | Tyr | Thr | Gly | Asn | Tyr | Thr | Gly | Asp | Thr | Pro | Gly | Asn | Leu | Pro | Asp |
| 25 | | | | | 30 | | | | | 35 | | | | | 40 |

| ccc | tac | ttc | tgg | tgg | gag | gcc | ggc | gcc | atg | ttc | ggc | acc | ctc | gtc | gac | 296 |
|---|---|---|---|---|---|---|---|---|---|---|---|---|---|---|---|---|
| Pro | Tyr | Phe | Trp | Trp | Glu | Ala | Gly | Ala | Met | Phe | Gly | Thr | Leu | Val | Asp |
| | | | | 45 | | | | | 50 | | | | | 55 |

| tac | tgg | gct | ctg | acc | ggc | gac | gag | tcc | tac | aac | gcc | atc | acc | ctc | caa | 344 |
|---|---|---|---|---|---|---|---|---|---|---|---|---|---|---|---|---|
| Tyr | Trp | Ala | Leu | Thr | Gly | Asp | Glu | Ser | Tyr | Asn | Ala | Ile | Thr | Leu | Gln |
| | | | 60 | | | | | 65 | | | | | 70 |

| gcc | atg | gtc | cat | cag | ggc | acc | gag | aag | ggc | gac | ttc | atg | ccg | cgg | aac | 392 |
|---|---|---|---|---|---|---|---|---|---|---|---|---|---|---|---|---|
| Ala | Met | Val | His | Gln | Gly | Thr | Glu | Lys | Gly | Asp | Phe | Met | Pro | Arg | Asn |
| | | 75 | | | | | 80 | | | | | 85 |

| cag | acc | cgg | acc | ctc | ggc | aac | gac | gac | caa | ggc | ttc | tgg | ggc | atg | gcg | 440 |
|---|---|---|---|---|---|---|---|---|---|---|---|---|---|---|---|---|
| Gln | Thr | Arg | Thr | Leu | Gly | Asn | Asp | Asp | Gln | Gly | Phe | Trp | Gly | Met | Ala |
| | 90 | | | | | 95 | | | | | 100 |

| gcc | atg | tcg | gcc | gcc | gag | aac | aac | ttc | ccc | aac | ccg | ccg | cac | gac | cag | 488 |
|---|---|---|---|---|---|---|---|---|---|---|---|---|---|---|---|---|
| Ala | Met | Ser | Ala | Ala | Glu | Asn | Asn | Phe | Pro | Asn | Pro | Pro | His | Asp | Gln |
| 105 | | | | | 110 | | | | | 115 | | | | | 120 |

| ccc | caa | tgg | ctc | gcc | ctc | gcc | cag | tcc | ctc | ttc | aac | cag | tgg | gcg | tcc | 536 |
|---|---|---|---|---|---|---|---|---|---|---|---|---|---|---|---|---|
| Pro | Gln | Trp | Leu | Ala | Leu | Ala | Gln | Ser | Leu | Phe | Asn | Gln | Trp | Ala | Ser |
| | | | | 125 | | | | | 130 | | | | | 135 |

| cgc | tgg | gag | ccc | gaa | acc | tgc | ggc | ggc | ggc | ctg | cgc | tgg | caa | atc | ttt | 584 |
|---|---|---|---|---|---|---|---|---|---|---|---|---|---|---|---|---|
| Arg | Trp | Glu | Pro | Glu | Thr | Cys | Gly | Gly | Gly | Leu | Arg | Trp | Gln | Ile | Phe |
| | | | 140 | | | | | 145 | | | | | 150 |

| gcc | ttc | aac | aac | ggc | ttc | aac | tac | aaa | aac | tcc | atc | tcc | aac | ggc | tgt | 632 |
|---|---|---|---|---|---|---|---|---|---|---|---|---|---|---|---|---|
| Ala | Phe | Asn | Asn | Gly | Phe | Asn | Tyr | Lys | Asn | Ser | Ile | Ser | Asn | Gly | Cys |
| | | 155 | | | | | 160 | | | | | 165 |

| ttc | ttc | aac | atc | gcc | gcc | cgc | ctg | gcc | cgc | tac | acg | ggc | aac | cag | acc | 680 |
|---|---|---|---|---|---|---|---|---|---|---|---|---|---|---|---|---|
| Phe | Phe | Asn | Ile | Ala | Ala | Arg | Leu | Ala | Arg | Tyr | Thr | Gly | Asn | Gln | Thr |
| | | 170 | | | | | 175 | | | | | 180 |

| tac | gcc | gac | tgg | gcc | gcc | cgc | atc | tgg | gac | tgg | gag | gag | ggc | atc | ggg | 728 |
|---|---|---|---|---|---|---|---|---|---|---|---|---|---|---|---|---|
| Tyr | Ala | Asp | Trp | Ala | Ala | Arg | Ile | Trp | Asp | Trp | Glu | Glu | Gly | Ile | Gly |
| 185 | | | | | 190 | | | | | 195 | | | | | 200 |

| ctg | atc | acg | ccc | gac | tac | gcc | gtg | cac | gac | ggc | gtc | ggc | atc | aac | cct | 776 |
|---|---|---|---|---|---|---|---|---|---|---|---|---|---|---|---|---|
| Leu | Ile | Thr | Pro | Asp | Tyr | Ala | Val | His | Asp | Gly | Val | Gly | Ile | Asn | Pro |
| | | | | 205 | | | | | 210 | | | | | 215 |

| ctg | aac | ggc | gag | tgc | ctg | gtc | ggc | agc | atg | gac | acg | aac | cag | tgg | acc | 824 |
|---|---|---|---|---|---|---|---|---|---|---|---|---|---|---|---|---|
| Leu | Asn | Gly | Glu | Cys | Leu | Val | Gly | Ser | Met | Asp | Thr | Asn | Gln | Trp | Thr |

```
                220                 225                 230
tac aac gcc ggc atc ttc ctc cac ggc gcg gcc gtc atg tac aac ctc        872
Tyr Asn Ala Gly Ile Phe Leu His Gly Ala Ala Val Met Tyr Asn Leu
            235                 240                 245 acc aac ggc agc gcc gac tgg cgc gcg cgc gtc gac ggc atc ctc tcc        920
Thr Asn Gly Ser Ala Asp Trp Arg Ala Arg Val Asp Gly Ile Leu Ser
250                 255                 260 aac acc atc aac acc ttt tac acc acc ccg gaa ccc ggc agc ccc gcc        968
Asn Thr Ile Asn Thr Phe Tyr Thr Thr Pro Glu Pro Gly Ser Pro Ala
265                 270                 275                 280 ggc gcc aac ccc gtc ctg agg gag ctc tgc gaa ggg ccc caa aac ttc       1016
Gly Ala Asn Pro Val Leu Arg Glu Leu Cys Glu Gly Pro Gln Asn Phe
            285                 290                 295 tgc aac atc gac cag cgc tcc ttc aaa ggc tac ctc acg cgc tgg ctg       1064
Cys Asn Ile Asp Gln Arg Ser Phe Lys Gly Tyr Leu Thr Arg Trp Leu
            300                 305                 310 gcc ggc acc tcc ctg ctc gcc ccg cac acc cag ccc gtc atc cag ccc       1112
Ala Gly Thr Ser Leu Leu Ala Pro His Thr Gln Pro Val Ile Gln Pro
            315                 320                 325 ctc ctg cgc tcc tcc gcc ctc gcc gcc gcc cac gct tgc tcc ggc ccg       1160
Leu Leu Arg Ser Ser Ala Leu Ala Ala Ala His Ala Cys Ser Gly Pro
330                 335                 340 acc cag ccc ccg gaa ttc aaa ggc cac acg gga acc gcc tgc ggt ctc       1208
Thr Gln Pro Pro Glu Phe Lys Gly His Thr Gly Thr Ala Cys Gly Leu
345                 350                 355                 360 cgc tgg acc acc gcc gcc ggg ttc gac ggc ctc gtc ggc gtc ggc gag       1256
Arg Trp Thr Thr Ala Ala Gly Phe Asp Gly Leu Val Gly Val Gly Glu
            365                 370                 375 cag atg aat gcc ttg tcg gcc gtc atg tac acg ctc gcc gcg cgc ccg       1304
Gln Met Asn Ala Leu Ser Ala Val Met Tyr Thr Leu Ala Ala Arg Pro
            380                 385                 390 ggc gcg ccg gag ccg ttg acc gcg gat acg ggc                           1337
Gly Ala Pro Glu Pro Leu Thr Ala Asp Thr Gly
            395                 400

<210> SEQ ID NO 53
<211> LENGTH: 423
<212> TYPE: PRT
<213> ORGANISM: Humicola insolens

<400> SEQUENCE: 53

Met Arg Leu Leu Pro Trp Leu Thr Ala Ser Leu Gly Val Leu Val Arg
-20                 -15                 -10                  -5

Ser Ala Ala Ala Ile Glu Leu Asp Leu Asp Asn Glu Glu Ser Ile Lys
        -1   1               5                  10

Ala Ala Ala Ser Thr Ile Ala Phe Gly Leu Val Arg Tyr Tyr Thr Gly
             15                 20                  25

Asn Tyr Thr Gly Asp Thr Pro Gly Asn Leu Pro Asp Pro Tyr Phe Trp
         30                 35                  40

Trp Glu Ala Gly Ala Met Phe Gly Thr Leu Val Asp Tyr Trp Ala Leu
45                  50                  55                  60

Thr Gly Asp Glu Ser Tyr Asn Ala Ile Thr Leu Gln Ala Met Val His
                65                  70                  75

Gln Gly Thr Glu Lys Gly Asp Phe Met Pro Arg Asn Gln Thr Arg Thr
            80                  85                  90

Leu Gly Asn Asp Asp Gln Gly Phe Trp Gly Met Ala Ala Met Ser Ala
         95                 100                 105

Ala Glu Asn Asn Phe Pro Asn Pro Pro His Asp Gln Pro Gln Trp Leu
```

```
                    110                 115                 120
Ala Leu Ala Gln Ser Leu Phe Asn Gln Trp Ala Ser Arg Trp Glu Pro
125                 130                 135                 140

Glu Thr Cys Gly Gly Gly Leu Arg Trp Gln Ile Phe Ala Phe Asn Asn
                    145                 150                 155

Gly Phe Asn Tyr Lys Asn Ser Ile Ser Asn Gly Cys Phe Phe Asn Ile
                160                 165                 170

Ala Ala Arg Leu Ala Arg Tyr Thr Gly Asn Gln Thr Tyr Ala Asp Trp
                175                 180                 185

Ala Ala Arg Ile Trp Asp Trp Glu Glu Gly Ile Gly Leu Ile Thr Pro
                190                 195                 200

Asp Tyr Ala Val His Asp Gly Val Gly Ile Asn Pro Leu Asn Gly Glu
205                 210                 215                 220

Cys Leu Val Gly Ser Met Asp Thr Asn Gln Trp Thr Tyr Asn Ala Gly
                    225                 230                 235

Ile Phe Leu His Gly Ala Ala Val Met Tyr Asn Leu Thr Asn Gly Ser
                240                 245                 250

Ala Asp Trp Arg Ala Arg Val Asp Gly Ile Leu Ser Asn Thr Ile Asn
                255                 260                 265

Thr Phe Tyr Thr Thr Pro Glu Pro Gly Ser Pro Ala Gly Ala Asn Pro
270                 275                 280

Val Leu Arg Glu Leu Cys Glu Gly Pro Gln Asn Phe Cys Asn Ile Asp
285                 290                 295                 300

Gln Arg Ser Phe Lys Gly Tyr Leu Thr Arg Trp Leu Ala Gly Thr Ser
                    305                 310                 315

Leu Leu Ala Pro His Thr Gln Pro Val Ile Gln Pro Leu Leu Arg Ser
                320                 325                 330

Ser Ala Leu Ala Ala Ala His Ala Cys Ser Gly Pro Thr Gln Pro Pro
                335                 340                 345

Glu Phe Lys Gly His Thr Gly Thr Ala Cys Gly Leu Arg Trp Thr Thr
                350                 355                 360

Ala Ala Gly Phe Asp Gly Leu Val Gly Val Gly Glu Gln Met Asn Ala
365                 370                 375                 380

Leu Ser Ala Val Met Tyr Thr Leu Ala Ala Arg Pro Gly Ala Pro Glu
                    385                 390                 395

Pro Leu Thr Ala Asp Thr Gly
                400

<210> SEQ ID NO 54
<211> LENGTH: 403
<212> TYPE: PRT
<213> ORGANISM: Humicola insolens

<400> SEQUENCE: 54

Ile Glu Leu Asp Leu Asp Asn Glu Glu Ser Ile Lys Ala Ala Ala Ser
1               5                   10                  15

Thr Ile Ala Phe Gly Leu Val Arg Tyr Tyr Thr Gly Asn Tyr Thr Gly
                20                  25                  30

Asp Thr Pro Gly Asn Leu Pro Asp Pro Tyr Phe Trp Trp Glu Ala Gly
            35                  40                  45

Ala Met Phe Gly Thr Leu Val Asp Tyr Trp Ala Leu Thr Gly Asp Glu
        50                  55                  60

Ser Tyr Asn Ala Ile Thr Leu Gln Ala Met Val His Gln Gly Thr Glu
65                  70                  75                  80
```

```
Lys Gly Asp Phe Met Pro Arg Asn Gln Thr Arg Leu Gly Asn Asp
                85                  90                  95

Asp Gln Gly Phe Trp Gly Met Ala Ala Met Ser Ala Ala Glu Asn Asn
            100                 105                 110

Phe Pro Asn Pro Pro His Asp Gln Pro Gln Trp Leu Ala Leu Ala Gln
            115                 120                 125

Ser Leu Phe Asn Gln Trp Ala Ser Arg Trp Glu Pro Glu Thr Cys Gly
    130                 135                 140

Gly Gly Leu Arg Trp Gln Ile Phe Ala Phe Asn Gly Phe Asn Tyr
145                 150                 155                 160

Lys Asn Ser Ile Ser Asn Gly Cys Phe Phe Asn Ile Ala Ala Arg Leu
                165                 170                 175

Ala Arg Tyr Thr Gly Asn Gln Thr Tyr Ala Asp Trp Ala Ala Arg Ile
            180                 185                 190

Trp Asp Trp Glu Glu Gly Ile Gly Leu Ile Thr Pro Asp Tyr Ala Val
            195                 200                 205

His Asp Gly Val Gly Ile Asn Pro Leu Asn Gly Glu Cys Leu Val Gly
    210                 215                 220

Ser Met Asp Thr Asn Gln Trp Thr Tyr Asn Ala Gly Ile Phe Leu His
225                 230                 235                 240

Gly Ala Ala Val Met Tyr Asn Leu Thr Asn Gly Ser Ala Asp Trp Arg
                245                 250                 255

Ala Arg Val Asp Gly Ile Leu Ser Asn Thr Ile Asn Thr Phe Tyr Thr
            260                 265                 270

Thr Pro Glu Pro Gly Ser Pro Ala Gly Ala Asn Pro Val Leu Arg Glu
            275                 280                 285

Leu Cys Glu Gly Pro Gln Asn Phe Cys Asn Ile Asp Gln Arg Ser Phe
    290                 295                 300

Lys Gly Tyr Leu Thr Arg Trp Leu Ala Gly Thr Ser Leu Leu Ala Pro
305                 310                 315                 320

His Thr Gln Pro Val Ile Gln Pro Leu Leu Arg Ser Ser Ala Leu Ala
                325                 330                 335

Ala Ala His Ala Cys Ser Gly Pro Thr Gln Pro Pro Glu Phe Lys Gly
            340                 345                 350

His Thr Gly Thr Ala Cys Gly Leu Arg Trp Thr Thr Ala Ala Gly Phe
            355                 360                 365

Asp Gly Leu Val Gly Val Gly Glu Gln Met Asn Ala Leu Ser Ala Val
    370                 375                 380

Met Tyr Thr Leu Ala Ala Arg Pro Gly Ala Pro Glu Pro Leu Thr Ala
385                 390                 395                 400

Asp Thr Gly
```

<210> SEQ ID NO 55
<211> LENGTH: 1605
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1605)
<220> FEATURE:
<221> NAME/KEY: sig_peptide
<222> LOCATION: (1)..(105)
<220> FEATURE:
<221> NAME/KEY: mat_peptide
<222> LOCATION: (106)..(1605)

```
<400> SEQUENCE: 55 atg gcc agt aag gtt aga aga aga ttc aag ctt atc gta ttg ctt gtt        48
Met Ala Ser Lys Val Arg Arg Arg Phe Lys Leu Ile Val Leu Leu Val
-35                 -30                 -25                 -20 gtt ctt gca ctc tcg atc agt acc cta tct cca agc gga atg cct cgc        96
Val Leu Ala Leu Ser Ile Ser Thr Leu Ser Pro Ser Gly Met Pro Arg
            -15                 -10                  -5 gcc cat gct ttt gaa gcg gag gat gcg aag acg gca atc gtt gcc tac       144
Ala His Ala Phe Glu Ala Glu Asp Ala Lys Thr Ala Ile Val Ala Tyr
         -1   1               5                  10 aat gat gca ttc tgg gat gca aac gcg aaa tac ttc tgg aaa tcc acc       192
Asn Asp Ala Phe Trp Asp Ala Asn Ala Lys Tyr Phe Trp Lys Ser Thr
 15                  20                  25 aat cgt acc gat tat cag gac ttt tgg ata gag gcc gag ctt tgg gag       240
Asn Arg Thr Asp Tyr Gln Asp Phe Trp Ile Glu Ala Glu Leu Trp Glu
 30                  35                  40                  45 ctc gtt atg gat gcc tat ctg cat aca tcg gac ccg gag ctc aag gcg       288
Leu Val Met Asp Ala Tyr Leu His Thr Ser Asp Pro Glu Leu Lys Ala
                 50                  55                  60 cag ctg cgg acc cag att gac gat gtg ttc gat gga gcc gta acg agg       336
Gln Leu Arg Thr Gln Ile Asp Asp Val Phe Asp Gly Ala Val Thr Arg
             65                  70                  75 tac ggc gag gac tgg aca tat aat ccg tat aac gat gac atc atg tgg       384
Tyr Gly Glu Asp Trp Thr Tyr Asn Pro Tyr Asn Asp Asp Ile Met Trp
         80                  85                  90 tgg gca atg gca agt gca aga gcc tat cag att acg aat gac gaa cgg       432
Trp Ala Met Ala Ser Ala Arg Ala Tyr Gln Ile Thr Asn Asp Glu Arg
     95                 100                 105 tat ttg gaa caa gcg gaa tat tat ttc aat tat gtc tat gat aat gaa       480
Tyr Leu Glu Gln Ala Glu Tyr Tyr Phe Asn Tyr Val Tyr Asp Asn Glu
110                 115                 120                 125 tgg gat act gaa ttt gcc gga ggc ggc att tgg tgg aaa agc gat gat       528
Trp Asp Thr Glu Phe Ala Gly Gly Gly Ile Trp Trp Lys Ser Asp Asp
                130                 135                 140 cgc acg aca aaa aat gca tgc atc aac ttt cct gcc gct caa acc gct       576
Arg Thr Thr Lys Asn Ala Cys Ile Asn Phe Pro Ala Ala Gln Thr Ala
            145                 150                 155 gtc ttt ttg tat aac gtt acc caa gac gaa caa tac ctg gat gca gcc       624
Val Phe Leu Tyr Asn Val Thr Gln Asp Glu Gln Tyr Leu Asp Ala Ala
        160                 165                 170 gaa acc atc tac cat tgg gga aaa aca ata ctg act gac ggc aac ggc       672
Glu Thr Ile Tyr His Trp Gly Lys Thr Ile Leu Thr Asp Gly Asn Gly
    175                 180                 185 aaa gta ttc gat cga att gaa acg caa aat gga gct att caa ggc gcg       720
Lys Val Phe Asp Arg Ile Glu Thr Gln Asn Gly Ala Ile Gln Gly Ala
190                 195                 200                 205 act cac tat aat caa ggt gcg ttt att ggg tca gcc gca ggt ctc tac       768
Thr His Tyr Asn Gln Gly Ala Phe Ile Gly Ser Ala Ala Gly Leu Tyr
                210                 215                 220 gag att acg gga gac acg gat tat ctg gac gat gcg atc aaa gcg gcc       816
Glu Ile Thr Gly Asp Thr Asp Tyr Leu Asp Asp Ala Ile Lys Ala Ala
            225                 230                 235 acg tat acg aag gag cat atg gtt gac gtc aac gga ctg ctc cga tat       864
Thr Tyr Thr Lys Glu His Met Val Asp Val Asn Gly Leu Leu Arg Tyr
        240                 245                 250 gag ggc cct aac gga gat ttg aag ggc ggc aaa acg att ctg ctg cgc       912
Glu Gly Pro Asn Gly Asp Leu Lys Gly Gly Lys Thr Ile Leu Leu Arg
    255                 260                 265 aac ctc ggc tat ttt caa gcg gcg ata gac gct cgc cag gaa gaa aat       960
Asn Leu Gly Tyr Phe Gln Ala Ala Ile Asp Ala Arg Gln Glu Glu Asn
```

```
                Asn Leu Gly Tyr Phe Gln Ala Ala Ile Asp Ala Arg Gln Glu Glu Asn
                270                 275                 280                 285 tac caa tcc ttc gcc gaa agc tac aat gag tgg ctg gct ttt aat gcc      1008
Tyr Gln Ser Phe Ala Glu Ser Tyr Asn Glu Trp Leu Ala Phe Asn Ala
                    290                 295                 300 gat atg gca tgg aac aat cgc aat gcg gcc aat ctc gtc gac ggc aac      1056
Asp Met Ala Trp Asn Asn Arg Asn Ala Ala Asn Leu Val Asp Gly Asn
                305                 310                 315 tgg gcg gga caa cag tta tcc ggc gcc atc gag tca tgg agc gcg gca      1104
Trp Ala Gly Gln Gln Leu Ser Gly Ala Ile Glu Ser Trp Ser Ala Ala
            320                 325                 330 gcg gcc gta caa gct ttg ata tcc cta aag ccg cag aac gcg gta cag      1152
Ala Ala Val Gln Ala Leu Ile Ser Leu Lys Pro Gln Asn Ala Val Gln
        335                 340                 345 ctg gga tat gcc gtt aag aac cct tat aac agg atc gaa gcg gaa agt      1200
Leu Gly Tyr Ala Val Lys Asn Pro Tyr Asn Arg Ile Glu Ala Glu Ser
350                 355                 360                 365 tac aat att ata aac ggc cct ggc ctg gag gac agc aat gaa ggc tcg      1248
Tyr Asn Ile Ile Asn Gly Pro Gly Leu Glu Asp Ser Asn Glu Gly Ser
                    370                 375                 380 caa caa ctg gcc ggt att cag gac agt cat tat gcg gca tat aaa aat      1296
Gln Gln Leu Ala Gly Ile Gln Asp Ser His Tyr Ala Ala Tyr Lys Asn
                385                 390                 395 gtc gat ttt ggt tcg gaa gat ggt gca agc ggt ttc att gcg cga gca      1344
Val Asp Phe Gly Ser Glu Asp Gly Ala Ser Gly Phe Ile Ala Arg Ala
            400                 405                 410 tcg agc gga acg ggc ggc ggc cag atc gaa atc aga ctg gat gct ttg      1392
Ser Ser Gly Thr Gly Gly Gly Gln Ile Glu Ile Arg Leu Asp Ala Leu
        415                 420                 425 gac gga cca aag gca ggt acg cta aat gta aat ggt acc gga ggc tgg      1440
Asp Gly Pro Lys Ala Gly Thr Leu Asn Val Asn Gly Thr Gly Gly Trp
430                 435                 440                 445 aac aac tac atc gac gcg gct gta ctg ctg aag gat gag caa ggg aat      1488
Asn Asn Tyr Ile Asp Ala Ala Val Leu Leu Lys Asp Glu Gln Gly Asn
                    450                 455                 460 ccg agt cct gtg acc ggc gta cac gat gtg tat ctg gtg ttt aag agg      1536
Pro Ser Pro Val Thr Gly Val His Asp Val Tyr Leu Val Phe Lys Arg
                465                 470                 475 aca aat gac aca tat cta ttc aat ctc aat tgg ttc caa ttt acg aag      1584
Thr Asn Asp Thr Tyr Leu Phe Asn Leu Asn Trp Phe Gln Phe Thr Lys
            480                 485                 490 gtc gat ccg acc ctg att tct                                          1605
Val Asp Pro Thr Leu Ile Ser
        495                 500

<210> SEQ ID NO 56
<211> LENGTH: 535
<212> TYPE: PRT
<213> ORGANISM: Artificial Sequence
<220> FEATURE:
<223> OTHER INFORMATION: Synthetic Construct

<400> SEQUENCE: 56

Met Ala Ser Lys Val Arg Arg Phe Lys Leu Ile Val Leu Leu Val
-35                 -30                 -25                 -20

Val Leu Ala Leu Ser Ile Ser Thr Leu Ser Pro Ser Gly Met Pro Arg
                    -15                 -10                 -5

Ala His Ala Phe Glu Ala Glu Asp Ala Lys Thr Ala Ile Val Ala Tyr
        -1  1                 5                   10

Asn Asp Ala Phe Trp Asp Ala Asn Ala Lys Tyr Phe Trp Lys Ser Thr
```

Asn Arg Thr Asp Tyr Gln Asp Phe Trp Ile Glu Ala Glu Leu Trp Glu
 30                  35                  40                  45

Leu Val Met Asp Ala Tyr Leu His Thr Ser Asp Pro Glu Leu Lys Ala
                 50                  55                  60

Gln Leu Arg Thr Gln Ile Asp Val Phe Asp Gly Ala Val Thr Arg
                 65                  70                  75

Tyr Gly Glu Asp Trp Thr Tyr Asn Pro Tyr Asn Asp Asp Ile Met Trp
             80                  85                  90

Trp Ala Met Ala Ser Ala Arg Ala Tyr Gln Ile Thr Asn Asp Glu Arg
             95                 100                 105

Tyr Leu Glu Gln Ala Glu Tyr Tyr Phe Asn Tyr Val Tyr Asp Asn Glu
110                 115                 120                 125

Trp Asp Thr Glu Phe Ala Gly Gly Ile Trp Trp Lys Ser Asp Asp
                130                 135                 140

Arg Thr Thr Lys Asn Ala Cys Ile Asn Phe Pro Ala Ala Gln Thr Ala
                145                 150                 155

Val Phe Leu Tyr Asn Val Thr Gln Asp Glu Gln Tyr Leu Asp Ala Ala
                160                 165                 170

Glu Thr Ile Tyr His Trp Gly Lys Thr Ile Leu Thr Asp Gly Asn Gly
            175                 180                 185

Lys Val Phe Asp Arg Ile Glu Thr Gln Asn Gly Ala Ile Gln Gly Ala
190                 195                 200                 205

Thr His Tyr Asn Gln Gly Ala Phe Ile Gly Ser Ala Ala Gly Leu Tyr
                210                 215                 220

Glu Ile Thr Gly Asp Thr Asp Tyr Leu Asp Asp Ala Ile Lys Ala Ala
                225                 230                 235

Thr Tyr Thr Lys Glu His Met Val Asp Val Asn Gly Leu Leu Arg Tyr
                240                 245                 250

Glu Gly Pro Asn Gly Asp Leu Lys Gly Gly Lys Thr Ile Leu Leu Arg
                255                 260                 265

Asn Leu Gly Tyr Phe Gln Ala Ala Ile Asp Ala Arg Gln Glu Glu Asn
270                 275                 280                 285

Tyr Gln Ser Phe Ala Glu Ser Tyr Asn Glu Trp Leu Ala Phe Asn Ala
                290                 295                 300

Asp Met Ala Trp Asn Asn Arg Asn Ala Ala Asn Leu Val Asp Gly Asn
                305                 310                 315

Trp Ala Gly Gln Gln Leu Ser Gly Ala Ile Glu Ser Trp Ser Ala Ala
                320                 325                 330

Ala Ala Val Gln Ala Leu Ile Ser Leu Lys Pro Gln Asn Ala Val Gln
                335                 340                 345

Leu Gly Tyr Ala Val Lys Asn Pro Tyr Asn Arg Ile Glu Ala Glu Ser
350                 355                 360                 365

Tyr Asn Ile Ile Asn Gly Pro Gly Leu Glu Asp Ser Asn Glu Gly Ser
                370                 375                 380

Gln Gln Leu Ala Gly Ile Gln Asp Ser His Tyr Ala Ala Tyr Lys Asn
                385                 390                 395

Val Asp Phe Gly Ser Glu Asp Gly Ala Ser Gly Phe Ile Ala Arg Ala
                400                 405                 410

Ser Ser Gly Thr Gly Gly Gln Ile Glu Ile Arg Leu Asp Ala Leu
                415                 420                 425

Asp Gly Pro Lys Ala Gly Thr Leu Asn Val Asn Gly Thr Gly Gly Trp
430                 435                 440                 445

-continued

```
Asn Asn Tyr Ile Asp Ala Ala Val Leu Leu Lys Asp Glu Gln Gly Asn
            450                 455                 460

Pro Ser Pro Val Thr Gly Val His Asp Val Tyr Leu Val Phe Lys Arg
        465                 470                 475

Thr Asn Asp Thr Tyr Leu Phe Asn Leu Asn Trp Phe Gln Phe Thr Lys
        480                 485                 490

Val Asp Pro Thr Leu Ile Ser
    495                 500

<210> SEQ ID NO 57
<211> LENGTH: 500
<212> TYPE: PRT
<213> ORGANISM: Artificial Sequence
<220> FEATURE:
<223> OTHER INFORMATION: Synthetic Construct

<400> SEQUENCE: 57

Phe Glu Ala Glu Asp Ala Lys Thr Ala Ile Val Ala Tyr Asn Asp Ala
1               5                   10                  15

Phe Trp Asp Ala Asn Ala Lys Tyr Phe Trp Lys Ser Thr Asn Arg Thr
            20                  25                  30

Asp Tyr Gln Asp Phe Trp Ile Glu Ala Glu Leu Trp Glu Leu Val Met
        35                  40                  45

Asp Ala Tyr Leu His Thr Ser Asp Pro Glu Leu Lys Ala Gln Leu Arg
    50                  55                  60

Thr Gln Ile Asp Asp Val Phe Asp Gly Ala Val Thr Arg Tyr Gly Glu
65                  70                  75                  80

Asp Trp Thr Tyr Asn Pro Tyr Asn Asp Ile Met Trp Trp Ala Met
                85                  90                  95

Ala Ser Ala Arg Ala Tyr Gln Ile Thr Asn Asp Glu Arg Tyr Leu Glu
            100                 105                 110

Gln Ala Glu Tyr Tyr Phe Asn Tyr Val Tyr Asp Asn Glu Trp Asp Thr
        115                 120                 125

Glu Phe Ala Gly Gly Gly Ile Trp Trp Lys Ser Asp Asp Arg Thr Thr
    130                 135                 140

Lys Asn Ala Cys Ile Asn Phe Pro Ala Ala Gln Thr Ala Val Phe Leu
145                 150                 155                 160

Tyr Asn Val Thr Gln Asp Glu Gln Tyr Leu Asp Ala Ala Glu Thr Ile
                165                 170                 175

Tyr His Trp Gly Lys Thr Ile Leu Thr Asp Gly Asn Gly Lys Val Phe
            180                 185                 190

Asp Arg Ile Glu Thr Gln Asn Gly Ala Ile Gln Gly Ala Thr His Tyr
        195                 200                 205

Asn Gln Gly Ala Phe Ile Gly Ser Ala Ala Gly Leu Tyr Glu Ile Thr
    210                 215                 220

Gly Asp Thr Asp Tyr Leu Asp Asp Ala Ile Lys Ala Ala Thr Tyr Thr
225                 230                 235                 240

Lys Glu His Met Val Asp Val Asn Gly Leu Leu Arg Tyr Glu Gly Pro
                245                 250                 255

Asn Gly Asp Leu Lys Gly Gly Lys Thr Ile Leu Leu Arg Asn Leu Gly
            260                 265                 270

Tyr Phe Gln Ala Ala Ile Asp Ala Arg Gln Glu Glu Asn Tyr Gln Ser
        275                 280                 285

Phe Ala Glu Ser Tyr Asn Glu Trp Leu Ala Phe Asn Ala Asp Met Ala
    290                 295                 300
```

```
Trp Asn Asn Arg Asn Ala Ala Asn Leu Val Asp Gly Asn Trp Ala Gly
305                 310                 315                 320

Gln Gln Leu Ser Gly Ala Ile Glu Ser Trp Ser Ala Ala Ala Ala Val
            325                 330                 335

Gln Ala Leu Ile Ser Leu Lys Pro Gln Asn Ala Val Gln Leu Gly Tyr
        340                 345                 350

Ala Val Lys Asn Pro Tyr Asn Arg Ile Glu Ala Glu Ser Tyr Asn Ile
    355                 360                 365

Ile Asn Gly Pro Gly Leu Glu Asp Ser Asn Glu Gly Ser Gln Gln Leu
370                 375                 380

Ala Gly Ile Gln Asp Ser His Tyr Ala Ala Tyr Lys Asn Val Asp Phe
385                 390                 395                 400

Gly Ser Glu Asp Gly Ala Ser Gly Phe Ile Ala Arg Ala Ser Ser Gly
                405                 410                 415

Thr Gly Gly Gly Gln Ile Glu Ile Arg Leu Asp Ala Leu Asp Gly Pro
            420                 425                 430

Lys Ala Gly Thr Leu Asn Val Asn Gly Thr Gly Trp Asn Asn Tyr
        435                 440                 445

Ile Asp Ala Ala Val Leu Leu Lys Asp Glu Gln Gly Asn Pro Ser Pro
450                 455                 460

Val Thr Gly Val His Asp Val Tyr Leu Val Phe Lys Arg Thr Asn Asp
465                 470                 475                 480

Thr Tyr Leu Phe Asn Leu Asn Trp Phe Gln Phe Thr Lys Val Asp Pro
                485                 490                 495

Thr Leu Ile Ser
            500

<210> SEQ ID NO 58
<211> LENGTH: 27
<212> TYPE: PRT
<213> ORGANISM: Artificial Sequence
<220> FEATURE:
<223> OTHER INFORMATION: Synthetic construct

<400> SEQUENCE: 58

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 59
<211> LENGTH: 8
<212> TYPE: PRT
<213> ORGANISM: Artificial Sequence
<220> FEATURE:
<223> OTHER INFORMATION: Synthetic construct

<400> SEQUENCE: 59

His His His His His His Pro Arg
1               5

<210> SEQ ID NO 60
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
```

```
<223> OTHER INFORMATION: Xaa = Tyr, Asn or Asp
<220> FEATURE:
<221> NAME/KEY: misc_feature
<222> LOCATION: (4)..(4)
<223> OTHER INFORMATION: Xaa = Gln, Ile, Asn, Leu, Glu, or Met

<400> SEQUENCE: 60

Xaa Asp Asp Xaa
1

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = Ile, Leu, Met or Val
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Tyr or Ser

<400> SEQUENCE: 61

Gly Gly Xaa Xaa Xaa
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Gly or Ala
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Ala, Val or Leu
<220> FEATURE:
<221> NAME/KEY: MISC_FEATURE
<222> LOCATION: (5)..(5)
<223> OTHER INFORMATION: Xaa = Met or Leu
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Met or Ala
<220> FEATURE:
<221> NAME/KEY: MISC_FEATURE
<222> LOCATION: (8)..(8)
<223> OTHER INFORMATION: Xaa = Ala, Thr, or Val
<220> FEATURE:
<221> NAME/KEY: MISC_FEATURE
<222> LOCATION: (9)..(9)
<223> OTHER INFORMATION: Xaa = Glu, Ala, Thr, or Val

<400> SEQUENCE: 62

Xaa Xaa Xaa Xaa Xaa Xaa Xaa Xaa Xaa
```

```
<210> SEQ ID NO 63
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = Glu or Gln
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Val or Leu
<220> FEATURE:
<221> NAME/KEY: MISC_FEATURE
<222> LOCATION: (6)..(6)
<223> OTHER INFORMATION: Xaa = Tyr or Phe

<400> SEQUENCE: 63

Leu Ala Xaa Xaa Xaa Xaa
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Arg or Lys
<220> FEATURE:
<221> NAME/KEY: MISC_FEATURE
<222> LOCATION: (2)..(2)
<223> OTHER INFORMATION: Xaa = Asn, Leu, or Thr
<220> FEATURE:
<221> NAME/KEY: MISC_FEATURE
<222> LOCATION: (3)..(5)
<223> OTHER INFORMATION: Xaa = Arg, Asn, Asp, Asx, Cys, Glu, Gln, Gly,
      His, Ile, Leu, Lys, Met, Phe, Pro, Ser, Thr, Trp, Tyr, or Val
<220> FEATURE:
<221> NAME/KEY: MISC_FEATURE
<222> LOCATION: (6)..(6)
<223> OTHER INFORMATION: Xaa = Asn, Thr, or Val
<220> FEATURE:
<221> NAME/KEY: MISC_FEATURE
<222> LOCATION: (7)..(7)
<223> OTHER INFORMATION: Xaa = Arg, Asn, Asp, Asx, Cys, Glu, Gln, Gly,
      His, Ile, Leu, Lys, Met, Phe, Pro, Ser, Thr, Trp, Tyr, or Val
<220> FEATURE:
<221> NAME/KEY: MISC_FEATURE
<222> LOCATION: (9)..(9)
<223> OTHER INFORMATION: Xaa = Gly, Thr, Leu, Tyr, Ile, Ser, Ala, Val,
      Phe, Asn or Met

<400> SEQUENCE: 64

Xaa Xaa Xaa Xaa Xaa Xaa Xaa Pro Xaa
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic construct
```

```
<400> SEQUENCE: 65

Lys Asn Thr Pro Ala Asn Ala Pro Ala
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa = Glu, Gln, or Asp
<220> FEATURE:
<221> NAME/KEY: MISC_FEATURE
<222> LOCATION: (3)..(3)
<223> OTHER INFORMATION: Xaa = Trp, Phe, or Tyr
<220> FEATURE:
<221> NAME/KEY: MISC_FEATURE
<222> LOCATION: (4)..(4)
<223> OTHER INFORMATION: Xaa = His or Gly

<400> SEQUENCE: 66

Asn Xaa Xaa Xaa Glu
1               5

<210> SEQ ID NO 67
<211> LENGTH: 299
<212> TYPE: PRT
<213> ORGANISM: Bacillus bogoriensis

<400> SEQUENCE: 67

Ala Asn Ser Gly Phe Tyr Val Ser Gly Thr Thr Leu Tyr Asp Ala Asn
1               5                   10                  15

Gly Asn Pro Phe Val Met Arg Gly Ile Asn His Gly His Ala Trp Tyr
            20                  25                  30

Lys Asp Gln Ala Thr Thr Ala Ile Glu Gly Ile Ala Asn Thr Gly Ala
        35                  40                  45

Asn Thr Val Arg Ile Val Leu Ser Asp Gly Gly Gln Trp Thr Lys Asp
    50                  55                  60

Asp Ile His Thr Val Arg Asn Leu Ile Ser Leu Ala Glu Asp Asn His
65                  70                  75                  80

Leu Val Ala Val Leu Glu Val His Asp Ala Thr Gly Tyr Asp Ser Ile
                85                  90                  95

Ala Ser Leu Asn Arg Ala Val Asp Tyr Trp Ile Glu Met Arg Ser Ala
            100                 105                 110

Leu Ile Gly Lys Glu Asp Thr Val Ile Ile Asn Ile Ala Asn Glu Trp
        115                 120                 125

Phe Gly Ser Trp Glu Gly Asp Ala Trp Ala Asp Gly Tyr Lys Gln Ala
    130                 135                 140

Ile Pro Arg Leu Arg Asn Ala Gly Leu Asn His Thr Leu Met Val Asp
145                 150                 155                 160

Ala Ala Gly Trp Gly Gln Phe Pro Gln Ser Ile His Asp Tyr Gly Arg
                165                 170                 175

Glu Val Phe Asn Ala Asp Pro Gln Arg Asn Thr Met Phe Ser Ile His
            180                 185                 190

Met Tyr Glu Tyr Ala Gly Gly Asn Ala Ser Gln Val Arg Thr Asn Ile
        195                 200                 205

Asp Arg Val Leu Asn Gln Asp Leu Ala Leu Val Ile Gly Glu Phe Gly
    210                 215                 220
```

His Arg His Thr Asn Gly Asp Val Asp Glu Ala Thr Ile Met Ser Tyr
225                 230                 235                 240

Ser Glu Gln Arg Gly Val Gly Trp Leu Ala Trp Ser Trp Lys Gly Asn
            245                 250                 255

Gly Pro Glu Trp Glu Tyr Leu Asp Leu Ser Asn Asp Trp Ala Gly Asn
            260                 265                 270

Asn Leu Thr Ala Trp Gly Asn Thr Ile Val Asn Gly Pro Tyr Gly Leu
            275                 280                 285

Arg Glu Thr Ser Arg Leu Ser Thr Val Phe Gln
            290                 295

<210> SEQ ID NO 68
<211> LENGTH: 297
<212> TYPE: PRT
<213> ORGANISM: Paenibacillus species

<400> SEQUENCE: 68

Met Ala Thr Gly Phe Tyr Val Ser Gly Asn Lys Leu Tyr Asp Ser Thr
1               5                   10                  15

Gly Lys Pro Phe Val Met Arg Gly Val Asn His Gly His Ser Trp Phe
            20                  25                  30

Lys Asn Asp Leu Asn Thr Ala Ile Pro Ala Ile Ala Lys Thr Gly Ala
            35                  40                  45

Asn Thr Val Arg Ile Val Leu Ser Asn Gly Ser Leu Tyr Thr Lys Asp
        50                  55                  60

Asp Leu Asn Ala Val Lys Asn Ile Ile Asn Val Val Asn Gln Asn Lys
65                  70                  75                  80

Met Ile Ala Val Leu Glu Val His Asp Ala Thr Gly Lys Asp Asp Tyr
                85                  90                  95

Asn Ser Leu Asp Ala Ala Val Asn Tyr Trp Ile Ser Ile Lys Glu Ala
            100                 105                 110

Leu Ile Gly Lys Glu Asp Arg Val Ile Val Asn Ile Ala Asn Glu Trp
            115                 120                 125

Tyr Gly Thr Trp Asn Gly Ser Ala Trp Ala Asp Gly Tyr Lys Lys Ala
130                 135                 140

Ile Pro Lys Leu Arg Asn Ala Gly Ile Lys Asn Thr Leu Ile Val Asp
145                 150                 155                 160

Ala Ala Gly Trp Gly Gln Phe Pro Gln Ser Ile Val Asp Tyr Gly Gln
                165                 170                 175

Ser Val Phe Ala Ala Asp Ser Gln Lys Asn Thr Val Phe Ser Ile His
            180                 185                 190

Met Tyr Glu Tyr Ala Gly Lys Asp Ala Ala Thr Val Lys Ala Asn Met
            195                 200                 205

Glu Asn Val Leu Asn Lys Gly Leu Ala Leu Ile Ile Gly Glu Phe Gly
210                 215                 220

Gly Tyr His Thr Asn Gly Asp Val Asp Glu Tyr Ala Ile Met Arg Tyr
225                 230                 235                 240

Gly Gln Glu Lys Gly Val Gly Trp Leu Ala Trp Ser Trp Tyr Gly Asn
            245                 250                 255

Ser Ser Gly Leu Asn Tyr Leu Asp Met Ala Thr Gly Pro Asn Gly Ser
            260                 265                 270

Leu Thr Ser Phe Gly Asn Thr Val Val Asn Asp Thr Tyr Gly Ile Lys
            275                 280                 285

Asn Thr Ser Gln Lys Ala Gly Ile Phe

```
                  290                 295

<210> SEQ ID NO 69
<211> LENGTH: 464
<212> TYPE: PRT
<213> ORGANISM: Bacillus hemicellulosilyticus

<400> SEQUENCE: 69

Gln Thr His Ser Gly Phe Tyr Ile Glu Gly Ser Thr Leu Tyr Asp Ala
1               5                   10                  15

Asn Gly Glu Pro Phe Val Met Arg Gly Ile Asn His Gly His Ala Trp
            20                  25                  30

Tyr Lys His Asp Ser Asn Val Ala Ile Pro Ala Ile Ala Asn Gln Gly
        35                  40                  45

Ala Asn Thr Ile Arg Ile Val Leu Ser Asp Gly Gly Gln Trp Ala Lys
    50                  55                  60

Asp Asp Ile Asn Thr Leu Asn Gln Val Leu Asp Leu Ala Glu Glu His
65                  70                  75                  80

Glu Met Ile Ala Val Val Glu Val His Asp Ala Thr Gly Ser Asn Ser
                85                  90                  95

Met Ala Asp Leu Asn Arg Ala Val Asp Tyr Trp Ile Glu Met Lys Asp
            100                 105                 110

Ala Leu Ile Gly Lys Glu Asp Arg Val Ile Ile Asn Ile Ala Asn Glu
        115                 120                 125

Trp Tyr Gly Ala Trp Asp Gly Gln Gly Trp Ala Asn Gly Tyr Lys Glu
    130                 135                 140

Val Ile Pro Arg Leu Arg Asn Ala Gly Phe Thr His Thr Leu Met Val
145                 150                 155                 160

Asp Ala Ala Gly Trp Gly Gln Tyr Pro Gln Ser Ile His Asp Tyr Gly
                165                 170                 175

Gln Glu Val Phe Asn Ala Asp Pro Leu Ala Asn Thr Met Phe Ser Ile
            180                 185                 190

His Met Tyr Glu Tyr Ala Gly Gly Asn Ala Ser Met Val Gln Ser Asn
        195                 200                 205

Ile Asp Gly Val Val Asp Gln Gly Leu Ala Leu Val Ile Gly Glu Phe
    210                 215                 220

Gly His Met His Thr Asp Gly Asp Val Asp Glu Ala Thr Ile Leu Ser
225                 230                 235                 240

Tyr Ser Gln Gln Arg Gly Val Gly Trp Leu Ala Trp Ser Trp Lys Gly
                245                 250                 255

Asn Gly Thr Gln Trp Glu Tyr Leu Asp Leu Ser Tyr Asp Trp Gln Gly
            260                 265                 270

Thr Asn Leu Thr Ser Trp Gly Asn Thr Ile Val His Gly Pro Asn Gly
        275                 280                 285

Leu Leu Glu Thr Ser Ile Pro Ser Ser Ile Phe His Thr Ala Pro Asn
    290                 295                 300

Asn Gly Asp Pro Pro His Asn Gly Asn Glu Thr Ile Leu Tyr Asp
305                 310                 315                 320

Phe Glu His Gly Thr Gln Gly Trp Ser Gly Ser Ser Leu Leu Gly Gly
                325                 330                 335

Pro Trp Thr Thr Asn Glu Trp Ser Thr Asn Gly Asn His Ser Leu Lys
            340                 345                 350

Ala Asp Ile Phe Leu Ser Ala Asn Ser Lys His Glu Leu Ala Lys Val
        355                 360                 365
```

```
Glu Asn Arg Asn Leu Ser Gly Tyr Ser Thr Leu Gln Ala Thr Val Arg
    370             375             380

His Ala His Trp Gly Asn Val Gly Asn Leu Thr Ala Arg Met Tyr Val
385             390             395             400

Lys Thr Gly Ser Asn Tyr Ser Trp Phe Asn Gly Asp Pro Ile Pro Val
            405             410             415

Asn Ser Ala Asn Gly Thr Thr Val Thr Leu Pro Leu Ser Ser Ile Pro
            420             425             430

Asn Leu Asn Asp Val Lys Glu Ile Gly Val Glu Phe Ile Gly Ala Ser
        435             440             445

Asn Ser Asn Gly Gln Thr Ala Ile Tyr Leu Asp His Val Thr Ile Gln
    450             455             460
```